US011150250B2

(12) United States Patent
Anderberg et al.

(10) Patent No.: US 11,150,250 B2
(45) Date of Patent: Oct. 19, 2021

(54) METHODS FOR DIAGNOSING ACUTE KIDNEY INJURY OR RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 13/061,413

(22) PCT Filed: Aug. 28, 2009

(86) PCT No.: PCT/US2009/055449
§ 371 (c)(1),
(2), (4) Date: Mar. 17, 2011

(87) PCT Pub. No.: WO2010/025424
PCT Pub. Date: Mar. 4, 2010

(65) Prior Publication Data
US 2011/0195429 A1    Aug. 11, 2011

Related U.S. Application Data

(60) Provisional application No. 61/092,733, filed on Aug. 28, 2008, provisional application No. 61/092,905, filed on Aug. 29, 2008, provisional application No. 61/093,247, filed on Aug. 29, 2008, provisional application No. 61/093,272, filed on Aug. 29, 2008, provisional application No. 61/092,926, filed on Aug. 29, 2008, provisional application No. 61/092,912, filed on Aug. 29, 2008, provisional application No. 61/093,262, filed on Aug. 29, 2008, provisional application No. 61/093,263, filed on Aug. 29, 2008, provisional application No. 61/093,264, filed on Aug. 29, 2008, provisional application No. 61/093,266, filed on Aug. 29, 2008, provisional application No. 61/093,154, filed on Aug. 29, 2008, provisional application No. 61/093,249, filed on Aug. 29, 2008, provisional application No. 61/093,244, filed on Aug. 29, 2008.

(51) Int. Cl.
*G01N 33/53* (2006.01)
*G01N 33/68* (2006.01)

(52) U.S. Cl.
CPC ... *G01N 33/6893* (2013.01); *G01N 2800/347* (2013.01)

(58) Field of Classification Search
CPC ... G01N 2800/347; G01N 33/53; G01N 33/68
See application file for complete search history.

(56) References Cited

U.S. PATENT DOCUMENTS

| 5,773,430 | A  | 6/1998  | Simon et al.       |
|-----------|----|---------|--------------------|
| 6,218,122 | B1 | 4/2001  | Friend et al.      |
| 6,664,385 | B1 | 12/2003 | Sanicola-Nadel et al. |
| 6,784,154 | B2 | 8/2004  | Westenfelder       |
| 6,861,404 | B1 | 3/2005  | Cohen et al.       |
| 6,941,172 | B2 | 9/2005  | Nachum             |
| 7,138,230 | B2 | 11/2006 | Hu et al.          |
| 7,141,382 | B1 | 11/2006 | Parikh et al.      |
| 7,235,358 | B2 | 6/2007  | Wohlgemuth et al.  |
| 7,608,413 | B1 | 10/2009 | Joseloff et al.    |
| 7,662,578 | B2 | 2/2010  | Devarajan          |
| 7,981,684 | B2 | 7/2011  | Levin et al.       |
| 7,998,744 | B2 | 8/2011  | Stevenson et al.   |
| 8,008,008 | B2 | 8/2011  | Parr et al.        |
| 8,071,293 | B2 | 12/2011 | High et al.        |
| 8,080,394 | B2 | 12/2011 | Levy et al.        |
| 8,241,861 | B1 | 8/2012  | Heinecke et al.    |
| 2003/0003588 | A1 | 1/2003 | Comper             |
| 2004/0053309 | A1 | 3/2004 | Holt et al.        |

(Continued)

FOREIGN PATENT DOCUMENTS

| CN | 1791797 A   | 6/2006 |
| CN | 101163971 A | 4/2008 |

(Continued)

OTHER PUBLICATIONS

Sharma et al. Two-dimensional fluorescence difference gel electrophoresis analysis of the urine proteome in human diabetic nephropathy. Proteomics. Jul. 2005;5(10):2648-55.*

(Continued)

*Primary Examiner* — Dong Jiang

(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using assays that detect one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, active caspase-3, and soluble platelet endothelial cell adhesion molecule as diagnostic and prognostic biomarkers in renal injuries.

8 Claims, No Drawings

Specification includes a Sequence Listing.

(56) References Cited

U.S. PATENT DOCUMENTS

| | | |
|---|---|---|
| 2004/0106155 A1 | 6/2004 | Comper |
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1* | 2/2007 | Shariat .................. 435/7.23 |
| 2007/0087387 A1 | 4/2007 | Devarajan et al. |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| EP | 0828159 A1 | 3/1998 |
| EP | 1905846 A2 | 4/2008 |
| EP | 2261660 A1 | 12/2010 |
| EP | 2480882 A1 | 8/2012 |
| EP | 2513649 A1 | 10/2012 |
| RU | 2180965 C1 | 3/2002 |
| SU | 1429031 A1 | 10/1988 |
| WO | 1998055508 A2 | 12/1998 |
| WO | 2003054004 A2 | 7/2003 |
| WO | 2003075016 A1 | 9/2003 |
| WO | 2004005934 A2 | 1/2004 |
| WO | 2005042719 A2 | 5/2005 |
| WO | 2005087264 A1 | 9/2005 |
| WO | 2006083986 A3 | 8/2006 |
| WO | 2007013919 A2 | 2/2007 |
| WO | 2007041623 A2 | 4/2007 |
| WO | 2008060607 A2 | 5/2008 |
| WO | 2008084331 A2 | 7/2008 |
| WO | 2008104804 A2 | 9/2008 |
| WO | 2008116867 A1 | 10/2008 |
| WO | 2008122670 A2 | 10/2008 |
| WO | 2008154238 A1 | 12/2008 |
| WO | 2009038742 A2 | 3/2009 |
| WO | 2010025424 A1 | 3/2010 |
| WO | 2010025434 A1 | 3/2010 |
| WO | 2010048346 A1 | 4/2010 |
| WO | 2010048347 A2 | 4/2010 |
| WO | 2010054389 A1 | 5/2010 |
| WO | 2010091236 A1 | 8/2010 |
| WO | 2010111746 A1 | 10/2010 |
| WO | 2010128158 A1 | 11/2010 |
| WO | 2011035323 A1 | 3/2011 |
| WO | 2011075744 A1 | 6/2011 |

OTHER PUBLICATIONS

Norman et al. Progressive renal disease: fibroblasts, extracellular matrix, and integrins. Exp Nephrol., Mar.-Apr. 1999;7(2):167-77.*

Svatek et al. Soluble Fas—a promising novel urinary marker for the detection of recurrent superficial bladder cancer.. Cancer. Apr. 15, 2006;106(8):1701-7.*

Ghoniem et al. Differential profile analysis of urinary cytokines in patients with overactive bladder. Int Urogynecol J (2011) 22:953-961.*

Parikh and Devarajan, New biomarkers of acute kidney injury. Crit Care Med 2008;36(4 Suppl):S159-S165.

Parikh et al., Urinary IL-18 is an early predictive biomarker of acute kidney injury after cardiac surgery. Kidney Int, 2006;70(1):199-203.

Perco et al., Protein biomarkers associated with acute renal failure and chronic kidney disease. Eur J Clin Invest. Nov. 2006;36(11):753-763.

Picard et al., Origin of renal myofibroblasts in the model of unilateral ureter obstruction in the rat. Histochem Cell Biol. Jul. 2008;130(1):141-155.

Price, Abrupt Changes in Prostate-Specific Antigen Concentration in Acute Renal Failure. Clin Chem. Jan. 1993;39(1):161-162.

Prozialeck and Edwards, Cell Adhesion Molecules in Chemically-Induced Renal Injury. Pharmacol Ther. Apr. 2007;114(1):74-93.

Radford et al. Predicting renal outcome in IgA nephropathy. J Am Soc Nephrol Feb. 1997;8(2):199-207.

Ramesh and Reeves, TNF-α mediates chemokine and cytokine expression and renal injury in cisplatin nephrotoxicity. J. Clin. Invest. Sep. 2002;110(6):835-842.

Ramesh et al., Endotoxin and cisplatin synergistically induce renal dysfunction and cytokine production in mice. Am J Physiol Renal Physiol. Jul. 2007;293(1):F325-F332.

Ramirez et al., Prospective Study on Autoantibodies Against Apolipoprotein H ( B2GPI) in Several Clinical Parameters From Patients With Terminal Renal Failure and Functioning Renal Transplants. Transplantation Proceedings Jul. 2009;41(6):2370-2372.

Ricci et al., The Rifle criteria and mortality in acute kidney injury: A systematic review. Kidney Int Mar. 2008;73(5):538-546.

Rosenkranz et al., P-selectin deficiency exacerbates experimental glomerulonephritis: a protective role for endothelial P-selectin in inflammation. J Clin Invest Mar. 1999;103(5):649-659.

Rouschop et al., Pre-transplant plasma and cellular levels of CD44 correlate with acute renal allograft rejection. Nephrol Dial Transplant Oct. 2005;20(10):2248-2254.

Rouschop et al., Renal expression of CD44 correlates with acute renal allograft rejection. Kidney Int. Sep. 2006;70(6):1127-1134.

Schena et al., EGF and MCP-1 Urinary Excretion Is a Suitable Prognostic Marker in Iga Nephropathy. J Am Soc of Nephrology; Meeting of the American Society of Nephrology. Sep. 1, 2002;13(Program and Abstracts Issue): 458A.

(56) References Cited

OTHER PUBLICATIONS

Schiffer et al., Activated Renal Macrophages Are Markers of Disease Onset and Disease Remission in Lupus Nephritis, J Immunol Feb. 1, 2008;180(3):1938-1947.

Schmaldienst et al., Angiogenin: a novel inhibitor of neutrophil-lactoferrin release during extracorporeal circulation. Kidney Blood Press Res. 2003;26(2):107-112.

Schmidt et al., Sexual hormone abnormalities in male patients with renal failure. Nephrol Dial Transplant. Mar. 2002;17(3):368-371.

Segawa et al., In situ expression and soluble form of P-selectin in human glomerulonephritis. Kidney Int. Oct. 1997;52(4):1054-1063.

Segerer et al., Chemokines, Chemokine Receptors, and Renal Disease: From Basic Science to Pathophysiologic and Therapeutic Studies. J Am Soc Nephrol Jan. 2000;11(1):152-176.

Severini and Aliberti, Diagnostic significance of urinary enzymes: Development of a high performance liquid chromatographic method for the measurement of urinary lysozyme. Clin Chim Acta Feb. 27, 1987;163(1):97-103.

Shlipak et al., Elevations of Inflammatory and Procoagulant Biomarkers in Elderly Persons With Renal Insufficiency. Circulation Jan. 2003;107(1):87-92.

Shoji et al., Plasma angiopoietin-like protein 3 (ANGPTL3) concentration is associated with uremic dyslipidemia. Atherosclerosis. Dec. 2009;207(2):579-584.

Stafford-Smith et al., Acute Kidney Injury and Chronic Kidney Disease After Cardiac Surgery. Adv Chronic Kidney Dis. Jul. 2008;15(3):257-277.

Stasko et al., Soluble P-Selectin During a Single Hemodialysis Session in Patients With Chronic Renal Failure and Erythropoietin Treatment. Clin Appl Thromb Hemost. Oct. 2007;13(4):410-415.

Stuard et al., Soluble adhesion molecules in chronic renal failure patients. Nephrol Dialysis Transplant. 1997;12(9):A100.

Supavekin et al., Differential gene expression following early renal ischemia/reperfusion. Kidney Int. May 2003;63(5):1714-1724.

Sutton et al., Injury of the renal microvascular endothelium alters barrier function after ischemia. Am J Physiol Renal Physiol Aug. 2003;285(2):F191-F198.

Sutton et al., Microvascular endothelial injury and dysfunction during ischemic acute renal failure. Kidney Int. Nov. 2002;62(5):1539-1549.

Sutton, Alteration of microvascular permeability in acute kidney injury. Microvasc Res. Jan. 2009;77(1):4-7.

Symon et al., The endogenous insulin-like growth factor system in radiocontrast nephropathy. Am. J. Physiol. Renal Physiol. Mar. 1998;274(3 Pt 2):F490-497.

Takada et al., The Cytokine-adhesion Molecule Cascade in Ischemia/Reperfusion Injury of the Rat Kidney. Inhibition by a Soluble P-selectin Ligand. J. Clin. Invest. Jun. 1997; 99(11):2682-2690.

Taulan et al., Comprehensive analysis of the renal transcriptional response to acute uranyl nitrate exposure. BMC Genomics Jan. 11, 2006;7(2) 14 pages.

Teppo et al., Soluble Intercellular Adhesion Molecule-1 (Sicam-1) after Kidney Transplantation: The Origin and Role of Urinary Sicam-1? Transplantation Apr. 27, 2001;71(8):1113-1119.

Thorburn et al., CXC and CC chemokines induced in human renal epithelial cells by inflammatory cytokines. APMIS Jul. 2009;117(7):477-487.

Timoshanko et al., Interleukin-12 from Intrinsic Cells Is an Effector of Renal Injury in Crescentic Glomerulonephritis. J. Am. Soc. Nephrol. Mar. 2001;12(3):464-471.

Torres et al., The ratio of epidermal growth factor to monocyte chemotactic peptide-1 in the urine predicts renal prognosis in IgA nephropathy. Kidney Int. Feb. 2008;73(3):327-333.

Vaidya and Bonventre, Mechanistic biomarkers for cytotoxic acute kidney injury. Expert Opin Drug Metab Toxicol. Oct. 2006;2(5):697-713.

Vaidya et al., Biomarkers of Acute Kidney Injury. Annu Rev Pharmacol Toxicol. Feb. 2008;48:463-493.

Vanhoutte et al., Biomarker discovery with SELDI-TOF MS in human urine associated with early renal injury: evaluation with computational analytical tools. Nephrol Dial Transplant Oct. 2007;22(10):2932-2943.

Villanueva et al., Ischemic acute renal failure induces the expression of a wide range of nephrogenic proteins. Am J Physiol Regul Integr Comp Physiol Apr. 2006;290(4):R861-R870.

Vonderscher, Biomarker of Drug Induced Kidney Injury Qualification for Regulatory Decision Making (CRADA). IOM/FDA, Silver Spring, MD Apr. 23, 2007:31 pp.

Waikar et al., Diagnosis, Epidemiology and Outcomes of Acute Kidney Injury. Clin J Am Soc Nephrol. May 2008;3(3):844-861.

Wan et al., The pathogenesis of septic acute renal failure. Curr Opin Crit Care Dec. 2003;9(6):496-502.

Wang et al., Netrin-1 and kidney injury. I. Netrin-1 protects against ischemia-reperfusion injury of the kidney. Am J Physiol Renal Physiol. Apr. 2008;294(4):F739-F747.

Wang et al., Validation of putative genomic biomarkers of nephrotoxicity in rats. Toxicology Apr. 18, 2008;246(2-3):91-100.

Wilson and Hadley, Urinary lysozyme. J Pediatr. Feb. 1950;36(2):199-211.

Winchester et al., Sorbents in Acute Renal Failure and End-Stage Renal Disease: Middle Molecule and Cytokine Removal. Blood Purif. 2004;22(1):73-77.

Yang et al. Frequency of anti-bactericidal/permeability-increasing protein (BPI) and anti-azurocidin in patients with renal disease. Clin. Exp. Immunol. Jul. 1996;105(1):125-131.

Yu et al., Urinary biomarkers trefoil factor 3 and albumin enable early detection of kidney tubular injury. Nat Biotechnol May 2010;128(5):470-477.

International Search Report and Written Opinion dated Jun. 3, 2011 in PCT/US2011/026759.

International Search Report and Written Opinion dated Sep. 7, 2012 in PCT/US2012/043279.

International Search Report and Written Opinion dated Dec. 15, 2011 in PCT/US2011/001126.

International Search Report and Written Opinion dated Nov. 25, 2011 in PCT/US2011/001127.

International Search Report and Written Opinion dated Nov. 25, 2011 in PCT/US2011/001128.

International Search Report and Written Opinion dated Nov. 25, 2011 in PCT/US2011/001125.

International Search Report and Written Opinion dated Jun. 20, 2012 in PCT/US2012/020572.

International Search Report and Written Opinion dated May 2, 2012 in PCT/US2012/022926.

International Search Report and Written Opinion dated Sep. 21, 2012 in PCT/US2012/045583.

Non Final Office Action issued by the USPTO in U.S. Appl. No. 13/061,446 dated Oct. 12, 2012.

Abd El Latif et al., Urinary epidermal growth factor excretion: A useful prognostic marker for progression of renal damage in children. J Med Sci Oct. 2007; 7(7): 1171-1176.

Abou-Shousha and Youssef, Interleukin-2 Regulatory Effect on P-Selectin and Interleukin-8 Production in Patients with Chronic Renal Failure. Egypt J Immunol. 2006;13(1):11-18.

Akcay et al., Mediators of Inflammation in Acute Kidney Injury. Mediators Inflamm. 2009;2009:137072 (12 pp).

Albright, Acute Renal Failure: A Practical Update. Mayo Clin. Proc. Jan. 2001;76(1):67-74.

Anders et al., Chemokines and chemokine receptors are involved in the resolution or progression of renal disease. Kidney Int. Feb. 2003;63(2):401-415.

Anilkumar et al., Trimeric assembly of the C-terminal region of Thrombospondin-1 or Thrombospondin-2 is necessary for cell spreading and fascin spike organisation. J Cell Sci. Jun. 1, 2002;115(Pt 11):2357-2366.

Arribas and Esselens, ADAM17 as a Therapeutic Target in Multiple Diseases. Curr Pharm Des. 2009;15(20):2319-2335.

Arrizabalaga et al., Tubular and Interstitial Expression of ICAM-1 as a Marker of Renal Injury in IgA Nephropathy. Am J Nephrol May-Jun. 2003;23(3):121-128.

(56) References Cited

OTHER PUBLICATIONS

Bagshaw et al., Urinary biomarkers in septic acute kidney injury. Intensive Care Med. Jul. 2007;33(7):1285-1296.
Bajwa et al., Immune Mechanisms and Novel Pharmacological Therapies of Acute Kidney Injury. Curr Drug Targets Dec. 2009;10(12):1196-1204.
Barrera-Chimal et al., Hsp72 is an early and sensitive biomarker to detect acute kidney injury. EMBO Mol Med. Jan. 2011;3(1):5-20.
Beushausen, NWG Biomarker Objectives. ILSI Health and Environmental Sciences Institute, ILSI-HESI Annual Meeting 2006:17 pp.
Bicik et al., Role of Transforming Growth Factor-.beta.2 in, and a Possible Transforming Growth Factor-beta2 Gene Polymorphism as a Marker of, Renal Dysfunction in Essential Hypertension: A Study in Turkish Patients, Current Therapeutic Research, 2005;44(4):266-278.
Biotrin International, Biotrin Biomarkers: How late do you want to detect preclinical kidney damage? Biotrin's acute kidney injury test (AKI Test). Biotrin's Preclinical Kidney Biomarkers: 8 pp.
Bonomini et al., Serum Levels of Soluble Adhesion Molecules in Chronic Renal Failure and Dialysis Patients. Nephron. Aug. 1998;79(4):399-407.
Bonventre and Zuk, Ischemic acute renal failure: An inflammatory disease? Kidney Int. Aug. 2004;66(2):480-485.
Bonventre, Dedifferentiation and Proliferation of Surviving Epithelial Cells in Acute Renal Failure. J Am Soc Nephrol Jun. 2003;14 Suppl 1:S55-S61.
Bonventre, Pathophysiology of Acute Kidney Injury: Roles of Potential Inhibitors of Inflammation. Contrib Nephrol. 2007; 156: 39-46.
Burne et al., IL-1 and TNF independent pathways mediate ICAM-1/VCAM-1 up-regulation in ischemia reperfusion injury. J Leukoc Biol. Aug. 2001;70(2):192-198.
Burne-Taney and Rabb, The role of adhesion molecules and T cells in ischemic renal injury. Curr Opin Nephrol Hypertens. Jan. 2003;12(1):85-90.
Canani et al., The Fatty Acid-Binding Protein-2 A54T Polymorphism Is Associated With Renal Disease in Patients With Type 2 Diabetes. Diabetes Nov. 2005;54(11):3326-3330.
Catania et al., Role of matrix metalloproteinases in renal pathophysiologies. Am J Physiol Renal Physiol Mar. 2007;292(3):F905-F911.
Coca et al., Biomarkers for the diagnosis and risk stratification of acute kidney injury: A systematic review. Kidney Int May 2008;73(9):1008-1016.
Cruz et al., North East Italian Prospective Hospital Renal Outcome Survey on Acute Kidney Injury (NEiPHROS-AKI): Targeting the Problem with the RIFLE Criteria. Clin J Amer. Soc. Nephrol. May 2007;2(3):418-425.
Daha and Van Kooten, Is the proximal tubular cell a proinflammatory cell? Nephrol Dial Transplant 2000;15 Suppl 6:41-43.
De Sa et al., Leukocyte, platelet and endothelial activation in patients with acute renal failure treated by intermittent hemodialysis. Am J Nephrol. Jul.-Aug. 2001;21(4):264-273.
Devarajan and Williams, Proteomics for Biomarker Discovery in Acute Kidney Injury. Semin Nephrol. Nov. 2007;27(6):637-651.
Devarajan, Cellular and molecular derangements in acute tubular necrosis. Curr Opin Pediatr. Apr. 2005;17(2):193-199.
Devarajan, Novel biomarkers for the early prediction of acute kidney injury. Cancer Therapy Sep. 2005;3:477-488.
Devarajan, Update on Mechanisms of Ischemic Acute Kidney Injury. J Am Soc Nephrol. Jun. 2006;17(6):1503-1520.
Domanski et al., Purine and Cytokine Concentrations in the Renal Vein of the Allograft During Reperfusion. Transplant Proc. Jun. 2007;39(5):1319-1322.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm.
Ferguson et al., Biomarkers of nephrotoxic acute kidney injury. Toxicology Mar. 20, 2008;245(3):182-193.
Frangogiannis, Chemokines in ischemia and reperfusion. Thromb Haemost May 2007;97(5):738-747.
Furuichi et al., Chemokine/chemokine receptor-mediated inflammation regulates pathologic changes from acute kidney injury to chronic kidney disease. Clin Exp Nephrol Feb. 2009;13(1):9-14.
Furuichi et al., Roles of chemokines in renal ischemia/reperfusion injury. Front Biosci. May 1, 2008;13:4021-4028.
Galkina and Ley, Leukocyte Recruitment and Vascular Injury in Diabetic Nephropathy. J Am Soc Nephrol. Feb. 2006;17(2):368-377.
Garcia et al., Adenosine A2A receptor activation and macrophagemediated experimental glomerulonephritis. FASEB J. Feb. 2008;22(2):445-454.
Gbadegesin et al., Plasma and urinary soluble adhesion molecule expression is increased during first documented acute pyelonephritis. Arch Dis Child. Mar. 2002;86(3):218-221.
Goes et al., Effect of Recombinant Human Insulin-Like Growth Factor-1 on the Inflammatory Response to Acute Renal Injury. J Am Soc Nephrol. May 1996;7(5):710-720.
Response dated May 16, 2012 to Extended European Search Report and Written Opinion in PCT/US2009/055449.
Extended European Search Report and Written Opinion dated Feb. 23, 2012 in PCT/US2009/065419.
Extended European Search Report and Written Opinion dated Jul. 27, 2012 in PCT/US2010/023294.
Extended European Search Report and Written Opinion dated Oct. 24, 2011 in PCT/US2009/055449.
Extended European Search Report and Written Opinion dated Feb. 22, 2012 in PCT/US2009/055460.
Extended European Search Report and Written Opinion dated Jul. 9, 2012 in PCT/US2009/061561.
Extended European Search Report and Written Opinion dated Aug. 23, 2012 in PCT/US2009/061562.
Extended European Search Report and Written Opinion dated Jul. 9, 2012 in PCT/US2010/023292.
Extended European Search Report and Written Opinion dated Aug. 23, 2012 in PCT/US2010/023297.
Extended European Search Report and Written Opinion dated Jun. 8, 2012 in PCT/US2009/063906.
International Preliminary Report on Patentability dated Oct. 21, 2011 in PCT/US2010/023297.
International Preliminary Report on Patentability dated Mar. 29, 2011 in PCT/US2010/049234.
International Preliminary Report on Patentability dated May 18, 2012 in PCT/US2010/055730.
International Preliminary Report on Patentability dated Mar. 10, 2011 in PCT/US2009/055449.
International Preliminary Report on Patentability dated Mar. 10, 2011 in PCT/US2009/055460.
International Preliminary Report on Patentability dated Aug. 16, 2012 in PCT/US2011/023830.
International Preliminary Report on Patentability dated Aug. 16, 2012 in PCT/US2011/023831.
International Preliminary Report on Patentability dated Aug. 16, 2012 in PCT/US2011/023832.
International Preliminary Report on Patentability dated Apr. 5, 2012 in PCT/US2010/049695.
International Preliminary Report on Patentability dated May 5, 2011 in PCT/US2009/061561.
International Preliminary Report on Patentability dated May 5, 2011 in PCT/US2009/061562.
International Preliminary Report on Patentability dated Jun. 3, 2011 in PCT/US2009/065419.
International Preliminary Report on Patentability dated Jul. 5, 2012 in PCT/US2010/061377.
International Preliminary Report on Patentability dated Aug. 18, 2011 in PCT/US2010/023292.
International Preliminary Report on Patentability dated Aug. 18, 2011 in PCT/US2010/023294.
International Preliminary Report on Patentability dated May 10, 2011 in PCT/US2009/063906.
International Search Report and Written Opinion dated Dec. 3, 2010 in PCT/US2010/049234.

(56) References Cited

OTHER PUBLICATIONS

International Search Report and Written Opinion dated Feb. 8, 2011 in PCT/US2010/055730.
International Search Report and Written Opinion dated Oct. 28, 2010 in PCT/US2010/044772.
International Search Report and Written Opinion dated Oct. 8, 2010 in PCT/US2010/044708.
International Search Report and Written Opinion dated Dec. 10, 2009 in PCT/US2009/055449.
International Search Report and Written Opinion dated Dec. 31, 2009 in PCT/US2009/055460.
International Search Report and Written Opinion dated Dec. 3, 2010 in PCT/US2010/049695.
International Search Report and Written Opinion dated Jan. 20, 2010 in PCT/US2009/061561.
International Search Report and Written Opinion dated Apr. 13, 2010 in PCT/US2009/061562.
International Search Report and Written Opinion dated Mar. 30, 2010 in PCT/US2009/065419.
International Search Report and Written Opinion dated Mar. 8, 2011 in PCT/US2010/061377.
International Search Report and Written Opinion dated Apr. 30, 2010 in PCT/US2010/023292.
International Search Report and Written Opinion dated Apr. 22, 2010 in PCT/US2010/023294.
International Search Report and Written Opinion dated Jun. 3, 2010 in PCT/US2010/023297.
International Search Report and Written Opinion dated Jan. 15, 2010 in PCT/US2009/063906.
International Search Report and Written Opinion dated Nov. 18, 2010 in PCT/US2010/046910.
International Search Report and Written Opinion dated Jan. 18, 2012 in PCT/US2011/053015.
International Search Report and Written Opinion dated Feb. 24, 2012 in PCT/US2011/055055.
International Search Report and Written Opinion dated Jan. 19, 2011 in PCT/US2010/055721.
International Search Report and Written Opinion dated May 10, 2012 in PCT/US2012/020571.
International Search Report and Written Opinion dated Apr. 27, 2011 in PCT/US2011/023830.
International Search Report and Written Opinion dated Apr. 27, 2011 in PCT/US2011/023831.
International Search Report and Written Opinion dated Apr. 29, 2011 in PCT/US2011/023832.
International Search Report and Written Opinion dated May 17, 2011 in PCT/US2011/026384.
International Search Report and Written Opinion from PCT/US2009/055449 dated Dec. 10, 2009.
Grigoryev et al., The Local and Systemic Inflammatory Transcriptome after Acute Kidney Injury. J Am Soc Nephrol. Mar. 2008;19(3):547-558.
Gümüs et al., Serum Levels of Total Acid Phosphatase, Prostatic Acid Phosphatase, Total and Free Prostate-Specific Antigen in Patients Within Chronic Hemodialysis Program. Braz J Urol, Mar.-Apr. 2001;27(2):133-135.
Gupta et al., Role of Protein C in Renal Dysfunction after Polymicrobial Sepsis. J Am Soc Nephrol. Mar. 2007;18 (3):860-867.
Han et al, Urinary biomarkers in the early diagnosis of acute kidney injury, Kidney Int. Apr. 2008;73(7):863-869.
Han et al., Upregulation of hyaluronan and its binding receptors in an experimental model of chronic cyclosporine nephropathy. Nephrology (Carlton). Mar. 2010;15(2):216-224.
Han, Biomarkers for Early Detection of Acute Kidney Injury. Nephrology Rounds Apr. 2008;6(4):6 pp.
Harris et al., Growth Factors and Cytokines in Acute Renal Failure. Adv Ren Replace Ther. Apr. 1997;4(2 Suppl):43-53.
He et al., Interleukin-18 binding protein transgenic mice are protected against ischemic acute kidney injury. Am J Physiol Renal Physiol. Nov. 2008;295(5):F1414-F1421.

Herget-Rosenthal et al., Early detection of acute renal failure by serum cystatin C. Kidney Int. Sep. 2004;66(3):1115-1122.
Hidaka et al., Urinary clusterin levels in the rat correlate with the severity of tubular damage and may help to differentiate between glomerular and tubular injuries. Cell Tissue Res. Dec. 2002;310(3):289-296.
Hirschberg et al. Factors Predicting Poor Outcome in Patients with Acute Renal Failure (ARF). J. Am. Soc. Nephrol. Sep. 1, 1996;7(9):1374.
Hoste et al., Rifle criteria for acute kidney injury are associated with hospital mortality in critically ill patients: a cohort analysis. Crit Care, 2006;10(3):R73 (10 pages).
Hugo and Daniel, Thrombospondin in Renal Disease. Nephron Exp Nephrol. 2009;111(3):e61-e66.
Hugo et al. ,Thrombospondin 1 precedes and predicts the development of tubulointerstitial fibrosis in glomerular disease in the rat. Kidney Int. Feb. 1998;53(2):302-311.
Jang and Rabb, The innate immune response in ischemic acute kidney injury. Clin Immunol. Jan. 2009;130(1):41-50.
Jonsson, The role of fibroblast growth factor 23 in renal disease. Nephrol. Dial. Transplant Mar. 2005;20(3):479-482.
Julian et al., Sources of Urinary Proteins and their Analysis by Urinary Proteomics for the Detection of Biomarkers of Disease. Proteomics Clin Appl., 2009;3(9):1029-1043.
Kadiroglu et al., The Evaluation of Effects of Demographic Features, Biochemical Parameters, and Cytokines on Clinical Outcomes in Patients with Acute Renal Failure. Ren Fail. 2007;29(4):503-508.
Kalousova et al., Soluble Receptor for Advanced Glycation End Products in Patients With Decreased Renal Function. Am. J. Kidney Dis.Mar. 2006;47(3): 406-411.
Kamata et al., Up-regulation of glomerular extracellular matrix and transforming growth factor-beta expression in RF/J mice. Kidney Int. Mar. 1999;55(3):864-876.
Kehoe et al. Elevated Plasma Renin Activity Associated with Renal Dysfunction. Nephron 1986;44:51-57 (abstract only).
Kellum et al. Definition and Classification of Acute Kidney Injury. Nephron Clin Pract 2008;109(4):c182-c187.
Kellum., Acute kidney injury, Crit Care Med, 2008;36(4):S141-S145.
Keyes and Bagshaw, Early diagnosis of acute kidney injury in critically ill patients. Expert Rev Mol Diagn. Jul. 2008;8(4):455-464.
Khanna et al., Expression of TGF-beta and fibrogenic genes in transplant recipients with tacrolimus and cyclosporine nephrotoxicity. Kidney Int. Dec. 2002;62(6):2257-2263.
Kharasch et al., Gene Expression Profiling of Nephrotoxicity from the Sevoflurane Degradation Product Fluoromethyl-2,2-difluoro-1-(trifluoromethyl)vinyl Ether ("Compound A") in Rats. Toxicol Sci. Apr. 2006;90(2):419-431.
Kiley and Chevalier, Urinary biomarkers: The future looks promising. Kidney Int. Jul. 2009;76( 2): 133-134.
Kilis-Pstrusinska et al., [Levels of selected soluble adhesion molecules in blood serum of children with chronic glomerulonephritis]. Pol Merkur Lekarski. Apr. 2001;10(58):247-249.
Kilis-Pstrusinska et al., Serum levels of soluble adhesion molecules in children with glomerulonephritis (GN). Nephrol Dialysis Transplant. Jun. 2001;16(6):A62.
Kinsey et al., Inflammation in Acute Kidney Injury. Nephron Exp Nephrol. 2008; 109(4):e102-e107.
Koo et al., Cadaver versus living donor kidneys: Impact of donor factors on antigen induction before transplantation. Kidney Int. Oct. 1999;56(4):1551-1559.
Landray et al., Inflammation, Endothelial Dysfunction, and Platelet Activation in Patients With Chronic Kidney Disease: The Chronic Renal Impairment in Birmingham (CRIB) Study. Am J Kidney Dis. Feb. 2004;43(2):244-253.
Lang et al., Heat Shock Protein 60 Is Released in Immune-Mediated Glomerulonephritis and Aggravates Disease: In Vivo Evidence for an Immunologic Danger Signal. J Am Soc Nephrol. Feb. 2005;16(2):383-391.
Larsson et al., Circulating concentration of FGF-23 increases as renal function declines in patients with chronic kidney disease, but

(56) References Cited

OTHER PUBLICATIONS does not change in response to variation in Phosphate intake in healthy volunteers. Kidney Int.Dec. 2003;64(6):2272-2279.
Liu et al., Predictive and pathogenetic value of plasma biomarkers for acute kidney injury in patients with acute lung injury. Crit Care Med Dec. 2007;35(12):2755-2761.
Liu et al., Serum Interleukin-6 and interleukin-8 are early biomarkers of acute kidney injury and predict prolonged mechanical ventilation in children undergoing cardiac surgery: a case-control study. Critical Care 2009;13(4):R104 (9 pp.).
Lopes-Virella et al., Urinary high density lipoprotein in minimal change glomerular disease and chronic glomerulopathies. Clin Chim Acta. May 16, 1979;94(1):73-81.
Lu et al., Increased Macrophage Infiltration and Fractalkine Expression in Cisplatin-Induced Acute Renal Failure in Mice. J Pharmacol Exp Ther. Jan. 2008;324(1):111-117.
Malyszko et al., Visfatin and apelin, new adipocytokines, and their relation to endothelial function in patients with chronic renal failure. Adv Med Sci. 2008;53(1):32-36.
Matousovic et al., IgA-containing immune complexes in the urine of IgA nephropathy patients. Nephrol Dial Transplant Sep. 2006;21(9):2478-2484.
Mattes, Experience With a Biomarker Consortium. CPath Predictive Safety Training Consortium, Critical Path Institute:48 pp.
Melnikov et al., Impaired IL-18 processing protects caspase-1-deficient mice from ischemic acute renal failure. J Clin Invest, May 2001;107(9):1145-1152.
Milford et al., Prognostic Markers in Diarrhoea-Associated Haemolytic-Uraemic Syndrome: Initial Neutrophil Count, Human Neutrophil Elastase and Von Willebrand Factor Antigen. Nephrol Dial Transplant 1991;6(4):232-237.
Montagna et al., Impairment of cellular redox status and membrane protein activities in kidneys from rats with ischemic acute renal failure. Biochim Biophys Acta Aug. 14, 1998;1407(2):99-108.
Musial et al., Soluble adhesion molecules in chronic renal failure (CRF) children treated conservatively. Nephrol Dialysis Transplant. 2002:17(Abstracts Suppl 1):232.
Nguyen et al., Heparin-Binding EGF-Like Growth Factor Is Up-Regulated in the Obstructed Kidney in a Cell- and Region-Specific Manner and Acts to Inhibit Apoptosis. Am J Pathol. Mar. 2000;156(3):889-898.
Nishiyama et al., Up-Regulation of Galectin-3 in Acute Renal Failure of the Rat. Am J Pathol. Sep. 2000;157(3):815-823.
Ohno et al., Prognostic significance of tenascin-C expression in clear cell renal cell carcinoma. Oncol Rep. 2008;20(3):511-516.
Ozer et al., A panel of urinary biomarkers to monitor reversibility of renal injury and a serum marker with improved potential to assess renal function. Nat Biotechnol. May 2010;28(5):486-494.
Yuen et al., Ischemic and Nephrotoxic Acute Renal Failure are Distinguished by their Broad Transcriptomic Responses. Physiol Genomics. May 16, 2006;25(3):375-386.
Zager et al. Proximal tubular cytochrome c efflux: Determinant, and potential marker, of mitochondrial injury. Kidney Int. Jun. 2004;65(6):2123-2134.
Extended European Search Report and Written Opinion issued in PCT/US2010044772 dated Dec. 3, 2012.
Voshol et al., Evaluation of Biomarker Discovery Approaches to Detect Protein Biomarkers of Acute Renal Allograft Rejection. J Proteome Res. Jul.-Aug. 2005;4(4):1192-1199.
Extended European Search Report and Written Opinion issued in PCT/US2010044708 dated Dec. 3, 2012.
Neziri et al., Cloning and molecular characterization of Dashurin encoded by C20orf116, a PCI-domain containing protein. Biochim Biophys Acta. Apr. 2010;1800(4):430-438.
Non Final Office Action issued by the US Patent and Trademark Office in U.S. Appl. No. 13/164,768 dated Dec. 18, 2012.
Non Final Office Action issued by the US Patent and Trademark Office in U.S. Appl. No. 13/061,413 dated Jan. 2, 2013.
Norman et al., Progressive Renal Disease: Fibroblasts, Extracellular Matrix, and Integrins. Exp Nephrol. Mar.-Apr. 1999;7(2):167-177.
International Search Report and Written Opinion issued in 200980154224.5 dated Nov. 23, 2012.
English Translation of International Search Report and Written Opinion issued in 200980154224.5 dated Nov. 23, 2012.
Zhu et al., Expression of Urinary Epidermal Growth Factor and Renal Function. J Clin Urol Dec. 31, 1998;13(8):374-379.
Zhu et al., Expression of Urinary Epidermal Growth Factor and Renal Function. J Clin Urol Dec. 31, 1998;13(8):374-379 (abstract English translation).
Sun et al., A Survey on the Relationship between the Epidermal Growth Factor and Renal Function. Int J Transpl Hemopurific Dec. 31, 2006;4(1):41-44.
Sun et al., A Survey on the Relationship between the Epidermal Growth Factor and Renal Function. Int J Transpl Hemopurific Dec. 31, 2006;4(1):41-44 (abstract English translation).
Non Final Office Action issued in 2009801542245 dated Dec. 17, 2012.
Non Final Office Action issued by the US Patent and Trademark Office in U.S. Appl. No. 13/125,360 dated Jan. 24, 2013.
Caron et al. Ischemic injury alters endothelial cell properties of kidney cortex:stimulation of MMP-9. Exp Cell Res. Oct. 15, 2005;301(1):105-116.
Non Final Office Action issued by the US Patent and Trademark Office in U.S. Appl. No. 13/508,363 dated Feb. 1, 2013.
Non Final Office Action issued by the US Patent and Trademark Office in U.S. Appl. No. 13/577,243 dated Feb. 14, 2013.
Non Final Office Action issued in Japanese Patent Application No. 2011-525262 dated Feb. 5, 2013.
Non Final Office Action issued in Japanese Patent Application No. 2011-525262 dated Feb. 5, 2013 (English translation).
International Preliminary Report on Patentability dated Sep. 7, 2012 in PCT/US2011/026384.
Non-Final Office Action issued by the US Patent and Trademark Office dated Nov. 16, 2012 in U.S. Appl. No. 13/389,351.
Non-Final Office Action issued by the US Patent and Trademark Office dated Nov. 27, 2012 in U.S. Appl. No. 13/130,474.
Flynn et al., Urinary excretion of beta2-glycoprotein-1 (apolipoprotein H) and other markers of tubular malfunction in "non-tubular" renal disease J Clin Pathol. Jul. 1992;45(7):561-567.
Kasahara et al Clinical Significance of Serum Oxidized Low-Density Lipoprotein/beta2-Giycoprotein I Complexes in Patients with Chronic Renal Diseases. Nephron Clin Pract. 2004;98(1):15-24.
Lapsley et al., Beta 2-glycoprotein-1 (apolipoprotein H) excretion in chronic renal tubular disorders: Comparison with other protein markers of tubular malfunction. J Clin Pathol. Oct. 1991;44(10):812-816.
Matsuda et al., Beta 2-Glycoprotein I—Dependent and -Independent Anticardiolipin Antibody in Patients with End-Stage Renal Disease. Thromb Res. Oct. 15, 1993;72(2):109-117.
Ramirez et al., Prospective Study on Autoantibodies Against Apolipoprotein H (beta2GPl) in Several Clinical Parameters From Patients With Terminal Renal Failure and Functioning Renal Transplants. Transplant Proc. Jul.-Aug. 2009;41(6):2370-2.
Zheng et al., Antiphospholipid antibody profiles in lupus nephritis with glomerular microthrombosis: a prospective study of 124 cases. Arthritis Res Ther. 2009;11(3):1-9.
International Search Report and Written Opinion issued in PCT/US2012/066152 dated Mar. 15, 2013.
Extended European Search Report and Written Opinion issued in EP 10817878 dated Apr. 15, 2013.
Mezzano et al., Endothelial Cell Markers in Chronic Uremia: Relationship with Hemostatic Defects and Severity of Renal Failure. Thromb Res. Dec. 15, 1997;88(6):465-472.
Tan et al., The level of urinary secretory immunoglobulin A (sIgA) of patients with IgA nephropathy is elevated and associated with pathological phenotypes. Clin Exp Immunol. Apr. 2009;156(1):111-116.
Zhang et al., The level of serum secretory IgA of patients with IgA nephropathy is elevated and associated with pathological phenotypes. Nephrol Dial Transplant Jan. 2008;23(1):207-212.
Search Report and Written Opinion issued by SIPO in 2009801406946 dated Apr. 15, 2013—includes English translation.

(56) References Cited

OTHER PUBLICATIONS

Office Action issued by SIPO in 2009801406946 dated May 29, 2013—includes English translation.
Search Report and Written Opinion issued in PCT/US2013/023479 dated May 15, 2013.
Choi et al., Expression of Vascular Endothelial Growth Factor-C and Its Receptor mRNA in the Rat Kidney With Ischemia-Reperfusion Injury. Clinical Kidney J. Jun. 2, 2011;4(Suppl 2):2 pages.
Cooper, Effect of Tobacco Smoking on Renal Function. Indian J Med Res Sep. 2006;124(3):261-268.
Extended European Search Report and Written Opinion issued in EP 10829198 dated May 21, 2013.
Senatorski et al., Urine activity of cathepsin B, collagenase and urine excretion of TGF-beta1 and fibronectin in membranous glomerulonephritis. Res Exp Med (Berl). Dec. 1998;198(4):199-206.
Schaefer et al., Urinary excretion of cathepsin B and cystatins as parameters of tubular damage. Kidney Int Suppl. Nov. 1994;47:S64-S67.
Kos et al., Cathepsins B,H and L and Their Inhibitors Stefin A and Cystatin C in Sera of Melanoma Patients. Clin Cancer Res. Oct. 1997;3(10):1815-1822.
Nambi et al., Down regulation of kidney neutral endopeptidase mRNA, protein and activity during acute renal failure: possible mechanism for ischemia-induced acute renal failure in rats? Mol Cell Biochem. Jul. 1999;197(1-2):53-59.
Li et al., Predictive value of RIFLE classification on prognosis of critically ill patients with acute kidney injury treated with continuous renal replacement therapy. Chin Med J (Engl). May 5, 2009;122(9):1020-1025.
Extended European Search Report and Written Opinion issued in EP 10829191 dated May 24, 2013.
Berahovich et al., Proteolytic activation of alternative CCR1 ligands in inflammation. J Immunol. Jun. 1, 2005;174(11):7341-7351.
Hatta et al., Cytokine Array Comparisons of Plasma from Cycling Fertile Women on Cycle Day 5 and Ovulation. Am J Reprod Immunol. Sep. 2009;62(3):158-164.
Office Action and Search Report issued by SIPO in Application No. 200980140805.3 dated Apr. 23, 2013—includes English Translation.
Mishra et al., Neutrophil gelatinase-associated lipocalin (NGAL) as a biomarker for acute renal injury after cardiac surgery. Lancet. Apr. 2-8, 2005;365(9466):1231-1238.
International Preliminary Report on Patentability issued in PCT/US2011/055055 dated May 24, 2013.
Extended European Search Report and Written Opinion issued in EP 10838357 dated Jun. 3, 2013.
Stenvinkel et al., High Serum Hyaluronan Indicates Poor Survival in Renal Replacement Therapy. Am J Kidney Dis. Dec. 1999;34(6):1083-1088.
Non-Final Office Action issued by the United States Patent and Trade Office in U.S. Appl. No. 13/577,242 dated Jun. 20, 2013.
Extended European Search Report and Written Opinion issued in EP 10818036 dated Jun. 6, 2013.
Extended European Search Report and Written Opinion issued in EP 11740470 dated Jun. 18, 2013.
Tary-Lehmann et al., Enzyme-Linked Immunosorbent Assay Spot Detection of Interferon-Gamma and Interleukin 5-Producing Cells as a Predictive Marker for Renal Allograft Failure. Transplantation. Jul. 27, 1998;66(2):219-224.
Kimmel et al., Immunologic function and survival in hemodialysis patients. Kidney Int. Jul. 1998;54(1):236-244.
Simmons et al., Plasma cytokine levels predict mortality in patients with acute renal failure. Kidney Int. Apr. 2004;65(4):1357-1365.
Search Report issued by SIPO in Application No. 200980149555.X dated May 23, 2013—includes English translation.
Cai, Detection and Application for the biomarker of Rental Injury in Early Stage. Laboratory Med Clinic. Jun. 2005;2(3):124-127—incl Engl transl abstract only.
Office Action issued by SIPO in Application No. 200980149555.X dated Jul. 1, 2013—includes English translation.
Search Report issued by in Application No. 201080014932.1 dated Jun. 9, 2013—includes English translation.
Office Action issued by SIPO in Application No. 201080014932.1 dated Jun. 25, 2013—includes English translation.
Jung et al., Diagnostic significance of urinary enzymes in detecting acute rejection crises in renal transplant recipients depending on expression of results illustrated through the example of alanine aminopeptidase. Clin Biochem. Aug. 1985;18(4):257-260.
Search Report issued by SIPO in Application No. 200980149636.X dated Jun. 17, 2013—includes English translation.
Office Action issued by SIPO in Application No. 200980149636.X dated Jul. 1, 2013—includes English translation.
Extended European Search Report and Written Opinion issued in EP 11740468 dated Jun. 13, 2013.
Fried et al., Inflammatory and Prothrombotic Markers and the Progression of Renal Disease in Elderly Individuals. J Am Soc Nephrol. Dec. 2004;15(12):3184-3191.
Edelstein, Biomarkers of Acute Kidney Injury. Adv Chronic Kidney Dis.Jul. 2008;15(3)222-234.
Extended European Search Report and Written Opinion issued in EP 11740469 dated Jun. 13, 2013.
Fujisaki et al., Infusion of radiocontrast agents induces exaggerated release of urinary endothelin in patients with impaired renal function. Clin Exp Nephrol. Dec. 2003;7(4):279-283.
Hirai et al., Plasma endothelin-1(ET-1) is a useful marker for renal dysfunction. Atheroscler Suppl. Jun. 19, 2006;7(3):60[Mo-P1:65].
Cottone et al., Endothelin-1 and F2-isoprostane relate to and predict renal dysfunction in hypertensive patients. Nephrol Dial Transpl. Feb. 2009;24(2):497-503.
Schulz et al., Endothelin-1 as an early prognostic marker in acute renal failure (ARF) and sepsis. Kidney Blood Press Res. 2000;23(3-5):341-342.
Search Report issued by SIPO in Application No. 201080057014.7 dated Jul. 8, 2013—includes English translation.
Office Action issued by SIPO in Application No. 201080057014.7 dated Jul. 18, 2013—includes English translation.
Extended European Search Report and Written Opinion issued in EP 10812639 dated Jul. 16, 2013.
Song et al., Expression of TRAIL, DR4, and DR5 in kidney and serum from patients receiving renal transplantation. Transplant Proc. Jun. 2004;36(5):1340-1343.
Extended European Search Report and Written Opinion issued in EP 10817878 dated Apr. 5, 2013.
Berahovich et al., Proteolytic activation of alternative CCR1 ligands in inflammation. J Immunol. Jun. 1, 2005;174(11):1341-7351.
Office Action and Search Report issued by SIPO in Application No. 200980140805.3 dated Apr. 16, 2013—includes English Translation.
Extended European Search Report and Written Opinion issued in EP application No. 09 810 695.8 dated Aug. 19, 2014.
Dalboni et al., High serum levels of soluble Fas (sFas) in CKD patients: Effects of renal clearance, reabsorption and synthesis. Int J Artif Organs. May 2008;31(5):405-410.
Dalboni et al., Soluble Fas: A Novel Marker of Inflammation in Uremia. Artif Organs. Aug. 2003;27(8):687-691.
Nguyen et al., Biomarkers for the early detection of acute kidney injury. Pediatr Nephrol. Dec. 2008;23(12):2151-2157.
Nishioka et al., Soluble FAS in Renal Allograft Recipients. Transplant Proc. Nov. 2000;32(7):1784.
Shou et al., Serum Levels of Soluble Fas and Disease Activity in Patients with IgA Nephropathy. Nephron. 1999;81(4):387-392.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm dated Jun. 12, 2008.
Harpur et al., Biological Qualification of Biomarkers of Chemical-Induced Renal Toxicity in Two Strains of Male Rat. Toxicol Sci. Aug. 2011;122(2):235-252.
Final Office Action issued by the United States Patent and Trademark Office in U.S. Appl. No. 13/061,446 dated Jun. 7, 2013.

(56) References Cited

OTHER PUBLICATIONS

Non Final Office Action issued by the United States Patent and Trademark Office in U.S. Appl. No. 13/125,454 dated Mar. 5, 2013.
Thaker et al., Identification of thrombospondin 1 (TSP-1) as a novel mediator of cell injury in kidney ischemia. J Clin Invest Dec. 2005;115(12):3451-3458.
Restriction Requirement issued by the United States Patent and Trademark Office in U.S. Appl. No. 13/061,413 dated Sep. 5, 2012.
Response to Restriction Requirement in U.S. Appl. No. 13/061,413 dated Oct. 16, 2012.
Response to Non Final Office Action issued in U.S. Appl. No. 13/061,413 dated Jul. 2, 2013.
Final Office Action issued by the United States Patent and Trademark Office in U.S. Appl. No. 13/061,413 dated Aug. 23, 2013.
Restriction Requirement issued by the United States Patent and Trademark Office in U.S. Appl. No. 13/148,031 dated Mar. 20, 2013.
Mast et al., Clinical utility of the soluble transferrin receptor and comparison with serum ferritin in several populations. Clin Chem. Jan. 1998;44(1):45-51.
Non Final Office Action issued by the United States Patent and Trademark Office in U.S. Appl. No. 13/389,363 dated Apr. 18, 2013.
Iglesias et al., Thyroid Dysfunction and Kidney Disease (Revised version). Eur J Endocrinol. Dec. 18, 2008:32 pages retrieved from URL://www.eje.org/content!early/2008/12/18/EJE-08.0837.full.pdf.
Rajashekar et al., Systemic diseases with renal manifestations. Prim Care. Jun. 2008;35(2):297-328.abstract retrieved from URL:www.ncbi.nlm.nih.gov/pubmed/18486717.
Rini et al., Renal cell carcinoma. Lancet. Mar. 28, 2009;373(9669):1119-1132.
Non Final Office Action issued by the United States Patent and Trademark Office in U.S. Appl. No. 13/125,360 dated Aug. 27, 2013.
Sharma et al. Two-dimensional fluorescence difference gel electrophoresis analysis of the urine proteome in human diabetic nephropathy. Proteomics. Jul. 2005;5(10):2648-2655.
Non Final Office Action issued by the United States Patent and Trademark Office in U.S. Appl. No. 13/130,474 dated Nov. 27, 2012.
Non Final Office Action issued by the United States Patent and Trademark Office in U.S. Appl. No. 13/148,030 dated May 1, 2013.
Malm et al., Changes in the plasma levels of vitamin K-dependent proteins C and S and of C4b-binding protein during pregnancy and oral contraception. Br J Haematol. Apr. 1988;68(4):437-443.
Matsuzaka et al., Relationship between vitamin K dependent coagulation factors and anticoagulants (protein C and protein S) in neonatal vitamin K deficiency. Arch Dis Child. Mar. 1993;68(3 Spec No):297-302.
International Search Report and Written Opinion issued in PCT/US2013/028005 dated Jun. 18, 2013.
Maddens et al., Chitinase-like Proteins are Candidate Biomarkers for Sepsis-induced Acute Kidney Injury. Mol Cell Proteomics. Jan. 10, 2012;11(6):1-13.
Restriction Requirement issued by the United States Patent and Trademark Office in U.S. Appl. No. 13/517,244 dated Jul. 1, 2013.
Extended European Search Report and Written Opinion issued in EP 11751238 dated Aug. 13, 2013.
Haase et al., A comparison of the RIFLE and Acute Kidney Injury Network classifications for cardiac surgery-associated acute kidney injury: A prospective cohort study. J Thorac Cardiovasc Surg. Dec. 2009;138(6):1370-1376.
Zaffanello M et al., Early diagnosis of acute kidney injury with urinary biomarkers in the newborn. J Matern Fetal Neonatal Med. 2009;22 Suppl 3:62-66.
Extended European Search Report and Written Opinion issued in EP 11748210 dated Aug. 16, 2013.
Calabrese et al., Oxidative stress and cellular stress response in diabetic nephropathy. Database Biosis [Online]. Biosciences Information Service Jan. 2007; XP002705326. Database accession No. PREV200800097004 (abstract):3 pages & Cell Stress Chaperones. 2007 Winter;12(4):299-306.
Musial et al., The Heat Shock Protein Profile in Children with Chronic Kidney Disease. Perit Dial Int. Mar.-Apr. 2010;30(2):227-232.
Tao et al., Expression of 60-kDa and Inducible 70-kDa Stress Proteins in Gentamicin-Induced Acute Renal Failure. Clin Exp Nephrol. Jul. 1997;1:254-260.
Awad et al., Compartmentalization of neutrophils in the kidney and lung following acute ischemic kidney injury. Kidney Int. Apr. 2009;75(7):689-698.
Bolisetty and Agarwal, Neutrophils in acute kidney injury: not neutral any more. Kidney Int. Apr. 2009;75(7):674-676.
Bonventre, Next-generation biomarkers for detecting kidney toxicity. Nat Biotechnol. May 2010;28(5):436-440.
Candiano et al., Repetitive Fragmentation Products of Albumin and (alpha)1-Antitrypsin in Glomerular Diseases Associated with Nephrotic Syndrome. J Am Soc Nephrol. Nov. 2006;17(11):3139-3148.
Faubel et al., Caspase-1-deficient mice are protected against cisplatin-induced apoptosis and acute tubular necrosis. Kidney Int. Dec. 2004;66(6):2202-2213.
Gupta et al., Distinct Functions of Activated Protein C Differentially Attenuate Acute Kidney Injury. J Am Soc Nephrol. Feb. 2009;20(2):267-277.
Hise et al., Control of the Epidermal Growth Factor Receptor and Its Ligands during Renal Injury. Nephron. May 2001;88(1):71-79.
Jang et al., B Cells Limit Repair after Ischemic Acute Kidney Injury. J Am Soc Nephrol. Apr. 2010;21(4):654-665.
Kunduzova et al., Involvement of Peripheral Benzodiazepine Receptor in the Oxidative Stress, Death-Signaling Pathways, and Renal Injury Induced by Ischemia-Reperfusion. J Am Soc Nephrol. Aug. 2004;15(8):2152-2160.
Kuzniar et al., Elastase deposits in the kidney and urinary elastase excretion in patients with glomerulonephritis evidence for neutrophil involvement in renal injury. Scand J Urol Nephrol. 2007;41(6):527-534.
Luyckx et al., Oncostatin M pathway plays a major role in the renal acute phase response. Am J Physiol Renal Physiol. Apr. 2009;296(4):F875-883.
Misseri et al., TNF-alpha mediates obstruction-induced renal tubular cell apoptosis and proapoptotic signaling. Am J Physiol Renal Physiol. Feb. 2005;288(2):F406-411.
Nogae et al., Induction of Apoptosis in Ischemia-Reperfusion Model of Mouse Kidney: Possible Involvement of Fas. J Am Soc Nephrol. Apr. 1998;9(4):620-631.
Parikh et al., Tubular proteinuria in acute kidney injury: a critical evaluation of current status and future promise. Ann Clin Biochem. Jul. 2010;47(Pt 4):301-312.
Singbartl et al., Blocking P-selectin protects from ischemia/reperfusion-induced acute renal failure. FASEB J. Jan. 2000;14(1):48-54.
Tadagavadi et al., Netrin-1 Regulates Th1/Th2/Th17 Cytokine Production and Inflammation through UNC5B Receptor and Protects Kidney against Ischemia-Reperfusion Injury. J Immunol. Sep. 15, 2010;185(6):3750-3758.
Varghese et al., Urine Biomarkers Predict the Cause of Glomerular Disease. J Am Soc Nephrol. Mar. 2007;18(3):913-922.
Wang et al., Endotoxemic acute renal failure is attenuated in caspase-1-deficient mice. Am J Physiol Renal Physiol. May 2005;288(5):F997-1004.
Wu et al., Elevated Urinary VCAM-1, P-Selectin, Soluble TNF Receptor-1, and CXC Chemokine Ligand 16 in Multiple Murine Lupus Strains and Human Lupus Nephritis. J Immunol. Nov. 15, 2007;179(10):7166-7175.
Wu et al., Excreted Urinary Mediators in an Animal Model of Experimental Immune Nephritis With Potential Pathogenic Significance. Arthritis Rheum. Mar. 2007;56(3):949-959.
Zhang et al., Biomarker Discovery for Lupus Nephritis Through Longitudinal Urine Proteomics. Kidney Int. Sep. 2008;74(6):799-807.
Zhang et al., Heat Shock Protein Expression Is Highly Sensitive to Ischemia-Reperfusion Injury in Rat Kidneys. Ann Clin Lab Sci. 2008 Winter;38(1):57-64.

(56) References Cited

OTHER PUBLICATIONS

Zhang et al., Urinary Peptide Patterns in Native Kidneys and Kidney Allografts. Transplantation. Jun. 27, 2009;87(12):1807-1813.
Office Action and Search Report issued by SIPO issued in Chinese Patent Application No. 200980140805.3 dated Dec. 4, 2013—incl English language translation.
Lorz et al., Proapoptotic Fas Ligand Is Expressed by Normal Kidney Tubular Epithelium and Injured Glomeruli. J Am Soc Nephrol. Jul. 2000;11(7):1266-1277.
Office Action and Search Report issued by SIPO in Chinese Patent Application No. 200980140805.3 dated May 30, 2014—incl English language translation.
Perianayagam et al., Serum soluble Fas (CD95) and Fas ligand profiles in chronic kidney failure. J Lab Clin Med. Oct. 2000;136(4):320-327.
"C-reaactive protein", US National Library of Medicine, retrieved from //www.nlm.nih.gov/medlineplus/ency/article/003356.htm, Jul. 31, 2015.
Devran et al., "C-reactive protein as a predictor of mortality in patients affected with severe sepsis in intensive care unit," Multidisciplinary Respiratory Medicine 2012, 7:47 http://www.mrmjournal.com/content/7/1/47.
Geersing et al., "Excluding venous thromboembolism using point of care D-dimer tests in outpatients: a diagnostic meta-analysis", BMJ 2009;339:b2990 doi:10.1136/bmj.b2990.
Indik and Alpert, "Detection of pulmonary embolism by D-dimer assay, spiral computed tomography, and magnetic resonance imaging", Prog Cardiovasc Dis. Jan.-Feb. 2000;42(4):261-72. Review.
Ridker, "C-Reactive Protein: A Simple Test to Help Predict Risk of Heart Attack and Stroke", Circulation. 2003;108: e81-e85, doi:10.1161/01.CIR.0000093381.57779.67.
"Prostate Cancer Screening Results from the Prostate, Lung, Colorectal, and Ovarian Cancer Randomized Screening Trial: Questions and Answers", National Cancer Institute, retrieved from http://www.cancer.gov/types/prostate/research/plco-screening-results-qa, Sep. 17, 2015.
James D. Faix, Biomarkers of Sepsis, Critical Reviews in Clinical Laboratory Sciences, 50:1, 23-26, 2013.
Office Action issued by the JPO in Japanese Patent Application No. 2015-208192 dated Aug. 16, 2016—incl Engl lang transl.
Office Action issued by KIPO in Korean Patent Application No. 10-2011-7006719 dated Jun. 15, 2016—incl Engl lang transl.
Extended European Search Report and Written Opinion issued in EP application No. 17185251 dated Oct. 19, 2017.
Davies et al., The Isolation of a Neutral Proteinase from the Urine of a Patient with Goodpasture's Syndrome. Biochem Soc Trans. 1978;6(5):947-949.
Kuzniar et al., Etiology of Increased Enzymuria in Different Morphological Forms of Glomerulonephritis. Nephron Physiol. 2004;98(1):p. 8-p. 14.
Mizutani et al., ON0-5046, Neutrophil Elastase Inhibitor, Reduces Ischemia/Reperfusion-Induced Acute Renal Injury by Inhibiting Leukocyte Activation in Rats. Anesthesiology Abstracts of Scientific Papers Annual Meeting, Oct. 16, 2000 Retrieved from the Internet: URL:http://www.asaabstracts.com/strands/asaabstracts/abstract.htm [retrieved on Oct. 4, 2017].
Shaefer et al., Leukocyte proteinases and proteinase inhibitors in the catabolism of acute renal failure. Kidney Int Suppl. Oct. 1987;22:S100-S103.
Office Action issued by SIPO in Chinese Patent Application No. 2015104282548 dated Jan. 12, 2017—incl Engl lang transl Search Report only.
"Rapidly progressive glomerulonephritis", TheFreeDictionary.com, Jun. 6, 2012, XP55029047, Retrieved from the Internet: URL: http://encyclopedia.thefreedictionary.com/Rapidly+progressing+glomerulonephritis [retrieved on Jun. 6, 2012].
Official Action dated Oct. 14, 2013, issued in Australian application (No. 2009285550).
Official Action dated Apr. 17, 2015, issued in Australian application (No. 2009285550).
Official Action dated Mar. 31, 2016, issued in Canadian application (No. 2,735,587).
Official Action dated Apr. 25, 2016, issued in Chinese Patent Application (201510428254.8).
Official Action dated Jul. 4, 2017, issued in Chinese Patent Application (201510428254.8).
Official action dated Jun. 13, 2012, in European Patent Application (No. 09 810 695.8).
Official action dated Jul. 9, 2015, in European Patent Application (No. 14151433.1).
Official action dated Feb. 1, 2016, in European Patent Application (No. 14151433.1).
Official action dated Sep. 19, 2018, in European Patent Application (No. 17185251.0).
Official action dated Jul. 31, 2017, in Indian Patent Application (No. 1671/CHENP/2011).
Official Action dated Nov. 19, 2013, in Japanese Patent Application (No. 2011-525260).
Official Action dated Sep. 30, 2014, in Japanese Patent Application (No. 2011-525260).
Official Action dated Jul. 19, 2016, in Japanese Patent Application (No. 2011-525260).
Official action dated May 5, 2011, in New Zealand Patent Application (No. 591437).
Official action dated Aug. 29, 2012, in New Zealand Patent Application (No. 591437).
Official action dated May 21, 2013, in New Zealand Patent Application (No. 591437).
Official action dated May 9, 2013, in New Zealand Patent Application (No. 610356).
Official action dated Feb. 24, 2015, in New Zealand Patent Application (No. 610356).
Official action dated Mar. 12, 2015, in New Zealand Patent Application (No. 610356).
Official action dated Feb. 24, 2015, in New Zealand Patent Application (No. 704822).

\* cited by examiner

SEQUENCE LISTING

```
<160> NUMBER OF SEQ ID NOS: 14

<210> SEQ ID NO 1
<211> LENGTH: 830
<212> TYPE: PRT
<213> ORGANISM: Homo sapiens

<400> SEQUENCE: 1

Met Ala Asn Cys Gln Ile Ala Ile Leu Tyr Gln Arg Phe Gln Arg Val
1               5                   10                  15

Val Phe Gly Ile Ser Gln Leu Leu Cys Phe Ser Ala Leu Ile Ser Glu
            20                  25                  30

Leu Thr Asn Gln Lys Glu Val Ala Ala Trp Thr Tyr His Tyr Ser Thr
        35                  40                  45

Lys Ala Tyr Ser Trp Asn Ile Ser Arg Lys Tyr Cys Gln Asn Arg Tyr
    50                  55                  60

Thr Asp Leu Val Ala Ile Gln Asn Lys Asn Glu Ile Asp Tyr Leu Asn
65                  70                  75                  80

Lys Val Leu Pro Tyr Tyr Ser Ser Tyr Tyr Trp Ile Gly Ile Arg Lys
                85                  90                  95

Asn Asn Lys Thr Trp Thr Trp Val Gly Thr Lys Lys Ala Leu Thr Asn
            100                 105                 110

Glu Ala Glu Asn Trp Ala Asp Asn Glu Pro Asn Asn Lys Arg Asn Asn
        115                 120                 125
```

```
Glu Asp Cys Val Glu Ile Tyr Ile Lys Ser Pro Ser Ala Pro Gly Lys
            130                 135                 140

Trp Asn Asp Glu His Cys Leu Lys Lys Lys His Ala Leu Cys Tyr Thr
145                 150                 155                 160

Ala Ser Cys Gln Asp Met Ser Cys Ser Lys Gln Gly Glu Cys Leu Glu
                165                 170                 175

Thr Ile Gly Asn Tyr Thr Cys Ser Cys Tyr Pro Gly Phe Tyr Gly Pro
            180                 185                 190

Glu Cys Glu Tyr Val Arg Glu Cys Gly Glu Leu Glu Leu Pro Gln His
        195                 200                 205

Val Leu Met Asn Cys Ser His Pro Leu Gly Asn Phe Ser Phe Asn Ser
210                 215                 220

Gln Cys Ser Phe His Cys Thr Asp Gly Tyr Gln Val Asn Gly Pro Ser
225                 230                 235                 240

Lys Leu Glu Cys Leu Ala Ser Gly Ile Trp Thr Asn Lys Pro Pro Gln
            245                 250                 255

Cys Leu Ala Ala Gln Cys Pro Pro Leu Lys Ile Pro Glu Arg Gly Asn
                260                 265                 270

Met Ile Cys Leu His Ser Ala Lys Ala Phe Gln His Gln Ser Ser Cys
        275                 280                 285

Ser Phe Ser Cys Glu Glu Gly Phe Ala Leu Val Gly Pro Glu Val Val
290                 295                 300

Gln Cys Thr Ala Ser Gly Val Trp Thr Ala Pro Ala Pro Val Cys Lys
305                 310                 315                 320

Ala Val Gln Cys Gln His Leu Glu Ala Pro Ser Glu Gly Thr Met Asp
            325                 330                 335

Cys Val His Pro Leu Thr Ala Phe Ala Tyr Gly Ser Ser Cys Lys Phe
                340                 345                 350

Glu Cys Gln Pro Gly Tyr Arg Val Arg Gly Leu Asp Met Leu Arg Cys
        355                 360                 365

Ile Asp Ser Gly His Trp Ser Ala Pro Leu Pro Thr Cys Glu Ala Ile
370                 375                 380

Ser Cys Glu Pro Leu Glu Ser Pro Val His Gly Ser Met Asp Cys Ser
385                 390                 395                 400

Pro Ser Leu Arg Ala Phe Gln Tyr Asp Thr Asn Cys Ser Phe Arg Cys
            405                 410                 415

Ala Glu Gly Phe Met Leu Arg Gly Ala Asp Ile Val Arg Cys Asp Asn
                420                 425                 430

Leu Gly Gln Trp Thr Ala Pro Ala Pro Val Cys Gln Ala Leu Gln Cys
        435                 440                 445

Gln Asp Leu Pro Val Pro Asn Glu Ala Arg Val Asn Cys Ser His Pro
450                 455                 460

Phe Gly Ala Phe Arg Tyr Gln Ser Val Cys Ser Phe Thr Cys Asn Glu
465                 470                 475                 480

Gly Leu Leu Leu Val Gly Ala Ser Val Leu Gln Cys Leu Ala Thr Gly
            485                 490                 495

Asn Trp Asn Ser Val Pro Pro Glu Cys Gln Ala Ile Pro Cys Thr Pro
                500                 505                 510

Leu Leu Ser Pro Gln Asn Gly Thr Met Thr Cys Val Gln Pro Leu Gly
        515                 520                 525

Ser Ser Ser Tyr Lys Ser Thr Cys Gln Phe Ile Cys Asp Glu Gly Tyr
530                 535                 540
```

```
Ser Leu Ser Gly Pro Glu Arg Leu Asp Cys Thr Arg Ser Gly Arg Trp
545                 550                 555                 560

Thr Asp Ser Pro Pro Met Cys Glu Ala Ile Lys Cys Pro Glu Leu Phe
                565                 570                 575

Ala Pro Glu Gln Gly Ser Leu Asp Cys Ser Asp Thr Arg Gly Glu Phe
            580                 585                 590

Asn Val Gly Ser Thr Cys His Phe Ser Cys Asn Asn Gly Phe Lys Leu
        595                 600                 605

Glu Gly Pro Asn Asn Val Glu Cys Thr Thr Ser Gly Arg Trp Ser Ala
    610                 615                 620

Thr Pro Pro Thr Cys Lys Gly Ile Ala Ser Leu Pro Thr Pro Gly Leu
625                 630                 635                 640

Gln Cys Pro Ala Leu Thr Thr Pro Gly Gln Gly Thr Met Tyr Cys Arg
                645                 650                 655

His His Pro Gly Thr Phe Gly Phe Asn Thr Thr Cys Tyr Phe Gly Cys
            660                 665                 670

Asn Ala Gly Phe Thr Leu Ile Gly Asp Ser Thr Leu Ser Cys Arg Pro
        675                 680                 685

Ser Gly Gln Trp Thr Ala Val Thr Pro Ala Cys Arg Ala Val Lys Cys
    690                 695                 700

Ser Glu Leu His Val Asn Lys Pro Ile Ala Met Asn Cys Ser Asn Leu
705                 710                 715                 720

Trp Gly Asn Phe Ser Tyr Gly Ser Ile Cys Ser Phe His Cys Leu Glu
                725                 730                 735

Gly Gln Leu Leu Asn Gly Ser Ala Gln Thr Ala Cys Gln Glu Asn Gly
            740                 745                 750

His Trp Ser Thr Thr Val Pro Thr Cys Gln Ala Gly Pro Leu Thr Ile
        755                 760                 765

Gln Glu Ala Leu Thr Tyr Phe Gly Gly Ala Val Ala Ser Thr Ile Gly
    770                 775                 780

Leu Ile Met Gly Gly Thr Leu Leu Ala Leu Leu Arg Lys Arg Phe Arg
785                 790                 795                 800

Gln Lys Asp Asp Gly Lys Cys Pro Leu Asn Pro His Ser His Leu Gly
                805                 810                 815

Thr Tyr Gly Val Phe Thr Asn Ala Ala Phe Asp Pro Ser Pro
            820                 825                 830

<210> SEQ ID NO 2
<211> LENGTH: 357
<212> TYPE: PRT
<213> ORGANISM: Homo sapiens

<400> SEQUENCE: 2

Met Gln Ser Val Gln Ser Thr Ser Phe Cys Leu Arg Lys Gln Cys Leu
1               5                   10                  15

Cys Leu Thr Phe Leu Leu Leu His Leu Leu Gly Gln Val Ala Ala Thr
                20                  25                  30

Gln Arg Cys Pro Pro Gln Cys Pro Gly Arg Cys Pro Ala Thr Pro Pro
            35                  40                  45

Thr Cys Ala Pro Gly Val Arg Ala Val Leu Asp Gly Cys Ser Cys Cys
        50                  55                  60

Leu Val Cys Ala Arg Gln Arg Gly Glu Ser Cys Ser Asp Leu Glu Pro
65                  70                  75                  80

Cys Asp Glu Ser Ser Gly Leu Tyr Cys Asp Arg Ser Ala Asp Pro Ser
                85                  90                  95
```

-continued

Asn Gln Thr Gly Ile Cys Thr Ala Val Glu Gly Asp Asn Cys Val Phe
            100                 105                 110

Asp Gly Val Ile Tyr Arg Ser Gly Glu Lys Phe Gln Pro Ser Cys Lys
            115                 120                 125

Phe Gln Cys Thr Cys Arg Asp Gly Gln Ile Gly Cys Val Pro Arg Cys
130                 135                 140

Gln Leu Asp Val Leu Leu Pro Glu Pro Asn Cys Pro Ala Pro Arg Lys
145                 150                 155                 160

Val Glu Val Pro Gly Glu Cys Cys Glu Lys Trp Ile Cys Gly Pro Asp
                165                 170                 175

Glu Glu Asp Ser Leu Gly Gly Leu Thr Leu Ala Ala Tyr Arg Pro Glu
            180                 185                 190

Ala Thr Leu Gly Val Glu Val Ser Asp Ser Ser Val Asn Cys Ile Glu
            195                 200                 205

Gln Thr Thr Glu Trp Thr Ala Cys Ser Lys Ser Cys Gly Met Gly Phe
        210                 215                 220

Ser Thr Arg Val Thr Asn Arg Asn Arg Gln Cys Glu Met Leu Lys Gln
225                 230                 235                 240

Thr Arg Leu Cys Met Val Arg Pro Cys Glu Gln Glu Pro Glu Gln Pro
                245                 250                 255

Thr Asp Lys Lys Gly Lys Lys Cys Leu Arg Thr Lys Lys Ser Leu Lys
            260                 265                 270

Ala Ile His Leu Gln Phe Lys Asn Cys Thr Ser Leu His Thr Tyr Lys
            275                 280                 285

Pro Arg Phe Cys Gly Val Cys Ser Asp Gly Arg Cys Cys Thr Pro His
        290                 295                 300

Asn Thr Lys Thr Ile Gln Ala Glu Phe Gln Cys Ser Pro Gly Gln Ile
305                 310                 315                 320

Val Lys Lys Pro Val Met Val Ile Gly Thr Cys Thr Cys His Thr Asn
                325                 330                 335

Cys Pro Lys Asn Asn Glu Ala Phe Leu Gln Glu Leu Glu Leu Lys Thr
            340                 345                 350

Thr Arg Gly Lys Met
            355

<210> SEQ ID NO 3
<211> LENGTH: 1210
<212> TYPE: PRT
<213> ORGANISM: Homo sapiens

<400> SEQUENCE: 3

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr

```
            100                 105                 110
Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525
```

```
Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
930                 935                 940
```

-continued

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 4
<211> LENGTH: 628
<212> TYPE: PRT
<213> ORGANISM: Homo sapiens

<400> SEQUENCE: 4

Met Gly Ser Cys Ala Arg Leu Leu Leu Leu Trp Gly Cys Thr Val Val
1               5                   10                  15

Ala Ala Gly Leu Ser Gly Val Ala Gly Val Ser Ser Arg Cys Glu Lys
            20                  25                  30

Ala Cys Asn Pro Arg Met Gly Asn Leu Ala Leu Gly Arg Lys Leu Trp
        35                  40                  45

Ala Asp Thr Thr Cys Gly Gln Asn Ala Thr Glu Leu Tyr Cys Phe Tyr
    50                  55                  60

Ser Glu Asn Thr Asp Leu Thr Cys Arg Gln Pro Lys Cys Asp Lys Cys
65                  70                  75                  80

Asn Ala Ala Tyr Pro His Leu Ala His Leu Pro Ser Ala Met Ala Asp
                85                  90                  95

```
Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
            115                 120                 125

His Leu Ile Val Met Phe Lys Ser Pro Arg Pro Ala Ala Met Val Leu
        130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Val Val Lys
                165                 170                 175

Lys Gly Ala Ile Cys Thr Ser Lys Tyr Ser Ser Pro Phe Pro Cys Thr
            180                 185                 190

Gly Gly Glu Val Ile Phe Lys Ala Leu Ser Pro Pro Tyr Asp Thr Glu
        195                 200                 205

Asn Pro Tyr Ser Ala Lys Val Gln Glu Gln Leu Lys Ile Thr Asn Leu
    210                 215                 220

Arg Val Gln Leu Leu Lys Arg Gln Ser Cys Pro Cys Gln Arg Asn Asp
225                 230                 235                 240

Leu Asn Glu Glu Pro Gln His Phe Thr His Tyr Ala Ile Tyr Asp Phe
                245                 250                 255

Ile Val Lys Gly Ser Cys Phe Cys Asn Gly His Ala Asp Gln Cys Ile
            260                 265                 270

Pro Val His Gly Phe Arg Pro Val Lys Ala Pro Gly Thr Phe His Met
        275                 280                 285

Val His Gly Lys Cys Met Cys Lys His Asn Thr Ala Gly Ser His Cys
        290                 295                 300

Gln His Cys Ala Pro Leu Tyr Asn Asp Arg Pro Trp Glu Ala Ala Asp
305                 310                 315                 320

Gly Lys Thr Gly Ala Pro Asn Glu Cys Arg Thr Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asp Asp Cys Gln His Asn Thr Glu Gly
            355                 360                 365

Gln Tyr Cys Gln Arg Cys Lys Pro Gly Phe Tyr Arg Asp Leu Arg Arg
    370                 375                 380

Pro Phe Ser Ala Pro Asp Ala Cys Lys Pro Cys Ser Cys His Pro Val
385                 390                 395                 400

Gly Ser Ala Val Leu Pro Ala Asn Ser Val Thr Phe Cys Asp Pro Ser
                405                 410                 415

Asn Gly Asp Cys Pro Cys Lys Pro Gly Val Ala Gly Arg Arg Cys Asp
            420                 425                 430

Arg Cys Met Val Gly Tyr Trp Gly Phe Gly Asp Tyr Gly Cys Arg Pro
        435                 440                 445

Cys Asp Cys Ala Gly Ser Cys Asp Pro Ile Thr Gly Asp Cys Ile Ser
    450                 455                 460

Ser His Thr Asp Ile Asp Trp Tyr His Glu Val Pro Asp Phe Arg Pro
465                 470                 475                 480

Val His Asn Lys Ser Glu Pro Ala Trp Glu Trp Asp Ala Gln Gly
                485                 490                 495

Phe Ser Ala Leu Leu His Ser Gly Lys Cys Glu Cys Lys Glu Gln Thr
            500                 505                 510
```

```
Leu Gly Asn Ala Lys Ala Phe Cys Gly Met Lys Tyr Ser Tyr Val Leu
        515                 520                 525

Lys Ile Lys Ile Leu Ser Ala His Asp Lys Gly Thr His Val Glu Val
    530                 535                 540

Asn Val Lys Ile Lys Lys Val Leu Lys Ser Thr Lys Leu Lys Ile Phe
545                 550                 555                 560

Arg Gly Lys Arg Thr Leu Tyr Pro Glu Ser Trp Thr Asp Arg Gly Cys
                565                 570                 575

Thr Cys Pro Ile Leu Asn Pro Gly Leu Glu Tyr Leu Val Ala Gly His
            580                 585                 590

Glu Asp Ile Arg Thr Gly Lys Leu Ile Val Asn Met Lys Ser Phe Val
        595                 600                 605

Gln His Trp Lys Pro Ser Leu Gly Arg Lys Val Met Asp Ile Leu Lys
    610                 615                 620

Arg Glu Cys Lys
625

<210> SEQ ID NO 5
<211> LENGTH: 406
<212> TYPE: PRT
<213> ORGANISM: Homo sapiens

<400> SEQUENCE: 5

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
            20                  25                  30

Cys Pro Lys Pro Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
    210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255
```

```
Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
    290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr
        355                 360                 365

Trp Tyr Ala Thr Gly Ile Leu Ser Phe Asp Lys Ser Cys Ala Val Ala
    370                 375                 380

Glu Tyr Gly Val Tyr Val Lys Val Thr Ser Ile Gln Asp Trp Val Gln
385                 390                 395                 400

Lys Thr Ile Ala Glu Asn
                405

<210> SEQ ID NO 6
<211> LENGTH: 418
<212> TYPE: PRT
<213> ORGANISM: Homo sapiens

<400> SEQUENCE: 6

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
```

```
            210                 215                 220
Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
                275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
                370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 7
<211> LENGTH: 267
<212> TYPE: PRT
<213> ORGANISM: Homo sapiens

<400> SEQUENCE: 7

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
                20                  25                  30

Gly Arg Arg Ala Arg Pro His Ala Trp Pro Phe Met Val Ser Leu Gln
            35                  40                  45

Leu Arg Gly Gly His Phe Cys Gly Ala Thr Leu Ile Ala Pro Asn Phe
        50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
                100                 105                 110

Asn Leu Leu Asn Asp Ile Val Ile Leu Gln Leu Asn Gly Ser Ala Thr
            115                 120                 125

Ile Asn Ala Asn Val Gln Val Ala Gln Leu Pro Ala Gln Gly Arg Arg
        130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
```

-continued

```
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
            245                 250                 255

Pro Arg Asp Pro Asp Pro Ala Ser Arg Thr His
        260                 265

<210> SEQ ID NO 8
<211> LENGTH: 335
<212> TYPE: PRT
<213> ORGANISM: Homo sapiens

<400> SEQUENCE: 8

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270
```

```
Gln Lys Val Gln Leu Leu Arg Asn Trp His Gln Leu His Gly Lys Lys
            275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 9
<211> LENGTH: 281
<212> TYPE: PRT
<213> ORGANISM: Homo sapiens

<400> SEQUENCE: 9

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 10
<211> LENGTH: 275
<212> TYPE: PRT
<213> ORGANISM: Homo sapiens
```

<400> SEQUENCE: 10

```
Met Ser Ser Phe Gly Tyr Arg Thr Leu Thr Val Ala Leu Phe Thr Leu
1               5                   10                  15

Ile Cys Cys Pro Gly Ser Asp Glu Lys Val Phe Glu Val His Val Arg
                20                  25                  30

Pro Lys Lys Leu Ala Val Glu Pro Lys Gly Ser Leu Glu Val Asn Cys
            35                  40                  45

Ser Thr Thr Cys Asn Gln Pro Glu Val Gly Gly Leu Glu Thr Ser Leu
        50                  55                  60

Asp Lys Ile Leu Leu Asp Glu Gln Ala Gln Trp Lys His Tyr Leu Val
65                  70                  75                  80

Ser Asn Ile Ser His Asp Thr Val Leu Gln Cys His Phe Thr Cys Ser
                85                  90                  95

Gly Lys Gln Glu Ser Met Asn Ser Asn Val Ser Val Tyr Gln Pro Pro
            100                 105                 110

Arg Gln Val Ile Leu Thr Leu Gln Pro Thr Leu Val Ala Val Gly Lys
        115                 120                 125

Ser Phe Thr Ile Glu Cys Arg Val Pro Thr Val Glu Pro Leu Asp Ser
130                 135                 140

Leu Thr Leu Phe Leu Phe Arg Gly Asn Glu Thr Leu His Tyr Glu Thr
145                 150                 155                 160

Phe Gly Lys Ala Ala Pro Ala Pro Gln Glu Ala Thr Ala Thr Phe Asn
                165                 170                 175

Ser Thr Ala Asp Arg Glu Asp Gly His Arg Asn Phe Ser Cys Leu Ala
            180                 185                 190

Val Leu Asp Leu Met Ser Arg Gly Gly Asn Ile Phe His Lys His Ser
        195                 200                 205

Ala Pro Lys Met Leu Glu Ile Tyr Glu Pro Val Ser Asp Ser Gln Met
210                 215                 220

Val Ile Ile Val Thr Val Val Ser Val Leu Leu Ser Leu Phe Val Thr
225                 230                 235                 240

Ser Val Leu Leu Cys Phe Ile Phe Gly Gln His Leu Arg Gln Gln Arg
                245                 250                 255

Met Gly Thr Tyr Gly Val Arg Ala Ala Trp Arg Arg Leu Pro Gln Ala
            260                 265                 270

Phe Arg Pro
        275
```

<210> SEQ ID NO 11
<211> LENGTH: 277
<212> TYPE: PRT
<213> ORGANISM: Homo sapiens

<400> SEQUENCE: 11

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
                20                  25                  30

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
        50                  55                  60

Ser Gly Thr Asp Val Asp Ala Ala Asn Leu Arg Glu Thr Phe Arg Asn
65                  70                  75                  80
```

```
Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 12
<211> LENGTH: 738
<212> TYPE: PRT
<213> ORGANISM: Homo sapiens

<400> SEQUENCE: 12

Met Gln Pro Arg Trp Ala Gln Gly Ala Thr Met Trp Leu Gly Val Leu
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Leu Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
```

```
                165                 170                 175
Leu Lys Arg Glu Lys Asn Ser Arg Asp Gln Asn Phe Val Ile Leu Glu
                180                 185                 190

Phe Pro Val Glu Glu Gln Asp Arg Val Leu Ser Phe Arg Cys Gln Ala
            195                 200                 205

Arg Ile Ile Ser Gly Ile His Met Gln Thr Ser Glu Ser Thr Lys Ser
        210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
            260                 265                 270

Gln Lys Asp Lys Ala Ile Val Ala His Asn Arg His Gly Asn Lys Ala
        275                 280                 285

Val Tyr Ser Val Met Ala Met Val Glu His Ser Gly Asn Tyr Thr Cys
        290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
            340                 345                 350

Pro Pro Ala Asn Phe Thr Ile Gln Lys Glu Asp Thr Ile Val Ser Gln
        355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
            420                 425                 430

Ser Ile Ser Gly Thr Leu Pro Ile Ser Tyr Gln Leu Leu Lys Thr Ser
        435                 440                 445

Lys Val Leu Glu Asn Ser Thr Lys Asn Ser Asn Asp Pro Ala Val Phe
    450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
                485                 490                 495

Ile Ala Pro Val Asp Glu Val Gln Ile Ser Ile Leu Ser Ser Lys Val
            500                 505                 510

Val Glu Ser Gly Glu Asp Ile Val Leu Gln Cys Ala Val Asn Glu Gly
        515                 520                 525

Ser Gly Pro Ile Thr Tyr Lys Phe Tyr Arg Glu Lys Glu Gly Lys Pro
    530                 535                 540

Phe Tyr Gln Met Thr Ser Asn Ala Thr Gln Ala Phe Trp Thr Lys Gln
545                 550                 555                 560

Lys Ala Ser Lys Glu Gln Glu Gly Glu Tyr Tyr Cys Thr Ala Phe Asn
                565                 570                 575

Arg Ala Asn His Ala Ser Ser Val Pro Arg Ser Lys Ile Leu Thr Val
            580                 585                 590
```

Arg Val Ile Leu Ala Pro Trp Lys Lys Gly Leu Ile Ala Val Val Ile
            595                 600                 605

Ile Gly Val Ile Ile Ala Leu Leu Ile Ile Ala Ala Lys Cys Tyr Phe
            610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
                645                 650                 655

Met Glu Ala Asn Ser His Tyr Gly His Asn Asp Val Arg Asn His
            660                 665                 670

Ala Met Lys Pro Ile Asn Asp Asn Lys Glu Pro Leu Asn Ser Asp Val
            675                 680                 685

Gln Tyr Thr Glu Val Gln Val Ser Ser Ala Glu Ser His Lys Asp Leu
            690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
                725                 730                 735

Gly Thr

<210> SEQ ID NO 13
<211> LENGTH: 205
<212> TYPE: PRT
<213> ORGANISM: Homo sapiens

<400> SEQUENCE: 13

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
        195                 200                 205

<210> SEQ ID NO 14

-continued

```
<211> LENGTH: 1210
<212> TYPE: PRT
<213> ORGANISM: Homo sapiens

<400> SEQUENCE: 14

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
```

```
             385                 390                 395                 400
        Ile Thr Gly Phe Leu Leu Ile Gln Ala Trp Pro Glu Asn Arg Thr Asp
                        405                 410                 415

Leu His Ala Phe Glu Asn Leu Glu Ile Ile Arg Gly Arg Thr Lys Gln
                        420                 425                 430

His Gly Gln Phe Ser Leu Ala Val Val Ser Leu Asn Ile Thr Ser Leu
                        435                 440                 445

Gly Leu Arg Ser Leu Lys Glu Ile Ser Asp Gly Asp Val Ile Ile Ser
                450                 455                 460

Gly Asn Lys Asn Leu Cys Tyr Ala Asn Thr Ile Asn Trp Lys Lys Leu
        465                 470                 475                 480

Phe Gly Thr Ser Gly Gln Lys Thr Lys Ile Ile Ser Asn Arg Gly Glu
                        485                 490                 495

Asn Ser Cys Lys Ala Thr Gly Gln Val Cys His Ala Leu Cys Ser Pro
                        500                 505                 510

Glu Gly Cys Trp Gly Pro Glu Pro Arg Asp Cys Val Ser Cys Arg Asn
                        515                 520                 525

Val Ser Arg Gly Arg Glu Cys Val Asp Lys Cys Asn Leu Leu Glu Gly
                530                 535                 540

Glu Pro Arg Glu Phe Val Glu Asn Ser Glu Cys Ile Gln Cys His Pro
        545                 550                 555                 560

Glu Cys Leu Pro Gln Ala Met Asn Ile Thr Cys Thr Gly Arg Gly Pro
                        565                 570                 575

Asp Asn Cys Ile Gln Cys Ala His Tyr Ile Asp Gly Pro His Cys Val
                        580                 585                 590

Lys Thr Cys Pro Ala Gly Val Met Gly Glu Asn Asn Thr Leu Val Trp
                        595                 600                 605

Lys Tyr Ala Asp Ala Gly His Val Cys His Leu Cys His Pro Asn Cys
                        610                 615                 620

Thr Tyr Gly Cys Thr Gly Pro Gly Leu Glu Gly Cys Pro Thr Asn Gly
        625                 630                 635                 640

Pro Lys Ile Pro Ser Ile Ala Thr Gly Met Val Gly Ala Leu Leu Leu
                        645                 650                 655

Leu Leu Val Val Ala Leu Gly Ile Gly Leu Phe Met Arg Arg Arg His
                        660                 665                 670

Ile Val Arg Lys Arg Thr Leu Arg Arg Leu Leu Gln Glu Arg Glu Leu
                        675                 680                 685

Val Glu Pro Leu Thr Pro Ser Gly Glu Ala Pro Asn Gln Ala Leu Leu
                        690                 695                 700

Arg Ile Leu Lys Glu Thr Glu Phe Lys Lys Ile Lys Val Leu Gly Ser
        705                 710                 715                 720

Gly Ala Phe Gly Thr Val Tyr Lys Gly Leu Trp Ile Pro Glu Gly Glu
                        725                 730                 735

Lys Val Lys Ile Pro Val Ala Ile Lys Glu Leu Arg Glu Ala Thr Ser
                        740                 745                 750

Pro Lys Ala Asn Lys Glu Ile Leu Asp Glu Ala Tyr Val Met Ala Ser
                        755                 760                 765

Val Asp Asn Pro His Val Cys Arg Leu Leu Gly Ile Cys Leu Thr Ser
                        770                 775                 780

Thr Val Gln Leu Ile Thr Gln Leu Met Pro Phe Gly Cys Leu Leu Asp
        785                 790                 795                 800

Tyr Val Arg Glu His Lys Asp Asn Ile Gly Ser Gln Tyr Leu Leu Asn
                        805                 810                 815
```

-continued

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
        850                 855                 860

Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

METHODS FOR DIAGNOSING ACUTE KIDNEY INJURY OR RENAL FAILURE

This application is filed under 35 U.S.C. § 371 as the U.S. national phase of International Application No. PCT/US2009/055449, filed Aug. 28, 2009, which designated the U.S. and claims the benefit of priority to U.S. Provisional Patent Application 61/092,733 filed Aug. 28, 2008, U.S. Provisional Patent Application 61/092,905 filed Aug. 29, 2008, U.S. Provisional Patent Application 61/092,912 filed Aug. 29, 2008, U.S. Provisional Patent Application 61/092,926 filed Aug. 29, 2008, U.S. Provisional Patent Application 61/093,154 filed Aug. 29, 2008, U.S. Provisional Patent Application 61/093,247 filed Aug. 29, 2008, U.S. Provisional Patent Application 61/093,249 filed Aug. 29, 2008, U.S. Provisional Patent Application 61/093,262 filed Aug. 29, 2008, U.S. Provisional Patent Application 61/093,263 filed Aug. 29, 2008, U.S. Provisional Patent Application 61/093,264 filed Aug. 29, 2008, U.S. Provisional Patent Application 61/093,266 filed Aug. 29, 2008, U.S. Provisional Patent Application 61/093,244 filed Aug. 29, 2008, and U.S. Provisional Patent Application 61/093,272 filed Aug. 29, 2008, the contents of which are hereby incorporated by reference in their entirety for all purposes.

SEQUENCE LISTING

The instant application contains a Sequence Listing which has been submitted in ASCII format via EFS-Web and is hereby incorporated by reference in its entirety. Said ASCII copy, created on Feb. 28, 2011, is named AST15400_SeqListing_txt, and is 65,536 bytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, $17^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, $47^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, $17^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |

-continued

| Type | Risk Factors |
|---|---|
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, caspase-3 (and most preferably active caspase-3), and soluble platelet endothelial cell adhesion molecule (collectively referred to herein as "kidney injury markers, and individually as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. The assay result(s), for example a measured concentration of one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, caspase-3 (and most preferably active caspase-3), and soluble platelet endothelial cell adhesion molecule is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example a measured concentration of one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, caspase-3 (and most preferably active caspase-3), and soluble platelet endothelial cell adhesion molecule is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example a measured concentration of one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, caspase-3 (and most preferably active caspase-3), and soluble platelet endothelial cell adhesion molecule is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example a measured concentration of one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, caspase-3 (and most preferably active caspase-3), and soluble platelet endothelial cell adhesion molecule is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more markers selected from the group consisting of soluble p-selectin, protein NOV homolog, soluble epidermal growth factor receptor, netrin-4, haptoglobin, heat shock protein beta-1, alpha-1-antitrypsin, leukocyte elastase, soluble tumor necrosis factor receptor superfamily member 6, soluble tumor necrosis factor ligand superfamily member 6, soluble intercellular adhesion molecule 2, caspase-3 (and most preferably active caspase-3), and soluble platelet endothelial cell adhesion molecule, or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmil/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "p-selectin" refers to one or more polypeptides present in a biological sample that are derived from the p-selectin precursor (Swiss-Prot P16109 (SEQ ID NO: 1)).

```
            10         20         30         40         50         60
    MANCQIAILY QRFQRVVFGI SQLLCFSALI SELTNQKEVA AWTYHYSTKA YSWNISRKYC 70         80         90        100        110        120
    QNRYTDLVAI QNKNEIDYLN KVLPYYSSYY WIGIRKNNKT WTWVGTKKAL TNEAENWADN 130        140        150        160        170        180
    EPNNKRNNED CVEIYIKSPS APGKWNDEHC LKKKHALCYT ASCQDMSCSK QGECLETIGN 190        200        210        220        230        240
    YTCSCYPGFY GPECEYVREC GELELPQHVL MNCSHPLGNF SFNSQCSFHC TDGYQVNGPS 250        260        270        280        290        300
    KLECLASGIW TNKPPQCLAA QCPPLKIPER GNMICLHSAK AFQHQSSCSF SCEEGFALVG 310        320        330        340        350        360
    PEVVQCTASG VWTAPAPVCK AVQCQHLEAP SEGTMDCVHP LTAFAYGSSC KFECQPGYRV 370        380        390        400        410        420
    RGLDMLRCID SGHWSAPLPT CEAISCEPLE SPVHGSMDCS PSLRAFQYDT NCSFRCAEGF 430        440        450        460        470        480
    MLRGADIVRC DNLGQWTAPA PVCQALQCQD LPVPNEARVN CSHPFGAFRY QSVCSFTCNE 490        500        510        520        530        540
    GLLLVGASVL QCLATGNWNS VPPECQAIPC TPLLSPQNGT MTCVQPLGSS SYKSTCQFIC 550        560        570        580        590        600
    DEGYSLSGPE RLDCTRSGRW TDSPPMCEAI KCPELFAPEQ GSLDCSDTRG EFNVGSTCHF 610        620        630        640        650        660
    SCNNGFKLEG PNNVECTTSG RWSATPPTCK GIASLPTPGL QCPALTTPGQ GTMYCRHHPG 670        680        690        700        710        720
    TFGFNTTCYF GCNAGFTLIG DSTLSCRPSG QWTAVTPACR AVKCSELHVN KPIAMNCSNL 730        740        750        760        770        780
    WGNFSYGSIC SFHCLEGQLL NGSAQTACQE NGHWSTTVPT CQAGPLTIQE ALTYFGGAVA 790        800        810        820        830
    STIGLIMGGT LLALLRKRFR QKDDGKCPLN PHSHLGTYGV FTNAAFDPSP
```

Most preferably, the p-selectin assay detects one or more soluble forms of p-selectin. P-selectin is a single-pass type I membrane protein having a large extracellular domain, most or all of which is present in soluble forms of p-selectin generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in p-selectin:

| Residues | Length | Domain ID |
|---|---|---|
| 1-41 | 41 | signal sequence |
| 42-830 | 789 | p-selectin |
| 42-771 | 730 | extracellular |
| 772-795 | 24 | transmembrane |
| 796-830 | 35 | cytoplasmic |

As used herein, the term "protein NOV homolog" refers to one or more polypeptides present in a biological sample that are derived from the protein NOV homolog precursor (Swiss-Prot P48745 (SEQ ID NO: 2)).

```
            10         20         30         40         50         60
    MQSVQSTSFC LRKQCLCLTF LLLHLLGQVA ATQRCPPQCP GRCPATPPTC APGVRAVLDG 70         80         90        100        110        120
    CSCCLVCARQ RGESCSDLEP CDESSGLYCD RSADPSNQTG ICTAVEGDNC VFDGVIYRSG 130        140        150        160        170        180
    EKFQPSCKFQ CTCRDGQIGC VPRCQLDVLL PEPNCPAPRK VEVPGECCEK WICGPDEEDS 190        200        210        220        230        240
    LGGLTLAAYR PEATLGVEVS DSSVNCIEQT TEWTACSKSC GMGFSTRVTN RNRQCEMLKQ 250        260        270        280        290        300
    TRLCMVRPCE QEPEQPTDKK GKKCLRTKKS LKAIHLQFKN CTSLHTYKPR FCGVCSDGRC 310        320        330        340        350
    CTPHNTKTIQ AEFQCSPGQI VKKPVMVIGT CTCHTNCPKN NEAFLQELEL KTTRGKM
```

The following domains have been identified in protein NOV homolog:

| Residues | Length | Domain ID |
|---|---|---|
| 1-31 | 31 | signal sequence |
| 32-357 | 326 | protein NOV homolog |

As used herein, the term "epidermal growth factor receptor" refers to one or more polypeptides present in a biological sample that are derived from the epidermal growth factor receptor precursor (Swiss-Prot P00533 (SEQ ID NO: 3)).

```
            10         20         30         40         50         60
    MRPSGTAGAA LLALLAALCP ASRALEEKKV CQGTSNKLTQ LGTFEDHFLS LQRMFNNCEV 70         80         90        100        110        120
    VLGNLEITYV QRNYDLSFLK TIQEVAGYVL IALNTVERIP LENLQIIRGN MYYENSYALA 130        140        150        160        170        180
    VLSNYDANKT GLKELPMRNL QEILHGAVRF SNNPALCNVE SIQWRDIVSS DFLSNMSMDF 190        200        210        220        230        240
    QNHLGSCQKC DPSCPNGSCW GAGEENCQKL TKIICAQQCS GRCRGKSPSD CCHNQCAAGC 250        260        270        280        290        300
    TGPRESDCLV CRKFRDEATC KDTCPPLMLY NPTTYQMDVN PEGKYSFGAT CVKKCPRNYV 310        320        330        340        350        360
    VTDHGSCVRA CGADSYEMEE DGVRKCKKCE GPCRKVCNGI GIGEFKDSLS INATNIKHFK 370        380        390        400        410        420
    NCTSISGDLH ILPVAFRGDS FTHTPPLDPQ ELDILKTVKE ITGFLLIQAW PENRTDLHAF 430        440        450        460        470        480
    ENLEIIRGRT KQHGQFSLAV VSLNITSLGL RSLKEISDGD VIISGNKNLC YANTINWKKL 490        500        510        520        530        540
    FGTSGQKTKI ISNRGENSCK ATGQVCHALC SPEGCWGPEP RDCVSCRNVS RGRECVDKCN 550        560        570        580        590        600
    LLEGEPREFV ENSECIQCHP ECLPQAMNIT CTGRGPDNCI QCAHYIDGPH CVKTCPAGVM 610        620        630        640        650        660
    GENNTLVWKY ADAGHVCHLC HPNCTYGCTG PGLEGCPTNG PKIPSIATGM VGALLLLLVV 670        680        690        700        710        720
    ALGIGLFMRR RHIVRKRTLR RLLQERELVE PLTPSGEAPN QALLRILKET EFKKIKVLGS 730        740        750        760        770        780
    GAFGTVYKGL WIPEGEKVKI PVAIKELREA TSPKANKEIL DEAYVMASVD NPHVCRLLGI 790        800        810        820        830        840
    CLTSTVQLIT QLMPFGCLLD YVREHKDNIG SQYLLNWCVQ IAKGMNYLED RRLVHRDLAA 850        860        870        880        890        900
    RNVLVKTPQH VKITDFGLAK LLGAEEKEYH AEGGKVPIKW MALESILHRI YTHQSDVWSY
```

```
             910        920        930        940        950        960
      GVTVWELMTF GSKPYDGIPA SEISSILEKG ERLPQPPICT IDVYMIMVKC WMIDADSRPK 970        980        990       1000       1010       1020
      FRELIIEFSK MARDPQRYLV IQGDERMHLP SPTDSNFYRA LMDEEDMDDV VDADEYLIPQ 1030       1040       1050       1060       1070       1080
      QGFFSSPSTS RTPLLSSLSA TSNNSTVACI DRNGLQSCPI KEDSFLQRYS SDPTGALTED 1090       1100       1110       1120       1130       1140
      SIDDTFLPVP EYINQSVPKR PAGSVQNPVY HNQPLNPAPS RDPHYQDPHS TAVGNPEYLN 1150       1160       1170       1180       1190       1200
      TVQPTCVNST FDSPAHWAQK GSHQISLDNP DYQQDFFPKE AKPNGIFKGS TAENAEYLRV

1210
      APQSSEFIGA
```

Most preferably, the epidermal growth factor receptor assay detects one or more soluble forms of epidermal growth factor receptor. Epidermal growth factor receptor is a single-pass type I membrane protein having a large extracellular domain, most or all of which is present in soluble forms of epidermal growth factor receptor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in epidermal growth factor receptor:

| Residues | Length | Domain ID |
|---|---|---|
| 1-24 | 24 | signal sequence |
| 25-1210 | 1186 | epidermal growth factor receptor |
| 25-645 | 621 | extracellular |
| 646-668 | 23 | transmembrane |
| 669-1210 | 542 | cytoplasmic |

As used herein, the term "netrin-4" refers to one or more polypeptides present in a biological sample that are derived from the netrin-4 precursor (Swiss-Prot Q9HB63 (SEQ ID NO: 4)).

```
                    10         20         30         40         50         60
            MGSCARLLLL WGCTVVAAGL SGVAGVSSRC EKACNPRMGN LALGRKLWAD TTCGQNATEL 70         80         90        100        110        120
            YCFYSENTDL TCRQPKCDKC NAAYPHLAHL PSAMADSSFR FPRTWWQSAE DVHREKIQLD 130        140        150        160        170        180
            LEAEFYFTHL IVMFKSPRPA AMVLDRSQDF GKTWKPYKYF ATNCSATFGL EDDVVKKGAI 190        200        210        220        230        240
            CTSKYSSPFP CTGGEVIFKA LSPPYDTENP YSAKVQEQLK ITNLRVQLLK RQSCPCQRND 250        260        270        280        290        300
            LNEEPQHFTH YAIYDFIVKG SCFCNGHADQ CIPVHGFRPV KAPGTFHMVH GKCMCKHNTA 310        320        330        340        350        360
            GSHCQHCAPL YNDRPWEAAD GKTGAPNECR TCKCNGHADT CHFDVNVWEA SGNRSGGVCD 370        380        390        400        410        420
            DCQHNTEGQY CQRCKPGFYR DLRRPFSAPD ACKPCSCHPV GSAVLPANSV TFCDPSNGDC 430        440        450        460        470        480
            PCKPGVAGRR CDRCMVGYWG FGDYGCRPCD CAGSCDPITG DCISSHTDID WYHEVPDFRP 490        500        510        520        530        540
            VHNKSEPAWE WEDAQGFSAL LHSGKCECKE QTLGNAKAFC GMKYSYVLKI KILSAHDKGT 550        560        570        580        590        600
            HVEVNVKIKK VLKSTKLKIF RGKRTLYPES WTDRGCTCPI LNPGLEYLVA GHEDIRTGKL 610        620
            IVNMKSFVQH WKPSLGRKVM DILKRECK
```

The following domains have been identified in netrin-4:

| Residues | Length | Domain ID |
|---|---|---|
| 1-18 | 18 | initiator methionine |
| 19-628 | 610 | netrin-4 |

As used herein, the term "haptoglobin" refers to one or more polypeptides present in a biological sample that are derived from the haptoglobin precursor (Swiss-Prot P00738 (SEQ ID NO: 5)).

```
         10         20         30         40         50         60
MSALGAVIAL LLWGQLFAVD SGNDVTDIAD DGCPKPPEIA HGYVEHSVRY QCKNYYKLRT 70         80         90        100        110        120
EGDGVYTLND KKQWINKAVG DKLPECEADD GCPKPPEIAH GYVEHSVRYQ CKNYYKLRTE 130        140        150        160        170        180
GDGVYTLNNE KQWINKAVGD KLPECEAVCG KPKNPANPVQ RILGGHLDAK GSFPWQAKMV 190        200        210        220        230        240
SHHNLTTGAT LINEQWLLTT AKNLFLNHSE NATAKDIAPT LTLYVGKKQL VEIEKVVLHP 250        260        270        280        290        300
NYSQVDIGLI KLKQKVSVNE RVMPICLPSK DYAEVGRVGY VSGWGRNANF KFTDHLKYVM 310        320        330        340        350        360
LPVADQDQCI RHYEGSTVPE KKTPKSPVGV QPILNEHTFC AGMSKYQEDT CYGDAGSAFA 370        380        390        400
VHDLEEDTWY ATGILSFDKS CAVAEYGVYV KVTSIQDWVQ KTIAEN
```

The following domains have been identified in haptoglobin:

| Residues | Length | Domain ID |
|---|---|---|
| 1-18 | 18 | signal sequence |
| 19-406 | 388 | haptoglobin |
| 19-160 | 142 | haptoglobin alpha chain |
| 162-406 | 245 | haptoglobin beta chain |

As used herein, the term "alpha-1-antitrypsin" refers to one or more polypeptides present in a biological sample that are derived from the alpha-1-antitrypsin precursor (Swiss-Prot P01009 (SEQ ID NO: 6)).

```
         10         20         30         40         50         60
MPSSVSWGIL LLAGLCCLVP VSLAEDPQGD AAQKTDTSHH DQDHPTFNKI TPNLAEFAFS 70         80         90        100        110        120
LYRQLAHQSN STNIFFSPVS IATAFAMLSL GTKADTHDEI LEGLNFNLTE IPEAQIHEGF 130        140        150        160        170        180
QELLRTLNQP DSQLQLTTGN GLFLSEGLKL VDKFLEDVKK LYHSEAFTVN FGDTEEAKKQ 190        200        210        220        230        240
INDYVEKGTQ GKIVDLVKEL DRDTVFALVN YIFFKGKWER PFEVKDTEEE DFHVDQVTTV 250        260        270        280        290        300
KVPMMKRLGM FNIQHCKKLS SWVLLMKYLG NATAIFFLPD EGKLQHLENE LTHDIITKFL 310        320        330        340        350        360
ENEDRRSASL HLPKLSITGT YDLKSVLGQL GITKVFSNGA DLSGVTEEAP LKLSKAVHKA 370        380        390        400        410
VLTIDEKGTE AAGAMFLEAI PMSIPPEVKF NKPFVFLMIE QNTKSPLFMG KVVNPTQK
```

The following domains have been identified in alpha-1-antitrypsin:

| Residues | Length | Domain ID |
|---|---|---|
| 1-24 | 24 | signal sequence |
| 25-418 | 394 | alpha-1-antitrypsin |

As used herein, the term "leukocyte elastase" refers to one or more polypeptides present in a biological sample that are derived from the leukocyte elastase precursor (Swiss-Prot P08246 (SEQ ID NO: 7)).

```
         10         20         30         40         50         60
MTLGRRLACL FLACVLPALL LGGTALASEI VGGRRARPHA WPFMVSLQLR GGHFCGATLI 70         80         90        100        110        120
APNFVMSAAH CVANVNVRAV RVVLGAHNLS RREPTRQVFA VQRIFENGYD PVNLLNDIVI 130        140        150        160        170        180
LQLNGSATIN ANVQVAQLPA QGRRLGNGVQ CLAMGWGLLG RNRGIASVLQ ELNVTVVTSL 190        200        210        220        230        240
CRRSNVCTLV RGRQAGVCFG DSGSPLVCNG LIHGIASFVR GGCASGLYPD AFAPVAQFVN 250        260
WIDSIIQRSE DNPCPHPRDP DPASRTH
```

The following domains have been identified in leukocyte elastase:

| Residues | Length | Domain ID |
|---|---|---|
| 1-27 | 315 | signal sequence |
| 28-29 | 2 | pro-peptide |
| 30-267 | 238 | leukocyte elastase |

As used herein, the term "tumor necrosis factor receptor superfamily member 6" refers to one or more polypeptides present in a biological sample that are derived from the tumor necrosis factor receptor superfamily member 6 precursor (Swiss-Prot P25445 (SEQ ID NO: 8)).

Most preferably, the tumor necrosis factor receptor superfamily member 6 assay detects one or more soluble forms of tumor necrosis factor receptor superfamily member 6. Tumor necrosis factor receptor superfamily member 6 is a single-pass type I membrane protein having a large extracellular domain, most or all of which is present in soluble forms of tumor necrosis factor receptor superfamily member 6 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in tumor necrosis factor receptor superfamily member 6:

| Residues | Length | Domain ID |
|---|---|---|
| 1-25 | 25 | signal sequence |
| 26-335 | 310 | tumor necrosis factor receptor superfamily member 6 |
| 26-173 | 148 | extracellular |
| 174-190 | 17 | transmembrane |
| 191-335 | 145 | cytoplasmic |

As used herein, the term "tumor necrosis factor ligand superfamily member 6" refers to one or more polypeptides present in a biological sample that are derived from the tumor necrosis factor ligand superfamily member 6 precursor (Swiss-Prot P48023 (SEQ ID NO: 9)).

```
         10         20         30         40         50         60
MLGIWTLLPL VLTSVARLSS KSVNAQVTDI NSKGLELRKT VTTVETQNLE GLHHDGQFCH 70         80         90        100        110        120
KPCPPGERKA RDCTVNGDEP DCVPCQEGKE YTDKAHFSSK CRRCRLCDEG HGLEVEINCT 130        140        150        160        170        180
RTQNTKCRCK PNFFCNSTVC EHCDPCTKCE HGIIKECTLT SNTKCKEEGS RSNLGWLCLL 190        200        210        220        230        240
LLPIPLIVWV KRKEVQKTCR KHRKENQGSH ESPTLNPETV AINLSDVDLS KYITTIAGVM 250        260        270        280        290        300
TLSQVKGFVR KNGVNEAKID EIKNDNVQDT AEQKVQLLRN WHQLHGKKEA YDTLIKDLKK 310        320        330
ANLCTLAEKI QTIILKDITS DSENSNFRNE IQSLV
```

```
          10         20         30         40         50         60
MQQPFNYPYP QIYWVDSSAS SPWAPPGTVL PCPTSVPRRP GQRRPPPPPP PPPLPPPPPP 70         80         90        100        110        120
PPLPPLPLPP LKKRGNHSTG LCLLVMFFMV LVALVGLGLG MFQLFHLQKE LAELRESTSQ 130        140        150        160        170        180
MHTASSLEKQ IGHPSPPPEK KELRKVAHLT GKSNSRSMPL EWEDTYGIVL LSGVKYKKGG 190        200        210        220        230        240
LVINETGLYF VYSKVYFRGQ SCNNLPLSHK VYMRNSKYPQ DLVMMEGKMM SYCTTGQMWA 250        260        270        280
RSSYLGAVFN LTSADHLYVN VSELSLVNFE ESQTFFGLYK L
```

Most preferably, the tumor necrosis factor ligand superfamily member 6 assay detects one or more soluble forms of tumor necrosis factor ligand superfamily member 6. Tumor necrosis factor ligand superfamily member 6 is a single-pass type II membrane protein having a large extracellular domain, most or all of which is present in soluble forms of tumor necrosis factor ligand superfamily member 6 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in tumor necrosis factor ligand superfamily member 6:

| Residues | Length | Domain ID |
|---|---|---|
| 1-281 | 281 | necrosis factor ligand superfamily member 6, membrane bound form |
| 130-281 | 152 | tumor necrosis factor ligand superfamily member 6, soluble form |
| 1-180 | 180 | cytoplasmic |
| 81-102 | 22 | membrane anchor signal |
| 103-281 | 179 | extracellular |

As used herein, the term "intercellular adhesion molecule 2" refers to one or more polypeptides present in a biological sample that are derived from the intercellular adhesion molecule 2 precursor (Swiss-Prot P13598 (SEQ ID NO: 10)).

Most preferably, the intercellular adhesion molecule 2 assay detects one or more soluble forms of intercellular adhesion molecule 2. Intercellular adhesion molecule 2 is a single-pass type I membrane protein having a large extracellular domain, most or all of which is present in soluble forms of intercellular adhesion molecule 2 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in intercellular adhesion molecule 2:

| Residues | Length | Domain ID |
|---|---|---|
| 1-21 | 21 | signal sequence |
| 22-275 | 254 | intercellular adhesion molecule 2 |
| 22-223 | 202 | extracellular |
| 224-248 | 25 | transmembrane |
| 249-275 | 27 | cytoplasmic |

As used herein, the term "caspase-3" refers to one or more polypeptides present in a biological sample that are derived from the caspase-3 precursor (Swiss-Prot P42574 (SEQ ID NO: 11)).

```
          10         20         30         40         50         60
MSSFGYRTLT VALFTLICCP GSDEKVFEVH VRPKKLAVEP KGSLEVNCST TCNQPEVGGL 70         80         90        100        110        120
ETSLDKILLD EQAQWKHYLV SNISHDTVLQ CHFTCSGKQE SMNSNVSVYQ PPRQVILTLQ 130        140        150        160        170        180
PTLVAVGKSF TIECRVPTVE PLDSLTLFLF RGNETLHYET FGKAAPAPQE ATATFNSTAD 190        200        210        220        230        240
REDGHRNFSC LAVLDLMSRG GNIFHKHSAP KMLEIYEPVS DSQMVIIVTV VSVLLSLFVT 250        260        270
SVLLCFIFGQ HLRQQRMGTY GVRAAWRRLP QAFRP
```

```
         10         20         30         40         50         60
MENTENSVDS KSIKNLEPKI IHGSESMDSG ISLDNSYKMD YPEMGLCIII NNKNFHKSTG 70         80         90        100        110        120
MTSRSGTDVD AANLRETFRN LKYEVRNKND LTREEIVELM RDVSKEDHSK RSSFVCVLLS 130        140        150        160        170        180
HGEEGIIFGT NGPVDLKKIT NFFRGDRCRS LTGKPKLFII QACRGTELDC GIETDSGVDD 190        200        210        220        230        240
DMACHKIPVE ADFLYAYSTA PGYYSWRNSK DGSWFIQSLC AMLKQYADKL EFMHILTRVN 250        260        270
RKVATEFESF SFDATFHAKK QIPCIVSMLT KELYFYH
```

The following domains have been identified in caspase-3:

| Residues | Length | Domain ID |
|---|---|---|
| 1-9 | 9 | Propeptide |
| 10-28 | 19 | propeptide |
| 29-175 | 147 | caspase-3 p17 subunit |
| 176-277 | 102 | caspase-3 p12 subunit |

Suitable assays may recognize only the p17 subunit of caspase-3, may recognize only the p12 subunit of caspase-3 (24 kDa) but not the full length caspase-3, may recognize only full length caspase-3, or may recognize one subunit and the full length full length caspase-3. In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length caspase-3 molecule and the assay result be expressed as a concentration of caspase-3, the signal from the assay is actually a result of all such "immunoreactive" polypeptides present in the sample.

As used herein, the term "platelet endothelial cell adhesion molecule" refers to one or more polypeptides present in a biological sample that are derived from the platelet endothelial cell adhesion molecule precursor (Swiss-Prot P16284 (SEQ ID NO: 12)).

```
         10         20         30         40         50         60
MQPRWAQGAT MWLGVLLTLL LCSSLEGQEN SFTINSVDMK SLPDWTVQNG KNLTLQCFAD 70         80         90        100        110        120
VSTTSHVKPQ HQMLFYKDDV LFYNISSMKS TESYFIPEVR IYDSGTYKCT VIVNNKEKTT 130        140        150        160        170        180
AEYQLLVEGV PSPRVTLDKK EAIQGGIVRV NCSVPEEKAP IHFTIEKLEL NEKMVKLKRE 190        200        210        220        230        240
KNSRDQNFVI LEFPVEEQDR VLSFRCQARI ISGIHMQTSE STKSELVTVT ESFSTPKFHI 250        260        270        280        290        300
SPTGMIMEGA QLHIKCTIQV THLAQEFPEI IIQKDKAIVA HNRHGNKAVY SVMAMVEHSG 310        320        330        340        350        360
NYTCKVESSR ISKVSSIVVN ITELFSKPEL ESSFTHLDQG ERLNLSCSIP GAPPANFTIQ 370        380        390        400        410        420
KEDTIVSQTQ DFTKIASKSD SGTYICTAGI DKVVKKSNTV QIVVCEMLSQ PRISYDAQFE 430        440        450        460        470        480
VIKGQTIEVR CESISGTLPI SYQLLKTSKV LENSTKNSND PAVFKDNPTE DVEYQCVADN 490        500        510        520        530        540
CHSHAKMLSE VLRVKVIAPV DEVQISILSS KVVESGEDIV LQCAVNEGSG PITYKFYREK 550        560        570        580        590        600
EGKPFYQMTS NATQAFWTKQ KASKEQEGEY YCTAFNRANH ASSVPRSKIL TVRVILAPWK 610        620        630        640        650        660
KGLIAVVIIG VIIALLIIAA KCYFLRKAKA KQMPVEMSRP AVPLLNSNNE KMSDPNMEAN 670        680        690        700        710        720
SHYGHNDDVR NHAMKPINDN KEPLNSDVQY TEVQVSSAES HKDLGKKDTE TVYSEVRKAV

730
PDAVESRYSR TEGSLDGT
```

Most preferably, the platelet endothelial cell adhesion molecule assay detects one or more soluble forms of platelet endothelial cell adhesion molecule. Platelet endothelial cell adhesion molecule is a single-pass type I membrane protein having a large extracellular domain, most or all of which is present in soluble forms of platelet endothelial cell adhesion molecule generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in platelet endothelial cell adhesion molecule:

| Residues | Length | Domain ID |
|---|---|---|
| 1-27 | 27 | signal sequence |
| 28-738 | 711 | platelet endothelial cell adhesion molecule |
| 28-601 | 574 | extracellular |
| 602-620 | 19 | transmembrane |
| 621-738 | 118 | cytoplasmic |

As used herein, the term "heat shock protein beta-1" refers to one or more polypeptides present in a biological sample that are derived from the heat shock protein beta-1 precursor (Swiss-Prot P04792 (SEQ ID NO: 13)).

```
            10         20         30         40         50         60
    MTERRVPFSL LRGPSWDPFR DWYPHSRLFD QAFGLPRLPE EWSQWLGGSS WPGYVRPLPP 70         80         90        100        110        120
    AAIESPAVAA PAYSRALSRQ LSSGVSEIRH TADRWRVSLD VNHFAPDELT VKTKDGVVEI 130        140        150        160        170        180
    TGKHEERQDE HGYISRCFTR KYTLPPGVDP TQVSSSLSPE GTLTVEAPMP KLATQSNEIT 190        200
    IPVTFESRAQ LGGPEAAKSD ETAAK
```

As used herein, the term "epidermal growth factor receptor" refers to one or more polypeptides present in a biological sample that are derived from the epidermal growth factor receptor precursor (Swiss-Prot P00533 (SEQ ID NO: 14)).

```
            10         20         30         40         50         60
    MRPSGTAGAA LLALLAALCP ASRALEEKKV CQGTSNKLTQ LGTFEDHFLS LQRMFNNCEV 70         80         90        100        110        120
    VLGNLEITYV QRNYDLSFLK TIQEVAGYVL IALNTVERIP LENLQIIRGN MYYENSYALA 130        140        150        160        170        180
    VLSNYDANKT GLKELPMRNL QEILHGAVRF SNNPALCNVE SIQWRDIVSS DFLSNMSMDF 190        200        210        220        230        240
    QNHLGSCQKC DPSCPNGSCW GAGEENCQKL TKIICAQQCS GRCRGKSPSD CCHNQCAAGC 250        260        270        280        290        300
    TGPRESDCLV CRKFRDEATC KDTCPPLMLY NPTTYQMDVN PEGKYSFGAT CVKKCPRNYV 310        320        330        340        350        360
    VTDHGSCVRA CGADSYEMEE DGVRKCKKCE GPCRKVCNGI GIGEFKDSLS INATNIKHFK 370        380        390        400        410        420
    NCTSISGDLH ILPVAFRGDS FTHTPPLDPQ ELDILKTVKE ITGFLLIQAW PENRTDLHAF 430        440        450        460        470        480
    ENLEIIRGRT KQHGQFSLAV VSLNITSLGL RSLKEISDGD VIISGNKNLC YANTINWKKL 490        500        510        520        530        540
    FGTSGQKTKI ISNRGENSCK ATGQVCHALC SPEGCWGPEP RDCVSCRNVS RGRECVDKCN 550        560        570        580        590        600
    LLEGEPREFV ENSECIQCHP ECLPQAMNIT CTGRGPDNCI QCAHYIDGPH CVKTCPAGVM 610        620        630        640        650        660
    GENNTLVWKY ADAGHVCHLC HPNCTYGCTG PGLEGCPTNG PKIPSIATGM VGALLLLLVV 670        680        690        700        710        720
    ALGIGLFMRR RHIVRKRTLR RLLQERELVE PLTPSGEAPN QALLRILKET EFKKIKVLGS 730        740        750        760        770        780
    GAFGTVYKGL WIPEGEKVKI PVAIKELREA TSPKANKEIL DEAYVMASVD NPHVCRLLGI 790        800        810        820        830        840
    CLTSTVQLIT QLMPFGCLLD YVREHKDNIG SQYLLNWCVQ IAKGMNYLED RRLVHRDLAA 850        860        870        880        890        900
    RNVLVKTPQH VKITDFGLAK LLGAEEKEYH AEGGKVPIKW MALESILHRI YTHQSDVWSY
```

-continued

```
       910        920        930        940        950        960
GVTVWELMTF GSKPYDGIPA SEISSILEKG ERLPQPPICT IDVYMIMVKC WMIDADSRPK 970        980        990       1000       1010       1020
FRELIIEFSK MARDPQRYLV IQGDERMHLP SPTDSNFYRA LMDEEDMDDV VDADEYLIPQ 1030       1040       1050       1060       1070       1080
QGFFSSPSTS RTPLLSSLSA TSNNSTVACI DRNGLQSCPI KEDSFLQRYS SDPTGALTED 1090       1100       1110       1120       1130       1140
SIDDTFLPVP EYINQSVPKR PAGSVQNPVY HNQPLNPAPS RDPHYQDPHS TAVGNPEYLN 1150       1160       1170       1180       1190       1200
TVQPTCVNST FDSPAHWAQK GSHQISLDNP DYQQDFFPKE AKPNGIFKGS TAENAEYLRV

1210
APQSSEFIGA
```

Most preferably, the epidermal growth factor receptor assay detects one or more soluble forms of epidermal growth factor receptor. Epidermal growth factor receptor is a single-pass type I membrane protein having a large extracellular domain, most or all of which is present in soluble forms of epidermal growth factor receptor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in epidermal growth factor receptor:

| Residues | Length | Domain ID |
|---|---|---|
| 1-24 | 24 | signal sequence |
| 25-1210 | 1186 | epidermal growth factor receptor |
| 25-645 | 621 | extracellular |
| 646-668 | 23 | transmembrane |
| 669-1210 | 542 | cytoplasmic |

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993);

Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5$^{th}$ percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cathepsin B (P07858); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., Nephrol. Dial. Transplant. 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.

Exclusion Criteria renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN −7.5%, risk of dialysis −0.04%; 6-10 total points=risk of CIN −14%, risk of dialysis −0.12%; 11-16 total points=risk of CIN −26.1%, risk of dialysis −1.09%; >16 total points=risk of CIN −57.3%, risk of dialysis −12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP <90 mmHg and/or need for vasopressor support to maintain MAP >60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients
expected to be hospitalized through acute care setting (ICU or ED) with a known risk factor for acute renal injury (e.g. sepsis, hypotension/shock (Shock=systolic BP <90 mmHg and/or the need for vasopressor support to maintain a MAP >60 mmHg and/or a documented drop in SBP >40 mmHg), major trauma, hemorrhage, or major surgery); and/or expected to be hospitalized to the ICU for at least 24 hours after enrollment.
Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HW) or a hepatitis virus;
meets only the SBP <90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Concentrations are expressed in the following examples as follows: soluble p-selectin-ng/mL; protein NOV homolog-pg·mL; netrin 4-ng/mL; haptoglobin-mg/mL; alpha-1-antitrypsin-mg/mL; leukocyte elastase-ng/mL; soluble tumor necrosis factor receptor superfamily member 6-pg/mL; soluble tumor necrosis factor ligand superfamily member 6-pg/mL; soluble intercellular adhesion molecule 2-units/mL; caspase 3 (active)-ng/mL; soluble platelet endothelial cell adhesion molecule-ng/mL; heat shock protein beta-1-ng/mL; soluble epidermal growth factor receptor-pg/mL.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels in urine samples collected for Cohort 1. Marker concentrations were measured in urine samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The following descriptive statistics were obtained:
Soluble p-Selectin:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 0.244 | 0.183 | 0.244 | 0.290 | 0.244 | 0.000 |
| average | 0.243 | 0.217 | 0.243 | 3.764 | 0.243 | 0.190 |
| stdev | 0.153 | 0.162 | 0.153 | 16.703 | 0.153 | na |
| p (t-test) |  | 0.527 |  | 0.134 |  | na |
| min | 0.000 | 0.000 | 0.000 | 0.000 | 0.000 | 0.190 |
| max | 0.662 | 0.662 | 0.662 | 82.167 | 0.662 | 0.190 |
| n (Samp) | 51 | 22 | 51 | 24 | 51 | 1 |
| n (Pat) | 40 | 22 | 40 | 24 | 40 | 1 |
| sCr only | | | | | | |
| median | 0.247 | 0.210 | 0.247 | 0.251 | 0.247 | 0.335 |
| average | 1.128 | 0.221 | 1.128 | 0.435 | 1.128 | 0.335 |
| stdev | 8.450 | 0.156 | 8.450 | 0.427 | 8.450 | 0.289 |
| p (t-test) |  | 0.794 |  | 0.830 |  | 0.895 |
| min | 0.000 | 0.068 | 0.000 | 0.000 | 0.000 | 0.130 |
| max | 82.167 | 0.499 | 82.167 | 1.244 | 82.167 | 0.539 |
| n (Samp) | 94 | 6 | 94 | 7 | 94 | 2 |
| n (Pat) | 74 | 6 | 74 | 7 | 74 | 2 |
| UO only | | | | | | |
| median | 0.196 | 0.190 | 0.196 | 0.325 | 0.196 | 0.344 |
| average | 0.210 | 0.218 | 0.210 | 4.057 | 0.210 | 0.394 |
| stdev | 0.141 | 0.164 | 0.141 | 17.449 | 0.141 | 0.336 |
| p (t-test) |  | 0.858 |  | 0.155 |  | 0.036 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| min | 0.000 | 0.000 | 0.000 | 0.019 | 0.000 | 0.068 |
| max | 0.662 | 0.662 | 0.662 | 82.167 | 0.662 | 0.818 |
| n (Samp) | 42 | 17 | 42 | 22 | 42 | 4 |
| n (Pat) | 33 | 17 | 33 | 22 | 33 | 4 |

Protein NOV Homolog:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| | sCr or UO | | | | | |
| median | 25253.378 | 52184.874 | 25253.378 | 60843.958 | 25253.378 | 66053.687 |
| average | 43022.422 | 62430.121 | 43022.422 | 83958.436 | 43022.422 | 66053.687 |
| stdev | 46997.024 | 56276.741 | 46997.024 | 70276.919 | 46997.024 | 23004.666 |
| p (t-test) | | 0.057 | | 0.001 | | 0.492 |
| min | 14.544 | 1226.994 | 14.544 | 3448.276 | 14.544 | 49786.932 |
| max | 227486.911 | 211725.664 | 227486.911 | 228010.471 | 227486.911 | 82320.442 |
| n (Samp) | 101 | 31 | 101 | 26 | 101 | 2 |
| n (Pat) | 50 | 31 | 50 | 26 | 50 | 2 |
| | sCr only | | | | | |
| median | 38059.701 | 33595.839 | 38059.701 | 71096.059 | 38059.701 | 11883.803 |
| average | 53718.274 | 48877.947 | 53718.274 | 71936.428 | 53718.274 | 38044.172 |
| stdev | 52989.113 | 55336.198 | 52989.113 | 65678.754 | 52989.113 | 45869.498 |
| p (t-test) | | 0.780 | | 0.298 | | 0.612 |
| min | 14.544 | 1226.994 | 14.544 | 2952.454 | 14.544 | 11240.310 |
| max | 228010.471 | 187781.350 | 228010.471 | 178982.301 | 228010.471 | 91008.403 |
| n (Samp) | 173 | 10 | 173 | 10 | 173 | 3 |
| n (Pat) | 94 | 10 | 94 | 10 | 94 | 3 |
| | UO only | | | | | |
| median | 23591.366 | 57512.315 | 23591.366 | 52352.941 | 23591.366 | 49786.932 |
| average | 34707.021 | 66292.036 | 34707.021 | 82763.046 | 34707.021 | 52148.495 |
| stdev | 34366.696 | 53041.733 | 34366.696 | 66472.787 | 34366.696 | 29735.062 |
| p (t-test) | | 0.001 | | 0.000 | | 0.272 |
| min | 14.544 | 3125.000 | 14.544 | 11821.705 | 14.544 | 17223.502 |
| max | 165265.487 | 211725.664 | 165265.487 | 228010.471 | 165265.487 | 82320.442 |
| n (Samp) | 78 | 25 | 78 | 23 | 78 | 5 |
| n (Pat) | 38 | 25 | 38 | 23 | 38 | 5 |

Netrin 4:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| | sCr or UO | | | | | |
| median | 0.007 | 0.007 | 0.007 | 0.011 | 0.007 | 0.000 |
| average | 0.037 | 0.014 | 0.037 | 0.011 | 0.037 | 0.126 |
| stdev | 0.071 | 0.015 | 0.071 | 0.016 | 0.071 | na |
| p (t-test) | | 0.276 | | 0.621 | | na |
| min | 0.000 | 0.000 | 0.000 | 0.000 | 0.000 | 0.126 |
| max | 0.262 | 0.050 | 0.262 | 0.023 | 0.262 | 0.126 |
| n (Samp) | 52 | 12 | 52 | 2 | 52 | 1 |
| n (Pat) | 36 | 12 | 36 | 2 | 36 | 1 |
| | sCr only | | | | | |
| median | 0.007 | 0.010 | 0.007 | 0.007 | 0.007 | 0.000 |
| average | 0.040 | 0.011 | 0.040 | 0.007 | 0.040 | 0.002 |
| stdev | 0.081 | 0.009 | 0.081 | 0.009 | 0.081 | na |
| p (t-test) | | 0.476 | | 0.563 | | na |
| min | 0.000 | 0.002 | 0.000 | 0.000 | 0.000 | 0.002 |
| max | 0.469 | 0.023 | 0.469 | 0.013 | 0.469 | 0.002 |
| n (Samp) | 86 | 4 | 86 | 2 | 86 | 1 |
| n (Pat) | 61 | 4 | 61 | 2 | 61 | 1 |
| | UO only | | | | | |
| median | 0.004 | 0.007 | 0.004 | 0.007 | 0.004 | 0.000 |
| average | 0.025 | 0.012 | 0.025 | 0.010 | 0.025 | 0.126 |
| stdev | 0.055 | 0.015 | 0.055 | 0.011 | 0.055 | na |
| p (t-test) | | 0.447 | | 0.648 | | na |
| min | 0.000 | 0.000 | 0.000 | 0.000 | 0.000 | 0.126 |
| max | 0.225 | 0.050 | 0.225 | 0.023 | 0.225 | 0.126 |
| n (Samp) | 38 | 11 | 38 | 3 | 38 | 1 |
| n (Pat) | 26 | 11 | 26 | 3 | 26 | 1 |

Haptoglobin:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 0.000 | 0.000 | 0.000 | 0.000 | 0.000 | 0.000 |
| average | 0.000 | 0.001 | 0.000 | 0.000 | 0.000 | 0.001 |
| stdev | 0.001 | 0.001 | 0.001 | 0.001 | 0.001 | 0.001 |
| p (t-test) |  | 0.420 |  | 0.964 |  | 0.124 |
| min | 0.000 | 0.000 | 0.000 | 0.000 | 0.000 | 0.000 |
| max | 0.007 | 0.005 | 0.007 | 0.004 | 0.007 | 0.004 |
| n (Samp) | 216 | 38 | 216 | 51 | 216 | 23 |
| n (Pat) | 77 | 38 | 77 | 51 | 77 | 23 |
| sCr only | | | | | | |
| median | 0.000 | 0.000 | 0.000 | 0.000 | 0.000 | 0.000 |
| average | 0.001 | 0.000 | 0.001 | 0.000 | 0.001 | 0.000 |
| stdev | 0.001 | 0.000 | 0.001 | 0.001 | 0.001 | 0.000 |
| p (t-test) |  | 0.403 |  | 0.705 |  | 0.560 |
| min | 0.000 | 0.000 | 0.000 | 0.000 | 0.000 | 0.000 |
| max | 0.007 | 0.002 | 0.007 | 0.003 | 0.007 | 0.001 |
| n (Samp) | 375 | 16 | 375 | 21 | 375 | 11 |
| n (Pat) | 127 | 16 | 127 | 21 | 127 | 11 |
| UO only | | | | | | |
| median | 0.000 | 0.000 | 0.000 | 0.000 | 0.000 | 0.000 |
| average | 0.000 | 0.001 | 0.000 | 0.000 | 0.000 | 0.001 |
| stdev | 0.001 | 0.001 | 0.001 | 0.001 | 0.001 | 0.001 |
| p (t-test) |  | 0.074 |  | 0.530 |  | 0.041 |
| min | 0.000 | 0.000 | 0.000 | 0.000 | 0.000 | 0.000 |
| max | 0.006 | 0.005 | 0.006 | 0.004 | 0.006 | 0.004 |
| n (Samp) | 181 | 34 | 181 | 45 | 181 | 23 |
| n (Pat) | 61 | 34 | 61 | 45 | 61 | 23 |

Alpha-1-Antitrypsin:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 0.001 | 0.001 | 0.001 | 0.001 | 0.001 | 0.001 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.065 |  | 0.133 |  | 0.365 |
| min | 0.000 | 0.000 | 0.000 | 0.000 | 0.000 | 0.000 |
| max | 0.005 | 0.005 | 0.005 | 0.003 | 0.005 | 0.003 |
| n (Samp) | 216 | 38 | 216 | 51 | 216 | 23 |
| n (Pat) | 77 | 38 | 77 | 51 | 77 | 23 |
| sCr only | | | | | | |
| median | 0.001 | 0.001 | 0.001 | 0.001 | 0.001 | 0.001 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.093 |  | 0.063 |  | 0.261 |
| min | 0.000 | 0.000 | 0.000 | 0.000 | 0.000 | 0.000 |
| max | 0.005 | 0.002 | 0.005 | 0.003 | 0.005 | 0.003 |
| n (Samp) | 375 | 16 | 375 | 21 | 375 | 11 |
| n (Pat) | 127 | 16 | 127 | 21 | 127 | 11 |
| UO only | | | | | | |
| median | 0.001 | 0.001 | 0.001 | 0.001 | 0.001 | 0.001 |
| average | 0.001 | 0.001 | 0.001 | 0.001 | 0.001 | 0.001 |
| Stdev | 0.001 | 0.001 | 0.001 | 0.001 | 0.001 | 0.001 |
| p (t-test) |  | 0.374 |  | 0.933 |  | 0.493 |
| min | 0.000 | 0.000 | 0.000 | 0.000 | 0.000 | 0.000 |
| max | 0.005 | 0.005 | 0.005 | 0.003 | 0.005 | 0.003 |
| n (Samp) | 181 | 34 | 181 | 45 | 181 | 23 |
| n (Pat) | 61 | 34 | 61 | 45 | 61 | 23 |

Leukocyte Elastase:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 23.999 | 42.003 | 23.999 | 34.568 | 23.999 | 23.410 |
| average | 34.066 | 49.753 | 34.066 | 47.135 | 34.066 | 36.253 |
| stdev | 31.889 | 41.280 | 31.889 | 41.324 | 31.889 | 34.715 |
| p (t-test) |  | 0.020 |  | 0.037 |  | 0.770 |
| min | 0.080 | 2.989 | 0.080 | 0.870 | 0.080 | 0.973 |
| max | 137.517 | 136.336 | 137.517 | 131.883 | 137.517 | 126.749 |
| n (Samp) | 103 | 36 | 103 | 46 | 103 | 23 |
| n (Pat) | 62 | 36 | 62 | 46 | 62 | 23 |
| sCr only | | | | | | |
| median | 34.568 | 33.123 | 34.568 | 31.179 | 34.568 | 43.691 |
| average | 43.827 | 42.392 | 43.827 | 38.160 | 43.827 | 55.480 |
| stdev | 37.819 | 36.409 | 37.819 | 38.649 | 37.819 | 44.934 |
| p (t-test) |  | 0.898 |  | 0.542 |  | 0.324 |
| min | 0.080 | 3.965 | 0.080 | 2.174 | 0.080 | 1.002 |
| max | 137.517 | 103.409 | 137.517 | 125.675 | 137.517 | 125.810 |
| n (Samp) | 226 | 12 | 226 | 18 | 226 | 11 |
| n (Pat) | 106 | 12 | 106 | 18 | 106 | 11 |
| UO only | | | | | | |
| median | 26.665 | 43.891 | 26.665 | 36.077 | 26.665 | 25.217 |
| average | 37.321 | 50.294 | 37.321 | 51.366 | 37.321 | 39.875 |
| stdev | 32.107 | 42.250 | 32.107 | 41.005 | 32.107 | 39.000 |
| p (t-test) |  | 0.078 |  | 0.037 |  | 0.750 |
| min | 0.080 | 2.989 | 0.080 | 0.870 | 0.080 | 0.973 |
| max | 137.517 | 136.336 | 137.517 | 131.883 | 137.517 | 126.749 |
| n (Samp) | 88 | 31 | 88 | 41 | 88 | 22 |
| n (Pat) | 50 | 31 | 50 | 41 | 50 | 22 |

Soluble Tumor Necrosis Factor Receptor Superfamily Member 6:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 282.634 | 542.790 | 282.634 | 491.935 | 282.634 | 662.625 |
| average | 424.230 | 571.252 | 424.230 | 657.667 | 424.230 | 611.976 |
| stdev | 418.752 | 456.904 | 418.752 | 549.928 | 418.752 | 164.637 |
| p (t-test) |  | 0.103 |  | 0.014 |  | 0.441 |
| min | 13.944 | 57.065 | 13.944 | 0.278 | 13.944 | 427.966 |
| max | 1765.586 | 1846.785 | 1765.586 | 2094.793 | 1765.586 | 745.338 |
| n (Samp) | 117 | 28 | 117 | 28 | 117 | 3 |
| n (Pat) | 48 | 28 | 48 | 28 | 48 | 3 |
| sCr only | | | | | | |
| median | 432.203 | 348.164 | 432.203 | 958.796 | 432.203 | 529.812 |
| average | 505.976 | 587.771 | 505.976 | 851.837 | 505.976 | 514.814 |
| stdev | 420.406 | 584.956 | 420.406 | 705.854 | 420.406 | 214.168 |
| p (t-test) |  | 0.576 |  | 0.012 |  | 0.967 |
| min | 0.278 | 57.065 | 0.278 | 21.169 | 0.278 | 254.294 |
| max | 2094.793 | 1648.865 | 2094.793 | 1870.324 | 2094.793 | 745.338 |
| n (Samp) | 194 | 9 | 194 | 11 | 194 | 4 |
| n (Pat) | 83 | 9 | 83 | 11 | 83 | 4 |
| UO only | | | | | | |
| median | 287.523 | 589.230 | 287.523 | 543.706 | 287.523 | 703.981 |
| average | 393.670 | 627.433 | 393.670 | 692.169 | 393.670 | 712.925 |
| stdev | 377.902 | 474.260 | 377.902 | 557.457 | 377.902 | 297.752 |
| p (t-test) |  | 0.015 |  | 0.002 |  | 0.046 |
| min | 13.944 | 108.491 | 13.944 | 0.278 | 13.944 | 348.164 |
| max | 1765.586 | 1846.785 | 1765.586 | 2094.793 | 1765.586 | 1082.777 |
| n (Samp) | 92 | 22 | 92 | 25 | 92 | 6 |
| n (Pat) | 38 | 22 | 38 | 25 | 38 | 6 |

Soluble Tumor Necrosis Factor Ligand Superfamily Member 6:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 0.158 | 1.290 | 0.158 | 1.418 | 0.158 | 0.300 |
| average | 0.915 | 1.454 | 0.915 | 2.059 | 0.915 | 0.300 |
| stdev | 2.398 | 1.331 | 2.398 | 2.492 | 2.398 | 0.200 |
| p (t-test) |  | 0.535 |  | 0.129 |  | 0.720 |
| min | 0.158 | 0.158 | 0.158 | 0.158 | 0.158 | 0.158 |
| max | 16.774 | 3.754 | 16.774 | 9.276 | 16.774 | 0.442 |
| n (Samp) | 78 | 8 | 78 | 12 | 78 | 2 |
| n (Pat) | 19 | 8 | 19 | 12 | 19 | 2 |
| sCr only | | | | | | |
| median | 0.158 | 0.158 | 0.158 | 0.627 | 0.158 | 0.812 |
| average | 1.356 | 0.441 | 1.356 | 0.976 | 1.356 | 1.007 |
| stdev | 2.585 | 0.566 | 2.585 | 1.005 | 2.585 | 0.684 |
| p (t-test) |  | 0.483 |  | 0.722 |  | 0.817 |
| min | 0.158 | 0.158 | 0.158 | 0.158 | 0.158 | 0.442 |
| max | 16.774 | 1.290 | 16.774 | 2.724 | 16.774 | 1.768 |
| n (Samp) | 118 | 4 | 118 | 6 | 118 | 3 |
| n (Pat) | 26 | 4 | 26 | 6 | 26 | 3 |
| UO only | | | | | | |
| median | 0.158 | 1.290 | 0.158 | 1.051 | 0.158 | 0.300 |
| average | 1.114 | 1.639 | 1.114 | 1.977 | 1.114 | 0.300 |
| stdev | 2.703 | 1.322 | 2.703 | 2.781 | 2.703 | 0.200 |
| p (t-test) |  | 0.616 |  | 0.355 |  | 0.674 |
| min | 0.158 | 0.158 | 0.158 | 0.158 | 0.158 | 0.158 |
| max | 16.774 | 3.754 | 16.774 | 9.276 | 16.774 | 0.442 |
| n (Samp) | 60 | 7 | 60 | 10 | 60 | 2 |
| n (Pat) | 14 | 7 | 14 | 10 | 14 | 2 |

Soluble Intercellular Adhesion Molecule 2:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 0.460 | 0.148 | 0.460 | 0.254 | 0.460 | 0.001 |
| average | 1.609 | 0.766 | 1.609 | 5.376 | 1.609 | 0.163 |
| stdev | 3.464 | 2.193 | 3.464 | 22.215 | 3.464 | na |
| p (t-test) |  | 0.220 |  | 0.118 |  | na |
| min | 0.001 | 0.001 | 0.001 | 0.006 | 0.001 | 0.163 |
| max | 30.484 | 11.883 | 30.484 | 113.267 | 30.484 | 0.163 |
| n (Samp) | 92 | 29 | 92 | 26 | 92 | 1 |
| n (Pat) | 48 | 29 | 48 | 26 | 48 | 1 |
| sCr only | | | | | | |
| median | 0.237 | 0.390 | 0.237 | 0.399 | 0.237 | 0.148 |
| average | 1.972 | 0.420 | 1.972 | 1.955 | 1.972 | 0.628 |
| stdev | 9.484 | 0.449 | 9.484 | 4.860 | 9.484 | 0.915 |
| p (t-test) |  | 0.607 |  | 0.995 |  | 0.807 |
| min | 0.001 | 0.006 | 0.001 | 0.012 | 0.001 | 0.054 |
| max | 113.267 | 1.308 | 113.267 | 15.738 | 113.267 | 1.684 |
| n (Samp) | 154 | 10 | 154 | 10 | 154 | 3 |
| n (Pat) | 89 | 10 | 89 | 10 | 89 | 3 |
| UO only | | | | | | |
| median | 0.507 | 0.103 | 0.507 | 0.201 | 0.507 | 0.470 |
| average | 1.804 | 0.752 | 1.804 | 5.218 | 1.804 | 0.603 |
| stdev | 4.188 | 2.418 | 4.188 | 23.024 | 4.188 | 0.505 |
| p (t-test) |  | 0.248 |  | 0.235 |  | 0.570 |
| min | 0.001 | 0.001 | 0.001 | 0.006 | 0.001 | 0.163 |
| max | 30.484 | 11.883 | 30.484 | 113.267 | 30.484 | 1.308 |
| n (Samp) | 70 | 24 | 70 | 24 | 70 | 4 |
| n (Pat) | 37 | 24 | 37 | 24 | 37 | 4 |

Caspase 3 (Active):

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 0.000 | 0.002 | 0.000 | 0.003 | 0.000 | 0.000 |
| Average | 0.004 | 0.005 | 0.004 | 0.016 | 0.004 | 0.014 |
| Stdev | 0.008 | 0.008 | 0.008 | 0.025 | 0.008 | na |
| p (t-test) |  | 0.541 |  | 0.003 |  | na |
| Min | 0.000 | 0.000 | 0.000 | 0.000 | 0.000 | 0.014 |
| Max | 0.041 | 0.034 | 0.041 | 0.095 | 0.041 | 0.014 |
| n (Samp) | 51 | 22 | 51 | 24 | 51 | 1 |
| n (Pat) | 40 | 22 | 40 | 24 | 40 | 1 |
| sCr only | | | | | | |
| median | 0.001 | 0.002 | 0.001 | 0.003 | 0.001 | 0.008 |
| average | 0.007 | 0.005 | 0.007 | 0.008 | 0.007 | 0.008 |
| stdev | 0.015 | 0.006 | 0.015 | 0.011 | 0.015 | 0.006 |
| p (t-test) |  | 0.703 |  | 0.878 |  | 0.908 |
| min | 0.000 | 0.000 | 0.000 | 0.000 | 0.000 | 0.005 |
| max | 0.095 | 0.013 | 0.095 | 0.028 | 0.095 | 0.012 |
| n (Samp) | 94 | 6 | 94 | 7 | 94 | 2 |
| n (Pat) | 74 | 6 | 74 | 7 | 74 | 2 |
| UO only | | | | | | |
| median | 0.000 | 0.003 | 0.000 | 0.004 | 0.000 | 0.009 |
| average | 0.004 | 0.006 | 0.004 | 0.017 | 0.004 | 0.008 |
| stdev | 0.008 | 0.009 | 0.008 | 0.026 | 0.008 | 0.007 |
| p (t-test) |  | 0.554 |  | 0.004 |  | 0.384 |
| min | 0.000 | 0.000 | 0.000 | 0.000 | 0.000 | 0.001 |
| max | 0.041 | 0.034 | 0.041 | 0.095 | 0.041 | 0.014 |
| n (Samp) | 42 | 17 | 42 | 22 | 42 | 4 |
| n (Pat) | 33 | 17 | 33 | 22 | 33 | 4 |

Soluble Platelet Endothelial Cell Adhesion Molecule:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 1.224 | 0.618 | 1.224 | 0.788 | 1.224 | na |
| average | 1.866 | 1.103 | 1.866 | 0.913 | 1.866 | na |
| stdev | 1.800 | 1.076 | 1.800 | 0.754 | 1.800 | na |
| p (t-test) |  | 0.206 |  | 0.371 |  | na |
| min | 0.002 | 0.212 | 0.002 | 0.229 | 0.002 | na |
| max | 7.216 | 3.281 | 7.216 | 1.722 | 7.216 | na |
| n (Samp) | 43 | 10 | 43 | 3 | 43 | 0 |
| n (Pat) | 26 | 10 | 26 | 3 | 26 | 0 |
| sCr only | | | | | | |
| median | 0.921 | 0.440 | 0.921 | 0.788 | 0.921 | 1.198 |
| average | 1.521 | 1.004 | 1.521 | 0.869 | 1.521 | 1.198 |
| stdev | 1.592 | 1.302 | 1.592 | 0.815 | 1.592 | 0.579 |
| p (t-test) |  | 0.482 |  | 0.486 |  | 0.777 |
| min | 0.002 | 0.212 | 0.002 | 0.097 | 0.002 | 0.788 |
| max | 7.216 | 3.281 | 7.216 | 1.722 | 7.216 | 1.607 |
| n (Samp) | 65 | 5 | 65 | 3 | 65 | 2 |
| n (Pat) | 41 | 5 | 41 | 3 | 41 | 2 |
| UO only | | | | | | |
| median | 1.378 | 0.618 | 1.378 | 1.224 | 1.378 | na |
| average | 1.959 | 1.108 | 1.959 | 1.058 | 1.959 | na |
| stdev | 1.608 | 1.088 | 1.608 | 0.760 | 1.608 | na |
| p (t-test) |  | 0.129 |  | 0.350 |  | na |
| min | 0.002 | 0.212 | 0.002 | 0.229 | 0.002 | na |
| max | 6.393 | 3.331 | 6.393 | 1.722 | 6.393 | na |
| n (Samp) | 30 | 10 | 30 | 3 | 30 | 0 |
| n (Pat) | 16 | 10 | 16 | 3 | 16 | 0 |

Heat Shock Protein Beta-1:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 1.490 | 1.616 | 1.490 | 1.088 | 1.490 | 0.086 |
| average | 2.984 | 5.803 | 2.984 | 1.088 | 2.984 | 1.546 |
| stdev | 4.947 | 11.437 | 4.947 | 0.710 | 4.947 | na |
| p (t-test) |  | 0.168 |  | 0.593 |  | na |
| min | 0.086 | 0.317 | 0.086 | 0.586 | 0.086 | 1.546 |
| max | 33.481 | 42.428 | 33.481 | 1.589 | 33.481 | 1.546 |
| n (Samp) | 54 | 14 | 54 | 2 | 54 | 1 |
| n (Pat) | 36 | 14 | 36 | 2 | 36 | 1 |
| sCr only | | | | | | |
| median | 1.533 | 5.412 | 1.533 | 1.259 | 1.533 | 0.905 |
| average | 3.203 | 10.462 | 3.203 | 1.259 | 3.203 | 0.905 |
| stdev | 5.494 | 15.904 | 5.494 | 0.468 | 5.494 | 0.561 |
| p (t-test) |  | 0.010 |  | 0.620 |  | 0.558 |
| min | 0.078 | 0.223 | 0.078 | 0.928 | 0.078 | 0.509 |
| max | 34.307 | 42.428 | 34.307 | 1.589 | 34.307 | 1.302 |
| n (Samp) | 88 | 6 | 88 | 2 | 88 | 2 |
| n (Pat) | 61 | 6 | 61 | 2 | 61 | 2 |
| UO only | | | | | | |
| median | 1.135 | 1.616 | 1.135 | 0.984 | 1.135 | 0.086 |
| average | 1.952 | 3.013 | 1.952 | 1.053 | 1.952 | 1.546 |
| stdev | 1.979 | 4.610 | 1.979 | 0.505 | 1.979 | na |
| p (t-test) |  | 0.245 |  | 0.442 |  | na |
| Min | 0.086 | 0.317 | 0.086 | 0.586 | 0.086 | 1.546 |
| max | 7.975 | 17.432 | 7.975 | 1.589 | 7.975 | 1.546 |
| n (Samp) | 40 | 13 | 40 | 3 | 40 | 1 |
| n (Pat) | 26 | 13 | 26 | 3 | 26 | 1 |

Soluble Epidermal Growth Factor Receptor:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 26.667 | 80.647 | 26.667 | 115.780 | 26.667 | 0.000 |
| average | 236.400 | 202.513 | 236.400 | 1553.848 | 236.400 | 47.329 |
| stdev | 470.310 | 281.585 | 470.310 | 6184.478 | 470.310 | na |
| p (t-test) |  | 0.755 |  | 0.132 |  | na |
| min | 0.000 | 0.000 | 0.000 | 0.000 | 0.000 | 47.329 |
| max | 2046.762 | 954.226 | 2046.762 | 29882.667 | 2046.762 | 47.329 |
| n (Samp) | 51 | 22 | 51 | 23 | 51 | 1 |
| n (Pat) | 40 | 22 | 40 | 23 | 40 | 1 |
| sCr only | | | | | | |
| median | 98.860 | 0.000 | 98.860 | 0.000 | 98.860 | 781.108 |
| average | 586.773 | 104.569 | 586.773 | 523.899 | 586.773 | 781.108 |
| stdev | 3099.913 | 162.125 | 3099.913 | 841.439 | 3099.913 | 191.895 |
| p (t-test) |  | 0.705 |  | 0.958 |  | 0.930 |
| min | 0.000 | 0.000 | 0.000 | 0.000 | 0.000 | 645.418 |
| max | 29882.667 | 323.886 | 29882.667 | 2186.810 | 29882.667 | 916.798 |
| n (Samp) | 93 | 6 | 93 | 7 | 93 | 2 |
| n (Pat) | 73 | 6 | 73 | 7 | 73 | 2 |
| UO only | | | | | | |
| median | 0.000 | 190.158 | 0.000 | 183.840 | 0.000 | 175.427 |
| average | 205.187 | 244.221 | 205.187 | 1682.860 | 205.187 | 328.289 |
| stdev | 474.101 | 302.208 | 474.101 | 6468.618 | 474.101 | 443.206 |
| p (t-test) |  | 0.755 |  | 0.143 |  | 0.621 |
| min | 0.000 | 0.000 | 0.000 | 0.000 | 0.000 | 0.000 |
| max | 2046.762 | 954.226 | 2046.762 | 29882.667 | 2046.762 | 962.300 |
| n (Samp) | 42 | 17 | 42 | 21 | 42 | 4 |
| n (Pat) | 33 | 17 | 33 | 21 | 33 | 4 |

In the following tables, the ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC <0.5 is indicative of a negative going marker for the comparison, and an AUC >0.5 is indicative of a positive going marker for the comparison.

Soluble p-Selectin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.42 | 0.072 | 51 | 22 | 1.727 |
| 24 hours | 0.59 | 0.072 | 51 | 24 | 0.214 |
| 48 hours | 0.40 | 0.269 | 51 | 1 | 1.285 |
| Cohort 1 v Cohort 2, adjudicated on serum creatinine | | | | | |
| 0 hours | 0.41 | 0.114 | 94 | 6 | 1.561 |
| 24 hours | 0.58 | 0.117 | 94 | 7 | 0.479 |
| 48 hours | 0.58 | 0.214 | 94 | 2 | 0.710 |
| Cohort 1 v Cohort 2, adjudicated on urine output | | | | | |
| 0 hours | 0.49 | 0.083 | 42 | 17 | 1.120 |
| 24 hours | 0.66 | 0.074 | 42 | 22 | 0.031 |
| 48 hours | 0.65 | 0.156 | 42 | 4 | 0.320 |

Protein NOV Homolog:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.62 | 0.060 | 101 | 31 | 0.050 |
| 24 hours | 0.69 | 0.062 | 101 | 26 | 0.003 |
| 48 hours | 0.79 | 0.192 | 101 | 2 | 0.129 |
| Cohort 1 v Cohort 2, adjudicated on serum creatinine | | | | | |
| 0 hours | 0.46 | 0.092 | 173 | 10 | 1.299 |
| 24 hours | 0.54 | 0.096 | 173 | 10 | 0.652 |
| 48 hours | 0.40 | 0.153 | 173 | 3 | 1.500 |
| Cohort 1 v Cohort 2, adjudicated on urine output | | | | | |
| 0 hours | 0.70 | 0.064 | 78 | 25 | 0.002 |
| 24 hours | 0.76 | 0.062 | 78 | 23 | 0.000 |
| 48 hours | 0.71 | 0.134 | 78 | 5 | 0.116 |

Netrin 4:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.57 | 0.095 | 52 | 12 | 0.462 |
| 24 hours | 0.40 | 0.192 | 52 | 2 | 1.402 |
| 48 hours | 0.88 | 0.221 | 52 | 1 | 0.082 |
| Cohort 1 v Cohort 2, adjudicated on serum creatinine | | | | | |
| 0 hours | 0.56 | 0.152 | 86 | 4 | 0.689 |
| 24 hours | 0.39 | 0.186 | 86 | 2 | 1.458 |
| 48 hours | 0.24 | 0.191 | 86 | 1 | 1.828 |

-continued

| Time prior max stage | AUC | SE | $n_{Cohort\ 1}$ | $n_{Cohort\ 2}$ | p |
|---|---|---|---|---|---|
| Cohort 1 v Cohort 2, adjudicated on urine output ||||||
| 0 hours | 0.54 | 0.101 | 38 | 11 | 0.678 |
| 24 hours | 0.51 | 0.176 | 38 | 3 | 0.941 |
| 48 hours | 0.92 | 0.189 | 38 | 1 | 0.026 |

Haptoglobin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.52 | 0.051 | 216 | 38 | 0.743 |
| 24 hours | 0.55 | 0.046 | 216 | 51 | 0.291 |
| 48 hours | 0.65 | 0.065 | 216 | 23 | 0.017 |
| Cohort 1 v Cohort 2, adjudicated on serum creatinine ||||||
| 0 hours | 0.40 | 0.067 | 375 | 16 | 1.865 |
| 24 hours | 0.52 | 0.065 | 375 | 21 | 0.777 |
| 48 hours | 0.56 | 0.091 | 375 | 11 | 0.519 |
| Cohort 1 v Cohort 2, adjudicated on urine output ||||||
| 0 hours | 0.57 | 0.055 | 181 | 34 | 0.202 |
| 24 hours | 0.56 | 0.049 | 181 | 45 | 0.224 |
| 48 hours | 0.60 | 0.066 | 181 | 23 | 0.116 |

Alpha-1-Antitrypsin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.44 | 0.049 | 216 | 38 | 1.816 |
| 24 hours | 0.45 | 0.044 | 216 | 51 | 1.741 |
| 48 hours | 0.49 | 0.063 | 216 | 23 | 1.134 |
| Cohort 1 v Cohort 2, adjudicated on serum creatinine ||||||
| 0 hours | 0.40 | 0.067 | 375 | 16 | 1.864 |
| 24 hours | 0.38 | 0.058 | 375 | 21 | 1.966 |
| 48 hours | 0.43 | 0.084 | 375 | 11 | 1.581 |
| Cohort 1 v Cohort 2, adjudicated on urine output ||||||
| 0 hours | 0.48 | 0.054 | 181 | 34 | 1.261 |
| 24 hours | 0.52 | 0.049 | 181 | 45 | 0.692 |
| 48 hours | 0.50 | 0.064 | 181 | 23 | 1.019 |

Leukocyte Elastase:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.60 | 0.056 | 103 | 36 | 0.071 |
| 24 hours | 0.58 | 0.052 | 103 | 46 | 0.121 |
| 48 hours | 0.52 | 0.067 | 103 | 23 | 0.771 |
| Cohort 1 v Cohort 2, adjudicated on serum creatinine ||||||
| 0 hours | 0.50 | 0.086 | 226 | 12 | 0.988 |
| 24 hours | 0.45 | 0.069 | 226 | 18 | 1.494 |
| 48 hours | 0.59 | 0.092 | 226 | 11 | 0.344 |
| Cohort 1 v Cohort 2, adjudicated on urine output ||||||
| 0 hours | 0.56 | 0.061 | 88 | 31 | 0.303 |
| 24 hours | 0.59 | 0.055 | 88 | 41 | 0.113 |
| 48 hours | 0.49 | 0.069 | 88 | 22 | 1.155 |

Soluble Tumor Necrosis Factor Receptor Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.63 | 0.062 | 117 | 28 | 0.040 |
| 24 hours | 0.65 | 0.061 | 117 | 28 | 0.015 |
| 48 hours | 0.76 | 0.163 | 117 | 3 | 0.106 |
| Cohort 1 v Cohort 2, adjudicated on serum creatinine ||||||
| 0 hours | 0.49 | 0.098 | 194 | 9 | 1.065 |
| 24 hours | 0.61 | 0.093 | 194 | 11 | 0.221 |
| 48 hours | 0.58 | 0.151 | 194 | 4 | 0.580 |
| Cohort 1 v Cohort 2, adjudicated on urine output ||||||
| 0 hours | 0.69 | 0.068 | 92 | 22 | 0.005 |
| 24 hours | 0.71 | 0.063 | 92 | 25 | 0.001 |
| 48 hours | 0.80 | 0.112 | 92 | 6 | 0.008 |

Soluble Tumor Necrosis Factor Ligand Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.70 | 0.108 | 78 | 8 | 0.065 |
| 24 hours | 0.78 | 0.082 | 78 | 12 | 0.001 |
| 48 hours | 0.54 | 0.212 | 78 | 2 | 0.868 |
| Cohort 1 v Cohort 2, adjudicated on serum creatinine ||||||
| 0 hours | 0.39 | 0.133 | 118 | 4 | 1.578 |
| 24 hours | 0.57 | 0.125 | 118 | 6 | 0.553 |
| 48 hours | 0.68 | 0.173 | 118 | 3 | 0.293 |
| Cohort 1 v Cohort 2, adjudicated on urine output ||||||
| 0 hours | 0.72 | 0.114 | 60 | 7 | 0.050 |
| 24 hours | 0.69 | 0.099 | 60 | 10 | 0.061 |
| 48 hours | 0.50 | 0.209 | 60 | 2 | 1.016 |

Soluble Intercellular Adhesion Molecule 2:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.36 | 0.056 | 92 | 29 | 1.987 |
| 24 hours | 0.44 | 0.062 | 92 | 26 | 1.671 |
| 48 hours | 0.38 | 0.258 | 92 | 1 | 1.356 |
| Cohort 1 v Cohort 2, adjudicated on serum creatinine ||||||
| 0 hours | 0.41 | 0.088 | 154 | 10 | 1.692 |
| 24 hours | 0.50 | 0.095 | 154 | 10 | 0.992 |
| 48 hours | 0.48 | 0.166 | 154 | 3 | 1.098 |
| Cohort 1 v Cohort 2, adjudicated on urine output ||||||
| 0 hours | 0.29 | 0.057 | 70 | 24 | 2.000 |
| 24 hours | 0.41 | 0.065 | 70 | 24 | 1.811 |
| 48 hours | 0.49 | 0.149 | 70 | 4 | 1.029 |

Caspase 3 (Active):

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.57 | 0.075 | 51 | 22 | 0.351 |
| 24 hours | 0.64 | 0.071 | 51 | 24 | 0.043 |
| 48 hours | 0.94 | 0.166 | 51 | 1 | 0.008 |
| Cohort 1 v Cohort 2, adjudicated on serum creatinine | | | | | |
| 0 hours | 0.53 | 0.124 | 94 | 6 | 0.813 |
| 24 hours | 0.55 | 0.116 | 94 | 7 | 0.680 |
| 48 hours | 0.75 | 0.203 | 94 | 2 | 0.223 |
| Cohort 1 v Cohort 2, adjudicated on urine output | | | | | |
| 0 hours | 0.59 | 0.084 | 42 | 17 | 0.302 |
| 24 hours | 0.69 | 0.073 | 42 | 22 | 0.010 |
| 48 hours | 0.77 | 0.143 | 42 | 4 | 0.058 |

Soluble Platelet Endothelial Cell Adhesion Molecule:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.37 | 0.093 | 43 | 10 | 1.832 |
| 24 hours | 0.37 | 0.154 | 43 | 3 | 1.593 |
| 48 hours | nd | nd | 43 | 0 | 0.211 |
| Cohort 1 v Cohort 2, adjudicated on serum creatinine | | | | | |
| 0 hours | 0.36 | 0.118 | 65 | 5 | 1.766 |
| 24 hours | 0.41 | 0.158 | 65 | 3 | 1.452 |
| 48 hours | 0.57 | 0.215 | 65 | 2 | 0.747 |
| Cohort 1 v Cohort 2, adjudicated on urine output | | | | | |
| 0 hours | 0.32 | 0.092 | 30 | 10 | 1.952 |
| 24 hours | 0.36 | 0.156 | 30 | 3 | 1.627 |
| 48 hours | nd | nd | 30 | 0 | 0.211 |

Heat Shock Protein Beta-1:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.54 | 0.088 | 54 | 14 | 0.674 |
| 24 hours | 0.38 | 0.187 | 54 | 2 | 1.481 |
| 48 hours | 0.56 | 0.302 | 54 | 1 | 0.854 |
| Cohort 1 v Cohort 2, adjudicated on serum creatinine | | | | | |
| 0 hours | 0.70 | 0.123 | 88 | 6 | 0.095 |
| 24 hours | 0.43 | 0.195 | 88 | 2 | 1.295 |
| 48 hours | 0.28 | 0.152 | 88 | 2 | 1.854 |
| Cohort 1 v Cohort 2, adjudicated on urine output | | | | | |
| 0 hours | 0.55 | 0.094 | 40 | 13 | 0.581 |
| 24 hours | 0.43 | 0.166 | 40 | 3 | 1.312 |
| 48 hours | 0.63 | 0.306 | 40 | 1 | 0.683 |

Soluble Epidermal Growth Factor Receptor:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.52 | 0.074 | 51 | 22 | 0.756 |
| 24 hours | 0.60 | 0.073 | 51 | 23 | 0.163 |
| 48 hours | 0.53 | 0.299 | 51 | 1 | 0.922 |
| Cohort 1 v Cohort 2, adjudicated on serum creatinine | | | | | |
| 0 hours | 0.37 | 0.108 | 93 | 6 | 1.768 |
| 24 hours | 0.49 | 0.113 | 93 | 7 | 1.038 |
| 48 hours | 0.87 | 0.163 | 93 | 2 | 0.023 |
| Cohort 1 v Cohort 2, adjudicated on urine output | | | | | |
| 0 hours | 0.61 | 0.084 | 42 | 17 | 0.169 |
| 24 hours | 0.69 | 0.074 | 42 | 21 | 0.011 |
| 48 hours | 0.66 | 0.155 | 42 | 4 | 0.301 |

Various threshold (or "cutoff") concentrations were selected, and the associated sensitivity and specificity for distinguishing cohort 1 from cohort 2, as shown in the following tables. OR is the odds ratio calculated for the particular cutoff concentration, and 95% CI is the confidence interval for the odds ratio.

Soluble p-Selectin:

| | | sCr or UO | | | | |
|---|---|---|---|---|---|---|
| Time prior AKI stag | Cutoff value | sens | spec | Quartile | OR | 95% CI of OR |
| 0 hours | 0.103709071 | 73% | 24% | 1 | | |
| | 0.086590607 | 82% | 18% | 2 | 3.4 | 1.0 11.7 |
| | 0.046882916 | 91% | 12% | 3 | 2.7 | 0.8 9.5 |
| | 0.316978593 | 14% | 73% | 4 | 2.7 | 0.8 9.5 |
| | 0.35046571 | 14% | 80% | | | |
| | 0.44303694 | 14% | 90% | | | |
| 24 hours | 0.134932873 | 71% | 25% | 1 | | |
| | 0.067535135 | 88% | 16% | 2 | 0.5 | 0.2 1.6 |
| | 0.018843437 | 92% | 8% | 3 | 0.5 | 0.2 1.6 |
| | 0.316978593 | 46% | 73% | 4 | 2.2 | 0.9 5.5 |
| | 0.35046571 | 42% | 80% | | | |
| | 0.44303694 | 29% | 90% | | | |
| 48 hours | 0.180141162 | 100% | 39% | 1 | | |
| | 0.180141162 | 100% | 39% | 2 | na | na na |
| | 0.180141162 | 100% | 39% | 3 | na | na na |
| | 0.316978593 | 0% | 73% | 4 | na | na na |
| | 0.35046571 | 0% | 80% | | | |
| | 0.44303694 | 0% | 90% | | | |
| | | sCr only | | | | |
| 0 hours | 0.067535135 | 83% | 13% | 1 | | |
| | 0.067535135 | 83% | 13% | 2 | 2.1 | 0.1 46.6 |
| | 0.046882916 | 100% | 11% | 3 | 1.0 | 0.0 59.3 |
| | 0.326917826 | 17% | 71% | 4 | 2.1 | 0.1 46.6 |
| | 0.382377815 | 17% | 81% | | | |
| | 0.478965584 | 17% | 90% | | | |
| 24 hours | 0.243665533 | 71% | 50% | 1 | | |
| | 0.067535135 | 86% | 13% | 2 | 0.5 | 0.0 10.7 |
| | 0 | 100% | 0% | 3 | 0.5 | 0.0 10.7 |
| | 0.326917826 | 43% | 71% | 4 | 1.5 | 0.2 9.1 |
| | 0.382377815 | 43% | 81% | | | |
| | 0.478965584 | 43% | 90% | | | |
| 48 hours | 0.119738536 | 100% | 22% | 1 | | |
| | 0.119738536 | 100% | 22% | 2 | 0.0 | 0.0 65535.0 |
| | 0.119738536 | 100% | 22% | 3 | 0.0 | 0.0 65535.0 |
| | 0.326917826 | 50% | 71% | 4 | 1.0 | 0.0 59.8 |
| | 0.382377815 | 50% | 81% | | | |
| | 0.478965584 | 50% | 90% | | | |
| | | UO only | | | | |
| 0 hours | 0.163424475 | 71% | 36% | 1 | | |
| | 0.101554867 | 82% | 26% | 2 | 2.7 | 0.7 10.4 |
| | 0.000000001 | 94% | 10% | 3 | 2.0 | 0.5 8.1 |
| | 0.26217594 | 18% | 71% | 4 | 1.1 | 0.2 5.7 |
| | 0.326917826 | 12% | 81% | | | |
| | 0.366600707 | 12% | 90% | | | |
| 24 hours | 0.134932873 | 73% | 31% | 1 | | |
| | 0.086590607 | 86% | 21% | 2 | 0.5 | 0.1 2.0 |
| | 0.067535135 | 91% | 17% | 3 | 0.7 | 0.2 2.5 |
| | 0.26217594 | 59% | 71% | 4 | 3.7 | 1.2 10.9 | sCr or UO (continued)

| Time prior AKI stag | Cutoff value | sens | spec | Quartile | OR | 95% CI of OR | |
|---|---|---|---|---|---|---|---|
| | 0.326917826 | 50% | 81% | | | | |
| | 0.366600707 | 45% | 90% | | | | |
| 48 hours | 0.180141162 | 75% | 48% | 1 | | | |
| | 0.046882916 | 100% | 14% | 2 | 0.9 | 0.0 | 66.6 |
| | 0.046882916 | 100% | 14% | 3 | 0.0 | 0.0 | 65535.0 |
| | 0.26217594 | 50% | 71% | 4 | 2.0 | 0.1 | 56.0 |
| | 0.326917826 | 50% | 81% | | | | |
| | 0.366600707 | 50% | 90% | | | | |

Protein NOV Homolog:

| Time prior AKI stage | Cutoff value | sens | spec | Quartile | OR | 95% CI of OR | |
|---|---|---|---|---|---|---|---|
| sCr or UO | | | | | | | |
| 0 hours | 22183.09859 | 71% | 47% | 1 | | | |
| | 14866.50485 | 81% | 31% | 2 | 1.8 | 0.8 | 3.9 |
| | 8817.829457 | 90% | 20% | 3 | 1.0 | 0.4 | 2.5 |
| | 42671.00977 | 58% | 70% | 4 | 3.6 | 1.8 | 7.4 |
| | 58743.84236 | 42% | 80% | | | | |
| | 126813.1868 | 13% | 90% | | | | |
| 24 hours | 26266.89189 | 73% | 51% | 1 | | | |
| | 17738.97059 | 81% | 39% | 2 | 1.0 | 0.3 | 3.0 |
| | 11355.6338 | 92% | 25% | 3 | 1.3 | 0.4 | 3.5 |
| | 42671.00977 | 65% | 70% | 4 | 4.6 | 2.0 | 10.4 |
| | 58743.84236 | 50% | 80% | | | | |
| | 126813.1868 | 27% | 90% | | | | |
| 48 hours | 47550.67568 | 100% | 75% | 1 | | | |
| | 47550.67568 | 100% | 75% | 2 | na | na | na |
| | 47550.67568 | 100% | 75% | 3 | na | na | na |
| | 42671.00977 | 100% | 70% | 4 | na | na | na |
| | 58743.84236 | 50% | 80% | | | | |
| | 126813.1868 | 0% | 90% | | | | |
| sCr only | | | | | | | |
| 0 hours | 17187.5 | 70% | 29% | 1 | | | |
| | 14964.78873 | 80% | 24% | 2 | 1.5 | 0.3 | 8.6 |
| | 6602.112676 | 90% | 8% | 3 | 1.0 | 0.1 | 7.8 |
| | 58169.29134 | 30% | 71% | 4 | 1.6 | 0.3 | 8.8 |
| | 85635.35912 | 10% | 80% | | | | |
| | 138681.3187 | 10% | 90% | | | | |
| 24 hours | 11355.6338 | 70% | 18% | 1 | | | |
| | 8538.732394 | 80% | 13% | 2 | 0.0 | 0.0 | 65535.0 |
| | 3125 | 90% | 2% | 3 | 0.5 | 0.1 | 2.2 |
| | 58169.29134 | 60% | 71% | 4 | 1.0 | 0.3 | 2.9 |
| | 85635.35912 | 40% | 80% | | | | |
| | 138681.3187 | 20% | 90% | | | | |
| 48 hours | 10937.5 | 100% | 18% | 1 | | | |
| | 10937.5 | 100% | 18% | 2 | 0.0 | 0.0 | 65535.0 |
| | 10937.5 | 100% | 18% | 3 | 0.0 | 0.0 | 65535.0 |
| | 58169.29134 | 33% | 71% | 4 | 2.0 | 0.1 | 42.5 |
| | 85635.35912 | 33% | 80% | | | | |
| | 138681.3187 | 0% | 90% | | | | |
| UO only | | | | | | | |
| 0 hours | 23968.4466 | 72% | 51% | 1 | | | |
| | 22150.73529 | 80% | 49% | 2 | 1.7 | 0.5 | 6.0 |
| | 9342.783505 | 92% | 22% | 3 | 1.3 | 0.4 | 5.0 |
| | 39780.40541 | 64% | 71% | 4 | 7.3 | 2.6 | 20.8 |
| | 47798.29545 | 60% | 81% | | | | |
| | 83977.90055 | 32% | 91% | | | | |
| 24 hours | 40390.87948 | 74% | 73% | 1 | | | |
| | 18658.08824 | 83% | 45% | 2 | 2.2 | 0.4 | 11.4 |
| | 14866.50485 | 91% | 33% | 3 | 2.9 | 0.6 | 13.6 |
| | 39780.40541 | 74% | 71% | 4 | 9.9 | 2.5 | 38.7 |
| | 47798.29545 | 61% | 81% | | | | |
| | 83977.90055 | 43% | 91% | | | | |
| 48 hours | 26491.47727 | 80% | 55% | 1 | | | |
| | 26491.47727 | 80% | 55% | 2 | na | na | na |
| | 17187.5 | 100% | 40% | 3 | na | na | na |
| | 39780.40541 | 60% | 71% | 4 | na | na | na |
| | 47798.29545 | 60% | 81% | | | | |
| | 83977.90055 | 0% | 91% | | | | |

Netrin 4:

| Time prior AKI stage | Cutoff value | sens | spec | Quartile | OR | 95% CI of OR | |
|---|---|---|---|---|---|---|---|
| sCr or UO | | | | | | | |
| 0 hours | 0.006865846 | 83% | 50% | 1 | | | |
| | 0.006865846 | 83% | 50% | 2 | 1.0 | 0.1 | 9.4 |
| | 0 | 100% | 0% | 3 | 3.2 | 0.6 | 17.2 |
| | 0.009466545 | 42% | 71% | 4 | 1.6 | 0.2 | 11.1 |
| | 0.059621711 | 0% | 83% | | | | |
| | 0.188419118 | 0% | 92% | | | | |
| 24 hours | 0 | 100% | 0% | 1 | | | |
| | 0 | 100% | 0% | 2 | 0.0 | 0.0 | 65535.0 |
| | 0 | 100% | 0% | 3 | 0.0 | 0.0 | 65535.0 |
| | 0.009466545 | 50% | 71% | 4 | 1.1 | 0.0 | 74.7 |
| | 0.059621711 | 0% | 83% | | | | |
| | 0.188419118 | 0% | 92% | | | | |
| 48 hours | 0.102163462 | 100% | 88% | 1 | | | |
| | 0.102163462 | 100% | 88% | 2 | na | na | na |
| | 0.102163462 | 100% | 88% | 3 | na | na | na |
| | 0.009466545 | 100% | 71% | 4 | na | na | na |
| | 0.059621711 | 100% | 83% | | | | |
| | 0.188419118 | 0% | 92% | | | | |
| sCr only | | | | | | | |
| 0 hours | 0.006865846 | 75% | 44% | 1 | | | |
| | 0.001144308 | 100% | 20% | 2 | 0.0 | 0.0 | 65535.0 |
| | 0.001144308 | 100% | 20% | 3 | 3.3 | 0.2 | 55.1 |
| | 0.012067244 | 50% | 71% | 4 | 0.0 | 0.0 | 65535.0 |
| | 0.050370066 | 0% | 80% | | | | |
| | 0.188419118 | 0% | 92% | | | | |
| 24 hours | 0 | 100% | 0% | 1 | | | |
| | 0 | 100% | 0% | 2 | na | na | na |
| | 0 | 100% | 0% | 3 | na | na | na |
| | 0.012067244 | 50% | 71% | 4 | na | na | na |
| | 0.050370066 | 0% | 80% | | | | |
| | 0.188419118 | 0% | 92% | | | | |
| 48 hours | 0.001144308 | 100% | 20% | 1 | | | |
| | 0.001144308 | 100% | 20% | 2 | na | na | na |
| | 0.001144308 | 100% | 20% | 3 | na | na | na |
| | 0.012067244 | 0% | 71% | 4 | na | na | na |
| | 0.050370066 | 0% | 80% | | | | |
| | 0.188419118 | 0% | 92% | | | | |
| UO only | | | | | | | |
| 0 hours | 0.006865846 | 73% | 58% | 1 | | | |
| | 0 | 100% | 0% | 2 | 0.0 | 0.0 | 65535.0 |
| | 0 | 100% | 0% | 3 | 2.1 | 0.5 | 10.0 |
| | 0.007336754 | 27% | 76% | 4 | 0.9 | 0.2 | 5.0 |
| | 0.013363487 | 18% | 82% | | | | |
| | 0.068873355 | 0% | 92% | | | | |
| 24 hours | 0 | 100% | 0% | 1 | | | |
| | 0 | 100% | 0% | 2 | 0.0 | 0.0 | 65535.0 |
| | 0 | 100% | 0% | 3 | 1.0 | 0.0 | 77.9 |
| | 0.007336754 | 33% | 76% | 4 | 0.9 | 0.0 | 68.6 |
| | 0.013363487 | 33% | 82% | | | | |
| | 0.068873355 | 0% | 92% | | | | |
| 48 hours | 0.068873355 | 100% | 92% | 1 | | | |
| | 0.068873355 | 100% | 92% | 2 | na | na | na |
| | 0.068873355 | 100% | 92% | 3 | na | na | na |
| | 0.007336754 | 100% | 76% | 4 | na | na | na |
| | 0.013363487 | 100% | 82% | | | | |
| | 0.068873355 | 100% | 92% | | | | |

Haptoglobin:

| Time prior AKI stage | Cutoff value | sens | spec | Quartile | OR | 95% CI of OR | |
|---|---|---|---|---|---|---|---|
| sCr or UO | | | | | | | |
| 0 hours | 0.0000193 | 71% | 30% | 1 | | | |
| | 0.00000305 | 82% | 11% | 2 | 0.8 | 0.5 | 1.3 |
| | 0 | 100% | 0% | 3 | 0.9 | 0.5 | 1.4 |
| | 0.000415 | 32% | 70% | 4 | 1.1 | 0.7 | 1.7 |
| | 0.000588 | 26% | 80% | | | | |
| | 0.00115 | 18% | 90% | | | | |
| 24 hours | 0.000067 | 71% | 44% | 1 | | | |
| | 0.0000337 | 80% | 36% | 2 | 1.9 | 1.2 | 3.0 |
| | 0 | 100% | 0% | 3 | 2.5 | 1.6 | 3.8 |
| | 0.000415 | 29% | 70% | 4 | 1.6 | 1.0 | 2.6 |
| | 0.000588 | 24% | 80% | | | | |
| | 0.00115 | 12% | 90% | | | | |
| 48 hours | 0.0000848 | 74% | 48% | 1 | | | |
| | 0.0000729 | 83% | 47% | 2 | 2.6 | 0.6 | 11.0 |
| | 0.000026 | 91% | 34% | 3 | 3.8 | 1.0 | 14.3 |
| | 0.000415 | 43% | 70% | 4 | 5.0 | 1.4 | 17.9 |
| | 0.000588 | 39% | 80% | | | | |
| | 0.00115 | 22% | 90% | | | | |
| sCr only | | | | | | | |
| 0 hours | 0.00000101 | 75% | 8% | 1 | | | |
| | 0 | 100% | 0% | 2 | 0.7 | 0.2 | 2.4 |
| | 0 | 100% | 0% | 3 | 0.5 | 0.1 | 2.2 |
| | 0.00048 | 31% | 70% | 4 | 1.8 | 0.8 | 4.1 |
| | 0.000763 | 13% | 80% | | | | |
| | 0.00137 | 6% | 90% | | | | |
| 24 hours | 0.0000757 | 71% | 43% | 1 | | | |
| | 0.0000669 | 81% | 39% | 2 | 1.0 | 0.4 | 2.8 |
| | 0 | 100% | 0% | 3 | 2.1 | 1.0 | 4.5 |
| | 0.00048 | 24% | 70% | 4 | 1.3 | 0.5 | 3.2 |
| | 0.000763 | 19% | 80% | | | | |
| | 0.00137 | 10% | 90% | | | | |
| 48 hours | 0.0000757 | 73% | 43% | 1 | | | |
| | 0.0000588 | 82% | 39% | 2 | 3.0 | 0.2 | 43.1 |
| | 0.000026 | 91% | 30% | 3 | 5.2 | 0.5 | 57.2 |
| | 0.00048 | 27% | 70% | 4 | 2.0 | 0.1 | 39.4 |
| | 0.000763 | 18% | 80% | | | | |
| | 0.00137 | 0% | 90% | | | | |
| UO only | | | | | | | |
| 0 hours | 0.0000533 | 71% | 41% | 1 | | | |
| | 0.0000146 | 82% | 28% | 2 | 1.6 | 0.8 | 2.9 |
| | 0.00000277 | 91% | 12% | 3 | 1.4 | 0.7 | 2.6 |
| | 0.000347 | 44% | 70% | 4 | 2.0 | 1.1 | 3.6 |
| | 0.000534 | 32% | 80% | | | | |
| | 0.00111 | 18% | 90% | | | | |
| 24 hours | 0.0000705 | 71% | 44% | 1 | | | |
| | 0.0000308 | 80% | 36% | 2 | 2.5 | 1.4 | 4.3 |
| | 0.00000794 | 91% | 19% | 3 | 2.8 | 1.6 | 4.8 |
| | 0.000347 | 33% | 70% | 4 | 2.2 | 1.3 | 3.9 |
| | 0.000534 | 22% | 80% | | | | |
| | 0.00111 | 11% | 90% | | | | |
| 48 hours | 0.0000737 | 74% | 45% | 1 | | | |
| | 0.0000533 | 83% | 41% | 2 | 1.7 | 0.6 | 5.4 |
| | 0 | 100% | 0% | 3 | 2.5 | 0.9 | 7.0 |
| | 0.000347 | 39% | 70% | 4 | 3.0 | 1.1 | 8.0 |
| | 0.000534 | 35% | 80% | | | | |
| | 0.00111 | 22% | 90% | | | | |

Alpha-1-Antitrypsin:

| Time prior AKI stage | Cutoff value | sens | spec | Quartile | OR | 95% CI of OR | |
|---|---|---|---|---|---|---|---|
| sCr or UO | | | | | | | |
| 0 hours | 0.000491 | 71% | 31% | 1 | | | |
| | 0.000315 | 82% | 20% | 2 | 5.3 | 2.2 | 12.7 |
| | 0.0000896 | 92% | 3% | 3 | 5.2 | 2.2 | 12.4 |
| | 0.00202 | 8% | 70% | 4 | 3.4 | 1.3 | 8.7 |
| | 0.00273 | 8% | 80% | | | | |
| | 0.00362 | 3% | 90% | | | | |
| 24 hours | 0.000491 | 71% | 31% | 1 | | | |
| | 0.000272 | 80% | 17% | 2 | 1.6 | 1.1 | 2.4 |
| | 0.000125 | 90% | 6% | 3 | 1.2 | 0.8 | 1.9 |
| | 0.00202 | 25% | 70% | 4 | 1.5 | 1.0 | 2.3 |
| | 0.00273 | 18% | 80% | | | | |
| | 0.00362 | 0% | 90% | | | | |
| 48 hours | 0.000569 | 74% | 33% | 1 | | | |
| | 0.000415 | 83% | 28% | 2 | 2.2 | 1.0 | 4.8 |
| | 0.00033 | 91% | 21% | 3 | 2.2 | 1.0 | 4.8 |
| | 0.00202 | 17% | 70% | 4 | 0.8 | 0.2 | 2.5 |
| | 0.00273 | 17% | 80% | | | | |
| | 0.00362 | 0% | 90% | | | | |
| sCr only | | | | | | | |
| 0 hours | 0.000499 | 75% | 28% | 1 | | | |
| | 0.000277 | 81% | 16% | 2 | na | na | na |
| | 0.0000896 | 94% | 4% | 3 | na | na | na |
| | 0.00191 | 0% | 70% | 4 | na | na | na |
| | 0.00264 | 0% | 80% | | | | |
| | 0.00309 | 0% | 90% | | | | |
| 24 hours | 0.000343 | 71% | 20% | 1 | | | |
| | 0.000173 | 81% | 9% | 2 | 3.1 | 0.8 | 12.0 |
| | 0.0000841 | 90% | 3% | 3 | 2.0 | 0.5 | 9.3 |
| | 0.00191 | 19% | 70% | 4 | 4.9 | 1.4 | 16.8 |
| | 0.00264 | 10% | 80% | | | | |
| | 0.00309 | 0% | 90% | | | | |
| 48 hours | 0.000587 | 73% | 31% | 1 | | | |
| | 0.00053 | 82% | 30% | 2 | 3.1 | 0.2 | 44.0 |
| | 0.000306 | 91% | 17% | 3 | 5.2 | 0.5 | 57.2 |
| | 0.00191 | 9% | 70% | 4 | 2.0 | 0.1 | 40.3 |
| | 0.00264 | 9% | 80% | | | | |
| | 0.00309 | 0% | 90% | | | | |
| UO only | | | | | | | |
| 0 hours | 0.00065 | 71% | 36% | 1 | | | |
| | 0.000371 | 82% | 23% | 2 | 2.0 | 1.1 | 3.7 |
| | 0.000275 | 91% | 15% | 3 | 1.8 | 1.0 | 3.3 |
| | 0.00181 | 18% | 70% | 4 | 1.2 | 0.6 | 2.4 |
| | 0.0024 | 12% | 80% | | | | |
| | 0.00297 | 6% | 90% | | | | |
| 24 hours | 0.000698 | 71% | 39% | 1 | | | |
| | 0.000429 | 80% | 27% | 2 | 1.2 | 0.8 | 2.0 |
| | 0.00016 | 91% | 7% | 3 | 1.4 | 0.9 | 2.3 |
| | 0.00181 | 31% | 70% | 4 | 1.5 | 1.0 | 2.4 |
| | 0.0024 | 27% | 80% | | | | |
| | 0.00297 | 0% | 90% | | | | |
| 48 hours | 0.00053 | 74% | 31% | 1 | | | |
| | 0.000429 | 83% | 27% | 2 | 1.9 | 0.8 | 4.4 |
| | 0.000409 | 91% | 25% | 3 | 2.2 | 1.0 | 5.0 |
| | 0.00181 | 22% | 70% | 4 | 1.0 | 0.3 | 2.9 |
| | 0.0024 | 17% | 80% | | | | |
| | 0.00297 | 0% | 90% | | | | |

Leukocyte Elastase:

| Time prior AKI stage | Cutoff value | sens | spec | Quartile | OR | 95% CI of OR | |
|---|---|---|---|---|---|---|---|
| sCr or UO | | | | | | | |
| 0 hours | 10.11904762 | 72% | 28% | 1 | | | |
| | 5.967620482 | 81% | 23% | 2 | 0.7 | 0.3 | 1.4 |
| | 3.949652778 | 92% | 15% | 3 | 0.8 | 0.4 | 1.6 |
| | 46.49621212 | 47% | 71% | 4 | 2.4 | 1.4 | 4.2 |
| | 61.598493 | 42% | 81% | | | | |
| | 76.74897119 | 33% | 90% | | | | |
| 24 hours | 13.34541063 | 72% | 38% | 1 | | | |
| | 5.095720721 | 80% | 17% | 2 | 0.6 | 0.3 | 1.0 |
| | 2.892287234 | 91% | 11% | 3 | 1.0 | 0.6 | 1.7 |
| | 46.49621212 | 39% | 71% | 4 | 1.9 | 1.2 | 3.0 |
| | 61.598493 | 37% | 81% | | | | |
| | 76.74897119 | 26% | 90% | | | | |

| Time prior AKI stage | Cutoff value | sens | spec | Quartile | OR | 95% CI of OR |
|---|---|---|---|---|---|---|
| 48 hours | 12.91130186 | 74% | 37% | 1 | | |
| | 8.935546875 | 83% | 27% | 2 | 2.3 | 0.9  5.5 |
| | 4.210069444 | 91% | 16% | 3 | 1.6 | 0.6  4.3 |
| | 46.49621212 | 26% | 71% | 4 | 1.3 | 0.4  3.5 |
| | 61.598493 | 22% | 81% | | | |
| | 76.74897119 | 13% | 90% | | | |
| sCr only | | | | | | |
| 0 hours | 18.29710145 | 75% | 37% | 1 | | |
| | 4.870495495 | 83% | 17% | 2 | 1.3 | 0.4  4.5 |
| | 3.965336134 | 92% | 13% | 3 | 0.7 | 0.1  3.6 |
| | 67.37516869 | 25% | 70% | 4 | 1.0 | 0.2  3.9 |
| | 81.89300412 | 17% | 80% | | | |
| | 99.65016146 | 17% | 90% | | | |
| 24 hours | 11.26644737 | 72% | 29% | 1 | | |
| | 3.949652778 | 83% | 13% | 2 | 1.4 | 0.4  4.6 |
| | 2.36037234 | 94% | 7% | 3 | 2.1 | 0.7  6.0 |
| | 67.37516869 | 17% | 70% | 4 | 1.7 | 0.6  5.3 |
| | 81.89300412 | 11% | 80% | | | |
| | 99.65016146 | 11% | 90% | | | |
| 48 hours | 21.94711538 | 73% | 40% | 1 | | |
| | 16.76755448 | 82% | 35% | 2 | 4.2 | 0.3  52.4 |
| | 16.00241546 | 91% | 35% | 3 | 2.0 | 0.1  41.2 |
| | 67.37516869 | 36% | 70% | 4 | 4.1 | 0.3  51.4 |
| | 81.89300412 | 36% | 80% | | | |
| | 99.65016146 | 18% | 90% | | | |
| UO only | | | | | | |
| 0 hours | 10.11904762 | 71% | 19% | 1 | | |
| | 6.624348958 | 81% | 17% | 2 | 0.1 | 0.0  0.5 |
| | 3.807773109 | 90% | 6% | 3 | 0.5 | 0.2  1.0 |
| | 47.90836653 | 48% | 70% | 4 | 1.5 | 0.8  2.6 |
| | 61.9752422 | 42% | 81% | | | |
| | 83.56950067 | 26% | 91% | | | |
| 24 hours | 18.29710145 | 71% | 40% | 1 | | |
| | 10.49254967 | 80% | 23% | 2 | 0.7 | 0.4  1.4 |
| | 3.689236111 | 90% | 5% | 3 | 1.0 | 0.5  1.8 |
| | 47.90836653 | 44% | 70% | 4 | 2.4 | 1.4  4.1 |
| | 61.9752422 | 39% | 81% | | | |
| | 83.56950067 | 24% | 91% | | | |
| 48 hours | 10.49254967 | 73% | 23% | 1 | | |
| | 5.176957831 | 82% | 11% | 2 | 0.5 | 0.2  1.3 |
| | 3.807773109 | 91% | 6% | 3 | 0.5 | 0.2  1.3 |
| | 47.90836653 | 32% | 70% | 4 | 1.1 | 0.5  2.2 |
| | 61.9752422 | 32% | 81% | | | |
| | 83.56950067 | 18% | 91% | | | |

Soluble Tumor Necrosis Factor Receptor Superfamily Member 6:

| Time prior AKI stage | Cutoff value | sens | spec | Quartile | OR | 95% CI of OR |
|---|---|---|---|---|---|---|
| sCr or UO | | | | | | |
| 0 hours | 206.5217391 | 71% | 39% | 1 | | |
| | 188.8586957 | 82% | 38% | 2 | 3.1 | 1.1  8.8 |
| | 110.8490566 | 93% | 19% | 3 | 1.4 | 0.4  4.9 |
| | 500.7385524 | 54% | 70% | 4 | 6.0 | 2.3  15.3 |
| | 597.4643423 | 39% | 80% | | | |
| | 1080.711354 | 11% | 91% | | | |
| 24 hours | 312.8531073 | 71% | 54% | 1 | | |
| | 294.7941889 | 82% | 53% | 2 | 1.3 | 0.5  3.5 |
| | 49.01960784 | 93% | 4% | 3 | 1.9 | 0.8  4.7 |
| | 500.7385524 | 50% | 70% | 4 | 3.8 | 1.7  8.5 |
| | 597.4643423 | 39% | 80% | | | |
| | 1080.711354 | 14% | 91% | | | |
| 48 hours | 421.9128329 | 100% | 62% | 1 | | |
| | 421.9128329 | 100% | 62% | 2 | na | na  na |
| | 421.9128329 | 100% | 62% | 3 | na | na  na |
| | 500.7385524 | 67% | 70% | 4 | na | na  na |
| | 597.4643423 | 67% | 80% | | | |
| | 1080.711354 | 0% | 91% | | | |
| sCr only | | | | | | |
| 0 hours | 154.8913043 | 78% | 22% | 1 | | |
| | 137.2093023 | 89% | 20% | 2 | 0.3 | 0.0  4.7 |
| | 49.01960784 | 100% | 4% | 3 | 0.7 | 0.1  3.6 |
| | 610.0443131 | 33% | 70% | 4 | 1.0 | 0.3  4.1 |
| | 779.9855491 | 33% | 80% | | | |
| | 1037.383178 | 22% | 90% | | | |
| 24 hours | 243.3628319 | 73% | 34% | 1 | | |
| | 92.39130435 | 82% | 10% | 2 | 0.3 | 0.0  4.7 |
| | 49.01960784 | 91% | 4% | 3 | 0.3 | 0.0  4.7 |
| | 610.0443131 | 55% | 70% | 4 | 2.1 | 0.7  6.0 |
| | 779.9855491 | 55% | 80% | | | |
| | 1037.383178 | 45% | 90% | | | |
| 48 hours | 438.8619855 | 75% | 51% | 1 | | |
| | 249.4158879 | 100% | 34% | 2 | na | na  na |
| | 249.4158879 | 100% | 34% | 3 | na | na  na |
| | 610.0443131 | 50% | 70% | 4 | na | na  na |
| | 779.9855491 | 0% | 80% | | | |
| | 1037.383178 | 0% | 90% | | | |
| UO only | | | | | | |
| 0 hours | 226.9021739 | 73% | 43% | 1 | | |
| | 203.4883721 | 82% | 39% | 2 | 3.4 | 0.8  14.7 |
| | 188.8586957 | 91% | 38% | 3 | 0.5 | 0.0  10.6 |
| | 483.6561743 | 64% | 71% | 4 | 10.6 | 2.8  39.9 |
| | 527.1041369 | 59% | 80% | | | |
| | 771.0413695 | 27% | 90% | | | |
| 24 hours | 354.2944785 | 72% | 59% | 1 | | |
| | 317.3652695 | 80% | 54% | 2 | 2.2 | 0.4  10.9 |
| | 294.7941889 | 92% | 52% | 3 | 3.5 | 0.8  15.2 |
| | 483.6561743 | 52% | 71% | 4 | 10.3 | 2.8  38.6 |
| | 527.1041369 | 52% | 80% | | | |
| | 771.0413695 | 28% | 90% | | | |
| 48 hours | 421.9128329 | 83% | 64% | 1 | | |
| | 421.9128329 | 83% | 64% | 2 | na | na  na |
| | 344.4309927 | 100% | 58% | 3 | na | na  na |
| | 483.6561743 | 67% | 71% | 4 | na | na  na |
| | 527.1041369 | 67% | 80% | | | |
| | 771.0413695 | 33% | 90% | | | |

Soluble Tumor Necrosis Factor Ligand Superfamily Member 6:

| Time prior AKI stage | Cutoff value | sens | spec | Quartile | OR | 95% CI of OR |
|---|---|---|---|---|---|---|
| sCr or UO | | | | | | |
| 0 hours | 0 | 100% | 0% | 1 | | |
| | 0 | 100% | 0% | 2 | na | na  na |
| | 0 | 100% | 0% | 3 | na | na  na |
| | 0.334480122 | 63% | 73% | 4 | na | na  na |
| | 0.993816254 | 63% | 86% | | | |
| | 1.767966361 | 38% | 92% | | | |
| 24 hours | 0.441696113 | 75% | 73% | 1 | | |
| | 0.334480122 | 83% | 73% | 2 | na | na  na |
| | 0 | 100% | 0% | 3 | na | na  na |
| | 0.334480122 | 83% | 73% | 4 | na | na  na |
| | 0.993816254 | 58% | 86% | | | |
| | 1.767966361 | 33% | 92% | | | |
| 48 hours | 0 | 100% | 0% | 1 | | |
| | 0 | 100% | 0% | 2 | na | na  na |
| | 0 | 100% | 0% | 3 | na | na  na |
| | 0.334480122 | 50% | 73% | 4 | na | na  na |
| | 0.993816254 | 0% | 86% | | | |
| | 1.767966361 | 0% | 92% | | | |
| sCr only | | | | | | |
| 0 hours | 0 | 100% | 0% | 1 | | |
| | 0 | 100% | 0% | 2 | 0.0 | 0.0  65535.0 |
| | 0 | 100% | 0% | 3 | 3.2 | 0.2  50.2 |
| | 0.993816254 | 25% | 73% | 4 | 0.0 | 0.0  65535.0 |

| Time prior AKI stage | Cutoff value | sens | spec | Quartile | OR | 95% CI of OR | |
|---|---|---|---|---|---|---|---|
| | 1.545936396 | 0% | 81% | | | | |
| | 3.20229682 | 0% | 91% | | | | |
| 24 hours | 0 | 100% | 0% | 1 | | | |
| | 0 | 100% | 0% | 2 | 0.0 | 0.0 | 65535.0 |
| | 0 | 100% | 0% | 3 | 1.0 | 0.1 | 8.1 |
| | 0.993816254 | 33% | 73% | 4 | 1.0 | 0.1 | 8.1 |
| | 1.545936396 | 33% | 81% | | | | |
| | 3.20229682 | 0% | 91% | | | | |
| 48 hours | 0.334480122 | 100% | 59% | 1 | | | |
| | 0.334480122 | 100% | 59% | 2 | na | na | na |
| | 0.334480122 | 100% | 59% | 3 | na | na | na |
| | 0.993816254 | 33% | 73% | 4 | na | na | na |
| | 1.545936396 | 33% | 81% | | | | |
| | 3.20229682 | 0% | 91% | | | | |
| | UO only | | | | | | |
| 0 hours | 0.993816254 | 71% | 82% | 1 | | | |
| | 0 | 100% | 0% | 2 | 0.0 | 0.0 | 65535.0 |
| | 0 | 100% | 0% | 3 | 0.0 | 0.0 | 65535.0 |
| | 0.812308869 | 71% | 75% | 4 | 2.9 | 0.5 | 15.6 |
| | 0.993816254 | 71% | 82% | | | | |
| | 1.767966361 | 43% | 90% | | | | |
| 24 hours | 0.334480122 | 70% | 68% | 1 | | | |
| | 0 | 100% | 0% | 2 | 2.0 | 0.1 | 48.3 |
| | 0 | 100% | 0% | 3 | 2.1 | 0.1 | 52.0 |
| | 0.812308869 | 50% | 75% | 4 | 6.2 | 0.4 | 85.0 |
| | 0.993816254 | 50% | 82% | | | | |
| | 1.767966361 | 30% | 90% | | | | |
| 48 hours | 0 | 100% | 0% | 1 | | | |
| | 0 | 100% | 0% | 2 | na | na | na |
| | 0 | 100% | 0% | 3 | na | na | na |
| | 0.812308869 | 0% | 75% | 4 | na | na | na |
| | 0.993816254 | 0% | 82% | | | | |
| | 1.767966361 | 0% | 90% | | | | |

Soluble Intercellular Adhesion Molecule 2:

| Time prior AKI stage | Cutoff value | sens | spec | Quartile | OR | 95% CI of OR | |
|---|---|---|---|---|---|---|---|
| | sCr or UO | | | | | | |
| 0 hours | 0.04233871 | 72% | 22% | 1 | | | |
| | 0.00133452 | 97% | 1% | 2 | 6.2 | 1.6 | 24.2 |
| | 0.00133452 | 97% | 1% | 3 | 6.2 | 1.6 | 24.2 |
| | 1.608510638 | 7% | 71% | 4 | 6.2 | 1.6 | 24.2 |
| | 2.846938776 | 3% | 80% | | | | |
| | 4.203488372 | 3% | 90% | | | | |
| 24 hours | 0.072580645 | 73% | 29% | 1 | | | |
| | 0.03125 | 85% | 20% | 2 | 1.4 | 0.5 | 3.8 |
| | 0.012096774 | 92% | 14% | 3 | 3.3 | 1.4 | 7.7 |
| | 1.608510638 | 15% | 71% | 4 | 2.1 | 0.8 | 5.3 |
| | 2.846938776 | 8% | 80% | | | | |
| | 4.203488372 | 8% | 90% | | | | |
| 48 hours | 0.161476868 | 100% | 38% | 1 | | | |
| | 0.161476868 | 100% | 38% | 2 | na | na | na |
| | 0.161476868 | 100% | 38% | 3 | na | na | na |
| | 1.608510638 | 0% | 71% | 4 | na | na | na |
| | 2.846938776 | 0% | 80% | | | | |
| | 4.203488372 | 0% | 90% | | | | |
| | sCr only | | | | | | |
| 0 hours | 0.00133452 | 100% | 1% | 1 | | | |
| | 0.00133452 | 100% | 1% | 2 | na | na | na |
| | 0.00133452 | 100% | 1% | 3 | na | na | na |
| | 1.066666667 | 10% | 70% | 4 | na | na | na |
| | 2.015151515 | 0% | 81% | | | | |
| | 3.42 | 0% | 90% | | | | |
| 24 hours | 0.041370107 | 80% | 23% | 1 | | | |
| | 0.041370107 | 80% | 23% | 2 | 0.3 | 0.0 | 4.8 |
| | 0.027217742 | 90% | 21% | 3 | 1.8 | 0.6 | 5.6 |
| | 1.066666667 | 10% | 70% | 4 | 0.3 | 0.0 | 4.8 |
| | 2.015151515 | 10% | 81% | | | | |
| | 3.42 | 10% | 90% | | | | |
| 48 hours | 0.04233871 | 100% | 25% | 1 | | | |
| | 0.04233871 | 100% | 25% | 2 | 0.0 | 0.0 | 65535.0 |
| | 0.04233871 | 100% | 25% | 3 | 2.1 | 0.1 | 44.2 |
| | 1.066666667 | 33% | 70% | 4 | 0.0 | 0.0 | 65535.0 |
| | 2.015151515 | 0% | 81% | | | | |
| | 3.42 | 0% | 90% | | | | |
| | UO only | | | | | | |
| 0 hours | 0.00133452 | 96% | 1% | 1 | | | |
| | 0.00133452 | 96% | 1% | 2 | 2.3 | 0.4 | 12.2 |
| | 0.00133452 | 96% | 1% | 3 | 6.6 | 1.6 | 27.2 |
| | 1.530612245 | 8% | 70% | 4 | 7.1 | 1.7 | 29.5 |
| | 2.326530612 | 4% | 80% | | | | |
| | 4.26 | 4% | 90% | | | | |
| 24 hours | 0.072580645 | 79% | 26% | 1 | | | |
| | 0.03125 | 83% | 17% | 2 | 0.4 | 0.1 | 1.7 |
| | 0.012096774 | 92% | 14% | 3 | 3.8 | 1.7 | 8.6 |
| | 1.530612245 | 21% | 70% | 4 | 1.1 | 0.4 | 2.9 |
| | 2.326530612 | 4% | 80% | | | | |
| | 4.26 | 4% | 90% | | | | |
| 48 hours | 0.25 | 75% | 39% | 1 | | | |
| | 0.161476868 | 100% | 36% | 2 | na | na | na |
| | 0.161476868 | 100% | 36% | 3 | na | na | na |
| | 1.530612245 | 0% | 70% | 4 | na | na | na |
| | 2.326530612 | 0% | 80% | | | | |
| | 4.26 | 0% | 90% | | | | |

Caspase 3 (Active):

| Time prior AKI stage | Cutoff value | sens | spec | Quartile | OR | 95% CI of OR | |
|---|---|---|---|---|---|---|---|
| | sCr or UO | | | | | | |
| 0 hours | 0 | 100% | 0% | 1 | | | |
| | 0 | 100% | 0% | 2 | 0.4 | 0.1 | 1.4 |
| | 0 | 100% | 0% | 3 | 1.0 | 0.4 | 2.7 |
| | 0.004194723 | 41% | 71% | 4 | 1.2 | 0.5 | 3.0 |
| | 0.006341002 | 32% | 80% | | | | |
| | 0.010457847 | 18% | 90% | | | | |
| 24 hours | 0.000279912 | 71% | 51% | 1 | | | |
| | 0 | 100% | 0% | 2 | 1.3 | 0.4 | 4.0 |
| | 0 | 100% | 0% | 3 | 1.3 | 0.4 | 4.0 |
| | 0.004194723 | 46% | 71% | 4 | 3.9 | 1.4 | 11.0 |
| | 0.006341002 | 42% | 80% | | | | |
| | 0.010457847 | 33% | 90% | | | | |
| 48 hours | 0.013171083 | 100% | 94% | 1 | | | |
| | 0.013171083 | 100% | 94% | 2 | na | na | na |
| | 0.013171083 | 100% | 94% | 3 | na | na | na |
| | 0.004194723 | 100% | 71% | 4 | na | na | na |
| | 0.006341002 | 100% | 80% | | | | |
| | 0.010457847 | 100% | 90% | | | | |
| | sCr only | | | | | | |
| 0 hours | 0 | 100% | 0% | 1 | | | |
| | 0 | 100% | 0% | 2 | 2.1 | 0.1 | 46.6 |
| | 0 | 100% | 0% | 3 | 1.0 | 0.0 | 59.3 |
| | 0.00531421 | 33% | 70% | 4 | 2.1 | 0.1 | 46.6 |
| | 0.008907421 | 33% | 81% | | | | |
| | 0.019515127 | 0% | 90% | | | | |
| 24 hours | 0 | 100% | 0% | 1 | | | |
| | 0 | 100% | 0% | 2 | na | na | na |
| | 0 | 100% | 0% | 3 | na | na | na |
| | 0.00531421 | 43% | 70% | 4 | na | na | na |
| | 0.008907421 | 43% | 81% | | | | |
| | 0.019515127 | 14% | 90% | | | | |
| 48 hours | 0.004313086 | 100% | 65% | 1 | | | |
| | 0.004313086 | 100% | 65% | 2 | na | na | na |
| | 0.004313086 | 100% | 65% | 3 | na | na | na |
| | 0.00531421 | 50% | 70% | 4 | na | na | na |
| | 0.008907421 | 50% | 81% | | | | |
| | 0.019515127 | 0% | 90% | | | | |

Soluble Platelet Endothelial Cell Adhesion Molecule:

| Time prior AKI stage | Cutoff value | sens | spec | Quartile | OR | 95% CI of OR | |
|---|---|---|---|---|---|---|---|
| | | UO only (continued) | | | | | |
| 0 hours | 0 | 100% | 0% | 1 | | | |
| | 0 | 100% | 0% | 2 | 0.4 | 0.1 | 2.4 |
| | 0 | 100% | 0% | 3 | 1.3 | 0.3 | 4.5 |
| | 0.004313086 | 41% | 71% | 4 | 1.7 | 0.5 | 5.7 |
| | 0.006922461 | 29% | 81% | | | | |
| | 0.012887702 | 12% | 90% | | | | |
| 24 hours | 0.001069236 | 73% | 60% | 1 | | | |
| | 0 | 100% | 0% | 2 | 0.3 | 0.1 | 1.7 |
| | 0 | 100% | 0% | 3 | 1.3 | 0.4 | 3.9 |
| | 0.004313086 | 50% | 71% | 4 | 2.8 | 1.0 | 8.2 |
| | 0.006922461 | 45% | 81% | | | | |
| | 0.012887702 | 36% | 90% | | | | |
| 48 hours | 0.002958621 | 75% | 67% | 1 | | | |
| | 0.000279912 | 100% | 55% | 2 | na | na | na |
| | 0.000279912 | 100% | 55% | 3 | na | na | na |
| | 0.004313086 | 50% | 71% | 4 | na | na | na |
| | 0.006922461 | 50% | 81% | | | | |
| | 0.012887702 | 50% | 90% | | | | |

Soluble Platelet Endothelial Cell Adhesion Molecule:

| Time prior AKI stage | Cutoff value | sens | spec | Quartile | OR | 95% CI of OR | |
|---|---|---|---|---|---|---|---|
| | | sCr or UO | | | | | |
| 0 hours | 0.440167683 | 70% | 21% | 1 | | | |
| | 0.229048295 | 80% | 14% | 2 | 0.5 | 0.0 | 13.1 |
| | 0.154344512 | 100% | 12% | 3 | 1.8 | 0.2 | 13.2 |
| | 2.492647059 | 20% | 72% | 4 | 2.7 | 0.4 | 17.0 |
| | 3.110294118 | 10% | 81% | | | | |
| | 4.564393939 | 0% | 93% | | | | |
| 24 hours | 0.154344512 | 100% | 12% | 1 | | | |
| | 0.154344512 | 100% | 12% | 2 | na | na | na |
| | 0.154344512 | 100% | 12% | 3 | na | na | na |
| | 2.492647059 | 0% | 72% | 4 | na | na | na |
| | 3.110294118 | 0% | 81% | | | | |
| | 4.564393939 | 0% | 93% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| | | sCr only | | | | | |
| 0 hours | 0.154344512 | 100% | 8% | 1 | | | |
| | 0.154344512 | 100% | 8% | 2 | 0.0 | 0.0 | 65535.0 |
| | 0.154344512 | 100% | 8% | 3 | 2.1 | 0.1 | 51.0 |
| | 1.650815217 | 20% | 71% | 4 | 2.3 | 0.1 | 54.8 |
| | 2.625 | 20% | 80% | | | | |
| | 4.109848485 | 0% | 91% | | | | |
| 24 hours | 0.040015244 | 100% | 5% | 1 | | | |
| | 0.040015244 | 100% | 5% | 2 | na | na | na |
| | 0.040015244 | 100% | 5% | 3 | na | na | na |
| | 1.650815217 | 33% | 71% | 4 | na | na | na |
| | 2.625 | 0% | 80% | | | | |
| | 4.109848485 | 0% | 91% | | | | |
| 48 hours | 0.786830357 | 100% | 45% | 1 | | | |
| | 0.786830357 | 100% | 45% | 2 | na | na | na |
| | 0.786830357 | 100% | 45% | 3 | na | na | na |
| | 1.650815217 | 0% | 71% | 4 | na | na | na |
| | 2.625 | 0% | 80% | | | | |
| | 4.109848485 | 0% | 91% | | | | |
| | | UO only | | | | | |
| 0 hours | 0.440167683 | 70% | 13% | 1 | | | |
| | 0.229048295 | 80% | 10% | 2 | 2.3 | 0.1 | 67.6 |
| | 0.154344512 | 100% | 7% | 3 | 2.3 | 0.1 | 67.6 |
| | 2.492647059 | 20% | 70% | 4 | 9.0 | 0.5 | 174.0 |
| | 3.110294118 | 10% | 80% | | | | |
| | 4.26199262 | 0% | 90% | | | | |
| 24 hours | 0.154344512 | 100% | 7% | 1 | | | |
| | 0.154344512 | 100% | 7% | 2 | na | na | na |
| | 0.154344512 | 100% | 7% | 3 | na | na | na |
| | 2.492647059 | 0% | 70% | 4 | na | na | na |
| | 3.110294118 | 0% | 80% | | | | |
| | 4.26199262 | 0% | 90% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |

Heat Shock Protein Beta-1:

| Time prior AKI stage | Cutoff value | sens | spec | Quartile | OR | 95% CI of OR | |
|---|---|---|---|---|---|---|---|
| | | sCr or UO | | | | | |
| 0 hours | 1.025390625 | 71% | 44% | 1 | | | |
| | 0.68359375 | 86% | 20% | 2 | 1.0 | 0.2 | 4.9 |
| | 0.390625 | 93% | 9% | 3 | 1.9 | 0.5 | 7.5 |
| | 2.412280702 | 29% | 70% | 4 | 1.0 | 0.2 | 4.9 |
| | 4.58511396 | 21% | 81% | | | | |
| | 6.43966763 | 14% | 91% | | | | |
| 24 hours | 0.581395349 | 100% | 19% | 1 | | | |
| | 0.581395349 | 100% | 19% | 2 | na | na | na |
| | 0.581395349 | 100% | 19% | 3 | na | na | na |
| | 2.412280702 | 0% | 70% | 4 | na | na | na |
| | 4.58511396 | 0% | 81% | | | | |
| | 6.43966763 | 0% | 91% | | | | |
| 48 hours | 1.519097222 | 100% | 56% | 1 | | | |
| | 1.519097222 | 100% | 56% | 2 | na | na | na |
| | 1.519097222 | 100% | 56% | 3 | na | na | na |
| | 2.412280702 | 0% | 70% | 4 | na | na | na |
| | 4.58511396 | 0% | 81% | | | | |
| | 6.43966763 | 0% | 91% | | | | |
| | | sCr only | | | | | |
| 0 hours | 1.683208155 | 83% | 57% | 1 | | | |
| | 1.683208155 | 83% | 57% | 2 | 0.0 | 0.0 | 65535.0 |
| | 0.110463627 | 100% | 5% | 3 | 1.0 | 0.0 | 60.2 |
| | 2.715933476 | 67% | 70% | 4 | 4.4 | 0.3 | 61.5 |
| | 4.258928571 | 67% | 81% | | | | |
| | 6.43966763 | 33% | 91% | | | | |
| 24 hours | 0.896990741 | 100% | 33% | 1 | | | |
| | 0.896990741 | 100% | 33% | 2 | na | na | na |
| | 0.896990741 | 100% | 33% | 3 | na | na | na |
| | 2.715933476 | 0% | 70% | 4 | na | na | na |
| | 4.258928571 | 0% | 81% | | | | |
| | 6.43966763 | 0% | 91% | | | | |
| 48 hours | 0.446428571 | 100% | 13% | 1 | | | |
| | 0.446428571 | 100% | 13% | 2 | na | na | na |
| | 0.446428571 | 100% | 13% | 3 | na | na | na |
| | 2.715933476 | 0% | 70% | 4 | na | na | na |
| | 4.258928571 | 0% | 81% | | | | |
| | 6.43966763 | 0% | 91% | | | | |
| | | UO only | | | | | |
| 0 hours | 0.882523148 | 77% | 38% | 1 | | | |
| | 0.581395349 | 85% | 20% | 2 | 0.6 | 0.1 | 4.5 |
| | 0.382620389 | 92% | 8% | 3 | 2.1 | 0.5 | 9.2 |
| | 1.978272532 | 31% | 70% | 4 | 0.9 | 0.2 | 4.9 |
| | 2.467105263 | 23% | 80% | | | | |
| | 3.926282051 | 15% | 90% | | | | |
| 24 hours | 0.581395349 | 100% | 20% | 1 | | | |
| | 0.581395349 | 100% | 20% | 2 | na | na | na |
| | 0.581395349 | 100% | 20% | 3 | na | na | na |
| | 1.978272532 | 0% | 70% | 4 | na | na | na |
| | 2.467105263 | 0% | 80% | | | | |
| | 3.926282051 | 0% | 90% | | | | |
| 48 hours | 1.519097222 | 100% | 63% | 1 | | | |
| | 1.519097222 | 100% | 63% | 2 | na | na | na |

-continued

| Time prior AKI stage | Cutoff value | sens | spec | Quartile | OR | 95% CI of OR | |
|---|---|---|---|---|---|---|---|
| | 1.519097222 | 100% | 63% | 3 | na | na | na |
| | 1.978272532 | 0% | 70% | 4 | na | na | na |
| | 2.467105263 | 0% | 80% | | | | |
| | 3.926282051 | 0% | 90% | | | | |

Soluble Epidermal Growth Factor Receptor:

| Time prior AKI stage | Cutoff value | sens | spec | Quartile | OR | 95% CI of OR | |
|---|---|---|---|---|---|---|---|
| | | | sCr or UO | | | | |
| 0 hours | 0 | 100% | 0% | 1 | | | |
| | 0 | 100% | 0% | 2 | 0.8 | 0.3 | 2.2 |
| | 0 | 100% | 0% | 3 | 0.4 | 0.1 | 1.4 |
| | 153.7521097 | 50% | 71% | 4 | 1.5 | 0.6 | 3.6 |
| | 249.1463853 | 36% | 80% | | | | |
| | 756.4365897 | 9% | 90% | | | | |
| 24 hours | 0 | 100% | 0% | 1 | | | |
| | 0 | 100% | 0% | 2 | 0.7 | 0.2 | 2.2 |
| | 0 | 100% | 0% | 3 | 0.7 | 0.2 | 2.4 |
| | 153.7521097 | 48% | 71% | 4 | 2.9 | 1.1 | 7.5 |
| | 249.1463853 | 43% | 80% | | | | |
| | 756.4365897 | 17% | 90% | | | | |
| 48 hours | 41.16691598 | 100% | 53% | 1 | | | |
| | 41.16691598 | 100% | 53% | 2 | na | na | na |
| | 41.16691598 | 100% | 53% | 3 | na | na | na |
| | 153.7521097 | 0% | 71% | 4 | na | na | na |
| | 249.1463853 | 0% | 80% | | | | |
| | 756.4365897 | 0% | 90% | | | | |
| | | | sCr only | | | | |
| 0 hours | 0 | 100% | 0% | 1 | | | |
| | 0 | 100% | 0% | 2 | 1.0 | 0.0 | 59.3 |
| | 0 | 100% | 0% | 3 | 4.6 | 0.3 | 63.1 |
| | 300.9850468 | 33% | 71% | 4 | 0.0 | 0.0 | 65535.0 |
| | 397.4771484 | 0% | 81% | | | | |
| | 921.4914927 | 0% | 90% | | | | |
| 24 hours | 0 | 100% | 0% | 1 | | | |
| | 0 | 100% | 0% | 2 | 0.0 | 0.0 | 65535.0 |
| | 0 | 100% | 0% | 3 | 1.0 | 0.2 | 4.4 |
| | 300.9850468 | 43% | 71% | 4 | 0.3 | 0.0 | 4.9 |
| | 397.4771484 | 29% | 81% | | | | |
| | 921.4914927 | 29% | 90% | | | | |
| 48 hours | 556.2664366 | 100% | 85% | 1 | | | |
| | 556.2664366 | 100% | 85% | 2 | na | na | na |
| | 556.2664366 | 100% | 85% | 3 | na | na | na |
| | 300.9850468 | 100% | 71% | 4 | na | na | na |
| | 397.4771484 | 100% | 81% | | | | |
| | 921.4914927 | 0% | 90% | | | | |
| | | | UO only | | | | |
| 0 hours | 0 | 100% | 0% | 1 | | | |
| | 0 | 100% | 0% | 2 | 1.3 | 0.3 | 6.0 |
| | 0 | 100% | 0% | 3 | 0.9 | 0.2 | 4.8 |
| | 98.85989481 | 59% | 71% | 4 | 3.2 | 0.8 | 12.5 |
| | 249.1463853 | 41% | 83% | | | | |
| | 666.4908125 | 12% | 90% | | | | |
| 24 hours | 48.27635621 | 71% | 62% | 1 | | | |
| | 0 | 100% | 0% | 2 | 0.1 | 0.0 | 1.9 |
| | 0 | 100% | 0% | 3 | 1.2 | 0.4 | 3.6 |
| | 98.85989481 | 57% | 71% | 4 | 2.6 | 0.9 | 7.6 |
| | 249.1463853 | 43% | 83% | | | | |
| | 666.4908125 | 19% | 90% | | | | |
| 48 hours | 41.16691598 | 75% | 60% | 1 | | | |
| | 0 | 100% | 0% | 2 | 0.0 | 0.0 | 65535.0 |
| | 0 | 100% | 0% | 3 | 1.0 | 0.0 | 74.6 |
| | 98.85989481 | 50% | 71% | 4 | 2.0 | 0.1 | 56.0 |
| | 249.1463853 | 50% | 83% | | | | |
| | 666.4908125 | 25% | 90% | | | | |

Example 7

Kidney Injury Markers for Evaluating Renal Status in Patients at RIFLE Stages 0 and R Patients were classified and analyzed as described in Example 6. However, patients that reached stage R but did not progress to stage I or F were grouped with patients from non-injury stage 0 in Cohort 1. Cohort 2 in this example included only patients that progressed to stage I or F. Marker concentrations in urine samples were included for Cohort 1. Marker concentrations in urine samples collected within 0, 24, and 48 hours of reaching stage I or F were included for Cohort 2.

The following descriptive statistics were obtained:

Soluble p-Selectin:

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| | | | sCr or UO | | | |
| median | 0.244 | 0.000 | 0.244 | 0.350 | 0.244 | 0.000 |
| average | 0.272 | 0.239 | 0.272 | 5.440 | 0.272 | 0.818 |
| stdev | 0.220 | na | 0.220 | 20.461 | 0.220 | na |
| p (t-test) | | na | | 0.011 | | na |
| min | 0.000 | 0.239 | 0.000 | 0.000 | 0.000 | 0.818 |
| max | 1.367 | 0.239 | 1.367 | 82.167 | 1.367 | 0.818 |
| n (Samp) | 99 | 1 | 99 | 16 | 99 | 1 |
| n (Pat) | 75 | 1 | 75 | 16 | 75 | 1 |
| | | | sCr only | | | |
| median | 0.251 | na | 0.251 | 0.514 | 0.251 | na |
| average | 0.995 | na | 0.995 | 0.465 | 0.995 | na |
| stdev | 7.673 | na | 7.673 | 0.202 | 7.673 | na |
| p (t-test) | | na | | 0.905 | | na |
| min | 0.000 | na | 0.000 | 0.244 | 0.000 | na |
| max | 82.167 | na | 82.167 | 0.639 | 82.167 | na |
| n (Samp) | 114 | 0 | 114 | 3 | 114 | 0 |
| n (Pat) | 88 | 0 | 88 | 3 | 88 | 0 |
| | | | UO only | | | |
| median | 0.202 | 0.000 | 0.202 | 0.317 | 0.202 | 0.666 |
| average | 0.253 | 0.239 | 0.253 | 5.769 | 0.253 | 0.666 |
| stdev | 0.206 | na | 0.206 | 21.135 | 0.206 | 0.215 |
| p (t-test) | | na | | 0.017 | | 0.006 |
| min | 0.000 | 0.239 | 0.000 | 0.000 | 0.000 | 0.514 |
| max | 1.367 | 0.239 | 1.367 | 82.167 | 1.367 | 0.818 |
| n (Samp) | 82 | 1 | 82 | 15 | 82 | 2 |
| n (Pat) | 62 | 1 | 62 | 15 | 62 | 2 |

Protein NOV Homolog:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 38059.701 | 37922.297 | 38059.701 | 52182.427 | 38059.701 | 29478.827 |
| average | 52501.927 | 43800.740 | 52501.927 | 66347.716 | 52501.927 | 40156.051 |
| stdev | 51579.286 | 42686.735 | 51579.286 | 64235.376 | 51579.286 | 42349.801 |
| p (t-test) |  | 0.620 |  | 0.293 |  | 0.681 |
| min | 14.544 | 1785.714 | 14.544 | 9600.515 | 14.544 | 4166.667 |
| max | 227486.911 | 139120.879 | 227486.911 | 228010.471 | 227486.911 | 86822.660 |
| n (Samp) | 167 | 9 | 167 | 18 | 167 | 3 |
| n (Pat) | 90 | 9 | 90 | 18 | 90 | 3 |
| sCr only | | | | | | |
| median | 37990.999 | 14.544 | 37990.999 | 71096.059 | 37990.999 | 49353.231 |
| average | 54176.796 | 51847.291 | 54176.796 | 80144.315 | 54176.796 | 49353.231 |
| stdev | 53334.647 | na | 53334.647 | 26378.749 | 53334.647 | 52989.774 |
| p (t-test) |  | na |  | 0.333 |  | 0.899 |
| min | 14.544 | 51847.291 | 14.544 | 59579.832 | 14.544 | 11883.803 |
| max | 228010.471 | 51847.291 | 228010.471 | 118805.310 | 228010.471 | 86822.660 |
| n (Samp) | 198 | 1 | 198 | 4 | 198 | 2 |
| n (Pat) | 110 | 1 | 110 | 4 | 110 | 2 |
| UO only | | | | | | |
| median | 38281.250 | 37922.297 | 38281.250 | 38168.932 | 38281.250 | 29478.827 |
| average | 48607.167 | 43800.740 | 48607.167 | 67966.748 | 48607.167 | 50816.935 |
| stdev | 45556.799 | 42686.735 | 45556.799 | 69694.118 | 45556.799 | 60224.503 |
| p (t-test) |  | 0.759 |  | 0.134 |  | 0.934 |
| min | 14.544 | 1785.714 | 14.544 | 9600.515 | 14.544 | 4166.667 |
| max | 226963.351 | 139120.879 | 226963.351 | 228010.471 | 226963.351 | 118805.310 |
| n (Samp) | 133 | 9 | 133 | 16 | 133 | 3 |
| n (Pat) | 71 | 9 | 71 | 16 | 71 | 3 |

Netrin 4:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 0.007 | 0.006 | 0.007 | 0.011 | 0.007 | 0.030 |
| average | 0.032 | 0.030 | 0.032 | 0.011 | 0.032 | 0.030 |
| stdev | 0.062 | 0.072 | 0.062 | 0.016 | 0.062 | 0.042 |
| p (t-test) |  | 0.939 |  | 0.644 |  | 0.965 |
| min | 0.000 | 0.000 | 0.000 | 0.000 | 0.000 | 0.000 |
| max | 0.262 | 0.207 | 0.262 | 0.023 | 0.262 | 0.060 |
| n (Samp) | 75 | 8 | 75 | 2 | 75 | 2 |
| n (Pat) | 55 | 8 | 55 | 2 | 55 | 2 |
| sCr only | | | | | | |
| median | 0.007 | 0.000 | 0.007 | na | 0.007 | 0.001 |
| average | 0.038 | 0.002 | 0.038 | na | 0.038 | 0.001 |
| stdev | 0.079 | na | 0.079 | na | 0.079 | 0.001 |
| p (t-test) |  | na |  | na |  | 0.506 |
| min | 0.000 | 0.002 | 0.000 | na | 0.000 | 0.000 |
| max | 0.469 | 0.002 | 0.469 | na | 0.469 | 0.002 |
| n (Samp) | 92 | 1 | 92 | 0 | 92 | 2 |
| n (Pat) | 67 | 1 | 67 | 0 | 67 | 2 |
| UO only | | | | | | |
| median | 0.007 | 0.006 | 0.007 | 0.011 | 0.007 | 0.000 |
| average | 0.024 | 0.030 | 0.024 | 0.011 | 0.024 | 0.060 |
| stdev | 0.049 | 0.072 | 0.049 | 0.016 | 0.049 | na |
| p (t-test) |  | 0.755 |  | 0.719 |  | na |
| min | 0.000 | 0.000 | 0.000 | 0.000 | 0.000 | 0.060 |
| max | 0.225 | 0.207 | 0.225 | 0.023 | 0.225 | 0.060 |
| n (Samp) | 58 | 8 | 58 | 2 | 58 | 1 |
| n (Pat) | 42 | 8 | 42 | 2 | 42 | 1 |

Alpha-1-Antitrypsin:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 0.001 | 0.001 | 0.001 | 0.001 | 0.001 | 0.000 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.467 |  | 0.240 |  | 0.286 |
| min | 0.000 | 0.000 | 0.000 | 0.000 | 0.000 | 0.000 |
| max | 0.005 | 0.003 | 0.005 | 0.003 | 0.005 | 0.003 |
| n (Samp) | 351 | 21 | 351 | 25 | 351 | 13 |
| n (Pat) | 121 | 21 | 121 | 25 | 121 | 13 |
| sCr only | | | | | | |
| median | 0.001 | 0.001 | 0.001 | 0.001 | 0.001 | 0.001 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.509 |  | 0.301 |  | 0.224 |
| min | 0.000 | 0.000 | 0.000 | 0.000 | 0.000 | 0.000 |
| max | 0.005 | 0.002 | 0.005 | 0.003 | 0.005 | 0.002 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| n (Samp) | 428 | 5 | 428 | 6 | 428 | 5 |
| n (Pat) | 146 | 5 | 146 | 6 | 146 | 5 |
| UO only | | | | | | |
| median | 0.001 | 0.001 | 0.001 | 0.001 | 0.001 | 0.001 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.923 |  | 0.480 |  | 0.566 |
| min | 0.000 | 0.000 | 0.000 | 0.000 | 0.000 | 0.000 |
| max | 0.005 | 0.003 | 0.005 | 0.003 | 0.005 | 0.003 |
| n (Samp) | 294 | 20 | 294 | 22 | 294 | 13 |
| n (Pat) | 96 | 20 | 96 | 22 | 96 | 13 |

Leukocyte Elastase:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 27.160 | 60.358 | 27.160 | 78.767 | 27.160 | 61.235 |
| average | 37.230 | 57.770 | 37.230 | 69.139 | 37.230 | 48.020 |
| stdev | 34.627 | 46.896 | 34.627 | 40.418 | 34.627 | 37.264 |
| p (t-test) |  | 0.024 |  | 0.000 |  | 0.279 |
| min | 0.080 | 0.678 | 0.080 | 2.106 | 0.080 | 0.899 |
| max | 137.517 | 136.336 | 137.517 | 125.592 | 137.517 | 110.014 |
| n (Samp) | 202 | 17 | 202 | 23 | 202 | 13 |
| n (Pat) | 106 | 17 | 106 | 23 | 106 | 13 |
| sCr only | | | | | | |
| median | 34.290 | 12.262 | 34.290 | 57.332 | 34.290 | 32.287 |
| average | 43.605 | 12.262 | 43.605 | 41.532 | 43.605 | 50.430 |
| stdev | 37.731 | 12.000 | 37.731 | 35.174 | 37.731 | 47.217 |
| p (t-test) |  | 0.242 |  | 0.903 |  | 0.690 |
| min | 0.080 | 3.776 | 0.080 | 3.950 | 0.080 | 1.002 |
| max | 137.517 | 20.747 | 137.517 | 78.767 | 137.517 | 125.810 |
| n (Samp) | 260 | 2 | 260 | 5 | 260 | 5 |
| n (Pat) | 125 | 2 | 125 | 5 | 125 | 5 |
| UO only | | | | | | |
| median | 27.498 | 60.358 | 27.498 | 79.904 | 27.498 | 57.332 |
| average | 39.360 | 57.677 | 39.360 | 69.880 | 39.360 | 49.239 |
| stdev | 35.376 | 46.899 | 35.376 | 41.313 | 35.376 | 35.461 |
| p (t-test) |  | 0.050 |  | 0.000 |  | 0.333 |
| min | 0.080 | 0.678 | 0.080 | 2.106 | 0.080 | 0.899 |
| max | 137.517 | 136.336 | 137.517 | 125.592 | 137.517 | 110.014 |
| n (Samp) | 174 | 17 | 174 | 21 | 174 | 13 |
| n (Pat) | 85 | 17 | 85 | 21 | 85 | 13 |

Soluble Tumor Necrosis Factor Receptor Superfamily Member 6:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 344.431 | 202.687 | 344.431 | 520.423 | 344.431 | 791.546 |
| average | 465.773 | 230.410 | 465.773 | 689.222 | 465.773 | 877.443 |
| stdev | 424.385 | 232.277 | 424.385 | 598.397 | 424.385 | 661.989 |
| p (t-test) |  | 0.219 |  | 0.041 |  | 0.036 |
| min | 13.944 | 26.930 | 13.944 | 0.278 | 13.944 | 98.864 |
| max | 2094.793 | 622.960 | 2094.793 | 2002.736 | 2094.793 | 1870.324 |
| n (Samp) | 189 | 5 | 189 | 18 | 189 | 5 |
| n (Pat) | 84 | 5 | 84 | 18 | 84 | 5 |
| sCr only | | | | | | |
| median | 390.719 | na | 390.719 | 1738.473 | 390.719 | 1062.309 |
| average | 492.914 | na | 492.914 | 1667.984 | 492.914 | 1062.309 |
| stdev | 417.039 | na | 417.039 | 348.507 | 417.039 | 1142.706 |
| p (t-test) |  | na |  | 0.000 |  | 0.059 |
| min | 0.278 | na | 0.278 | 1192.256 | 0.278 | 254.294 |
| max | 2094.793 | na | 2094.793 | 2002.736 | 2094.793 | 1870.324 |
| n (Samp) | 225 | 0 | 225 | 4 | 225 | 2 |
| n (Pat) | 98 | 0 | 98 | 4 | 98 | 2 |
| UO only | | | | | | |
| median | 380.682 | 202.687 | 380.682 | 460.539 | 380.682 | 791.546 |
| average | 474.759 | 230.410 | 474.759 | 481.530 | 474.759 | 903.926 |
| stdev | 409.593 | 232.277 | 409.593 | 312.181 | 409.593 | 712.370 |
| p (t-test) |  | 0.188 |  | 0.949 |  | 0.026 |
| min | 13.944 | 26.930 | 13.944 | 0.278 | 13.944 | 98.864 |
| max | 2094.793 | 622.960 | 2094.793 | 1120.160 | 2094.793 | 2002.736 |
| n (Samp) | 148 | 5 | 148 | 16 | 148 | 5 |
| n (Pat) | 68 | 5 | 68 | 16 | 68 | 5 |

Soluble Tumor Necrosis Factor Ligand Superfamily Member 6:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 0.158 | 0.724 | 0.158 | 0.812 | 0.158 | 0.627 |
| average | 1.092 | 2.030 | 1.092 | 1.187 | 1.092 | 2.716 |
| stdev | 2.393 | 3.037 | 2.393 | 0.976 | 2.393 | 4.378 |
| p (t-test) |  | 0.447 |  | 0.917 |  | 0.199 |
| min | 0.158 | 0.158 | 0.158 | 0.158 | 0.158 | 0.334 |
| max | 16.774 | 6.515 | 16.774 | 2.724 | 16.774 | 9.276 |
| n (Samp) | 109 | 4 | 109 | 7 | 109 | 4 |
| n (Pat) | 27 | 4 | 27 | 7 | 27 | 4 |
| sCr only | | | | | | |
| median | 0.158 | na | 0.158 | 1.441 | 0.158 | 1.105 |
| average | 1.278 | na | 1.278 | 1.441 | 1.278 | 1.105 |
| stdev | 2.489 | na | 2.489 | 1.814 | 2.489 | 0.938 |
| p (t-test) |  | na |  | 0.927 |  | 0.922 |
| min | 0.158 | na | 0.158 | 0.158 | 0.158 | 0.442 |
| max | 16.774 | na | 16.774 | 2.724 | 16.774 | 1.768 |
| n (Samp) | 133 | 0 | 133 | 2 | 133 | 2 |
| n (Pat) | 32 | 0 | 32 | 2 | 32 | 2 |
| UO only | | | | | | |
| median | 0.158 | 0.724 | 0.158 | 0.812 | 0.158 | 0.812 |
| average | 1.294 | 2.030 | 1.294 | 1.085 | 1.294 | 3.474 |
| stdev | 2.661 | 3.037 | 2.661 | 0.749 | 2.661 | 5.030 |
| p (t-test) |  | 0.592 |  | 0.862 |  | 0.180 |
| min | 0.158 | 0.158 | 0.158 | 0.158 | 0.158 | 0.334 |
| max | 16.774 | 6.515 | 16.774 | 2.098 | 16.774 | 9.276 |
| n (Samp) | 82 | 4 | 82 | 5 | 82 | 3 |
| n (Pat) | 20 | 4 | 20 | 5 | 20 | 3 |

Soluble Intercellular Adhesion Molecule 2:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 0.360 | 0.006 | 0.360 | 0.133 | 0.360 | 0.330 |
| average | 1.329 | 0.268 | 1.329 | 7.349 | 1.329 | 0.546 |
| stdev | 3.057 | 0.603 | 3.057 | 26.578 | 3.057 | 0.650 |
| p (t-test) |  | 0.301 |  | 0.008 |  | 0.659 |
| min | 0.001 | 0.001 | 0.001 | 0.006 | 0.001 | 0.031 |
| max | 30.484 | 1.810 | 30.484 | 113.267 | 30.484 | 1.276 |
| n (Samp) | 148 | 9 | 148 | 18 | 148 | 3 |
| n (Pat) | 85 | 9 | 85 | 18 | 85 | 3 |
| sCr only | | | | | | |
| median | 0.254 | 0.001 | 0.254 | 0.186 | 0.254 | 0.042 |
| average | 1.860 | 0.006 | 1.860 | 0.331 | 1.860 | 0.042 |
| stdev | 8.870 | na | 8.870 | 0.424 | 8.870 | 0.016 |
| p (t-test) |  | na |  | 0.731 |  | 0.773 |
| min | 0.001 | 0.006 | 0.001 | 0.006 | 0.001 | 0.031 |
| max | 113.267 | 0.006 | 113.267 | 0.945 | 113.267 | 0.054 |
| n (Samp) | 179 | 1 | 179 | 4 | 179 | 2 |
| n (Pat) | 104 | 1 | 104 | 4 | 104 | 2 |
| UO only | | | | | | |
| median | 0.360 | 0.006 | 0.360 | 0.133 | 0.360 | 0.330 |
| average | 1.330 | 0.268 | 1.330 | 8.203 | 1.330 | 0.570 |
| stdev | 3.327 | 0.603 | 3.327 | 28.170 | 3.327 | 0.623 |
| p (t-test) |  | 0.343 |  | 0.011 |  | 0.694 |
| min | 0.001 | 0.001 | 0.001 | 0.006 | 0.001 | 0.103 |
| max | 30.484 | 1.810 | 30.484 | 113.267 | 30.484 | 1.276 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| n (Samp) | 117 | 9 | 117 | 16 | 117 | 3 |
| n (Pat) | 68 | 9 | 68 | 16 | 68 | 3 |

Heat Shock Protein Beta-1:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 1.533 | 1.493 | 1.533 | 1.616 | 1.533 | 1.795 |
| average | 3.434 | 1.754 | 3.434 | 2.869 | 3.434 | 1.795 |
| stdev | 6.360 | 1.423 | 6.360 | 3.104 | 6.360 | 0.291 |
| p (t-test) |  | 0.460 |  | 0.879 |  | 0.718 |
| min | 0.086 | 0.078 | 0.086 | 0.586 | 0.086 | 1.589 |
| max | 42.428 | 3.819 | 42.428 | 6.404 | 42.428 | 2.001 |
| n (Samp) | 78 | 8 | 78 | 3 | 78 | 2 |
| n (Pat) | 56 | 8 | 56 | 3 | 56 | 2 |
| sCr only | | | | | | |
| median | 1.516 | 0.078 | 1.516 | 0.078 | 1.516 | 1.049 |
| average | 3.460 | 4.420 | 3.460 | 6.404 | 3.460 | 1.049 |
| stdev | 6.642 | na | 6.642 | na | 6.642 | 0.764 |
| p (t-test) |  | na |  | na |  | 0.611 |
| min | 0.078 | 4.420 | 0.078 | 6.404 | 0.078 | 0.509 |
| max | 42.428 | 4.420 | 42.428 | 6.404 | 42.428 | 1.589 |
| n (Samp) | 96 | 1 | 96 | 1 | 96 | 2 |
| n (Pat) | 69 | 1 | 69 | 1 | 69 | 2 |
| UO only | | | | | | |
| median | 1.476 | 1.493 | 1.476 | 1.101 | 1.476 | 0.086 |
| average | 2.292 | 1.754 | 2.292 | 1.101 | 2.292 | 2.001 |
| stdev | 2.701 | 1.423 | 2.701 | 0.728 | 2.701 | na |
| p (t-test) |  | 0.583 |  | 0.539 |  | na |
| min | 0.086 | 0.078 | 0.086 | 0.586 | 0.086 | 2.001 |
| max | 17.432 | 3.819 | 17.432 | 1.616 | 17.432 | 2.001 |
| n (Samp) | 61 | 8 | 61 | 2 | 61 | 1 |
| n (Pat) | 43 | 8 | 43 | 2 | 43 | 1 |

In the following tables, the ability to distinguish cohort 1 (subjects remaining in RIFLE 0 or R) from Cohort 2 (subjects progressing to RIFLE I or F) was determined using ROC analysis.

Soluble p-Selectin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.49 | 0.290 | 99 | 1 | 1.028 |
| 24 hours | 0.65 | 0.079 | 99 | 16 | 0.059 |
| 48 hours | 0.98 | 0.099 | 99 | 1 | 0.000 |
| Cohort 1 v Cohort 2, adjudicated on serum creatinine | | | | | |
| 0 hours | nd | nd | 114 | 0 | 0.211 |
| 24 hours | 0.78 | 0.161 | 114 | 3 | 0.085 |
| 48 hours | nd | nd | 114 | 0 | 0.211 |

| Time prior max stage | AUC | SE | n_Cohort 1 | n_Cohort 2 | p |
|---|---|---|---|---|---|
| Cohort 1 v Cohort 2, adjudicated on urine output | | | | | |
| 0 hours | 0.55 | 0.300 | 82 | 1 | 0.855 |
| 24 hours | 0.66 | 0.082 | 82 | 15 | 0.046 |
| 48 hours | 0.95 | 0.107 | 82 | 2 | 0.000 |

Protein NOV Homolog:

| Time prior max stage | AUC | SE | n_Cohort 1 | n_Cohort 2 | p |
|---|---|---|---|---|---|
| Cohort 1 v Cohort 2, adjudicated on serum creatinine measurements or urine output | | | | | |
| 0 hours | 0.45 | 0.096 | 167 | 9 | 1.376 |
| 24 hours | 0.58 | 0.074 | 167 | 18 | 0.301 |
| 48 hours | 0.43 | 0.159 | 167 | 3 | 1.345 |
| Cohort 1 v Cohort 2, adjudicated on serum creatinine | | | | | |
| 0 hours | 0.64 | 0.301 | 198 | 1 | 0.638 |
| 24 hours | 0.76 | 0.141 | 198 | 4 | 0.067 |
| 48 hours | 0.50 | 0.206 | 198 | 2 | 1.000 |
| Cohort 1 v Cohort 2, adjudicated on urine output | | | | | |
| 0 hours | 0.46 | 0.097 | 133 | 9 | 1.350 |
| 24 hours | 0.57 | 0.078 | 133 | 16 | 0.393 |
| 48 hours | 0.46 | 0.164 | 133 | 3 | 1.187 |

Netrin 4:

| Time prior max stage | AUC | SE | n_Cohort 1 | n_Cohort 2 | p |
|---|---|---|---|---|---|
| Cohort 1 v Cohort 2, adjudicated on serum creatinine measurements or urine output | | | | | |
| 0 hours | 0.41 | 0.101 | 75 | 8 | 1.614 |
| 24 hours | 0.40 | 0.189 | 75 | 2 | 1.415 |
| 48 hours | 0.44 | 0.198 | 75 | 2 | 1.238 |
| Cohort 1 v Cohort 2, adjudicated on serum creatinine | | | | | |
| 0 hours | 0.23 | 0.188 | 92 | 1 | 1.842 |
| 24 hours | nd | nd | 92 | 0 | 0.211 |
| 48 hours | 0.14 | 0.093 | 92 | 2 | 2.000 |
| Cohort 1 v Cohort 2, adjudicated on urine output | | | | | |
| 0 hours | 0.44 | 0.106 | 58 | 8 | 1.411 |
| 24 hours | 0.42 | 0.195 | 58 | 2 | 1.325 |
| 48 hours | 0.87 | 0.231 | 58 | 1 | 0.109 |

Alpha-1-Antitrypsin:

| Time prior max stage | AUC | SE | n_Cohort 1 | n_Cohort 2 | p |
|---|---|---|---|---|---|
| Cohort 1 v Cohort 2, adjudicated on serum creatinine measurements or urine output | | | | | |
| 0 hours | 0.49 | 0.064 | 351 | 21 | 1.156 |
| 24 hours | 0.43 | 0.057 | 351 | 25 | 1.782 |
| 48 hours | 0.41 | 0.075 | 351 | 13 | 1.763 |
| Cohort 1 v Cohort 2, adjudicated on serum creatinine | | | | | |
| 0 hours | 0.43 | 0.122 | 428 | 5 | 1.430 |
| 24 hours | 0.37 | 0.103 | 428 | 6 | 1.804 |
| 48 hours | 0.35 | 0.110 | 428 | 5 | 1.829 |

| Time prior max stage | AUC | SE | n_Cohort 1 | n_Cohort 2 | p |
|---|---|---|---|---|---|
| Cohort 1 v Cohort 2, adjudicated on urine output | | | | | |
| 0 hours | 0.54 | 0.068 | 294 | 20 | 0.557 |
| 24 hours | 0.46 | 0.062 | 294 | 22 | 1.519 |
| 48 hours | 0.44 | 0.078 | 294 | 13 | 1.524 |

Leukocyte Elastase:

| Time prior max stage | AUC | SE | n_Cohort 1 | n_Cohort 2 | p |
|---|---|---|---|---|---|
| Cohort 1 v Cohort 2, adjudicated on serum creatinine measurements or urine output | | | | | |
| 0 hours | 0.62 | 0.075 | 202 | 17 | 0.107 |
| 24 hours | 0.72 | 0.063 | 202 | 23 | 0.000 |
| 48 hours | 0.57 | 0.085 | 202 | 13 | 0.424 |
| Cohort 1 v Cohort 2, adjudicated on serum creatinine | | | | | |
| 0 hours | 0.25 | 0.139 | 260 | 2 | 1.925 |
| 24 hours | 0.48 | 0.129 | 260 | 5 | 1.135 |
| 48 hours | 0.54 | 0.133 | 260 | 5 | 0.782 |
| Cohort 1 v Cohort 2, adjudicated on urine output | | | | | |
| 0 hours | 0.60 | 0.076 | 174 | 17 | 0.165 |
| 24 hours | 0.71 | 0.066 | 174 | 21 | 0.002 |
| 48 hours | 0.58 | 0.086 | 174 | 13 | 0.357 |

Soluble Tumor Necrosis Factor Receptor Superfamily Member 6:

| Time prior max stage | AUC | SE | n_Cohort 1 | n_Cohort 2 | p |
|---|---|---|---|---|---|
| Cohort 1 v Cohort 2, adjudicated on serum creatinine measurements or urine output | | | | | |
| 0 hours | 0.31 | 0.104 | 189 | 5 | 1.925 |
| 24 hours | 0.61 | 0.073 | 189 | 18 | 0.122 |
| 48 hours | 0.72 | 0.131 | 189 | 5 | 0.092 |
| Cohort 1 v Cohort 2, adjudicated on serum creatinine | | | | | |
| 0 hours | nd | nd | 225 | 0 | 0.211 |
| 24 hours | 0.97 | 0.060 | 225 | 4 | 0.000 |
| 48 hours | 0.68 | 0.211 | 225 | 2 | 0.406 |
| Cohort 1 v Cohort 2, adjudicated on urine output | | | | | |
| 0 hours | 0.29 | 0.100 | 148 | 5 | 1.961 |
| 24 hours | 0.55 | 0.078 | 148 | 16 | 0.553 |
| 48 hours | 0.72 | 0.132 | 148 | 5 | 0.101 |

Soluble Tumor Necrosis Factor Ligand Superfamily Member 6:

| Time prior max stage | AUC | SE | n_Cohort 1 | n_Cohort 2 | p |
|---|---|---|---|---|---|
| Cohort 1 v Cohort 2, adjudicated on serum creatinine measurements or urine output | | | | | |
| 0 hours | 0.60 | 0.153 | 109 | 4 | 0.523 |
| 24 hours | 0.66 | 0.115 | 109 | 7 | 0.154 |
| 48 hours | 0.76 | 0.143 | 109 | 4 | 0.073 |
| Cohort 1 v Cohort 2, adjudicated on serum creatinine | | | | | |
| 0 hours | nd | nd | 133 | 0 | 0.211 |
| 24 hours | 0.58 | 0.213 | 133 | 2 | 0.718 |
| 48 hours | 0.73 | 0.206 | 133 | 2 | 0.274 |

-continued

| Time prior max stage | AUC | SE | $n_{Cohort\ 1}$ | $n_{Cohort\ 2}$ | p |
|---|---|---|---|---|---|
| Cohort 1 v Cohort 2, adjudicated on urine output | | | | | |
| 0 hours | 0.57 | 0.153 | 82 | 4 | 0.654 |
| 24 hours | 0.65 | 0.137 | 82 | 5 | 0.266 |
| 48 hours | 0.74 | 0.167 | 82 | 3 | 0.152 |

Soluble Intercellular Adhesion Molecule 2:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.22 | 0.063 | 148 | 9 | 2.000 |
| 24 hours | 0.44 | 0.070 | 148 | 18 | 1.582 |
| 48 hours | 0.45 | 0.163 | 148 | 3 | 1.218 |
| Cohort 1 v Cohort 2, adjudicated on serum creatinine | | | | | |
| 0 hours | 0.08 | 0.080 | 179 | 1 | 2.000 |
| 24 hours | 0.40 | 0.134 | 179 | 4 | 1.536 |
| 48 hours | 0.24 | 0.137 | 179 | 2 | 1.938 |
| Cohort 1 v Cohort 2, adjudicated on urine output | | | | | |
| 0 hours | 0.22 | 0.063 | 117 | 9 | 2.000 |
| 24 hours | 0.44 | 0.074 | 117 | 16 | 1.591 |
| 48 hours | 0.49 | 0.169 | 117 | 3 | 1.040 |

Heat Shock Protein Beta-1:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.43 | 0.102 | 78 | 8 | 1.509 |
| 24 hours | 0.54 | 0.174 | 78 | 3 | 0.835 |
| 48 hours | 0.57 | 0.214 | 78 | 2 | 0.742 |
| Cohort 1 v Cohort 2, adjudicated on serum creatinine | | | | | |
| 0 hours | 0.81 | 0.263 | 96 | 1 | 0.235 |
| 24 hours | 0.90 | 0.211 | 96 | 1 | 0.061 |
| 48 hours | 0.33 | 0.169 | 96 | 2 | 1.691 |
| Cohort 1 v Cohort 2, adjudicated on urine output | | | | | |
| 0 hours | 0.46 | 0.107 | 61 | 8 | 1.285 |
| 24 hours | 0.39 | 0.188 | 61 | 2 | 1.443 |
| 48 hours | 0.67 | 0.301 | 61 | 1 | 0.568 |

Various threshold (or "cutoff") concentrations were selected, and the associated sensitivity and specificity for distinguishing cohort 1 from cohort 2, as shown in the following tables. OR is the odds ratio calculated for the particular cutoff concentration, and 95% CI is the confidence interval for the odds ratio.

Soluble p-Selectin:

| Time prior AKI stage | Cutoff value | sens | spec | Quartile | OR | 95% CI of OR | |
|---|---|---|---|---|---|---|---|
| sCr or UO | | | | | | | |
| 0 hours | 0.227269073 | 100% | 48% | 1 | | | |
| | 0.227269073 | 100% | 48% | 2 | na | na | na |
| | 0.227269073 | 100% | 48% | 3 | na | na | na |
| | 0.326917826 | 0% | 72% | 4 | na | na | na |
| | 0.382377815 | 0% | 81% | | | | |
| | 0.512077136 | 0% | 91% | | | | |
| 24 hours | 0.23913407 | 75% | 49% | 1 | | | |
| | 0.180141162 | 81% | 38% | 2 | 1.5 | 0.3 | 8.9 |
| | 0.086590607 | 94% | 16% | 3 | 1.5 | 0.3 | 8.9 |
| | 0.326917826 | 50% | 72% | 4 | 5.0 | 1.2 | 20.0 |
| | 0.382377815 | 44% | 81% | | | | |
| | 0.512077136 | 19% | 91% | | | | |
| 48 hours | 0.743604394 | 100% | 98% | 1 | | | |
| | 0.743604394 | 100% | 98% | 2 | na | na | na |
| | 0.743604394 | 100% | 98% | 3 | na | na | na |
| | 0.326917826 | 100% | 72% | 4 | na | na | na |
| | 0.382377815 | 100% | 81% | | | | |
| | 0.512077136 | 100% | 91% | | | | |
| sCr only | | | | | | | |
| 0 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| 24 hours | 0.23913407 | 100% | 48% | 1 | | | |
| | 0.23913407 | 100% | 48% | 2 | na | na | na |
| | 0.23913407 | 100% | 48% | 3 | na | na | na |
| | 0.326917826 | 67% | 70% | 4 | na | na | na |
| | 0.412971955 | 67% | 82% | | | | |
| | 0.512077136 | 67% | 90% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| UO only | | | | | | | |
| 0 hours | 0.227269073 | 100% | 55% | 1 | | | |
| | 0.227269073 | 100% | 55% | 2 | na | na | na |
| | 0.227269073 | 100% | 55% | 3 | na | na | na |
| | 0.299537531 | 0% | 71% | 4 | na | na | na |
| | 0.35046571 | 0% | 80% | | | | |
| | 0.498556372 | 0% | 90% | | | | |
| 24 hours | 0.250763181 | 73% | 63% | 1 | | | |
| | 0.180141162 | 80% | 43% | 2 | 1.0 | 0.1 | 8.5 |
| | 0.086590607 | 93% | 18% | 3 | 2.2 | 0.4 | 11.5 |
| | 0.299537531 | 53% | 71% | 4 | 4.3 | 1.0 | 18.4 |
| | 0.35046571 | 47% | 80% | | | | |
| | 0.498556372 | 20% | 90% | | | | |
| 48 hours | 0.512077136 | 100% | 91% | 1 | | | |
| | 0.512077136 | 100% | 91% | 2 | na | na | na |
| | 0.512077136 | 100% | 91% | 3 | na | na | na |
| | 0.299537531 | 100% | 71% | 4 | na | na | na |
| | 0.35046571 | 100% | 80% | | | | |
| | 0.498556372 | 100% | 90% | | | | |

Protein NOV Homolog:

| Time prior AKI stage | Cutoff value | sens | spec | Quartile | OR | 95% CI of OR | |
|---|---|---|---|---|---|---|---|
| sCr or UO | | | | | | | |
| 0 hours | 20680.14706 | 78% | 36% | 1 | | | |
| | 1785.714286 | 89% | 1% | 2 | 1.0 | 0.1 | 7.8 |
| | 1226.993865 | 100% | 1% | 3 | 1.5 | 0.3 | 8.6 |
| | 57899.15966 | 22% | 70% | 4 | 1.0 | 0.1 | 7.8 |

-continued

| Time prior AKI stage | Cutoff value | sens | spec | Quartile | OR | 95% CI of OR | |
|---|---|---|---|---|---|---|---|
| | 85359.11602 | 11% | 80% | | | | |
| | 138681.3187 | 11% | 90% | | | | |
| 24 hours | 19393.38235 | 72% | 35% | 1 | | | |
| | 15230.58252 | 83% | 27% | 2 | 1.7 | 0.6 | 5.5 |
| | 10937.5 | 94% | 20% | 3 | 1.7 | 0.6 | 5.5 |
| | 57899.15966 | 44% | 70% | 4 | 1.7 | 0.5 | 5.3 |
| | 85359.11602 | 28% | 80% | | | | |
| | 138681.3187 | 11% | 90% | | | | |
| 48 hours | 3673.245614 | 100% | 4% | 1 | | | |
| | 3673.245614 | 100% | 4% | 2 | 0.0 | 0.0 | 65535.0 |
| | 3673.245614 | 100% | 4% | 3 | 1.0 | 0.0 | 55.3 |
| | 57899.15966 | 33% | 70% | 4 | 1.0 | 0.0 | 56.7 |
| | 85359.11602 | 33% | 80% | | | | |
| | 138681.3187 | 0% | 90% | | | | |
| | sCr only | | | | | | |
| 0 hours | 49915.54054 | 100% | 64% | 1 | | | |
| | 49915.54054 | 100% | 64% | 2 | na | na | na |
| | 49915.54054 | 100% | 64% | 3 | na | na | na |
| | 58743.84236 | 0% | 70% | 4 | na | na | na |
| | 87315.27094 | 0% | 80% | | | | |
| | 138716.8142 | 0% | 90% | | | | |
| 24 hours | 66633.85827 | 75% | 73% | 1 | | | |
| | 58743.84236 | 100% | 70% | 2 | na | na | na |
| | 58743.84236 | 100% | 70% | 3 | na | na | na |
| | 58743.84236 | 100% | 70% | 4 | na | na | na |
| | 87315.27094 | 25% | 80% | | | | |
| | 138716.8142 | 0% | 90% | | | | |
| 48 hours | 11821.70543 | 100% | 20% | 1 | | | |
| | 11821.70543 | 100% | 20% | 2 | 0.0 | 0.0 | 65535.0 |
| | 11821.70543 | 100% | 20% | 3 | 0.0 | 0.0 | 65535.0 |
| | 58743.84236 | 50% | 70% | 4 | 1.0 | 0.0 | 54.6 |
| | 87315.27094 | 0% | 80% | | | | |
| | 138716.8142 | 0% | 90% | | | | |
| | UO only | | | | | | |
| 0 hours | 20680.14706 | 78% | 36% | 1 | | | |
| | 1785.714286 | 89% | 1% | 2 | 1.0 | 0.1 | 8.2 |
| | 14.54359673 | 100% | 1% | 3 | 1.5 | 0.3 | 8.9 |
| | 56594.48819 | 22% | 71% | 4 | 1.0 | 0.1 | 8.2 |
| | 81932.77311 | 11% | 80% | | | | |
| | 104450.2618 | 11% | 90% | | | | |
| 24 hours | 16084.55882 | 75% | 29% | 1 | | | |
| | 15230.58252 | 81% | 26% | 2 | 1.8 | 0.6 | 5.7 |
| | 10760.30928 | 94% | 19% | 3 | 1.0 | 0.2 | 4.1 |
| | 56594.48819 | 38% | 71% | 4 | 1.7 | 0.5 | 5.5 |
| | 81932.77311 | 31% | 80% | | | | |
| | 104450.2618 | 25% | 90% | | | | |
| 48 hours | 3673.245614 | 100% | 4% | 1 | | | |
| | 3673.245614 | 100% | 4% | 2 | 0.0 | 0.0 | 65535.0 |
| | 3673.245614 | 100% | 4% | 3 | 1.0 | 0.0 | 56.8 |
| | 56594.48819 | 33% | 71% | 4 | 1.0 | 0.0 | 56.8 |
| | 81932.77311 | 33% | 80% | | | | |
| | 104450.2618 | 33% | 90% | | | | |

Netrin 4:

| Time prior AKI stage | Cutoff value | sens | spec | Quartile | OR | 95% CI of OR | |
|---|---|---|---|---|---|---|---|
| | sCr or UO | | | | | | |
| 0 hours | 0 | 100% | 0% | 1 | | | |
| | 0 | 100% | 0% | 2 | 0.0 | 0.0 | 65535.0 |
| | 0 | 100% | 0% | 3 | 1.6 | 0.3 | 10.0 |
| | 0.012067244 | 25% | 71% | 4 | 1.7 | 0.3 | 10.7 |
| | 0.031866776 | 13% | 80% | | | | |
| | 0.102163462 | 13% | 91% | | | | |
| 24 hours | 0 | 100% | 0% | 1 | | | |
| | 0 | 100% | 0% | 2 | 0.0 | 0.0 | 65535.0 |
| | 0 | 100% | 0% | 3 | 0.0 | 0.0 | 65535.0 |
| | 0.012067244 | 50% | 71% | 4 | 1.1 | 0.0 | 65.8 |
| | 0.031866776 | 0% | 80% | | | | |
| | 0.102163462 | 0% | 91% | | | | |
| 48 hours | 0 | 100% | 0% | 1 | | | |
| | 0 | 100% | 0% | 2 | 0.0 | 0.0 | 65535.0 |
| | 0 | 100% | 0% | 3 | 0.0 | 0.0 | 65535.0 |
| | 0.012067244 | 50% | 71% | 4 | 1.1 | 0.0 | 65.8 |
| | 0.031866776 | 50% | 80% | | | | |
| | 0.102163462 | 0% | 91% | | | | |
| | sCr only | | | | | | |
| 0 hours | 0.001144308 | 100% | 20% | 1 | | | |
| | 0.001144308 | 100% | 20% | 2 | na | na | na |
| | 0.001144308 | 100% | 20% | 3 | na | na | na |
| | 0.012067244 | 0% | 71% | 4 | na | na | na |

| Time prior AKI stage | Cutoff value | sens | spec | Quartile | OR | 95% CI of OR |
|---|---|---|---|---|---|---|
| | 0.050370066 | 0% | 82% | | | |
| | 0.170036765 | 0% | 90% | | | |
| 24 hours | 0 | na | na | 1 | | |
| | 0 | na | na | 2 | na | na na |
| | 0 | na | na | 3 | na | na na |
| | 0 | na | na | 4 | na | na na |
| | 0 | na | na | | | |
| | 0 | na | na | | | |
| 48 hours | 0 | 100% | 0% | 1 | | |
| | 0 | 100% | 0% | 2 | na | na na |
| | 0 | 100% | 0% | 3 | na | na na |
| | 0.012067244 | 0% | 71% | 4 | na | na na |
| | 0.050370066 | 0% | 82% | | | |
| | 0.170036765 | 0% | 90% | | | |
| UO only | | | | | | |
| 0 hours | 0 | 100% | 0% | 1 | | |
| | 0 | 100% | 0% | 2 | 1.1 | 0.1 10.0 |
| | 0 | 100% | 0% | 3 | 0.5 | 0.0 11.4 |
| | 0.007336754 | 25% | 72% | 4 | 1.7 | 0.3 11.7 |
| | 0.028711718 | 13% | 81% | | | |
| | 0.068873355 | 13% | 91% | | | |
| 24 hours | 0 | 100% | 0% | 1 | | |
| | 0 | 100% | 0% | 2 | 0.0 | 0.0 65535.0 |
| | 0 | 100% | 0% | 3 | 0.0 | 0.0 65535.0 |
| | 0.007336754 | 50% | 72% | 4 | 1.0 | 0.0 66.7 |
| | 0.028711718 | 0% | 81% | | | |
| | 0.068873355 | 0% | 91% | | | |
| 48 hours | 0.050370066 | 100% | 86% | 1 | | |
| | 0.050370066 | 100% | 86% | 2 | na | na na |
| | 0.050370066 | 100% | 86% | 3 | na | na na |
| | 0.007336754 | 100% | 72% | 4 | na | na na |
| | 0.028711718 | 100% | 81% | | | |
| | 0.068873355 | 0% | 91% | | | |

Alpha-1-Antitrypsin:

| Time prior AKI stage | Cutoff value | sens | spec | Quartile | OR | 95% CI of OR |
|---|---|---|---|---|---|---|
| sCr or UO | | | | | | |
| 0 hours | 0.000755 | 71% | 40% | 1 | | |
| | 0.000539 | 81% | 32% | 2 | 3.2 | 1.3 8.0 |
| | 0.0000896 | 90% | 4% | 3 | 1.7 | 0.6 5.1 |
| | 0.00179 | 24% | 70% | 4 | 1.3 | 0.4 4.4 |
| | 0.00258 | 14% | 80% | | | |
| | 0.00295 | 0% | 90% | | | |
| 24 hours | 0.000315 | 72% | 19% | 1 | | |
| | 0.000181 | 80% | 11% | 2 | 1.2 | 0.6 2.6 |
| | 0.000125 | 92% | 7% | 3 | 1.0 | 0.4 2.3 |
| | 0.00179 | 24% | 70% | 4 | 1.9 | 1.0 3.6 |
| | 0.00258 | 16% | 80% | | | |
| | 0.00295 | 0% | 90% | | | |
| 48 hours | 0.000409 | 77% | 26% | 1 | | |
| | 0.000283 | 85% | 17% | 2 | 0.7 | 0.1 3.5 |
| | 0.000225 | 92% | 13% | 3 | 1.7 | 0.6 5.1 |
| | 0.00179 | 23% | 70% | 4 | 1.0 | 0.3 3.9 |
| | 0.00258 | 23% | 80% | | | |
| | 0.00295 | 0% | 90% | | | |
| sCr only | | | | | | |
| 0 hours | 0.000539 | 80% | 30% | 1 | | |
| | 0.000539 | 80% | 30% | 2 | na | na na |
| | 0.0000896 | 100% | 4% | 3 | na | na na |
| | 0.00179 | 40% | 70% | 4 | na | na na |
| | 0.00258 | 0% | 80% | | | |
| | 0.00291 | 0% | 90% | | | |
| 24 hours | 0.000361 | 83% | 22% | 1 | | |
| | 0.000361 | 83% | 22% | 2 | 0.0 | 0.0 65535.0 |
| | 0.0000657 | 100% | 2% | 3 | 3.1 | 0.2 43.3 |
| | 0.00179 | 17% | 70% | 4 | 2.0 | 0.1 40.0 |
| | 0.00258 | 17% | 80% | | | |
| | 0.00291 | 0% | 90% | | | |

| Time prior AKI stage | Cutoff value | sens | spec | Quartile | OR | 95% CI of OR |
|---|---|---|---|---|---|---|
| 48 hours | 0.000283 | 80% | 16% | 1 | | |
| | 0.000283 | 80% | 16% | 2 | na | na na |
| | 0.000178 | 100% | 10% | 3 | na | na na |
| | 0.00179 | 0% | 70% | 4 | na | na na |
| | 0.00258 | 0% | 80% | | | |
| | 0.00291 | 0% | 90% | | | |
| UO only | | | | | | |
| 0 hours | 0.000972 | 70% | 48% | 1 | | |
| | 0.00065 | 80% | 33% | 2 | 1.3 | 0.4 4.4 |
| | 0.000313 | 90% | 17% | 3 | 2.9 | 1.1 7.4 |
| | 0.00179 | 30% | 70% | 4 | 1.7 | 0.6 5.1 |
| | 0.0024 | 25% | 80% | | | |
| | 0.0029 | 5% | 90% | | | |
| 24 hours | 0.000313 | 73% | 17% | 1 | | |
| | 0.00018 | 82% | 10% | 2 | 1.2 | 0.6 2.6 |
| | 0.000126 | 91% | 6% | 3 | 0.8 | 0.3 2.0 |
| | 0.00179 | 27% | 70% | 4 | 1.4 | 0.7 3.0 |
| | 0.0024 | 18% | 80% | | | |
| | 0.0029 | 0% | 90% | | | |
| 48 hours | 0.000429 | 77% | 25% | 1 | | |
| | 0.000409 | 85% | 24% | 2 | 0.2 | 0.0 2.9 |
| | 0.000225 | 92% | 11% | 3 | 1.3 | 0.5 3.2 |
| | 0.00179 | 31% | 70% | 4 | 0.8 | 0.2 2.5 |
| | 0.0024 | 31% | 80% | | | |
| | 0.0029 | 0% | 90% | | | |

Leukocyte Elastase:

| Time prior AKI stage | Cutoff value | sens | spec | Quartile | OR | 95% CI of OR |
|---|---|---|---|---|---|---|
| sCr or UO | | | | | | |
| 0 hours | 20.21791768 | 71% | 45% | 1 | | |
| | 8.935546875 | 82% | 27% | 2 | 1.0 | 0.2 3.9 |
| | 3.708584337 | 94% | 13% | 3 | 1.3 | 0.4 4.5 |
| | 49.6875 | 53% | 70% | 4 | 2.5 | 0.9 6.8 |
| | 69.99461787 | 41% | 80% | | | |
| | 90.38461538 | 29% | 90% | | | |
| 24 hours | 40.4467169 | 74% | 63% | 1 | | |
| | 18.29710145 | 83% | 43% | 2 | 0.7 | 0.1 3.6 |
| | 3.949652778 | 91% | 14% | 3 | 1.4 | 0.4 4.6 |
| | 49.6875 | 70% | 70% | 4 | 5.8 | 2.4 13.8 |
| | 69.99461787 | 57% | 80% | | | |
| | 90.38461538 | 43% | 90% | | | |
| 48 hours | 5.152027027 | 77% | 18% | 1 | | |
| | 4.210069444 | 85% | 15% | 2 | 0.0 | 0.0 65535.0 |
| | 0.987617925 | 92% | 4% | 3 | 0.7 | 0.2 2.4 |
| | 49.6875 | 54% | 70% | 4 | 1.5 | 0.6 3.8 |
| | 69.99461787 | 23% | 80% | | | |
| | 90.38461538 | 15% | 90% | | | |
| sCr only | | | | | | |
| 0 hours | 3.708584337 | 100% | 12% | 1 | | |
| | 3.708584337 | 100% | 12% | 2 | na | na na |
| | 3.708584337 | 100% | 12% | 3 | na | na na |
| | 65.21634615 | 0% | 70% | 4 | na | na na |
| | 79.90397805 | 0% | 80% | | | |
| | 99.65016146 | 0% | 90% | | | |
| 24 hours | 3.949652778 | 80% | 13% | 1 | | |
| | 3.949652778 | 80% | 13% | 2 | 2.1 | 0.1 41.4 |
| | 3.860294118 | 100% | 13% | 3 | 0.0 | 0.0 65535.0 |
| | 65.21634615 | 20% | 70% | 4 | 2.1 | 0.1 41.4 |
| | 79.90397805 | 0% | 80% | | | |
| | 99.65016146 | 0% | 90% | | | |
| 48 hours | 30.80296896 | 80% | 50% | 1 | | |
| | 30.80296896 | 80% | 50% | 2 | 2.0 | 0.1 40.8 |
| | 0.987617925 | 100% | 4% | 3 | 1.0 | 0.0 53.5 |
| | 65.21634615 | 20% | 70% | 4 | 1.0 | 0.0 52.7 |
| | 79.90397805 | 20% | 80% | | | |
| | 99.65016146 | 20% | 90% | | | |

| Time prior AKI stage | Cutoff value | sens | spec | Quartile | OR | 95% CI of OR | |
|---|---|---|---|---|---|---|---|
| UO only | | | | | | | |
| 0 hours | 17.47596154 | 71% | 40% | 1 | | | |
| | 8.963815789 | 82% | 24% | 2 | 0.5 | 0.1 | 2.2 |
| | 3.708584337 | 94% | 8% | 3 | 1.0 | 0.3 | 2.8 |
| | 54.73484848 | 53% | 70% | 4 | 1.8 | 0.8 | 4.4 |
| | 73.59396433 | 41% | 80% | | | | |
| | 95.2689243 | 29% | 90% | | | | |
| 24 hours | 40.4467169 | 71% | 60% | 1 | | | |
| | 18.29710145 | 81% | 41% | 2 | 1.5 | 0.3 | 8.4 |
| | 12.5 | 90% | 30% | 3 | 2.0 | 0.4 | 9.7 |
| | 54.73484848 | 67% | 70% | 4 | 7.5 | 2.2 | 25.7 |
| | 73.59396433 | 57% | 80% | | | | |
| | 95.2689243 | 33% | 90% | | | | |
| 48 hours | 20.21791768 | 77% | 43% | 1 | | | |
| | 5.152027027 | 85% | 15% | 2 | 0.3 | 0.0 | 4.6 |
| | 4.210069444 | 92% | 11% | 3 | 1.0 | 0.2 | 4.0 |
| | 54.73484848 | 54% | 70% | 4 | 2.1 | 0.7 | 6.1 |
| | 73.59396433 | 15% | 80% | | | | |
| | 95.2689243 | 15% | 90% | | | | |

Soluble Tumor Necrosis Factor Receptor Superfamily Member 6:

| Time prior AKI stage | Cutoff value | sens | spec | Quartile | OR | 95% CI of OR | |
|---|---|---|---|---|---|---|---|
| sCr or UO | | | | | | | |
| 0 hours | 92.39130435 | 80% | 13% | 1 | | | |
| | 92.39130435 | 80% | 13% | 2 | 0.0 | 0.0 | 65535.0 |
| | 24.82199367 | 100% | 2% | 3 | 2.0 | 0.1 | 42.0 |
| | 539.044289 | 20% | 70% | 4 | 2.1 | 0.1 | 42.9 |
| | 679.5520231 | 0% | 80% | | | | |
| | 1037.383178 | 0% | 90% | | | | |
| 24 hours | 302.3952096 | 72% | 45% | 1 | | | |
| | 226.9021739 | 83% | 37% | 2 | 1.0 | 0.2 | 3.9 |
| | 78.94736842 | 94% | 9% | 3 | 1.7 | 0.6 | 5.3 |
| | 539.044289 | 50% | 70% | 4 | 2.5 | 0.9 | 6.9 |
| | 679.5520231 | 33% | 80% | | | | |
| | 1037.383178 | 22% | 90% | | | | |
| 48 hours | 539.044289 | 80% | 70% | 1 | | | |
| | 539.044289 | 80% | 70% | 2 | 0.0 | 0.0 | 65535.0 |
| | 95.83333333 | 100% | 14% | 3 | 1.0 | 0.0 | 54.8 |
| | 539.044289 | 80% | 70% | 4 | 3.1 | 0.2 | 45.5 |
| | 679.5520231 | 60% | 80% | | | | |
| | 1037.383178 | 40% | 90% | | | | |
| sCr only | | | | | | | |
| 0 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| 24 hours | 1522.427441 | 75% | 96% | 1 | | | |
| | 1187.39255 | 100% | 93% | 2 | na | na | na |
| | 1187.39255 | 100% | 93% | 3 | na | na | na |
| | 597.4643423 | 100% | 70% | 4 | na | na | na |
| | 779.6005706 | 100% | 80% | | | | |
| | 1037.383178 | 100% | 90% | | | | |
| 48 hours | 249.4158879 | 100% | 36% | 1 | | | |
| | 249.4158879 | 100% | 36% | 2 | na | na | na |
| | 249.4158879 | 100% | 36% | 3 | na | na | na |
| | 597.4643423 | 50% | 70% | 4 | na | na | na |
| | 779.6005706 | 50% | 80% | | | | |
| | 1037.383178 | 50% | 90% | | | | |
| UO only | | | | | | | |
| 0 hours | 92.39130435 | 80% | 11% | 1 | | | |
| | 92.39130435 | 80% | 11% | 2 | 0.0 | 0.0 | 65535.0 |
| | 24.82199367 | 100% | 2% | 3 | 2.1 | 0.1 | 44.4 |
| | 549.9286733 | 20% | 70% | 4 | 2.1 | 0.1 | 44.4 |
| | 675.0369276 | 0% | 80% | | | | |
| | 1010.680908 | 0% | 91% | | | | |
| 24 hours | 294.7941889 | 75% | 40% | 1 | | | |
| | 226.9021739 | 81% | 32% | 2 | 1.0 | 0.2 | 4.1 |
| | 78.94736842 | 94% | 8% | 3 | 1.8 | 0.6 | 5.6 |
| | 549.9286733 | 44% | 70% | 4 | 1.8 | 0.6 | 5.6 |
| | 675.0369276 | 25% | 80% | | | | |
| | 1010.680908 | 6% | 91% | | | | |
| 48 hours | 539.044289 | 80% | 70% | 1 | | | |
| | 539.044289 | 80% | 70% | 2 | 0.0 | 0.0 | 65535.0 |
| | 95.83333333 | 100% | 11% | 3 | 1.0 | 0.0 | 56.0 |
| | 549.9286733 | 60% | 70% | 4 | 3.1 | 0.2 | 46.8 |
| | 675.0369276 | 60% | 80% | | | | |
| | 1010.680908 | 40% | 91% | | | | |

Soluble Tumor Necrosis Factor Ligand Superfamily Member 6:

| Time prior AKI stage | Cutoff value | sens | spec | Quartile | OR | 95% CI of OR | |
|---|---|---|---|---|---|---|---|
| sCr or UO | | | | | | | |
| 0 hours | 0 | 100% | 0% | 1 | | | |
| | 0 | 100% | 0% | 2 | na | na | na |
| | 0 | 100% | 0% | 3 | na | na | na |
| | 0.812308869 | 50% | 73% | 4 | na | na | na |
| | 1.290137615 | 25% | 83% | | | | |
| | 2.723623853 | 25% | 91% | | | | |
| 24 hours | 0.441696113 | 71% | 69% | 1 | | | |
| | 0 | 100% | 0% | 2 | 1.0 | 0.0 | 58.0 |
| | 0 | 100% | 0% | 3 | 2.1 | 0.1 | 45.2 |
| | 0.812308869 | 43% | 73% | 4 | 3.2 | 0.2 | 51.0 |
| | 1.290137615 | 43% | 83% | | | | |
| | 2.723623853 | 25% | 91% | | | | |
| 48 hours | 0.334480122 | 75% | 68% | 1 | | | |
| | 0.173611111 | 100% | 63% | 2 | na | na | na |
| | 0.173611111 | 100% | 63% | 3 | na | na | na |
| | 0.812308869 | 25% | 73% | 4 | na | na | na |
| | 1.290137615 | 25% | 83% | | | | |
| | 2.723623853 | 25% | 91% | | | | |
| sCr only | | | | | | | |
| 0 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| 24 hours | 0 | 100% | 0% | 1 | | | |
| | 0 | 100% | 0% | 2 | na | na | na |
| | 0 | 100% | 0% | 3 | na | na | na |
| | 0.993816254 | 50% | 74% | 4 | na | na | na |
| | 1.545936396 | 50% | 81% | | | | |
| | 3.20229682 | 0% | 91% | | | | |
| 48 hours | 0.334480122 | 100% | 62% | 1 | | | |
| | 0.334480122 | 100% | 62% | 2 | na | na | na |
| | 0.334480122 | 100% | 62% | 3 | na | na | na |
| | 0.993816254 | 50% | 74% | 4 | na | na | na |
| | 1.545936396 | 50% | 81% | | | | |
| | 3.20229682 | 0% | 91% | | | | |
| UO only | | | | | | | |
| 0 hours | 0 | 100% | 0% | 1 | | | |
| | 0 | 100% | 0% | 2 | na | na | na |
| | 0 | 100% | 0% | 3 | na | na | na |
| | 0.993816254 | 50% | 76% | 4 | na | na | na |
| | 1.290137615 | 25% | 80% | | | | |
| | 3.201452599 | 25% | 90% | | | | |
| 24 hours | 0.441696113 | 80% | 63% | 1 | | | |
| | 0.441696113 | 80% | 63% | 2 | na | na | na |
| | 0 | 100% | 0% | 3 | na | na | na |
| | 0.993816254 | 40% | 76% | 4 | na | na | na |

-continued

| Time prior AKI stage | Cutoff value | sens | spec | Quartile | OR | 95% CI of OR | |
|---|---|---|---|---|---|---|---|
| | 1.290137615 | 40% | 80% | | | | |
| | 3.201452599 | 0% | 90% | | | | |
| 48 hours | 0.173611111 | 100% | 56% | 1 | | | |
| | 0.173611111 | 100% | 56% | 2 | na | na | na |
| | 0.173611111 | 100% | 56% | 3 | na | na | na |
| | 0.993816254 | 33% | 76% | 4 | na | na | na |
| | 1.290137615 | 33% | 80% | | | | |
| | 3.201452599 | 33% | 90% | | | | |

Soluble Intercellular Adhesion Molecule 2:

| Time prior AKI stage | Cutoff value | sens | spec | Quartile | OR | 95% CI of OR | |
|---|---|---|---|---|---|---|---|
| | | sCr or UO | | | | | |
| 0 hours | 0.00133452 | 89% | 1% | 1 | | | |
| | 0.00133452 | 89% | 1% | 2 | 1.0 | 0.0 | 57.3 |
| | 0 | 100% | 0% | 3 | 0.0 | 0.0 | 65535.0 |
| | 1.115384615 | 11% | 70% | 4 | 8.5 | 0.8 | 89.6 |
| | 2.015151515 | 0% | 80% | | | | |
| | 3.42 | 0% | 91% | | | | |
| 24 hours | 0.075892857 | 72% | 28% | 1 | | | |
| | 0.012096774 | 83% | 16% | 2 | 0.2 | 0.0 | 2.2 |
| | 0.00133452 | 100% | 1% | 3 | 1.5 | 0.7 | 3.2 |
| | 1.115384615 | 28% | 70% | 4 | 1.0 | 0.4 | 2.5 |
| | 2.015151515 | 11% | 80% | | | | |
| | 3.42 | 11% | 91% | | | | |
| 48 hours | 0.027217742 | 100% | 17% | 1 | | | |
| | 0.027217742 | 100% | 17% | 2 | na | na | na |
| | 0.027217742 | 100% | 17% | 3 | na | na | na |
| | 1.115384615 | 33% | 70% | 4 | na | na | na |
| | 2.015151515 | 0% | 80% | | | | |
| | 3.42 | 0% | 91% | | | | |
| | | sCr only | | | | | |
| 0 hours | 0.00133452 | 100% | 1% | 1 | | | |
| | 0.00133452 | 100% | 1% | 2 | na | na | na |
| | 0.00133452 | 100% | 1% | 3 | na | na | na |
| | 1.066666667 | 0% | 71% | 4 | na | na | na |
| | 1.744897959 | 0% | 80% | | | | |
| | 3.39 | 0% | 91% | | | | |
| 24 hours | 0.087701613 | 75% | 35% | 1 | | | |
| | 0.00133452 | 100% | 1% | 2 | na | na | na |
| | 0.00133452 | 100% | 1% | 3 | na | na | na |
| | 1.066666667 | 0% | 71% | 4 | na | na | na |
| | 1.744897959 | 0% | 80% | | | | |
| | 3.39 | 0% | 91% | | | | |
| 48 hours | 0.027217742 | 100% | 21% | 1 | | | |
| | 0.027217742 | 100% | 21% | 2 | na | na | na |
| | 0.027217742 | 100% | 21% | 3 | na | na | na |
| | 1.066666667 | 0% | 71% | 4 | na | na | na |
| | 1.744897959 | 0% | 80% | | | | |
| | 3.39 | 0% | 91% | | | | |
| | | UO only | | | | | |
| 0 hours | 0.00133452 | 89% | 1% | 1 | | | |
| | 0.00133452 | 89% | 1% | 2 | 1.0 | 0.0 | 59.2 |
| | 0 | 100% | 0% | 3 | 0.0 | 0.0 | 65535.0 |
| | 1.066666667 | 11% | 71% | 4 | 9.0 | 0.8 | 98.2 |
| | 1.685106383 | 11% | 80% | | | | |
| | 3.296511628 | 0% | 91% | | | | |
| 24 hours | 0.053571429 | 75% | 22% | 1 | | | |
| | 0.012096774 | 81% | 15% | 2 | 0.0 | 0.0 | 65535.0 |
| | 0.00133452 | 100% | 1% | 3 | 1.3 | 0.5 | 3.0 |
| | 1.066666667 | 31% | 71% | 4 | 1.0 | 0.4 | 2.6 |
| | 1.685106383 | 25% | 80% | | | | |
| | 3.296511628 | 13% | 91% | | | | |
| 48 hours | 0.087701613 | 100% | 27% | 1 | | | |
| | 0.087701613 | 100% | 27% | 2 | na | na | na |
| | 0.087701613 | 100% | 27% | 3 | na | na | na |
| | 1.066666667 | 33% | 71% | 4 | na | na | na |
| | 1.685106383 | 0% | 80% | | | | |
| | 3.296511628 | 0% | 91% | | | | |

Heat Shock Protein Beta-1:

| Time prior AKI stage | Cutoff value | sens | spec | Quartile | OR | 95% CI of OR | |
|---|---|---|---|---|---|---|---|
| | | sCr or UO | | | | | |
| 0 hours | 0.882523148 | 75% | 28% | 1 | | | |
| | 0.286565061 | 88% | 5% | 2 | 1.1 | 0.1 | 9.1 |
| | 0 | 100% | 0% | 3 | 1.0 | 0.1 | 8.6 |
| | 2.715933476 | 25% | 71% | 4 | 1.1 | 0.1 | 9.1 |
| | 4.478276353 | 0% | 81% | | | | |
| | 6.43966763 | 0% | 91% | | | | |
| 24 hours | 0.581395349 | 100% | 17% | 1 | | | |
| | 0.581395349 | 100% | 17% | 2 | 0.0 | 0.0 | 65535.0 |
| | 0.581395349 | 100% | 17% | 3 | 1.0 | 0.0 | 61.9 |
| | 2.715933476 | 33% | 71% | 4 | 1.0 | 0.0 | 58.5 |
| | 4.478276353 | 33% | 81% | | | | |
| | 6.43966763 | 0% | 91% | | | | |
| 48 hours | 1.575912017 | 100% | 53% | 1 | | | |
| | 1.575912017 | 100% | 53% | 2 | na | na | na |
| | 1.575912017 | 100% | 53% | 3 | na | na | na |
| | 2.715933476 | 0% | 71% | 4 | na | na | na |
| | 4.478276353 | 0% | 81% | | | | |
| | 6.43966763 | 0% | 91% | | | | |
| | | sCr only | | | | | |
| 0 hours | 4.258928571 | 100% | 81% | 1 | | | |
| | 4.258928571 | 100% | 81% | 2 | na | na | na |
| | 4.258928571 | 100% | 81% | 3 | na | na | na |
| | 2.713815789 | 100% | 71% | 4 | na | na | na |
| | 3.926282051 | 100% | 80% | | | | |
| | 6.43966763 | 0% | 91% | | | | |
| 24 hours | 5.973214286 | 100% | 90% | 1 | | | |
| | 5.973214286 | 100% | 90% | 2 | na | na | na |
| | 5.973214286 | 100% | 90% | 3 | na | na | na |
| | 2.713815789 | 100% | 71% | 4 | na | na | na |
| | 3.926282051 | 100% | 80% | | | | |
| | 6.43966763 | 0% | 91% | | | | |
| 48 hours | 0.446428571 | 100% | 13% | 1 | | | |
| | 0.446428571 | 100% | 13% | 2 | na | na | na |
| | 0.446428571 | 100% | 13% | 3 | na | na | na |
| | 2.713815789 | 0% | 71% | 4 | na | na | na |
| | 3.926282051 | 0% | 80% | | | | |
| | 6.43966763 | 0% | 91% | | | | |
| | | UO only | | | | | |
| 0 hours | 0.882523148 | 75% | 30% | 1 | | | |
| | 0.286565061 | 88% | 5% | 2 | 1.1 | 0.1 | 9.8 |
| | 0 | 100% | 0% | 3 | 1.1 | 0.1 | 9.8 |
| | 2.110745614 | 38% | 70% | 4 | 1.1 | 0.1 | 9.8 |
| | 3.169642857 | 25% | 80% | | | | |
| | 5.332977208 | 0% | 90% | | | | |
| 24 hours | 0.581395349 | 100% | 18% | 1 | | | |
| | 0.581395349 | 100% | 18% | 2 | na | na | na |
| | 0.581395349 | 100% | 18% | 3 | na | na | na |
| | 2.110745614 | 0% | 70% | 4 | na | na | na |
| | 3.169642857 | 0% | 80% | | | | |
| | 5.332977208 | 0% | 90% | | | | |
| 48 hours | 1.978272532 | 100% | 67% | 1 | | | |
| | 1.978272532 | 100% | 67% | 2 | na | na | na |
| | 1.978272532 | 100% | 67% | 3 | na | na | na |
| | 2.110745614 | 0% | 70% | 4 | na | na | na |
| | 3.169642857 | 0% | 80% | | | | |
| | 5.332977208 | 0% | 90% | | | | |

Example 8

Kidney Injury Markers for Evaluating Renal Status in Patients Progressing from Stage R to Stages I and F Patients were classified and analyzed as described in Example 6, but only those patients that reached Stage R were included in this example. Cohort 1 contained patients that reached stage R but did not progress to stage I or F within 10 days, and Cohort 2 included only patients that progressed to stage I or F. Marker concentrations in urine samples collected within 12 hours of reaching stage R were included in the analysis for both Cohort 1 and 2.

The following descriptive statistics were obtained

Alpha-1-Antitrypsin:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 0.001 | 0.001 | 0.001 | 0.001 | 0.001 | 0.001 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.563 |  | 0.563 |  | 0.563 |
| min | 0.000 | 0.000 | 0.000 | 0.000 | 0.000 | 0.000 |
| max | 0.005 | 0.003 | 0.005 | 0.003 | 0.005 | 0.003 |
| n (Samp) | 33 | 16 | 33 | 16 | 33 | 16 |
| n (Pat) | 33 | 16 | 33 | 16 | 33 | 16 |
| sCr only | | | | | | |
| median | 0.001 | 0.002 | 0.001 | 0.002 | 0.001 | 0.002 |
| average | 0.001 | 0.002 | 0.001 | 0.002 | 0.001 | 0.002 |
| stdev | 0.001 | 0.001 | 0.001 | 0.001 | 0.001 | 0.001 |
| p (t-test) |  | 0.035 |  | 0.035 |  | 0.035 |
| min | 0.000 | 0.001 | 0.000 | 0.001 | 0.000 | 0.001 |
| max | 0.003 | 0.003 | 0.003 | 0.003 | 0.003 | 0.003 |
| n (Samp) | 14 | 5 | 14 | 5 | 14 | 5 |
| n (Pat) | 14 | 5 | 14 | 5 | 14 | 5 |
| UO only | | | | | | |
| median | 0.001 | 0.001 | 0.001 | 0.001 | 0.001 | 0.001 |
| average | 0.001 | 0.001 | 0.001 | 0.001 | 0.001 | 0.001 |
| stdev | 0.001 | 0.001 | 0.001 | 0.001 | 0.001 | 0.001 |
| p (t-test) |  | 0.179 |  | 0.179 |  | 0.179 |
| min | 0.000 | 0.000 | 0.000 | 0.000 | 0.000 | 0.000 |
| max | 0.005 | 0.002 | 0.005 | 0.002 | 0.005 | 0.002 |
| n (Samp) | 25 | 13 | 25 | 13 | 25 | 13 |
| n (Pat) | 25 | 13 | 25 | 13 | 25 | 13 |

Leukocyte Elastase:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 28.438 | 71.179 | 28.438 | 71.179 | 28.438 | 71.179 |
| average | 39.562 | 69.189 | 39.562 | 69.189 | 39.562 | 69.189 |
| stdev | 37.684 | 40.182 | 37.684 | 40.182 | 37.684 | 40.182 |
| p (t-test) |  | 0.013 |  | 0.013 |  | 0.013 |
| min | 2.989 | 3.950 | 2.989 | 3.950 | 2.989 | 3.950 |
| max | 125.675 | 124.623 | 125.675 | 124.623 | 125.675 | 124.623 |
| n (Samp) | 33 | 17 | 33 | 17 | 33 | 17 |
| n (Pat) | 33 | 17 | 33 | 17 | 33 | 17 |
| sCr only | | | | | | |
| median | 37.273 | 57.332 | 37.273 | 57.332 | 37.273 | 57.332 |
| average | 44.713 | 55.067 | 44.713 | 55.067 | 44.713 | 55.067 |
| stdev | 37.604 | 38.895 | 37.604 | 38.895 | 37.604 | 38.895 |
| p (t-test) |  | 0.616 |  | 0.616 |  | 0.616 |
| min | 3.965 | 4.010 | 3.965 | 4.010 | 3.965 | 4.010 |
| max | 118.380 | 103.409 | 118.380 | 103.409 | 118.380 | 103.409 |
| n (Samp) | 12 | 5 | 12 | 5 | 12 | 5 |
| n (Pat) | 12 | 5 | 12 | 5 | 12 | 5 |
| UO only | | | | | | |
| median | 22.957 | 73.466 | 22.957 | 73.466 | 22.957 | 73.466 |
| average | 40.248 | 66.363 | 40.248 | 66.363 | 40.248 | 66.363 |
| stdev | 40.543 | 42.234 | 40.543 | 42.234 | 40.543 | 42.234 |
| p (t-test) |  | 0.067 |  | 0.067 |  | 0.067 |
| min | 2.989 | 3.776 | 2.989 | 3.776 | 2.989 | 3.776 |
| max | 125.675 | 124.623 | 125.675 | 124.623 | 125.675 | 124.623 |
| n (Samp) | 24 | 14 | 24 | 14 | 24 | 14 |
| n (Pat) | 24 | 14 | 24 | 14 | 24 | 14 |

Soluble Tumor Necrosis Factor Receptor Superfamily Member 6:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 509.986 | 522.008 | 509.986 | 522.008 | 509.986 | 522.008 |
| average | 571.908 | 730.530 | 571.908 | 730.530 | 571.908 | 730.530 |
| stdev | 432.649 | 577.043 | 432.649 | 577.043 | 432.649 | 577.043 |
| p (t-test) |  | 0.339 |  | 0.339 |  | 0.339 |
| min | 57.065 | 225.000 | 57.065 | 225.000 | 57.065 | 225.000 |
| max | 1846.785 | 2002.736 | 1846.785 | 2002.736 | 1846.785 | 2002.736 |
| n (Samp) | 29 | 12 | 29 | 12 | 29 | 12 |
| n (Pat) | 29 | 12 | 29 | 12 | 29 | 12 |
| Cr only | | | | | | |
| median | 317.365 | 1480.020 | 317.365 | 1480.020 | 317.365 | 1480.020 |
| average | 412.409 | 1327.735 | 412.409 | 1327.735 | 412.409 | 1327.735 |
| stdev | 357.389 | 711.474 | 357.389 | 711.474 | 357.389 | 711.474 |
| p (t-test) |  | 0.005 |  | 0.005 |  | 0.005 |

-continued

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| min | 57.065 | 348.164 | 57.065 | 348.164 | 57.065 | 348.164 |
| max | 1082.777 | 2002.736 | 1082.777 | 2002.736 | 1082.777 | 2002.736 |
| n (Samp) | 11 | 4 | 11 | 4 | 11 | 4 |
| n (Pat) | 11 | 4 | 11 | 4 | 11 | 4 |
|  | | UO only | | | | |
| median | 615.549 | 416.168 | 615.549 | 416.168 | 615.549 | 416.168 |
| average | 663.825 | 582.789 | 663.825 | 582.789 | 663.825 | 582.789 |
| stdev | 445.268 | 477.453 | 445.268 | 477.453 | 445.268 | 477.453 |
| p (t-test) |  | 0.671 |  | 0.671 |  | 0.671 |
| min | 108.491 | 225.000 | 108.491 | 225.000 | 108.491 | 225.000 |
| max | 1846.785 | 1648.865 | 1846.785 | 1648.865 | 1846.785 | 1648.865 |
| n (Samp) | 21 | 8 | 21 | 8 | 21 | 8 |
| n (Pat) | 21 | 8 | 21 | 8 | 21 | 8 |

In the following tables, the ability to distinguish cohort 1 (subjects remaining in RIFLE R) from Cohort 2 (subjects progressing to RIFLE I or F) was determined using ROC analysis.

Alpha-1-Antitrypsin:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.48 | 0.088 | 33 | 16 | 1.153 |
| 24 hours | 0.48 | 0.088 | 33 | 16 | 1.153 |
| 48 hours | 0.48 | 0.088 | 33 | 16 | 1.153 |
| Cohort 1 v Cohort 2, adjudicated on serum creatinine | | | | | |
| 0 hours | 0.81 | 0.127 | 14 | 5 | 0.013 |
| 24 hours | 0.81 | 0.127 | 14 | 5 | 0.013 |
| 48 hours | 0.81 | 0.127 | 14 | 5 | 0.013 |
| Cohort 1 v Cohort 2, adjudicated on urine output | | | | | |
| 0 hours | 0.39 | 0.095 | 25 | 13 | 1.750 |
| 24 hours | 0.39 | 0.095 | 25 | 13 | 1.750 |
| 48 hours | 0.39 | 0.095 | 25 | 13 | 1.750 |

Leukocyte Elastase:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.70 | 0.082 | 33 | 17 | 0.015 |
| 24 hours | 0.70 | 0.082 | 33 | 17 | 0.015 |
| 48 hours | 0.70 | 0.082 | 33 | 17 | 0.015 |
| Cohort 1 v Cohort 2, adjudicated on serum creatinine | | | | | |
| 0 hours | 0.58 | 0.159 | 12 | 5 | 0.600 |
| 24 hours | 0.58 | 0.159 | 12 | 5 | 0.600 |
| 48 hours | 0.58 | 0.159 | 12 | 5 | 0.600 |
| Cohort 1 v Cohort 2, adjudicated on urine output | | | | | |
| 0 hours | 0.67 | 0.094 | 24 | 14 | 0.077 |
| 24 hours | 0.67 | 0.094 | 24 | 14 | 0.077 |
| 48 hours | 0.67 | 0.094 | 24 | 14 | 0.077 |

Soluble Tumor Necrosis Factor Receptor Superfamily Member 6:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.58 | 0.101 | 29 | 12 | 0.442 |
| 24 hours | 0.58 | 0.101 | 29 | 12 | 0.442 |
| 48 hours | 0.58 | 0.101 | 29 | 12 | 0.442 |
| Cohort 1 v Cohort 2, adjudicated on serum creatinine | | | | | |
| 0 hours | 0.91 | 0.106 | 11 | 4 | 0.000 |
| 24 hours | 0.91 | 0.106 | 11 | 4 | 0.000 |
| 48 hours | 0.91 | 0.106 | 11 | 4 | 0.000 |
| Cohort 1 v Cohort 2, adjudicated on urine output | | | | | |
| 0 hours | 0.40 | 0.116 | 21 | 8 | 1.589 |
| 24 hours | 0.40 | 0.116 | 21 | 8 | 1.589 |
| 48 hours | 0.40 | 0.116 | 21 | 8 | 1.589 |

Various threshold (or "cutoff") concentrations were selected, and the associated sensitivity and specificity for distinguishing cohort 1 from cohort 2, as shown in the following tables. OR is the odds ratio calculated for the particular cutoff concentration, and 95% CI is the confidence interval for the odds ratio:

Alpha-1-Antitrypsin:

| Time prior AKI stage | Cutoff value | sens | spec | Quartile | OR | 95% CI of OR | |
| --- | --- | --- | --- | --- | --- | --- | --- |
| | | | sCr or UO | | | | |
| 0 hours | 0.000361 | 75% | 27% | 1 | | | |
|  | 0.000283 | 81% | 24% | 2 | 0.8 | 0.2 | 3.6 |
|  | 0.000126 | 94% | 18% | 3 | 1.6 | 0.4 | 6.4 |
|  | 0.00164 | 25% | 73% | 4 | 1.1 | 0.3 | 4.8 |
|  | 0.00202 | 6% | 82% |  | | | |
|  | 0.0028 | 0% | 97% |  | | | |
| 24 hours | 0.000361 | 75% | 27% | 1 | | | |
|  | 0.000283 | 81% | 24% | 2 | 0.8 | 0.2 | 3.6 |
|  | 0.000126 | 94% | 18% | 3 | 1.6 | 0.4 | 6.4 |
|  | 0.00164 | 25% | 73% | 4 | 1.1 | 0.3 | 4.8 |
|  | 0.00202 | 6% | 82% |  | | | |
|  | 0.0028 | 0% | 97% |  | | | |
| 48 hours | 0.000361 | 75% | 27% | 1 | | | |
|  | 0.000283 | 81% | 24% | 2 | 0.8 | 0.2 | 3.6 |
|  | 0.000126 | 94% | 18% | 3 | 1.6 | 0.4 | 6.4 |
|  | 0.00164 | 25% | 73% | 4 | 1.1 | 0.3 | 4.8 |

-continued

| Time prior AKI stage | Cutoff value | sens | spec | Quartile | OR | 95% CI of OR |
|---|---|---|---|---|---|---|
|  | 0.00202 | 6% | 82% |  |  |  |
|  | 0.0028 | 0% | 97% |  |  |  |
| sCr only |  |  |  |  |  |  |
| 0 hours | 0.00135 | 80% | 86% | 1 |  |  |
|  | 0.00135 | 80% | 86% | 2 | na | na na |
|  | 0.000814 | 100% | 57% | 3 | na | na na |
|  | 0.000935 | 80% | 71% | 4 | na | na na |
|  | 0.00135 | 80% | 86% |  |  |  |
|  | 0.00175 | 20% | 93% |  |  |  |
| 24 hours | 0.00135 | 80% | 86% | 1 |  |  |
|  | 0.00135 | 80% | 86% | 2 | na | na na |
|  | 0.000814 | 100% | 57% | 3 | na | na na |
|  | 0.000935 | 80% | 71% | 4 | na | na na |
|  | 0.00135 | 80% | 86% |  |  |  |
|  | 0.00175 | 20% | 93% |  |  |  |
| 48 hours | 0.00135 | 80% | 86% | 1 |  |  |
|  | 0.00135 | 80% | 86% | 2 | na | na na |
|  | 0.000814 | 100% | 57% | 3 | na | na na |
|  | 0.000935 | 80% | 71% | 4 | na | na na |
|  | 0.00135 | 80% | 86% |  |  |  |
|  | 0.00175 | 20% | 93% |  |  |  |
| UO only |  |  |  |  |  |  |
| 0 hours | 0.000283 | 77% | 20% | 1 |  |  |
|  | 0.000184 | 85% | 16% | 2 | 1.1 | 0.1 13.7 |
|  | 0.000126 | 92% | 16% | 3 | 4.0 | 0.5 29.8 |
|  | 0.00164 | 15% | 72% | 4 | 3.2 | 0.4 26.3 |
|  | 0.00202 | 0% | 80% |  |  |  |
|  | 0.0028 | 0% | 96% |  |  |  |
| 24 hours | 0.000283 | 77% | 20% | 1 |  |  |
|  | 0.000184 | 85% | 16% | 2 | 1.1 | 0.1 13.7 |
|  | 0.000126 | 92% | 16% | 3 | 4.0 | 0.5 29.8 |
|  | 0.00164 | 15% | 72% | 4 | 3.2 | 0.4 26.3 |
|  | 0.00202 | 0% | 80% |  |  |  |
|  | 0.0028 | 0% | 96% |  |  |  |
| 48 hours | 0.000283 | 77% | 20% | 1 |  |  |
|  | 0.000184 | 85% | 16% | 2 | 1.1 | 0.1 13.7 |
|  | 0.000126 | 92% | 16% | 3 | 4.0 | 0.5 29.8 |
|  | 0.00164 | 15% | 72% | 4 | 3.2 | 0.4 26.3 |
|  | 0.00202 | 0% | 80% |  |  |  |
|  | 0.0028 | 0% | 96% |  |  |  |

Leukocyte Elastase:

| Time prior AKI stage | Cutoff value | sens | spec | Quartile | OR | 95% CI of OR |
|---|---|---|---|---|---|---|
| sCr or UO |  |  |  |  |  |  |
| 0 hours | 55.8934338 | 71% | 73% | 1 |  |  |
|  | 28.4375 | 82% | 52% | 2 | 1.5 | 0.2 11.4 |
|  | 3.965336134 | 94% | 9% | 3 | 5.0 | 0.8 31.1 |
|  | 55.8934338 | 71% | 73% | 4 | 4.3 | 0.7 25.5 |
|  | 81.89300412 | 35% | 82% |  |  |  |
|  | 97.87405813 | 29% | 91% |  |  |  |
| 24 hours | 55.8934338 | 71% | 73% | 1 |  |  |
|  | 28.4375 | 82% | 52% | 2 | 1.5 | 0.2 11.4 |
|  | 3.965336134 | 94% | 9% | 3 | 5.0 | 0.8 31.1 |
|  | 55.8934338 | 71% | 73% | 4 | 4.3 | 0.7 25.5 |
|  | 81.89300412 | 35% | 82% |  |  |  |
|  | 97.87405813 | 29% | 91% |  |  |  |
| 48 hours | 55.8934338 | 71% | 73% | 1 |  |  |
|  | 28.4375 | 82% | 52% | 2 | 1.5 | 0.2 11.4 |
|  | 3.965336134 | 94% | 9% | 3 | 5.0 | 0.8 31.1 |
|  | 55.8934338 | 71% | 73% | 4 | 4.3 | 0.7 25.5 |
|  | 81.89300412 | 35% | 82% |  |  |  |
|  | 97.87405813 | 29% | 91% |  |  |  |
| sCr only |  |  |  |  |  |  |
| 0 hours | 19.39903846 | 80% | 42% | 1 |  |  |
|  | 19.39903846 | 80% | 42% | 2 | 1.0 | 0.0 186.2 |
|  | 3.965336134 | 100% | 8% | 3 | 1.0 | 0.0 186.2 |
|  | 65.40865385 | 40% | 75% | 4 | 2.0 | 0.0 139.7 |
|  | 71.17868676 | 40% | 83% |  |  |  |
|  | 101.4800861 | 20% | 92% |  |  |  |
| 24 hours | 19.39903846 | 80% | 42% | 1 |  |  |
|  | 19.39903846 | 80% | 42% | 2 | 1.0 | 0.0 186.2 |
|  | 3.965336134 | 100% | 8% | 3 | 1.0 | 0.0 186.2 |
|  | 65.40865385 | 40% | 75% | 4 | 2.0 | 0.0 139.7 |
|  | 71.17868676 | 40% | 83% |  |  |  |
|  | 101.4800861 | 20% | 92% |  |  |  |
| 48 hours | 19.39903846 | 80% | 42% | 1 |  |  |
|  | 19.39903846 | 80% | 42% | 2 | 1.0 | 0.0 186.2 |
|  | 3.965336134 | 100% | 8% | 3 | 1.0 | 0.0 186.2 |
|  | 65.40865385 | 40% | 75% | 4 | 2.0 | 0.0 139.7 |
|  | 71.17868676 | 40% | 83% |  |  |  |
|  | 101.4800861 | 20% | 92% |  |  |  |
| UO only |  |  |  |  |  |  |
| 0 hours | 36.17788462 | 71% | 58% | 1 |  |  |
|  | 10.20281457 | 86% | 46% | 2 | 1.5 | 0.2 13.4 |
|  | 3.776041667 | 93% | 8% | 3 | 2.8 | 0.3 23.8 |
|  | 55.8934338 | 64% | 71% | 4 | 3.5 | 0.5 27.0 |
|  | 92.52400549 | 36% | 83% |  |  |  |
|  | 97.87405813 | 29% | 92% |  |  |  |
| 24 hours | 36.17788462 | 71% | 58% | 1 |  |  |
|  | 10.20281457 | 86% | 46% | 2 | 1.5 | 0.2 13.4 |
|  | 3.776041667 | 93% | 8% | 3 | 2.8 | 0.3 23.8 |
|  | 55.8934338 | 64% | 71% | 4 | 3.5 | 0.5 27.0 |
|  | 92.52400549 | 36% | 83% |  |  |  |
|  | 97.87405813 | 29% | 92% |  |  |  |
| 48 hours | 36.17788462 | 71% | 58% | 1 |  |  |
|  | 10.20281457 | 86% | 46% | 2 | 1.5 | 0.2 13.4 |
|  | 3.776041667 | 93% | 8% | 3 | 2.8 | 0.3 23.8 |
|  | 55.8934338 | 64% | 71% | 4 | 3.5 | 0.5 27.0 |
|  | 92.52400549 | 36% | 83% |  |  |  |
|  | 97.87405813 | 29% | 92% |  |  |  |

Soluble Tumor Necrosis Factor Receptor Superfamily Member 6:

| Time prior AKI stage | Cutoff value | sens | spec | Quartile | OR | 95% CI of OR |
|---|---|---|---|---|---|---|
| sCr or UO |  |  |  |  |  |  |
| 0 hours | 344.3113772 | 75% | 38% | 1 |  |  |
|  | 243.2065217 | 83% | 31% | 2 | 2.7 | 0.3 20.5 |
|  | 225 | 92% | 28% | 3 | 1.0 | 0.1 11.6 |
|  | 698.2881598 | 33% | 72% | 4 | 2.3 | 0.3 16.8 |
|  | 857.3692552 | 25% | 83% |  |  |  |
|  | 1273.352436 | 17% | 93% |  |  |  |
| 24 hours | 344.3113772 | 75% | 38% | 1 |  |  |
|  | 243.2065217 | 83% | 31% | 2 | 2.7 | 0.3 20.5 |
|  | 225 | 92% | 28% | 3 | 1.0 | 0.1 11.6 |
|  | 698.2881598 | 33% | 72% | 4 | 2.3 | 0.3 16.8 |

-continued

| Time prior AKI stage | Cutoff value | sens | spec | Quartile | OR | 95% CI of OR | |
|---|---|---|---|---|---|---|---|
| 48 hours | 857.3692552 | 25% | 83% | | | | |
| | 1273.352436 | 17% | 93% | | | | |
| | 344.3113772 | 75% | 38% | 1 | | | |
| | 243.2065217 | 83% | 31% | 2 | 2.7 | 0.3 | 20.5 |
| | 225 | 92% | 28% | 3 | 1.0 | 0.1 | 11.6 |
| | 698.2881598 | 33% | 72% | 4 | 2.3 | 0.3 | 16.8 |
| | 857.3692552 | 25% | 83% | | | | |
| | 1273.352436 | 17% | 93% | | | | |
| sCr only | | | | | | | |
| 0 hours | 1082.777036 | 75% | 100% | 1 | | | |
| | 344.3113772 | 100% | 64% | 2 | na | na | na |
| | 344.3113772 | 100% | 64% | 3 | na | na | na |
| | 427.7912621 | 75% | 73% | 4 | na | na | na |
| | 670.3645008 | 75% | 82% | | | | |
| | 1010.680908 | 75% | 91% | | | | |
| 24 hours | 1082.777036 | 75% | 100% | 1 | | | |
| | 344.3113772 | 100% | 64% | 2 | na | na | na |
| | 344.3113772 | 100% | 64% | 3 | na | na | na |
| | 427.7912621 | 75% | 73% | 4 | na | na | na |
| | 670.3645008 | 75% | 82% | | | | |
| | 1010.680908 | 75% | 91% | | | | |
| 48 hours | 1082.777036 | 75% | 100% | 1 | | | |
| | 344.3113772 | 100% | 64% | 2 | na | na | na |
| | 344.3113772 | 100% | 64% | 3 | na | na | na |
| | 427.7912621 | 75% | 73% | 4 | na | na | na |
| | 670.3645008 | 75% | 82% | | | | |
| | 1010.680908 | 75% | 91% | | | | |
| UO only | | | | | | | |
| 0 hours | 243.2065217 | 75% | 24% | 1 | | | |
| | 225 | 88% | 19% | 2 | 0.0 | 0.0 | 65535.0 |
| | 206.5217391 | 100% | 19% | 3 | 4.0 | 0.3 | 46.4 |
| | 722.027972 | 25% | 71% | 4 | 1.2 | 0.1 | 17.5 |
| | 857.3692552 | 13% | 81% | | | | |
| | 1273.352436 | 13% | 90% | | | | |
| 24 hours | 243.2065217 | 75% | 24% | 1 | | | |
| | 225 | 88% | 19% | 2 | 0.0 | 0.0 | 65535.0 |
| | 206.5217391 | 100% | 19% | 3 | 4.0 | 0.3 | 46.4 |
| | 722.027972 | 25% | 71% | 4 | 1.2 | 0.1 | 17.5 |
| | 857.3692552 | 13% | 81% | | | | |
| | 1273.352436 | 13% | 90% | | | | |
| 48 hours | 243.2065217 | 75% | 24% | 1 | | | |
| | 225 | 88% | 19% | 2 | 0.0 | 0.0 | 65535.0 |
| | 206.5217391 | 100% | 19% | 3 | 4.0 | 0.3 | 46.4 |
| | 722.027972 | 25% | 71% | 4 | 1.2 | 0.1 | 17.5 |
| | 857.3692552 | 13% | 81% | | | | |
| | 1273.352436 | 13% | 90% | | | | |

Example 9

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels in blood samples collected for Cohort 1. Marker concentrations were measured in the plasma component of the blood samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The following descriptive statistics were obtained:
Soluble p-Selectin:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 70.572 | 83.841 | 70.572 | 69.671 | 70.572 | na |
| average | 71.352 | 85.322 | 71.352 | 72.002 | 71.352 | na |
| stdev | 31.877 | 25.092 | 31.877 | 39.791 | 31.877 | na |
| p (t-test) |  | 0.266 |  | 0.953 |  | na |
| min | 26.445 | 56.486 | 26.445 | 27.323 | 26.445 | na |
| max | 148.265 | 119.078 | 148.265 | 195.149 | 148.265 | na |
| n (Samp) | 26 | 8 | 26 | 17 | 26 | 0 |
| n (Pat) | 25 | 8 | 25 | 17 | 25 | 0 |
| sCr only | | | | | | |
| median | 69.882 | 63.763 | 69.882 | 48.651 | 69.882 | 22.994 |
| average | 75.831 | 63.763 | 75.831 | 62.269 | 75.831 | 104.567 |
| stdev | 39.565 | 10.291 | 39.565 | 27.300 | 39.565 | na |
| p (t-test) |  | 0.672 |  | 0.331 |  | na |
| min | 22.994 | 56.486 | 22.994 | 34.538 | 22.994 | 104.567 |
| max | 196.760 | 71.039 | 196.760 | 106.261 | 196.760 | 104.567 |
| n (Samp) | 47 | 2 | 47 | 9 | 47 | 1 |
| n (Pat) | 44 | 2 | 44 | 9 | 44 | 1 |
| UO only | | | | | | |
| median | 71.039 | 96.643 | 71.039 | 69.671 | 71.039 | 26.445 |
| average | 69.479 | 87.362 | 69.479 | 76.898 | 69.479 | 71.409 |
| stdev | 32.279 | 26.376 | 32.279 | 43.557 | 32.279 | na |
| p (t-test) |  | 0.187 |  | 0.566 |  | na |
| min | 26.445 | 56.486 | 26.445 | 27.323 | 26.445 | 71.409 |
| max | 148.265 | 119.078 | 148.265 | 195.149 | 148.265 | 71.409 |
| n (Samp) | 27 | 7 | 27 | 11 | 27 | 1 |
| n (Pat) | 25 | 7 | 25 | 11 | 25 | 1 |

Protein NOV Homolog:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 7867.816 | 10136.555 | 7867.816 | 11134.454 | 7867.816 | 14.544 |
| average | 32628.823 | 11619.711 | 32628.823 | 11746.019 | 32628.823 | 13928.571 |
| stdev | 118993.020 | 7490.315 | 118993.020 | 9009.294 | 118993.020 | na |
| p (t-test) |  | 0.422 |  | 0.436 |  | na |
| min | 14.544 | 1362.398 | 14.544 | 730.519 | 14.544 | 13928.571 |
| max | 1005084.746 | 29632.588 | 1005084.746 | 32110.092 | 1005084.746 | 13928.571 |
| n (Samp) | 82 | 21 | 82 | 20 | 82 | 1 |
| n (Pat) | 47 | 21 | 47 | 20 | 47 | 1 |
| sCr only | | | | | | |
| median | 8560.924 | 15515.485 | 8560.924 | 11263.342 | 8560.924 | 21232.057 |
| average | 24336.406 | 20501.633 | 24336.406 | 13302.341 | 24336.406 | 28699.397 |
| stdev | 93316.115 | 16311.708 | 93316.115 | 9797.524 | 93316.115 | 19613.823 |
| p (t-test) |  | 0.908 |  | 0.684 |  | 0.936 |
| min | 14.544 | 1362.398 | 14.544 | 730.519 | 14.544 | 13916.016 |
| max | 1005084.746 | 54988.124 | 1005084.746 | 39449.541 | 1005084.746 | 50950.119 |
| n (Samp) | 135 | 8 | 135 | 12 | 135 | 3 |
| n (Pat) | 78 | 8 | 78 | 12 | 78 | 3 |
| UO only | | | | | | |
| median | 9195.402 | 12646.484 | 9195.402 | 11449.580 | 9195.402 | 13629.325 |
| average | 36969.265 | 13836.073 | 36969.265 | 15641.491 | 36969.265 | 13629.325 |
| stdev | 130178.851 | 8858.174 | 130178.851 | 13967.881 | 130178.851 | 423.199 |
| p (t-test) |  | 0.420 |  | 0.544 |  | 0.802 |
| min | 14.544 | 1542.208 | 14.544 | 974.026 | 14.544 | 13330.078 |
| max | 1005084.746 | 32827.476 | 1005084.746 | 48955.614 | 1005084.746 | 13928.571 |
| n (Samp) | 68 | 21 | 68 | 14 | 68 | 2 |
| n (Pat) | 37 | 21 | 37 | 14 | 37 | 2 |

Netrin 4:

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| median | 0.012 | 0.016 | 0.012 | 0.023 | 0.012 | 0.005 |
| average | 0.332 | 0.024 | 0.332 | 0.064 | 0.332 | 0.038 |
| stdev | 1.597 | 0.018 | 1.597 | 0.084 | 1.597 | na |
| p (t-test) | | 0.492 | | 0.774 | | na |
| min | 0.005 | 0.007 | 0.005 | 0.008 | 0.005 | 0.038 |
| max | 8.584 | 0.062 | 8.584 | 0.161 | 8.584 | 0.038 |
| n (Samp) | 56 | 13 | 56 | 3 | 56 | 1 |
| n (Pat) | 37 | 13 | 37 | 3 | 37 | 1 |
| sCr only | | | | | | |
| median | 0.013 | 0.037 | 0.013 | 0.027 | 0.013 | 0.012 |
| average | 0.220 | 0.035 | 0.220 | 0.070 | 0.220 | 0.012 |
| stdev | 1.279 | 0.017 | 1.279 | 0.078 | 1.279 | 0.007 |
| p (t-test) | | 0.725 | | 0.840 | | 0.820 |
| min | 0.005 | 0.009 | 0.005 | 0.023 | 0.005 | 0.007 |
| max | 8.584 | 0.053 | 8.584 | 0.161 | 8.584 | 0.017 |
| n (Samp) | 88 | 6 | 88 | 3 | 88 | 2 |
| n (Pat) | 61 | 6 | 61 | 3 | 61 | 2 |
| UO only | | | | | | |
| median | 0.011 | 0.018 | 0.011 | 0.019 | 0.011 | 0.005 |
| average | 0.437 | 0.024 | 0.437 | 0.017 | 0.437 | 0.038 |
| stdev | 1.861 | 0.018 | 1.861 | 0.008 | 1.861 | na |
| p (t-test) | | 0.413 | | 0.701 | | na |
| min | 0.005 | 0.007 | 0.005 | 0.008 | 0.005 | 0.038 |
| max | 8.584 | 0.062 | 8.584 | 0.023 | 8.584 | 0.038 |
| n (Samp) | 41 | 14 | 41 | 3 | 41 | 1 |
| n (Pat) | 27 | 14 | 27 | 3 | 27 | 1 |

Haptoglobin:

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| median | 2.650 | 1.820 | 2.650 | 1.910 | 2.650 | 2.400 |
| average | 3.055 | 2.257 | 3.055 | 2.372 | 3.055 | 2.704 |
| stdev | 2.226 | 1.750 | 2.226 | 1.940 | 2.226 | 2.157 |
| p (t-test) | | 0.044 | | 0.044 | | 0.481 |
| min | 0.000 | 0.000 | 0.000 | 0.000 | 0.000 | 0.021 |
| max | 12.700 | 7.060 | 12.700 | 8.540 | 12.700 | 8.970 |
| n (Samp) | 221 | 35 | 221 | 51 | 221 | 22 |
| n (Pat) | 80 | 35 | 80 | 51 | 80 | 22 |
| sCr only | | | | | | |
| median | 2.465 | 1.640 | 2.465 | 1.910 | 2.465 | 1.985 |
| average | 2.759 | 2.213 | 2.759 | 2.473 | 2.759 | 1.804 |
| stdev | 2.083 | 2.136 | 2.083 | 2.067 | 2.083 | 0.796 |
| p (t-test) | | 0.306 | | 0.540 | | 0.149 |
| min | 0.000 | 0.000 | 0.000 | 0.000 | 0.000 | 0.703 |
| max | 12.700 | 8.320 | 12.700 | 8.870 | 12.700 | 2.730 |
| n (Samp) | 386 | 16 | 386 | 21 | 386 | 10 |
| n (Pat) | 129 | 16 | 129 | 21 | 129 | 10 |
| UO only | | | | | | |
| median | 2.190 | 1.620 | 2.190 | 2.160 | 2.190 | 2.670 |
| average | 2.571 | 2.144 | 2.571 | 2.446 | 2.571 | 2.863 |
| stdev | 2.000 | 1.724 | 2.000 | 2.021 | 2.000 | 2.289 |
| p (t-test) | | 0.245 | | 0.709 | | 0.533 |
| min | 0.000 | 0.019 | 0.000 | 0.000 | 0.000 | 0.021 |
| max | 12.700 | 7.060 | 12.700 | 8.540 | 12.700 | 8.970 |
| n (Samp) | 183 | 34 | 183 | 45 | 183 | 21 |
| n (Pat) | 65 | 34 | 65 | 45 | 65 | 21 |

Alpha-1-Antitrypsin:

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| median | 3.510 | 2.460 | 3.510 | 2.160 | 3.510 | 2.200 |
| average | 3.655 | 2.645 | 3.655 | 2.428 | 3.655 | 2.550 |
| stdev | 1.505 | 0.889 | 1.505 | 1.053 | 1.505 | 1.005 |
| p (t-test) | | 0.000 | | 0.000 | | 0.001 |
| min | 1.080 | 1.310 | 1.080 | 0.854 | 1.080 | 1.080 |
| max | 8.930 | 5.090 | 8.930 | 5.640 | 8.930 | 5.060 |
| n (Samp) | 221 | 35 | 221 | 51 | 221 | 22 |
| n (Pat) | 80 | 35 | 80 | 51 | 80 | 22 |
| sCr only | | | | | | |
| median | 3.040 | 2.505 | 3.040 | 2.390 | 3.040 | 2.670 |
| average | 3.311 | 2.854 | 3.311 | 2.558 | 3.311 | 2.701 |
| stdev | 1.455 | 1.465 | 1.455 | 1.354 | 1.455 | 1.386 |
| p (t-test) | | 0.220 | | 0.021 | | 0.191 |
| min | 0.769 | 1.220 | 0.769 | 0.968 | 0.769 | 0.737 |
| max | 8.930 | 6.700 | 8.930 | 5.580 | 8.930 | 5.060 |
| n (Samp) | 386 | 16 | 386 | 21 | 386 | 10 |
| n (Pat) | 129 | 16 | 129 | 21 | 129 | 10 |
| UO only | | | | | | |
| median | 3.240 | 2.550 | 3.240 | 2.170 | 3.240 | 2.160 |
| average | 3.533 | 2.860 | 3.533 | 2.553 | 3.533 | 2.438 |
| stdev | 1.410 | 1.092 | 1.410 | 1.086 | 1.410 | 0.910 |
| p (t-test) | | 0.009 | | 0.000 | | 0.001 |
| min | 1.080 | 1.310 | 1.080 | 0.854 | 1.080 | 1.080 |
| max | 8.230 | 6.250 | 8.230 | 5.640 | 8.230 | 5.060 |
| n (Samp) | 183 | 34 | 183 | 45 | 183 | 21 |
| n (Pat) | 65 | 34 | 65 | 45 | 65 | 21 |

Leukocyte Elastase:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 222.772 | 297.398 | 222.772 | 368.959 | 222.772 | 393.443 |
| average | 247.491 | 329.042 | 247.491 | 354.958 | 247.491 | 400.478 |
| stdev | 152.139 | 200.493 | 152.139 | 180.003 | 152.139 | 216.536 |
| p (t-test) |  | 0.021 |  | 0.000 |  | 0.000 |
| min | 8.409 | 48.240 | 8.409 | 1.849 | 8.409 | 80.793 |
| max | 1032.377 | 874.180 | 1032.377 | 816.803 | 1032.377 | 954.508 |
| n (Samp) | 84 | 31 | 84 | 46 | 84 | 22 |
| n (Pat) | 49 | 31 | 49 | 46 | 49 | 22 |
| sCr only | | | | | | |
| median | 264.962 | 408.843 | 264.962 | 328.996 | 264.962 | 373.327 |
| average | 304.658 | 485.313 | 304.658 | 314.930 | 304.658 | 397.912 |
| stdev | 184.125 | 424.976 | 184.125 | 181.513 | 184.125 | 260.693 |
| p (t-test) |  | 0.003 |  | 0.821 |  | 0.128 |
| min | 8.409 | 79.573 | 8.409 | 1.849 | 8.409 | 80.793 |
| max | 1032.377 | 1644.672 | 1032.377 | 689.754 | 1032.377 | 954.508 |
| n (Samp) | 200 | 12 | 200 | 18 | 200 | 10 |
| n (Pat) | 90 | 12 | 90 | 18 | 90 | 10 |
| UO only | | | | | | |
| median | 234.419 | 286.321 | 234.419 | 373.606 | 234.419 | 373.327 |
| average | 287.226 | 321.020 | 287.226 | 362.698 | 287.226 | 373.328 |
| stdev | 192.885 | 191.749 | 192.885 | 167.926 | 192.885 | 172.453 |
| p (t-test) |  | 0.435 |  | 0.044 |  | 0.073 |
| min | 8.409 | 48.240 | 8.409 | 36.724 | 8.409 | 82.317 |
| max | 1032.377 | 861.088 | 1032.377 | 816.803 | 1032.377 | 742.213 |
| n (Samp) | 76 | 27 | 76 | 37 | 76 | 20 |
| n (Pat) | 44 | 27 | 44 | 37 | 44 | 20 |

Soluble Tumor Necrosis Factor Receptor Superfamily Member 6:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 8865.415 | 12729.659 | 8865.415 | 10371.517 | 8865.415 | 10338.807 |
| average | 9989.544 | 12480.031 | 9989.544 | 11454.723 | 9989.544 | 10338.807 |
| stdev | 4535.217 | 4126.782 | 4535.217 | 3896.751 | 4535.217 | 4906.249 |
| p (t-test) |  | 0.037 |  | 0.156 |  | 0.914 |
| min | 3586.165 | 6493.109 | 3586.165 | 6171.516 | 3586.165 | 6869.565 |
| max | 21411.765 | 18935.447 | 21411.765 | 18618.347 | 21411.765 | 13808.050 |
| n (Samp) | 97 | 17 | 97 | 23 | 97 | 2 |
| n (Pat) | 34 | 17 | 34 | 23 | 34 | 2 |
| sCr only | | | | | | |
| median | 9860.870 | 15705.689 | 9860.870 | 9953.178 | 9860.870 | 12004.530 |
| average | 10987.374 | 14748.081 | 10987.374 | 11852.762 | 10987.374 | 12374.972 |
| stdev | 4642.075 | 3913.248 | 4642.075 | 3851.215 | 4642.075 | 1288.436 |
| p (t-test) |  | 0.052 |  | 0.500 |  | 0.607 |
| min | 3586.165 | 8367.072 | 3586.165 | 6202.144 | 3586.165 | 11312.336 |
| max | 21494.904 | 18437.146 | 21494.904 | 18618.347 | 21494.904 | 13808.050 |
| n (Samp) | 155 | 6 | 155 | 14 | 155 | 3 |
| n (Pat) | 56 | 6 | 56 | 14 | 56 | 3 |
| UO only | | | | | | |
| median | 8909.217 | 12729.659 | 8909.217 | 10828.803 | 8909.217 | 9831.547 |
| average | 9531.137 | 12459.768 | 9531.137 | 11236.077 | 9531.137 | 10169.720 |
| stdev | 3917.481 | 4106.211 | 3917.481 | 3615.748 | 3917.481 | 3481.582 |
| p (t-test) |  | 0.010 |  | 0.112 |  | 0.782 |
| min | 3586.165 | 6493.109 | 3586.165 | 6171.516 | 3586.165 | 6869.565 |
| max | 20557.276 | 18935.447 | 20557.276 | 18369.196 | 20557.276 | 13808.050 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| n (Samp) | 78 | 15 | 78 | 16 | 78 | 3 |
| n (Pat) | 29 | 15 | 29 | 16 | 29 | 3 |

Soluble Tumor Necrosis Factor Ligand Superfamily Member 6:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 42.775 | 39.610 | 42.775 | 55.696 | 42.775 | 49.616 |
| average | 51.446 | 48.676 | 51.446 | 66.236 | 51.446 | 49.616 |
| stdev | 28.498 | 31.762 | 28.498 | 37.719 | 28.498 | 5.370 |
| p (t-test) |  | 0.776 |  | 0.114 |  | 0.928 |
| min | 12.326 | 13.368 | 12.326 | 23.077 | 12.326 | 45.819 |
| max | 140.754 | 114.547 | 140.754 | 124.129 | 140.754 | 53.413 |
| n (Samp) | 77 | 10 | 77 | 12 | 77 | 2 |
| n (Pat) | 19 | 10 | 19 | 12 | 19 | 2 |
| sCr only | | | | | | |
| median | 43.362 | 37.796 | 43.362 | 41.424 | 43.362 | 44.816 |
| average | 53.571 | 32.283 | 53.571 | 58.881 | 53.571 | 37.263 |
| stdev | 31.254 | 12.032 | 31.254 | 37.415 | 31.254 | 13.960 |
| p (t-test) |  | 0.133 |  | 0.666 |  | 0.371 |
| min | 11.820 | 13.368 | 11.820 | 18.750 | 11.820 | 21.154 |
| max | 140.754 | 41.424 | 140.754 | 120.509 | 140.754 | 45.819 |
| n (Samp) | 117 | 5 | 117 | 7 | 117 | 3 |
| n (Pat) | 26 | 5 | 26 | 7 | 26 | 3 |
| UO only | | | | | | |
| median | 42.996 | 48.707 | 42.996 | 47.702 | 42.996 | 49.616 |
| average | 51.980 | 53.996 | 51.980 | 58.968 | 51.980 | 49.616 |
| stdev | 29.050 | 32.850 | 29.050 | 34.286 | 29.050 | 5.370 |
| p (t-test) |  | 0.857 |  | 0.496 |  | 0.910 |
| min | 12.326 | 20.673 | 12.326 | 23.077 | 12.326 | 45.819 |
| max | 140.754 | 114.547 | 140.754 | 124.129 | 140.754 | 53.413 |
| n (Samp) | 58 | 8 | 58 | 10 | 58 | 2 |
| n (Pat) | 14 | 8 | 14 | 10 | 14 | 2 |

Soluble Intercellular Adhesion Molecule 2:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 381.659 | 332.808 | 381.659 | 207.029 | 381.659 | na |
| average | 453.439 | 471.326 | 453.439 | 175.035 | 453.439 | na |
| stdev | 309.507 | 297.611 | 309.507 | 116.425 | 309.507 | na |
| p (t-test) |  | 0.863 |  | 0.131 |  | na |
| min | 1.944 | 115.768 | 1.944 | 45.957 | 1.944 | na |
| max | 1343.415 | 920.780 | 1343.415 | 272.118 | 1343.415 | na |
| n (Samp) | 47 | 11 | 47 | 3 | 47 | 0 |
| n (Pat) | 26 | 11 | 26 | 3 | 26 | 0 |
| sCr only | | | | | | |
| median | 352.709 | 274.877 | 352.709 | 207.029 | 352.709 | 571.024 |
| average | 437.179 | 299.470 | 437.179 | 214.280 | 437.179 | 571.024 |
| stdev | 300.781 | 95.717 | 300.781 | 172.063 | 300.781 | 371.283 |
| p (t-test) |  | 0.314 |  | 0.208 |  | 0.538 |
| min | 1.944 | 193.610 | 1.944 | 45.957 | 1.944 | 308.488 |
| max | 1343.415 | 445.517 | 1343.415 | 389.854 | 1343.415 | 833.561 |
| n (Samp) | 72 | 5 | 72 | 3 | 72 | 2 |
| n (Pat) | 43 | 5 | 43 | 3 | 43 | 2 |
| UO only | | | | | | |
| median | 354.483 | 392.230 | 354.483 | 272.118 | 354.483 | na |
| average | 492.930 | 482.921 | 492.930 | 312.819 | 492.930 | na |
| stdev | 322.471 | 281.363 | 322.471 | 130.973 | 322.471 | na |
| p (t-test) |  | 0.925 |  | 0.349 |  | na |
| min | 34.681 | 115.768 | 34.681 | 207.029 | 34.681 | na |
| max | 1343.415 | 920.780 | 1343.415 | 459.310 | 1343.415 | na |
| n (Samp) | 33 | 12 | 33 | 3 | 33 | 0 |
| n (Pat) | 16 | 12 | 16 | 3 | 16 | 0 |

Soluble Platelet Endothelial Cell Adhesion Molecule:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 73.208 | 64.207 | 73.208 | 52.986 | 73.208 | na |
| average | 77.246 | 84.781 | 77.246 | 67.004 | 77.246 | na |
| stdev | 29.337 | 47.540 | 29.337 | 29.571 | 29.337 | na |
| p (t-test) |  | 0.502 |  | 0.561 |  | na |
| min | 40.444 | 39.576 | 40.444 | 47.048 | 40.444 | na |
| max | 184.615 | 193.269 | 184.615 | 100.978 | 184.615 | na |
| n (Samp) | 47 | 11 | 47 | 3 | 47 | 0 |
| n (Pat) | 26 | 11 | 26 | 3 | 26 | 0 |
| sCr only | | | | | | |
| median | 74.467 | 64.207 | 74.467 | 95.531 | 74.467 | 95.310 |
| average | 84.898 | 70.258 | 84.898 | 83.165 | 84.898 | 95.310 |
| stdev | 37.172 | 25.772 | 37.172 | 26.277 | 37.172 | 30.532 |
| p (t-test) |  | 0.391 |  | 0.937 |  | 0.697 |
| min | 39.576 | 43.771 | 39.576 | 52.986 | 39.576 | 73.720 |
| max | 200.481 | 112.255 | 200.481 | 100.978 | 200.481 | 116.899 |
| n (Samp) | 72 | 5 | 72 | 3 | 72 | 2 |
| n (Pat) | 43 | 5 | 43 | 3 | 43 | 2 |
| UO only | | | | | | |
| median | 73.464 | 78.271 | 73.464 | 52.986 | 73.464 | na |
| average | 75.845 | 85.411 | 75.845 | 62.838 | 75.845 | na |
| stdev | 26.038 | 45.034 | 26.038 | 22.404 | 26.038 | na |
| p (t-test) |  | 0.380 |  | 0.410 |  | na |
| min | 42.620 | 39.576 | 42.620 | 47.048 | 42.620 | na |
| max | 158.173 | 193.269 | 158.173 | 88.480 | 158.173 | na |
| n (Samp) | 33 | 12 | 33 | 3 | 33 | 0 |
| n (Pat) | 16 | 12 | 16 | 3 | 16 | 0 |

Heat Shock Protein Beta-1:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 83.383 | 62.505 | 83.383 | 57.533 | 83.383 | 3.449 |
| average | 129.932 | 68.022 | 129.932 | 50.652 | 129.932 | 16.349 |
| stdev | 127.748 | 57.697 | 127.748 | 28.391 | 127.748 | na |
| p (t-test) |  | 0.082 |  | 0.291 |  | na |
| min | 3.449 | 8.406 | 3.449 | 19.454 | 3.449 | 16.349 |
| max | 683.847 | 211.848 | 683.847 | 74.970 | 683.847 | 16.349 |
| n (Samp) | 57 | 14 | 57 | 3 | 57 | 1 |
| n (Pat) | 37 | 14 | 37 | 3 | 37 | 1 |
| sCr only | | | | | | |
| median | 76.472 | 84.460 | 76.472 | 62.650 | 76.472 | 468.268 |
| average | 117.716 | 143.771 | 117.716 | 65.051 | 117.716 | 468.268 |
| stdev | 123.501 | 193.557 | 123.501 | 8.963 | 123.501 | 488.226 |
| p (t-test) |  | 0.631 |  | 0.464 |  | 0.000 |
| min | 3.449 | 9.395 | 3.449 | 57.533 | 3.449 | 123.040 |
| max | 683.847 | 533.475 | 683.847 | 74.970 | 683.847 | 813.496 |
| n (Samp) | 91 | 6 | 91 | 3 | 91 | 2 |
| n (Pat) | 62 | 6 | 62 | 3 | 62 | 2 |
| UO only | | | | | | |
| median | 88.186 | 35.469 | 88.186 | 57.533 | 88.186 | 14.768 |
| average | 136.091 | 57.330 | 136.091 | 178.691 | 136.091 | 16.349 |
| stdev | 130.907 | 57.559 | 130.907 | 243.575 | 130.907 | na |
| p (t-test) |  | 0.029 |  | 0.609 |  | na |
| min | 14.768 | 8.406 | 14.768 | 19.454 | 14.768 | 16.349 |
| max | 683.847 | 211.848 | 683.847 | 459.086 | 683.847 | 16.349 |
| n (Samp) | 42 | 15 | 42 | 3 | 42 | 1 |
| n (Pat) | 27 | 15 | 27 | 3 | 27 | 1 |

In the following tables, the ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC <0.5 is indicative of a negative going marker for the comparison, and an AUC >0.5 is indicative of a positive going marker for the comparison.

Soluble p-Selectin:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.63 | 0.119 | 26 | 8 | 0.293 |
| 24 hours | 0.47 | 0.091 | 26 | 17 | 1.236 |
| 48 hours | nd | nd | 26 | 0 | 0.211 |
| Cohort 1 v Cohort 2, adjudicated on serum creatinine | | | | | |
| 0 hours | 0.43 | 0.198 | 47 | 2 | 1.293 |
| 24 hours | 0.41 | 0.100 | 47 | 9 | 1.626 |
| 48 hours | 0.81 | 0.267 | 47 | 1 | 0.247 |
| Cohort 1 v Cohort 2, adjudicated on urine output | | | | | |
| 0 hours | 0.67 | 0.123 | 27 | 7 | 0.161 |
| 24 hours | 0.51 | 0.105 | 27 | 11 | 0.962 |
| 48 hours | 0.56 | 0.307 | 27 | 1 | 0.856 |

Protein NOV Homolog:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.56 | 0.072 | 82 | 21 | 0.379 |
| 24 hours | 0.56 | 0.073 | 82 | 20 | 0.447 |
| 48 hours | 0.74 | 0.287 | 82 | 1 | 0.396 |
| Cohort 1 v Cohort 2, adjudicated on serum creatinine | | | | | |
| 0 hours | 0.70 | 0.106 | 135 | 8 | 0.057 |
| 24 hours | 0.60 | 0.090 | 135 | 12 | 0.262 |
| 48 hours | 0.85 | 0.142 | 135 | 3 | 0.014 |
| Cohort 1 v Cohort 2, adjudicated on urine output | | | | | |
| 0 hours | 0.60 | 0.073 | 68 | 21 | 0.187 |
| 24 hours | 0.58 | 0.087 | 68 | 14 | 0.370 |
| 48 hours | 0.74 | 0.204 | 68 | 2 | 0.235 |

Netrin 4:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.56 | 0.091 | 56 | 13 | 0.482 |
| 24 hours | 0.63 | 0.178 | 56 | 3 | 0.482 |
| 48 hours | 0.79 | 0.275 | 56 | 1 | 0.299 |
| Cohort 1 v Cohort 2, adjudicated on serum creatinine | | | | | |
| 0 hours | 0.73 | 0.120 | 88 | 6 | 0.050 |
| 24 hours | 0.81 | 0.153 | 88 | 3 | 0.042 |
| 48 hours | 0.35 | 0.175 | 88 | 2 | 1.619 |

-continued

| Time prior max stage | AUC | SE | $n_{Cohort\ 1}$ | $n_{Cohort\ 2}$ | p |
|---|---|---|---|---|---|
| Cohort 1 v Cohort 2, adjudicated on urine output ||||||
| 0 hours | 0.63 | 0.090 | 41 | 14 | 0.147 |
| 24 hours | 0.60 | 0.180 | 41 | 3 | 0.572 |
| 48 hours | 0.83 | 0.257 | 41 | 1 | 0.200 |

Haptoglobin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.40 | 0.049 | 221 | 35 | 1.955 |
| 24 hours | 0.41 | 0.042 | 221 | 51 | 1.971 |
| 48 hours | 0.45 | 0.062 | 221 | 22 | 1.601 |
| Cohort 1 v Cohort 2, adjudicated on serum creatinine ||||||
| 0 hours | 0.40 | 0.068 | 386 | 16 | 1.843 |
| 24 hours | 0.45 | 0.062 | 386 | 21 | 1.620 |
| 48 hours | 0.37 | 0.081 | 386 | 10 | 1.888 |
| Cohort 1 v Cohort 2, adjudicated on urine output ||||||
| 0 hours | 0.44 | 0.052 | 183 | 34 | 1.716 |
| 24 hours | 0.48 | 0.048 | 183 | 45 | 1.396 |
| 48 hours | 0.54 | 0.068 | 183 | 21 | 0.589 |

Alpha-1-Antitrypsin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.29 | 0.042 | 221 | 35 | 2.000 |
| 24 hours | 0.25 | 0.033 | 221 | 51 | 2.000 |
| 48 hours | 0.28 | 0.049 | 221 | 22 | 2.000 |
| Cohort 1 v Cohort 2, adjudicated on serum creatinine ||||||
| 0 hours | 0.39 | 0.066 | 386 | 16 | 1.905 |
| 24 hours | 0.34 | 0.054 | 386 | 21 | 1.997 |
| 48 hours | 0.38 | 0.083 | 386 | 10 | 1.842 |
| Cohort 1 v Cohort 2, adjudicated on urine output ||||||
| 0 hours | 0.35 | 0.048 | 183 | 34 | 1.998 |
| 24 hours | 0.28 | 0.038 | 183 | 45 | 2.000 |
| 48 hours | 0.26 | 0.049 | 183 | 21 | 2.000 |

Leukocyte Elastase:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.63 | 0.061 | 84 | 31 | 0.027 |
| 24 hours | 0.70 | 0.050 | 84 | 46 | 0.000 |
| 48 hours | 0.73 | 0.066 | 84 | 22 | 0.001 |
| Cohort 1 v Cohort 2, adjudicated on serum creatinine ||||||
| 0 hours | 0.64 | 0.089 | 200 | 12 | 0.117 |
| 24 hours | 0.54 | 0.073 | 200 | 18 | 0.564 |
| 48 hours | 0.61 | 0.097 | 200 | 10 | 0.254 |
| Cohort 1 v Cohort 2, adjudicated on urine output ||||||
| 0 hours | 0.57 | 0.066 | 76 | 27 | 0.282 |
| 24 hours | 0.65 | 0.057 | 76 | 37 | 0.006 |
| 48 hours | 0.67 | 0.072 | 76 | 20 | 0.020 |

Soluble Tumor Necrosis Factor Receptor Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.67 | 0.076 | 97 | 17 | 0.027 |
| 24 hours | 0.62 | 0.068 | 97 | 23 | 0.077 |
| 48 hours | 0.52 | 0.210 | 97 | 2 | 0.922 |
| Cohort 1 v Cohort 2, adjudicated on serum creatinine ||||||
| 0 hours | 0.74 | 0.119 | 155 | 6 | 0.046 |
| 24 hours | 0.57 | 0.083 | 155 | 14 | 0.403 |
| 48 hours | 0.66 | 0.174 | 155 | 3 | 0.371 |
| Cohort 1 v Cohort 2, adjudicated on urine output ||||||
| 0 hours | 0.70 | 0.080 | 78 | 15 | 0.013 |
| 24 hours | 0.65 | 0.080 | 78 | 16 | 0.071 |
| 48 hours | 0.58 | 0.176 | 78 | 3 | 0.662 |

Soluble Tumor Necrosis Factor Ligand Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.45 | 0.095 | 77 | 10 | 1.368 |
| 24 hours | 0.62 | 0.092 | 77 | 12 | 0.193 |
| 48 hours | 0.60 | 0.215 | 77 | 2 | 0.651 |
| Cohort 1 v Cohort 2, adjudicated on serum creatinine ||||||
| 0 hours | 0.30 | 0.103 | 117 | 5 | 1.945 |
| 24 hours | 0.54 | 0.115 | 117 | 7 | 0.703 |
| 48 hours | 0.38 | 0.151 | 117 | 3 | 1.554 |
| Cohort 1 v Cohort 2, adjudicated on urine output ||||||
| 0 hours | 0.52 | 0.111 | 58 | 8 | 0.876 |
| 24 hours | 0.57 | 0.102 | 58 | 10 | 0.492 |
| 48 hours | 0.57 | 0.216 | 58 | 2 | 0.749 |

Soluble Intercellular Adhesion Molecule 2:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output ||||||
| 0 hours | 0.50 | 0.098 | 47 | 11 | 0.976 |
| 24 hours | 0.17 | 0.093 | 47 | 3 | 2.000 |
| 48 hours | nd | nd | 47 | 0 | 0.211 |
| Cohort 1 v Cohort 2, adjudicated on serum creatinine ||||||
| 0 hours | 0.36 | 0.117 | 72 | 5 | 1.764 |
| 24 hours | 0.27 | 0.124 | 72 | 3 | 1.938 |
| 48 hours | 0.61 | 0.216 | 72 | 2 | 0.607 |
| Cohort 1 v Cohort 2, adjudicated on urine output ||||||
| 0 hours | 0.50 | 0.098 | 33 | 12 | 1.020 |
| 24 hours | 0.31 | 0.143 | 33 | 3 | 1.808 |
| 48 hours | nd | nd | 33 | 0 | 0.211 |

Soluble Platelet Endothelial Cell Adhesion Molecule:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.49 | 0.097 | 47 | 11 | 1.087 |
| 24 hours | 0.39 | 0.157 | 47 | 3 | 1.515 |
| 48 hours | nd | nd | 47 | 0 | 0.211 |
| Cohort 1 v Cohort 2, adjudicated on serum creatinine | | | | | |
| 0 hours | 0.38 | 0.120 | 72 | 5 | 1.686 |
| 24 hours | 0.55 | 0.175 | 72 | 3 | 0.762 |
| 48 hours | 0.64 | 0.215 | 72 | 2 | 0.508 |
| Cohort 1 v Cohort 2, adjudicated on urine output | | | | | |
| 0 hours | 0.52 | 0.099 | 33 | 12 | 0.848 |
| 24 hours | 0.35 | 0.153 | 33 | 3 | 1.661 |
| 48 hours | nd | nd | 33 | 0 | 0.211 |

Heat Shock Protein Beta-1:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.34 | 0.076 | 57 | 14 | 1.965 |
| 24 hours | 0.26 | 0.122 | 57 | 3 | 1.953 |
| 48 hours | 0.08 | 0.081 | 57 | 1 | 2.000 |
| Cohort 1 v Cohort 2, adjudicated on serum creatinine | | | | | |
| 0 hours | 0.52 | 0.123 | 91 | 6 | 0.894 |
| 24 hours | 0.45 | 0.163 | 91 | 3 | 1.255 |
| 48 hours | 0.84 | 0.176 | 91 | 2 | 0.053 |
| Cohort 1 v Cohort 2, adjudicated on urine output | | | | | |
| 0 hours | 0.25 | 0.067 | 42 | 15 | 2.000 |
| 24 hours | 0.42 | 0.164 | 42 | 3 | 1.372 |
| 48 hours | 0.04 | 0.044 | 42 | 1 | 2.000 |

Various threshold (or "cutoff") concentrations were selected, and the associated sensitivity and specificity for distinguishing cohort 1 from cohort 2, as shown in the following tables. OR is the odds ratio calculated for the particular cutoff concentration, and 95% CI is the confidence interval for the odds ratio.

Soluble p-Selectin:

| Time prior AKI stage | Cutoff value | sens | spec | Quartile | OR | 95% CI of OR |
|---|---|---|---|---|---|---|
| | sCr or UO | | | | | |
| 0 hours | 62.1755931 | 75% | 38% | 1 | | |
| | 56.48600789 | 88% | 35% | 2 | na | na na |
| | 49.50570666 | 100% | 35% | 3 | na | na na |
| | 85.18918315 | 50% | 73% | 4 | na | na na |
| | 100.9858993 | 25% | 81% | | | |
| | 111.8621122 | 25% | 92% | | | |
| 24 hours | 45.08916942 | 71% | 31% | 1 | | |
| | 36.15698737 | 82% | 15% | 2 | 1.0 | 0.2 4.7 |
| | 32.86446282 | 94% | 15% | 3 | 1.5 | 0.3 6.5 |
| | 85.18918315 | 24% | 73% | 4 | 1.2 | 0.2 5.7 |
| | 100.9858993 | 12% | 81% | | | |
| | 111.8621122 | 6% | 92% | | | |
| 48 hours | 0 | na | na | 1 | | |
| | 0 | na | na | 2 | na | na na |
| | 0 | na | na | 3 | na | na na |
| | 0 | na | na | 4 | na | na na |
| | 0 | na | na | | | |
| | 0 | na | na | | | |

| Time prior AKI stage | Cutoff value | sens | spec | Quartile | OR | 95% CI of OR |
|---|---|---|---|---|---|---|
| | sCr only | | | | | |
| 0 hours | 52.7973052 | 100% | 32% | 1 | | |
| | 52.7973052 | 100% | 32% | 2 | na | na na |
| | 52.7973052 | 100% | 32% | 3 | na | na na |
| | 87.65153768 | 0% | 70% | 4 | na | na na |
| | 104.3602943 | 0% | 81% | | | |
| | 116.8580315 | 0% | 91% | | | |
| 24 hours | 39.57955124 | 78% | 21% | 1 | | |
| | 34.53796343 | 89% | 15% | 2 | 0.5 | 0.0 12.0 |
| | 32.86446282 | 100% | 15% | 3 | 1.6 | 0.2 11.8 |
| | 87.65153768 | 22% | 70% | 4 | 1.6 | 0.2 11.8 |
| | 104.3602943 | 11% | 81% | | | |
| | 116.8580315 | 0% | 91% | | | |
| 48 hours | 104.3602943 | 100% | 81% | 1 | | |
| | 104.3602943 | 100% | 81% | 2 | na | na na |
| | 104.3602943 | 100% | 81% | 3 | na | na na |
| | 87.65153768 | 100% | 70% | 4 | na | na na |
| | 104.3602943 | 100% | 81% | | | |
| | 116.8580315 | 0% | 91% | | | |
| | UO only | | | | | |
| 0 hours | 62.1755931 | 71% | 44% | 1 | | |
| | 56.48600789 | 86% | 41% | 2 | na | na na |
| | 49.50570666 | 100% | 41% | 3 | na | na na |
| | 84.57719926 | 57% | 70% | 4 | na | na na |
| | 100.9858993 | 29% | 81% | | | |
| | 111.8621122 | 29% | 93% | | | |
| 24 hours | 62.1755931 | 73% | 44% | 1 | | |
| | 49.50570666 | 82% | 41% | 2 | 2.3 | 0.3 18.6 |
| | 36.15698737 | 91% | 19% | 3 | 1.8 | 0.2 16.4 |
| | 84.57719926 | 18% | 70% | 4 | 0.9 | 0.1 10.5 |
| | 100.9858993 | 9% | 81% | | | |
| | 111.8621122 | 9% | 93% | | | |
| 48 hours | 71.26241682 | 100% | 56% | 1 | | |
| | 71.26241682 | 100% | 56% | 2 | na | na na |
| | 71.26241682 | 100% | 56% | 3 | na | na na |
| | 84.57719926 | 0% | 70% | 4 | na | na na |
| | 100.9858993 | 0% | 81% | | | |
| | 111.8621122 | 0% | 93% | | | |

Protein NOV Homolog:

| Time prior AKI stage | Cutoff value | sens | spec | Quartile | OR | 95% CI of OR |
|---|---|---|---|---|---|---|
| | sCr or UO | | | | | |
| 0 hours | 6465.517241 | 71% | 44% | 1 | | |
| | 5128.205128 | 81% | 33% | 2 | 0.7 | 0.2 2.6 |
| | 1785.714286 | 90% | 11% | 3 | 2.3 | 0.9 6.0 |
| | 11607.14286 | 48% | 71% | 4 | 1.6 | 0.6 4.3 |
| | 16845.70313 | 19% | 80% | | | |
| | 37140.57508 | 0% | 90% | | | |
| 24 hours | 7500 | 70% | 48% | 1 | | |
| | 5128.205128 | 80% | 33% | 2 | 0.7 | 0.2 2.6 |
| | 1461.038960 | 90% | 10% | 3 | 2.5 | 1.0 6.3 |
| | 11607.14286 | 35% | 71% | 4 | 1.3 | 0.4 3.6 |
| | 16845.70313 | 15% | 80% | | | |
| | 37140.57508 | 0% | 90% | | | |
| 48 hours | 13916.01563 | 100% | 74% | 1 | | |
| | 13916.01563 | 100% | 74% | 2 | na | na na |
| | 13916.01563 | 100% | 74% | 3 | na | na na |
| | 11607.14286 | 100% | 71% | 4 | na | na na |
| | 16845.70313 | 0% | 80% | | | |
| | 37140.57508 | 0% | 90% | | | |
| | sCr only | | | | | |
| 0 hours | 12978.4689 | 75% | 72% | 1 | | |
| | 10057.47126 | 88% | 57% | 2 | 0.0 | 0.0 65535.0 |
| | 1209.128065 | 100% | 6% | 3 | 3.1 | 0.2 47.4 |
| | 12619.61722 | 75% | 70% | 4 | 4.3 | 0.3 55.5 |
| | 16566.98565 | 38% | 80% | | | |
| | 29632.58786 | 25% | 90% | | | |

-continued

| Time prior AKI stage | Cutoff value | sens | spec | Quartile | OR | 95% CI of OR | |
|---|---|---|---|---|---|---|---|
| 24 hours | 9339.08046 | 75% | 53% | 1 | | | |
| | 7500 | 83% | 44% | 2 | 2.0 | 0.1 | 42.3 |
| | 5970.149254 | 92% | 36% | 3 | 6.8 | 0.6 | 75.1 |
| | 12619.61722 | 42% | 70% | 4 | 3.1 | 0.2 | 47.2 |
| | 16566.98565 | 17% | 80% | | | | |
| | 29632.58786 | 8% | 90% | | | | |
| 48 hours | 13232.42188 | 100% | 73% | 1 | | | |
| | 13232.42188 | 100% | 73% | 2 | na | na | na |
| | 13232.42188 | 100% | 73% | 3 | na | na | na |
| | 12619.61722 | 100% | 70% | 4 | na | na | na |
| | 16566.98565 | 67% | 80% | | | | |
| | 29632.58786 | 33% | 90% | | | | |
| UO only | | | | | | | |
| 0 hours | 9500 | 71% | 53% | 1 | | | |
| | 6089.74359 | 81% | 31% | 2 | 1.0 | 0.3 | 3.3 |
| | 2830.981183 | 90% | 16% | 3 | 1.7 | 0.6 | 4.8 |
| | 11607.14286 | 57% | 72% | 4 | 2.0 | 0.7 | 5.4 |
| | 16845.70313 | 29% | 82% | | | | |
| | 49738.90339 | 0% | 91% | | | | |
| 24 hours | 8189.655172 | 71% | 47% | 1 | | | |
| | 2588.555858 | 86% | 15% | 2 | 0.6 | 0.1 | 3.8 |
| | 1461.038961 | 93% | 7% | 3 | 1.9 | 0.5 | 6.9 |
| | 11607.14286 | 43% | 72% | 4 | 1.3 | 0.3 | 5.3 |
| | 16845.70313 | 29% | 82% | | | | |
| | 49738.90339 | 0% | 91% | | | | |
| 48 hours | 12978.4689 | 100% | 74% | 1 | | | |
| | 12978.4689 | 100% | 74% | 2 | na | na | na |
| | 12978.4689 | 100% | 74% | 3 | na | na | na |
| | 11607.14286 | 100% | 72% | 4 | na | na | na |
| | 16845.70313 | 0% | 82% | | | | |
| | 49738.90339 | 0% | 91% | | | | |

Netrin 4:

| Time prior AKI stage | Cutoff value | sens | spec | Quartile | OR | 95% CI of OR | |
|---|---|---|---|---|---|---|---|
| sCr or UO | | | | | | | |
| 0 hours | 0.01015625 | 77% | 36% | 1 | | | |
| | 0.009315718 | 85% | 32% | 2 | 1.6 | 0.2 | 10.8 |
| | 0.006669207 | 92% | 11% | 3 | 1.6 | 0.2 | 10.8 |
| | 0.019901762 | 46% | 71% | 4 | 2.9 | 0.6 | 15.1 |
| | 0.04140625 | 15% | 80% | | | | |
| | 0.106860632 | 0% | 91% | | | | |
| 24 hours | 0.007727812 | 100% | 20% | 1 | | | |
| | 0.007727812 | 100% | 20% | 2 | 0.0 | 0.0 | 65535.0 |
| | 0.007727812 | 100% | 20% | 3 | 0.9 | 0.0 | 62.6 |
| | 0.019901762 | 67% | 71% | 4 | 0.9 | 0.0 | 62.6 |
| | 0.04140625 | 33% | 80% | | | | |
| | 0.106860632 | 33% | 91% | | | | |
| 48 hours | 0.03671875 | 100% | 79% | 1 | | | |
| | 0.03671875 | 100% | 79% | 2 | na | na | na |
| | 0.03671875 | 100% | 79% | 3 | na | na | na |
| | 0.019901762 | 100% | 71% | 4 | na | na | na |
| | 0.04140625 | 0% | 80% | | | | |
| | 0.106860632 | 0% | 91% | | | | |
| sCr only | | | | | | | |
| 0 hours | 0.020431064 | 83% | 72% | 1 | | | |
| | 0.020431064 | 83% | 72% | 2 | na | na | na |
| | 0.009315718 | 100% | 31% | 3 | na | na | na |
| | 0.019901762 | 83% | 70% | 4 | na | na | na |
| | 0.031546409 | 67% | 81% | | | | |
| | 0.0671875 | 0% | 91% | | | | |
| 24 hours | 0.021489668 | 100% | 74% | 1 | | | |
| | 0.021489668 | 100% | 74% | 2 | na | na | na |
| | 0.021489668 | 100% | 74% | 3 | na | na | na |
| | 0.019901762 | 100% | 70% | 4 | na | na | na |
| | 0.031546409 | 33% | 81% | | | | |
| | 0.0671875 | 33% | 91% | | | | |
| 48 hours | 0.00625 | 100% | 5% | 1 | | | |
| | 0.00625 | 100% | 5% | 2 | na | na | na |
| | 0.00625 | 100% | 5% | 3 | na | na | na |
| | 0.019901762 | 0% | 70% | 4 | na | na | na |
| | 0.031546409 | 0% | 81% | | | | |
| | 0.0671875 | 0% | 91% | | | | |
| UO only | | | | | | | |
| 0 hours | 0.0109375 | 71% | 51% | 1 | | | |
| | 0.00984502 | 86% | 39% | 2 | 1.5 | 0.2 | 11.0 |
| | 0.006669207 | 93% | 12% | 3 | 1.5 | 0.2 | 11.0 |
| | 0.015138042 | 57% | 71% | 4 | 4.1 | 0.7 | 23.3 |
| | 0.019901762 | 50% | 80% | | | | |
| | 0.100574713 | 0% | 90% | | | | |
| 24 hours | 0.007727812 | 100% | 22% | 1 | | | |
| | 0.007727812 | 100% | 22% | 2 | 0.0 | 0.0 | 65535.0 |
| | 0.007727812 | 100% | 22% | 3 | 1.0 | 0.0 | 74.6 |
| | 0.015138042 | 67% | 71% | 4 | 1.0 | 0.0 | 74.6 |
| | 0.019901762 | 33% | 80% | | | | |
| | 0.100574713 | 0% | 90% | | | | |
| 48 hours | 0.021489668 | 100% | 83% | 1 | | | |
| | 0.021489668 | 100% | 83% | 2 | na | na | na |
| | 0.021489668 | 100% | 83% | 3 | na | na | na |
| | 0.015138042 | 100% | 71% | 4 | na | na | na |
| | 0.019901762 | 100% | 80% | | | | |
| | 0.100574713 | 0% | 90% | | | | |

Haptoglobin:

| Time prior AKI stage | Cutoff value | sens | spec | Quartile | OR | 95% CI of OR | |
|---|---|---|---|---|---|---|---|
| sCr or UO | | | | | | | |
| 0 hours | 0.863 | 71% | 16% | 1 | | | |
| | 0.695 | 80% | 13% | 2 | 3.1 | 1.5 | 6.5 |
| | 0.227 | 91% | 8% | 3 | 1.8 | 0.8 | 4.3 |
| | 3.74 | 20% | 70% | 4 | 3.8 | 1.9 | 7.8 |
| | 4.65 | 9% | 80% | | | | |
| | 6.38 | 3% | 90% | | | | |
| 24 hours | 1.16 | 71% | 23% | 1 | | | |
| | 0.662 | 80% | 13% | 2 | 1.3 | 0.8 | 2.0 |
| | 0.213 | 90% | 7% | 3 | 1.9 | 1.2 | 2.8 |
| | 3.74 | 22% | 70% | 4 | 2.0 | 1.3 | 3.0 |
| | 4.65 | 12% | 80% | | | | |
| | 6.38 | 6% | 90% | | | | |
| 48 hours | 1.43 | 73% | 28% | 1 | | | |
| | 1.27 | 82% | 24% | 2 | 1.6 | 0.6 | 3.8 |
| | 0.739 | 91% | 14% | 3 | 1.8 | 0.8 | 4.3 |
| | 3.74 | 18% | 70% | 4 | 1.3 | 0.5 | 3.4 |
| | 4.65 | 9% | 80% | | | | |
| | 6.38 | 9% | 90% | | | | |
| sCr only | | | | | | | |
| 0 hours | 0.875 | 75% | 20% | 1 | | | |
| | 0.864 | 81% | 20% | 2 | 0.3 | 0.0 | 4.7 |
| | 0.275 | 94% | 10% | 3 | 2.1 | 0.7 | 5.7 |
| | 3.48 | 25% | 70% | 4 | 2.1 | 0.8 | 5.8 |
| | 4.15 | 13% | 80% | | | | |
| | 5.55 | 6% | 90% | | | | |
| 24 hours | 1.44 | 71% | 31% | 1 | | | |
| | 1.16 | 81% | 26% | 2 | 0.5 | 0.1 | 2.2 |
| | 0.815 | 90% | 19% | 3 | 3.0 | 1.5 | 6.0 |
| | 3.48 | 19% | 70% | 4 | 1.0 | 0.4 | 2.8 |
| | 4.15 | 14% | 80% | | | | |
| | 5.55 | 10% | 90% | | | | |
| 48 hours | 1.39 | 70% | 30% | 1 | | | |
| | 1.03 | 80% | 23% | 2 | na | na | na |
| | 0.703 | 90% | 16% | 3 | na | na | na |
| | 3.48 | 0% | 70% | 4 | na | na | na |
| | 4.15 | 0% | 80% | | | | |
| | 5.55 | 0% | 90% | | | | |
| UO only | | | | | | | |
| 0 hours | 0.852 | 71% | 20% | 1 | | | |
| | 0.413 | 82% | 9% | 2 | 0.8 | 0.4 | 1.4 |

-continued

| Time prior AKI stage | Cutoff value | sens | spec | Quartile | OR | 95% CI of OR | |
|---|---|---|---|---|---|---|---|
| | 0.227 | 91% | 9% | 3 | 0.6 | 0.3 | 1.2 |
| | 3.24 | 29% | 70% | 4 | 1.5 | 0.9 | 2.3 |
| | 3.95 | 15% | 80% | | | | |
| | 5.33 | 3% | 90% | | | | |
| 24 hours | 0.945 | 71% | 22% | 1 | | | |
| | 0.662 | 80% | 15% | 2 | 1.3 | 0.8 | 2.0 |
| | 0.213 | 91% | 8% | 3 | 0.9 | 0.5 | 1.4 |
| | 3.24 | 31% | 70% | 4 | 1.5 | 1.0 | 2.3 |
| | 3.95 | 18% | 80% | | | | |
| | 5.33 | 9% | 90% | | | | |
| 48 hours | 1.43 | 71% | 35% | 1 | | | |
| | 1.27 | 81% | 31% | 2 | 1.3 | 0.5 | 3.4 |
| | 0.662 | 90% | 15% | 3 | 1.9 | 0.8 | 4.4 |
| | 3.24 | 29% | 70% | 4 | 1.3 | 0.5 | 3.4 |
| | 3.95 | 24% | 80% | | | | |
| | 5.33 | 10% | 90% | | | | |

Alpha-1-Antitrypsin:

| Time prior AKI stage | Cutoff value | sens | spec | Quartile | OR | 95% CI of OR | |
|---|---|---|---|---|---|---|---|
| | | | sCr or UO | | | | |
| 0 hours | 2.13 | 71% | 18% | 1 | | | |
| | 1.86 | 83% | 11% | 2 | 3.2 | 0.8 | 12.6 |
| | 1.61 | 91% | 4% | 3 | 7.9 | 2.4 | 26.3 |
| | 4.38 | 6% | 70% | 4 | 8.7 | 2.6 | 28.6 |
| | 4.88 | 3% | 81% | | | | |
| | 5.68 | 0% | 90% | | | | |
| 24 hours | 1.89 | 71% | 11% | 1 | | | |
| | 1.75 | 80% | 9% | 2 | 1.7 | 0.6 | 5.2 |
| | 1.48 | 90% | 3% | 3 | 6.7 | 2.9 | 15.5 |
| | 4.38 | 8% | 70% | 4 | 14.3 | 6.4 | 31.9 |
| | 4.88 | 6% | 81% | | | | |
| | 5.68 | 0% | 90% | | | | |
| 48 hours | 1.92 | 73% | 11% | 1 | | | |
| | 1.75 | 82% | 9% | 2 | 3.1 | 0.2 | 45.3 |
| | 1.46 | 91% | 2% | 3 | 6.5 | 0.6 | 69.0 |
| | 4.38 | 5% | 70% | 4 | 15.0 | 1.7 | 134.9 |
| | 4.88 | 5% | 81% | | | | |
| | 5.68 | 0% | 90% | | | | |
| | | | sCr only | | | | |
| 0 hours | 1.85 | 75% | 15% | 1 | | | |
| | 1.59 | 88% | 6% | 2 | 1.5 | 0.3 | 8.2 |
| | 1.52 | 94% | 5% | 3 | 2.6 | 0.6 | 10.6 |
| | 3.96 | 19% | 70% | 4 | 3.2 | 0.8 | 12.2 |
| | 4.6 | 13% | 80% | | | | |
| | 5.42 | 6% | 90% | | | | |
| 24 hours | 1.75 | 71% | 12% | 1 | | | |
| | 1.32 | 81% | 4% | 2 | 2.6 | 0.6 | 10.6 |
| | 1.13 | 90% | 2% | 3 | 2.0 | 0.5 | 9.2 |
| | 3.96 | 14% | 70% | 4 | 5.5 | 1.6 | 18.6 |
| | 4.6 | 10% | 80% | | | | |
| | 5.42 | 10% | 90% | | | | |
| 48 hours | 1.67 | 70% | 9% | 1 | | | |
| | 1.46 | 80% | 4% | 2 | 3.1 | 0.2 | 43.5 |
| | 1.42 | 90% | 4% | 3 | 2.0 | 0.1 | 39.8 |
| | 3.96 | 20% | 70% | 4 | 4.1 | 0.3 | 49.8 |
| | 4.6 | 10% | 80% | | | | |
| | 5.42 | 0% | 90% | | | | |
| | | | UO only | | | | |
| 0 hours | 2.24 | 74% | 21% | 1 | | | |
| | 2.12 | 82% | 18% | 2 | 1.3 | 0.5 | 3.4 |
| | 1.76 | 91% | 10% | 3 | 4.5 | 2.2 | 9.1 |
| | 4.25 | 15% | 70% | 4 | 3.3 | 1.5 | 6.9 |
| | 4.76 | 12% | 80% | | | | |
| | 5.53 | 3% | 90% | | | | |
| 24 hours | 1.93 | 71% | 13% | 1 | | | |
| | 1.84 | 80% | 11% | 2 | 0.8 | 0.3 | 2.0 |
| | 1.67 | 91% | 5% | 3 | 3.4 | 1.8 | 6.3 |
| | 4.25 | 11% | 70% | 4 | 6.5 | 3.7 | 11.6 |

-continued

| Time prior AKI stage | Cutoff value | sens | spec | Quartile | OR | 95% CI of OR | |
|---|---|---|---|---|---|---|---|
| | 4.76 | 7% | 80% | | | | |
| | 5.53 | 4% | 90% | | | | |
| 48 hours | 1.92 | 71% | 13% | 1 | | | |
| | 1.84 | 81% | 11% | 2 | 2.0 | 0.1 | 41.8 |
| | 1.59 | 90% | 4% | 3 | 6.7 | 0.6 | 71.3 |
| | 4.25 | 5% | 70% | 4 | 15.4 | 1.7 | 140.6 |
| | 4.76 | 5% | 80% | | | | |
| | 5.53 | 0% | 90% | | | | |

Leukocyte Elastase:

| Time prior AKI stage | Cutoff value | sens | spec | Quartile | OR | 95% CI of OR | |
|---|---|---|---|---|---|---|---|
| | | | sCr or UO | | | | |
| 0 hours | 202.8023599 | 71% | 44% | 1 | | | |
| | 161.5932642 | 81% | 32% | 2 | 1.2 | 0.5 | 2.9 |
| | 106.737013 | 90% | 10% | 3 | 1.2 | 0.5 | 2.9 |
| | 284.3698854 | 55% | 70% | 4 | 4.3 | 2.0 | 9.1 |
| | 314.3939394 | 48% | 81% | | | | |
| | 449.5901639 | 19% | 90% | | | | |
| 24 hours | 262.2749591 | 72% | 63% | 1 | | | |
| | 198.9247312 | 80% | 44% | 2 | 0.8 | 0.4 | 1.7 |
| | 93.49593496 | 91% | 7% | 3 | 2.1 | 1.2 | 4.0 |
| | 284.3698854 | 67% | 70% | 4 | 6.3 | 3.4 | 11.6 |
| | 314.3939394 | 63% | 81% | | | | |
| | 449.5901639 | 24% | 90% | | | | |
| 48 hours | 263.9405204 | 73% | 64% | 1 | | | |
| | 198.9247312 | 82% | 44% | 2 | 2.1 | 0.4 | 10.7 |
| | 161.5932642 | 91% | 32% | 3 | 1.6 | 0.3 | 9.5 |
| | 284.3698854 | 59% | 70% | 4 | 11.1 | 2.9 | 43.1 |
| | 314.3939394 | 59% | 81% | | | | |
| | 449.5901639 | 45% | 90% | | | | |
| | | | sCr only | | | | |
| 0 hours | 240.6088083 | 75% | 45% | 1 | | | |
| | 220.1370757 | 83% | 38% | 2 | 1.0 | 0.1 | 7.7 |
| | 96.96969697 | 92% | 9% | 3 | 1.0 | 0.1 | 7.7 |
| | 356.3829787 | 58% | 70% | 4 | 3.3 | 0.8 | 13.0 |
| | 447.9508197 | 42% | 80% | | | | |
| | 524.1803279 | 25% | 90% | | | | |
| 24 hours | 237.4631268 | 72% | 44% | 1 | | | |
| | 116.4772727 | 83% | 12% | 2 | 0.7 | 0.2 | 2.4 |
| | 8.408874046 | 94% | 1% | 3 | 1.3 | 0.5 | 3.3 |
| | 356.3829787 | 50% | 70% | 4 | 1.5 | 0.6 | 3.7 |
| | 447.9508197 | 17% | 80% | | | | |
| | 524.1803279 | 11% | 90% | | | | |
| 48 hours | 328.9962825 | 70% | 65% | 1 | | | |
| | 151.9255875 | 80% | 22% | 2 | 0.0 | 0.0 | 65535.0 |
| | 106.737013 | 90% | 10% | 3 | 1.0 | 0.2 | 4.0 |
| | 356.3829787 | 60% | 70% | 4 | 1.3 | 0.4 | 4.5 |
| | 447.9508197 | 40% | 80% | | | | |
| | 524.1803279 | 30% | 90% | | | | |
| | | | UO only | | | | |
| 0 hours | 202.8023599 | 70% | 42% | 1 | | | |
| | 161.5932642 | 81% | 30% | 2 | 1.9 | 0.7 | 5.1 |
| | 106.737013 | 93% | 9% | 3 | 2.3 | 0.9 | 6.0 |
| | 321.0227273 | 44% | 71% | 4 | 2.3 | 0.9 | 6.0 |
| | 436.1833953 | 19% | 80% | | | | |
| | 546.3114754 | 11% | 91% | | | | |
| 24 hours | 262.2749591 | 70% | 57% | 1 | | | |
| | 199.1580311 | 81% | 42% | 2 | 2.4 | 1.0 | 6.0 |
| | 95.37337662 | 92% | 8% | 3 | 4.5 | 1.9 | 10.6 |
| | 321.0227273 | 65% | 71% | 4 | 4.9 | 2.1 | 11.3 |
| | 436.1833953 | 35% | 80% | | | | |
| | 546.3114754 | 14% | 91% | | | | |
| 48 hours | 262.2749591 | 70% | 57% | 1 | | | |
| | 221.8264249 | 80% | 46% | 2 | 6.1 | 0.5 | 76.8 |
| | 176.4896373 | 90% | 32% | 3 | 7.7 | 0.6 | 91.6 |
| | 321.0227273 | 55% | 71% | 4 | 11.5 | 1.0 | 128.4 |

-continued

| Time prior AKI stage | Cutoff value | sens | spec | Quartile | OR | 95% CI of OR | |
|---|---|---|---|---|---|---|---|
| | 436.1833953 | 40% | 80% | | | | |
| | 546.3114754 | 20% | 91% | | | | |

Soluble Tumor Necrosis Factor Receptor Superfamily Member 6:

| Time prior AKI stage | Cutoff value | sens | spec | Quartile | OR | 95% CI of OR | |
|---|---|---|---|---|---|---|---|
| | | | sCr or UO | | | | |
| 0 hours | 9249.617152 | 71% | 55% | 1 | | | |
| | 7408.695652 | 82% | 38% | 2 | 1.5 | 0.3 | 8.9 |
| | 6660.869565 | 94% | 25% | 3 | 2.2 | 0.4 | 11.0 |
| | 11694.11765 | 65% | 70% | 4 | 5.0 | 1.2 | 20.0 |
| | 13937.00787 | 47% | 80% | | | | |
| | 17611.54856 | 6% | 91% | | | | |
| 24 hours | 8652.37366 | 74% | 47% | 1 | | | |
| | 8295.302013 | 83% | 46% | 2 | 2.3 | 0.7 | 7.0 |
| | 6335.57047 | 91% | 22% | 3 | 1.8 | 0.5 | 6.0 |
| | 11694.11765 | 39% | 70% | 4 | 3.9 | 1.4 | 10.9 |
| | 13937.00787 | 26% | 80% | | | | |
| | 17611.54856 | 9% | 91% | | | | |
| 48 hours | 6660.869565 | 100% | 25% | 1 | | | |
| | 6660.869565 | 100% | 25% | 2 | na | na | na |
| | 6660.869565 | 100% | 25% | 3 | na | na | na |
| | 11694.11765 | 50% | 70% | 4 | na | na | na |
| | 13937.00787 | 0% | 80% | | | | |
| | 17611.54856 | 0% | 91% | | | | |
| | | | sCr only | | | | |
| 0 hours | 12043.34365 | 83% | 65% | 1 | | | |
| | 12043.34365 | 83% | 65% | 2 | na | na | na |
| | 8295.302013 | 100% | 35% | 3 | na | na | na |
| | 13171.64179 | 67% | 70% | 4 | na | na | na |
| | 16117.64706 | 50% | 80% | | | | |
| | 17795.27559 | 33% | 90% | | | | |
| 24 hours | 9019.908116 | 71% | 43% | 1 | | | |
| | 8652.37366 | 86% | 37% | 2 | 6.8 | 0.6 | 74.5 |
| | 8295.302013 | 93% | 35% | 3 | 2.1 | 0.1 | 42.7 |
| | 13171.64179 | 43% | 70% | 4 | 5.4 | 0.5 | 62.6 |
| | 16117.64706 | 7% | 80% | | | | |
| | 17795.27559 | 7% | 90% | | | | |
| 48 hours | 11286.08924 | 100% | 61% | 1 | | | |
| | 11286.08924 | 100% | 61% | 2 | na | na | na |
| | 11286.08924 | 100% | 61% | 3 | na | na | na |
| | 13171.64179 | 33% | 70% | 4 | na | na | na |
| | 16117.64706 | 0% | 80% | | | | |
| | 17795.27559 | 0% | 90% | | | | |
| | | | UO only | | | | |
| 0 hours | 9249.617152 | 73% | 56% | 1 | | | |
| | 7366.003063 | 80% | 35% | 2 | 1.0 | 0.1 | 8.6 |
| | 6660.869565 | 93% | 23% | 3 | 1.0 | 0.1 | 8.6 |
| | 10517.64706 | 67% | 71% | 4 | 6.3 | 1.5 | 26.1 |
| | 12211.76471 | 60% | 81% | | | | |
| | 16258.82353 | 20% | 91% | | | | |
| 24 hours | 8630.672926 | 75% | 46% | 1 | | | |
| | 8145.539906 | 81% | 40% | 2 | 1.5 | 0.2 | 9.3 |
| | 6294.027565 | 94% | 21% | 3 | 2.9 | 0.6 | 14.1 |
| | 10517.64706 | 50% | 71% | 4 | 3.5 | 0.8 | 15.8 |
| | 12211.76471 | 38% | 81% | | | | |
| | 16258.82353 | 13% | 91% | | | | |
| 48 hours | 6660.869565 | 100% | 23% | 1 | | | |
| | 6660.869565 | 100% | 23% | 2 | 0.0 | 0.0 | 65535.0 |
| | 6660.869565 | 100% | 23% | 3 | 1.0 | 0.0 | 61.9 |
| | 10517.64706 | 33% | 71% | 4 | 1.0 | 0.0 | 58.5 |
| | 12211.76471 | 33% | 81% | | | | |
| | 16258.82353 | 0% | 91% | | | | |

Soluble Tumor Necrosis Factor Ligand Superfamily Member 6:

| Time prior AKI stage | Cutoff value | sens | spec | Quartile | OR | 95% CI of OR | |
|---|---|---|---|---|---|---|---|
| | | | sCr or UO | | | | |
| 0 hours | 26.44230769 | 70% | 17% | 1 | | | |
| | 25.96153846 | 80% | 17% | 2 | 1.0 | 0.1 | 8.6 |
| | 20.39930556 | 90% | 10% | 3 | 1.0 | 0.1 | 8.6 |
| | 57.22128378 | 40% | 70% | 4 | 2.4 | 0.4 | 12.7 |
| | 69.12878788 | 20% | 81% | | | | |
| | 101.4808362 | 10% | 91% | | | | |
| 24 hours | 40.11524823 | 75% | 44% | 1 | | | |
| | 28.3203125 | 83% | 19% | 2 | 0.3 | 0.0 | 5.0 |
| | 27.77777778 | 92% | 19% | 3 | 1.0 | 0.2 | 4.5 |
| | 57.22128378 | 50% | 70% | 4 | 1.8 | 0.5 | 6.2 |
| | 69.12878788 | 33% | 81% | | | | |
| | 101.4808362 | 25% | 91% | | | | |
| 48 hours | 45.45454545 | 100% | 56% | 1 | | | |
| | 45.45454545 | 100% | 56% | 2 | na | na | na |
| | 45.45454545 | 100% | 56% | 3 | na | na | na |
| | 57.22128378 | 0% | 70% | 4 | na | na | na |
| | 69.12878788 | 0% | 81% | | | | |
| | 101.4808362 | 0% | 91% | | | | |
| | | | sCr only | | | | |
| 0 hours | 27.1577381 | 80% | 21% | 1 | | | |
| | 27.1577381 | 80% | 21% | 2 | na | na | na |
| | 12.32638889 | 100% | 2% | 3 | na | na | na |
| | 60.06205674 | 0% | 70% | 4 | na | na | na |
| | 86.2369338 | 0% | 80% | | | | |
| | 105.8362369 | 0% | 91% | | | | |
| 24 hours | 40.11524823 | 71% | 43% | 1 | | | |
| | 27.77777778 | 86% | 24% | 2 | 1.0 | 0.1 | 8.1 |
| | 17.78846154 | 100% | 9% | 3 | 0.5 | 0.0 | 10.4 |
| | 60.06205674 | 43% | 70% | 4 | 1.0 | 0.1 | 8.1 |
| | 86.2369338 | 29% | 80% | | | | |
| | 105.8362369 | 14% | 91% | | | | |
| 48 hours | 20.39930556 | 100% | 12% | 1 | | | |
| | 20.39930556 | 100% | 12% | 2 | na | na | na |
| | 20.39930556 | 100% | 12% | 3 | na | na | na |
| | 60.06205674 | 0% | 70% | 4 | na | na | na |
| | 86.2369338 | 0% | 80% | | | | |
| | 105.8362369 | 0% | 91% | | | | |
| | | | UO only | | | | |
| 0 hours | 26.44230769 | 75% | 21% | 1 | | | |
| | 25.96153846 | 88% | 21% | 2 | 0.3 | 0.0 | 4.9 |
| | 20.39930556 | 100% | 14% | 3 | 0.6 | 0.1 | 4.2 |
| | 57.84574468 | 50% | 71% | 4 | 0.6 | 0.1 | 3.9 |
| | 69.12878788 | 25% | 81% | | | | |
| | 102.7874564 | 13% | 91% | | | | |
| 24 hours | 40.11524823 | 70% | 40% | 1 | | | |
| | 39.2287234 | 80% | 38% | 2 | 1.6 | 0.2 | 10.8 |
| | 25.96153846 | 90% | 21% | 3 | 1.0 | 0.1 | 9.2 |
| | 57.84574468 | 40% | 71% | 4 | 1.6 | 0.2 | 10.8 |
| | 69.12878788 | 20% | 81% | | | | |
| | 102.7874564 | 20% | 91% | | | | |
| 48 hours | 45.45454545 | 100% | 53% | 1 | | | |
| | 45.45454545 | 100% | 53% | 2 | na | na | na |
| | 45.45454545 | 100% | 53% | 3 | na | na | na |
| | 57.84574468 | 0% | 71% | 4 | na | na | na |
| | 69.12878788 | 0% | 81% | | | | |
| | 102.7874564 | 0% | 91% | | | | |

Soluble Intercellular Adhesion Molecule 2:

| Time prior AKI stage | Cutoff value | sens | spec | Quartile | OR | 95% CI of OR | |
|---|---|---|---|---|---|---|---|
| | | | sCr or UO | | | | |
| 0 hours | 296.9458128 | 73% | 30% | 1 | | | |
| | 239.6166134 | 82% | 21% | 2 | 0.9 | 0.2 | 4.8 |
| | 205.8785942 | 91% | 19% | 3 | 0.6 | 0.1 | 4.4 |
| | 547.3170732 | 36% | 70% | 4 | 0.9 | 0.2 | 4.8 |

-continued

| Time prior AKI stage | Cutoff value | sens | spec | Quartile | OR | 95% CI of OR | |
|---|---|---|---|---|---|---|---|
| | 693.6585366 | 27% | 81% | | | | |
| | 783.804878 | 27% | 91% | | | | |
| 24 hours | 43.61702128 | 100% | 6% | 1 | | | |
| | 43.61702128 | 100% | 6% | 2 | na | na | na |
| | 43.61702128 | 100% | 6% | 3 | na | na | na |
| | 547.3170732 | 0% | 70% | 4 | na | na | na |
| | 693.6585366 | 0% | 81% | | | | |
| | 783.804878 | 0% | 91% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| sCr only | | | | | | | |
| 0 hours | 239.6166134 | 80% | 25% | 1 | | | |
| | 239.6166134 | 80% | 25% | 2 | na | na | na |
| | 191.5294118 | 100% | 18% | 3 | na | na | na |
| | 516.8780488 | 0% | 71% | 4 | na | na | na |
| | 693.6585366 | 0% | 81% | | | | |
| | 889.1707317 | 0% | 90% | | | | |
| 24 hours | 45.31914894 | 100% | 6% | 1 | | | |
| | 45.31914894 | 100% | 6% | 2 | na | na | na |
| | 45.31914894 | 100% | 6% | 3 | na | na | na |
| | 516.8780488 | 0% | 71% | 4 | na | na | na |
| | 693.6585366 | 0% | 81% | | | | |
| | 889.1707317 | 0% | 90% | | | | |
| 48 hours | 307.9802956 | 100% | 35% | 1 | | | |
| | 307.9802956 | 100% | 35% | 2 | na | na | na |
| | 307.9802956 | 100% | 35% | 3 | na | na | na |
| | 516.8780488 | 50% | 71% | 4 | na | na | na |
| | 693.6585366 | 50% | 81% | | | | |
| | 889.1707317 | 0% | 90% | | | | |
| UO only | | | | | | | |
| 0 hours | 296.9458128 | 75% | 24% | 1 | | | |
| | 221.5974441 | 83% | 12% | 2 | 1.7 | 0.3 | 8.8 |
| | 205.8785942 | 92% | 12% | 3 | 0.7 | 0.1 | 5.3 |
| | 690.1463415 | 25% | 73% | 4 | 1.1 | 0.2 | 6.6 |
| | 711.804878 | 25% | 82% | | | | |
| | 783.804878 | 25% | 91% | | | | |
| 24 hours | 205.8785942 | 100% | 12% | 1 | | | |
| | 205.8785942 | 100% | 12% | 2 | na | na | na |
| | 205.8785942 | 100% | 12% | 3 | na | na | na |
| | 690.1463415 | 0% | 73% | 4 | na | na | na |
| | 711.804878 | 0% | 82% | | | | |
| | 783.804878 | 0% | 91% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |

Soluble Platelet Endothelial Cell Adhesion Molecule:

| Time prior AKI stage | Cutoff value | sens | spec | Quartile | OR | 95% CI of OR | |
|---|---|---|---|---|---|---|---|
| sCr or UO | | | | | | | |
| 0 hours | 57.08191126 | 73% | 23% | 1 | | | |
| | 43.72693727 | 82% | 9% | 2 | 0.2 | 0.0 | 3.4 |
| | 40.44368601 | 91% | 2% | 3 | 0.7 | 0.2 | 3.0 |
| | 84.31372549 | 36% | 70% | 4 | 0.8 | 0.2 | 3.4 |
| | 90.92178771 | 36% | 81% | | | | |
| | 123.7745098 | 18% | 91% | | | | |
| 24 hours | 46.58703072 | 100% | 11% | 1 | | | |
| | 46.58703072 | 100% | 11% | 2 | 0.0 | 0.0 | 65535.0 |
| | 46.58703072 | 100% | 11% | 3 | 0.0 | 0.0 | 65535.0 |
| | 84.31372549 | 33% | 70% | 4 | 2.4 | 0.1 | 65.0 |
| | 90.92178771 | 33% | 81% | | | | |
| | 123.7745098 | 0% | 91% | | | | |

-continued

| Time prior AKI stage | Cutoff value | sens | spec | Quartile | OR | 95% CI of OR | |
|---|---|---|---|---|---|---|---|
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| sCr only | | | | | | | |
| 0 hours | 57.84132841 | 80% | 22% | 1 | | | |
| | 57.84132841 | 80% | 22% | 2 | 0.0 | 0.0 | 65535.0 |
| | 43.72693727 | 100% | 8% | 3 | 2.2 | 0.1 | 52.6 |
| | 90.92178771 | 20% | 71% | 4 | 2.2 | 0.1 | 52.6 |
| | 107.5980392 | 20% | 81% | | | | |
| | 130.726257 | 0% | 90% | | | | |
| 24 hours | 49.91467577 | 100% | 18% | 1 | | | |
| | 49.91467577 | 100% | 18% | 2 | 0.0 | 0.0 | 65535.0 |
| | 49.91467577 | 100% | 18% | 3 | 0.9 | 0.0 | 59.6 |
| | 90.92178771 | 67% | 71% | 4 | 0.9 | 0.0 | 59.6 |
| | 107.5980392 | 0% | 81% | | | | |
| | 130.726257 | 0% | 90% | | | | |
| 48 hours | 73.46416382 | 100% | 47% | 1 | | | |
| | 73.46416382 | 100% | 47% | 2 | na | na | na |
| | 73.46416382 | 100% | 47% | 3 | na | na | na |
| | 90.92178771 | 50% | 71% | 4 | na | na | na |
| | 107.5980392 | 50% | 81% | | | | |
| | 130.726257 | 0% | 90% | | | | |
| UO only | | | | | | | |
| 0 hours | 57.08191126 | 75% | 27% | 1 | | | |
| | 43.72693727 | 83% | 9% | 2 | 1.0 | 0.2 | 6.0 |
| | 39.57564576 | 92% | 0% | 3 | 0.6 | 0.1 | 4.8 |
| | 85.04901961 | 33% | 73% | 4 | 1.3 | 0.3 | 6.8 |
| | 88.82681564 | 33% | 82% | | | | |
| | 106.0055866 | 25% | 91% | | | | |
| 24 hours | 43.72693727 | 100% | 9% | 1 | | | |
| | 43.72693727 | 100% | 9% | 2 | 0.0 | 0.0 | 65535.0 |
| | 43.72693727 | 100% | 9% | 3 | 0.0 | 0.0 | 65535.0 |
| | 85.04901961 | 33% | 73% | 4 | 2.3 | 0.1 | 73.1 |
| | 88.82681564 | 0% | 82% | | | | |
| | 106.0055866 | 0% | 91% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |

Heat Shock Protein Beta-1:

| Time prior AKI stage | Cutoff value | sens | spec | Quartile | OR | 95% CI of OR | |
|---|---|---|---|---|---|---|---|
| sCr or UO | | | | | | | |
| 0 hours | 21.90563725 | 71% | 12% | 1 | | | |
| | 12.86204268 | 86% | 5% | 2 | 6.5 | 0.5 | 89.6 |
| | 8.860518293 | 93% | 4% | 3 | 2.1 | 0.1 | 51.0 |
| | 139.0050167 | 7% | 70% | 4 | 9.3 | 0.7 | 122.4 |
| | 189.9923313 | 7% | 81% | | | | |
| | 290.1168969 | 0% | 91% | | | | |
| 24 hours | 16.34933775 | 100% | 9% | 1 | | | |
| | 16.34933775 | 100% | 9% | 2 | na | na | na |
| | 16.34933775 | 100% | 9% | 3 | na | na | na |
| | 139.0050167 | 0% | 70% | 4 | na | na | na |
| | 189.9923313 | 0% | 81% | | | | |
| | 290.1168969 | 0% | 91% | | | | |
| 48 hours | 14.76753049 | 100% | 7% | 1 | | | |
| | 14.76753049 | 100% | 7% | 2 | na | na | na |
| | 14.76753049 | 100% | 7% | 3 | na | na | na |
| | 139.0050167 | 0% | 70% | 4 | na | na | na |
| | 189.9923313 | 0% | 81% | | | | |
| | 290.1168969 | 0% | 91% | | | | |

-continued

| Time prior AKI stage | Cutoff value | sens | spec | Quartile | OR | 95% CI of OR | |
|---|---|---|---|---|---|---|---|
| sCr only | | | | | | | |
| 0 hours | 50.49668874 | 83% | 35% | 1 | | | |
| | 50.49668874 | 83% | 35% | 2 | 1.0 | 0.0 | 59.8 |
| | 8.860518293 | 100% | 3% | 3 | 3.3 | 0.2 | 53.6 |
| | 135.1610429 | 17% | 71% | 4 | 1.0 | 0.0 | 57.1 |
| | 184.5735786 | 17% | 80% | | | | |
| | 273.1137088 | 17% | 90% | | | | |
| 24 hours | 57.1192053 | 100% | 41% | 1 | | | |
| | 57.1192053 | 100% | 41% | 2 | na | na | na |
| | 57.1192053 | 100% | 41% | 3 | na | na | na |
| | 135.1610429 | 0% | 71% | 4 | na | na | na |
| | 184.5735786 | 0% | 80% | | | | |
| | 273.1137088 | 0% | 90% | | | | |
| 48 hours | 116.9425087 | 100% | 68% | 1 | | | |
| | 116.9425087 | 100% | 68% | 2 | na | na | na |
| | 116.9425087 | 100% | 68% | 3 | na | na | na |
| | 135.1610429 | 50% | 71% | 4 | na | na | na |
| | 184.5735786 | 50% | 80% | | | | |
| | 273.1137088 | 50% | 90% | | | | |
| UO only | | | | | | | |
| 0 hours | 15.33917683 | 73% | 2% | 1 | | | |
| | 14.76753049 | 80% | 2% | 2 | 5.6 | 0.3 | 90.8 |
| | 8.40585443 | 93% | 0% | 3 | 2.3 | 0.1 | 59.8 |
| | 139.0050167 | 7% | 71% | 4 | 18.7 | 1.3 | 270.0 |
| | 184.5735786 | 7% | 81% | | | | |
| | 290.1168969 | 0% | 90% | | | | |
| 24 hours | 16.34933775 | 100% | 5% | 1 | | | |
| | 16.34933775 | 100% | 5% | 2 | 0.0 | 0.0 | 65535.0 |
| | 16.34933775 | 100% | 5% | 3 | 1.1 | 0.0 | 80.6 |
| | 139.0050167 | 33% | 71% | 4 | 1.1 | 0.0 | 80.6 |
| | 184.5735786 | 33% | 81% | | | | |
| | 290.1168969 | 33% | 90% | | | | |
| 48 hours | 14.76753049 | 100% | 2% | 1 | | | |
| | 14.76753049 | 100% | 2% | 2 | na | na | na |
| | 14.76753049 | 100% | 2% | 3 | na | na | na |
| | 139.0050167 | 0% | 71% | 4 | na | na | na |
| | 184.5735786 | 0% | 81% | | | | |
| | 290.1168969 | 0% | 90% | | | | |

Example 10

Kidney Injury Markers for Evaluating Renal Status in Patients at RIFLE Stages 0 and R Patients were classified and analyzed as described in Example 9. However, patients that reached stage R but did not progress to stage I or F were grouped with patients from non-injury stage 0 in Cohort 1. Cohort 2 in this example included only patients that progressed to stage I or F. Marker concentrations in the plasma component of blood samples were included for Cohort 1. Marker concentrations the plasma component of blood samples collected within 0, 24, and 48 hours of reaching stage I or F were included for Cohort 2.

The following descriptive statistics were obtained:

Soluble p-Selectin:

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| median | 70.461 | na | 70.461 | 66.772 | 70.461 | 26.445 |
| average | 75.507 | na | 75.507 | 69.173 | 75.507 | 71.409 |
| stdev | 38.443 | na | 38.443 | 29.437 | 38.443 | na |
| p (t-test) | | na | | 0.585 | | na |
| min | 26.445 | na | 26.445 | 24.586 | 26.445 | 71.409 |
| max | 196.760 | na | 196.760 | 115.156 | 196.760 | 71.409 |
| n (Samp) | 46 | 0 | 46 | 13 | 46 | 1 |
| n (Pat) | 43 | 0 | 43 | 13 | 43 | 1 |
| sCr only | | | | | | |
| median | 69.882 | na | 69.882 | 69.660 | 69.882 | na |
| average | 73.421 | na | 73.421 | 73.920 | 73.421 | na |
| stdev | 36.672 | na | 36.672 | 30.436 | 36.672 | na |
| p (t-test) | | na | | 0.982 | | na |
| min | 22.994 | na | 22.994 | 45.839 | 22.994 | na |
| max | 196.760 | na | 196.760 | 106.261 | 196.760 | na |
| n (Samp) | 59 | 0 | 59 | 3 | 59 | 0 |
| n (Pat) | 54 | 0 | 54 | 3 | 54 | 0 |
| UO only | | | | | | |
| median | 70.355 | na | 70.355 | 59.964 | 70.355 | 26.445 |
| average | 75.995 | na | 75.995 | 65.611 | 75.995 | 71.409 |
| stdev | 40.724 | na | 40.724 | 27.299 | 40.724 | na |
| p (t-test) | | na | | 0.396 | | na |
| min | 26.445 | na | 26.445 | 24.586 | 26.445 | 71.409 |
| max | 196.760 | na | 196.760 | 115.156 | 196.760 | 71.409 |
| n (Samp) | 40 | 0 | 40 | 13 | 40 | 1 |
| n (Pat) | 37 | 0 | 37 | 13 | 37 | 1 |

Protein NOV Homolog:

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| median | 9608.193 | 10919.540 | 9608.193 | 10031.513 | 9608.193 | 13217.703 |
| average | 25945.538 | 17907.223 | 25945.538 | 10960.289 | 25945.538 | 11866.502 |
| stdev | 96388.752 | 20623.132 | 96388.752 | 8150.749 | 96388.752 | 2438.316 |
| p (t-test) | | 0.804 | | 0.524 | | 0.801 |
| min | 14.544 | 1668.937 | 14.544 | 974.026 | 14.544 | 9051.724 |
| max | 1005084.746 | 66983.373 | 1005084.746 | 28035.144 | 1005084.746 | 13330.078 |
| n (Samp) | 126 | 9 | 126 | 17 | 126 | 3 |
| n (Pat) | 73 | 9 | 73 | 17 | 73 | 3 |

-continued

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr only | | | | | | |
| median | 9500.000 | 42441.842 | 9500.000 | 22900.391 | 9500.000 | 32083.911 |
| average | 23261.410 | 42441.842 | 23261.410 | 21955.843 | 23261.410 | 32083.911 |
| stdev | 86639.057 | 17743.121 | 86639.057 | 11402.433 | 86639.057 | 26680.847 |
| p (t-test) |  | 0.755 |  | 0.973 |  | 0.886 |
| min | 14.544 | 29895.561 | 14.544 | 9401.261 | 14.544 | 13217.703 |
| max | 1005084.746 | 54988.124 | 1005084.746 | 39449.541 | 1005084.746 | 50950.119 |
| n (Samp) | 157 | 2 | 157 | 5 | 157 | 2 |
| n (Pat) | 91 | 2 | 91 | 5 | 91 | 2 |
| UO only | | | | | | |
| median | 10345.733 | 10919.540 | 10345.733 | 8245.798 | 10345.733 | 11190.901 |
| average | 29628.248 | 17907.223 | 29628.248 | 9443.692 | 29628.248 | 11190.901 |
| stdev | 106698.517 | 20623.132 | 106698.517 | 8129.900 | 106698.517 | 3025.253 |
| p (t-test) |  | 0.744 |  | 0.467 |  | 0.808 |
| min | 14.544 | 1668.937 | 14.544 | 974.026 | 14.544 | 9051.724 |
| max | 1005084.746 | 66983.373 | 1005084.746 | 28035.144 | 1005084.746 | 13330.078 |
| n (Samp) | 102 | 9 | 102 | 15 | 102 | 2 |
| n (Pat) | 57 | 9 | 57 | 15 | 57 | 2 |

Netrin 4:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 0.013 | 0.027 | 0.013 | 0.030 | 0.013 | 0.021 |
| average | 0.238 | 0.043 | 0.238 | 0.057 | 0.238 | 0.021 |
| stdev | 1.340 | 0.055 | 1.340 | 0.070 | 1.340 | 0.004 |
| p (t-test) |  | 0.665 |  | 0.789 |  | 0.820 |
| min | 0.005 | 0.007 | 0.005 | 0.008 | 0.005 | 0.018 |
| max | 8.584 | 0.184 | 8.584 | 0.161 | 8.584 | 0.023 |
| n (Samp) | 80 | 9 | 80 | 4 | 80 | 2 |
| n (Pat) | 58 | 9 | 58 | 4 | 58 | 2 |
| sCr only | | | | | | |
| median | 0.014 | 0.037 | 0.014 | 0.100 | 0.014 | 0.020 |
| average | 0.200 | 0.037 | 0.200 | 0.100 | 0.200 | 0.020 |
| stdev | 1.212 | 0.022 | 1.212 | 0.086 | 1.212 | 0.004 |
| p (t-test) |  | 0.850 |  | 0.908 |  | 0.835 |
| min | 0.005 | 0.021 | 0.005 | 0.039 | 0.005 | 0.017 |
| max | 8.584 | 0.053 | 8.584 | 0.161 | 8.584 | 0.023 |
| n (Samp) | 98 | 2 | 98 | 2 | 98 | 2 |
| n (Pat) | 70 | 2 | 70 | 2 | 70 | 2 |
| UO only | | | | | | |
| median | 0.012 | 0.027 | 0.012 | 0.014 | 0.012 | 0.005 |
| average | 0.296 | 0.043 | 0.296 | 0.014 | 0.296 | 0.018 |
| stdev | 1.520 | 0.055 | 1.520 | 0.009 | 1.520 | na |
| p (t-test) |  | 0.622 |  | 0.796 |  | na |
| min | 0.005 | 0.007 | 0.005 | 0.008 | 0.005 | 0.018 |
| max | 8.584 | 0.184 | 8.584 | 0.020 | 8.584 | 0.018 |
| n (Samp) | 62 | 9 | 62 | 2 | 62 | 1 |
| n (Pat) | 45 | 9 | 45 | 2 | 45 | 1 |

Alpha-1-Antitrypsin:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 3.150 | 2.460 | 3.150 | 2.240 | 3.150 | 1.680 |
| average | 3.383 | 2.733 | 3.383 | 2.341 | 3.383 | 2.216 |
| stdev | 1.482 | 1.286 | 1.482 | 1.105 | 1.482 | 1.258 |
| p (t-test) |  | 0.041 |  | 0.001 |  | 0.005 |
| min | 0.854 | 1.270 | 0.854 | 0.737 | 0.854 | 1.080 |
| max | 8.930 | 6.130 | 8.930 | 5.540 | 8.930 | 5.580 |
| n (Samp) | 356 | 23 | 356 | 25 | 356 | 13 |
| n (Pat) | 121 | 23 | 121 | 25 | 121 | 13 |
| sCr only | | | | | | |
| median | 3.030 | 2.280 | 3.030 | 2.340 | 3.030 | 2.440 |
| average | 3.276 | 3.182 | 3.276 | 3.039 | 3.276 | 3.082 |
| stdev | 1.454 | 2.030 | 1.454 | 1.774 | 1.454 | 1.513 |
| p (t-test) |  | 0.876 |  | 0.670 |  | 0.767 |
| min | 0.769 | 1.540 | 0.769 | 1.130 | 0.769 | 1.680 |
| max | 8.930 | 6.700 | 8.930 | 5.540 | 8.930 | 5.580 |
| n (Samp) | 441 | 6 | 441 | 7 | 441 | 5 |
| n (Pat) | 146 | 6 | 146 | 7 | 146 | 5 |
| UO only | | | | | | |
| median | 3.040 | 2.460 | 3.040 | 2.155 | 3.040 | 1.550 |
| average | 3.286 | 2.849 | 3.286 | 2.249 | 3.286 | 1.895 |
| stdev | 1.385 | 1.459 | 1.385 | 0.934 | 1.385 | 0.761 |
| p (t-test) |  | 0.155 |  | 0.000 |  | 0.000 |
| min | 0.854 | 1.270 | 0.854 | 0.737 | 0.854 | 1.080 |
| max | 8.230 | 6.250 | 8.230 | 5.470 | 8.230 | 3.110 |
| n (Samp) | 293 | 22 | 293 | 24 | 293 | 13 |
| n (Pat) | 97 | 22 | 97 | 24 | 97 | 13 |

Leukocyte Elastase:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 245.772 | 344.108 | 245.772 | 328.996 | 245.772 | 356.383 |
| average | 292.672 | 430.527 | 292.672 | 349.494 | 292.672 | 343.889 |
| stdev | 192.477 | 365.913 | 192.477 | 222.177 | 192.477 | 147.123 |
| p (t-test) |  | 0.011 |  | 0.230 |  | 0.349 |
| min | 1.849 | 117.281 | 1.849 | 32.619 | 1.849 | 112.301 |
| max | 1032.377 | 1644.672 | 1032.377 | 861.088 | 1032.377 | 580.606 |
| n (Samp) | 176 | 17 | 176 | 19 | 176 | 13 |
| n (Pat) | 88 | 17 | 88 | 19 | 88 | 13 |
| sCr only | | | | | | |
| median | 269.909 | 754.508 | 269.909 | 390.753 | 269.909 | 426.508 |
| average | 310.018 | 970.631 | 310.018 | 345.086 | 310.018 | 385.000 |
| stdev | 192.041 | 596.125 | 192.041 | 107.963 | 192.041 | 97.033 |
| p (t-test) |  | 0.000 |  | 0.685 |  | 0.386 |
| min | 1.849 | 512.712 | 1.849 | 219.883 | 1.849 | 241.888 |
| max | 1032.377 | 1644.672 | 1032.377 | 449.195 | 1032.377 | 480.738 |
| n (Samp) | 230 | 3 | 230 | 5 | 230 | 5 |
| n (Pat) | 106 | 3 | 106 | 5 | 106 | 5 |
| UO only | | | | | | |
| median | 254.910 | 293.033 | 254.910 | 328.996 | 254.910 | 331.015 |
| average | 306.181 | 356.872 | 306.181 | 363.019 | 306.181 | 433.999 |
| stdev | 197.948 | 224.078 | 197.948 | 243.399 | 197.948 | 407.742 |
| p (t-test) |  | 0.324 |  | 0.252 |  | 0.053 |
| min | 1.849 | 117.281 | 1.849 | 32.619 | 1.849 | 112.301 |
| max | 1032.377 | 955.328 | 1032.377 | 861.088 | 1032.377 | 1644.672 |
| n (Samp) | 154 | 17 | 154 | 19 | 154 | 12 |
| n (Pat) | 75 | 17 | 75 | 19 | 75 | 12 |

Soluble Tumor Necrosis Factor Receptor Superfamily Member 6:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 9249.617 | 15198.188 | 9249.617 | 12198.142 | 9249.617 | 9831.547 |
| average | 10423.034 | 15527.259 | 10423.034 | 11740.844 | 10423.034 | 10889.450 |
| stdev | 4473.287 | 1478.048 | 4473.287 | 3647.663 | 4473.287 | 2958.338 |
| p (t-test) |  | 0.012 |  | 0.244 |  | 0.818 |
| min | 3586.165 | 14117.647 | 3586.165 | 6493.109 | 3586.165 | 8489.828 |
| max | 21494.904 | 17244.582 | 21494.904 | 18618.347 | 21494.904 | 16036.240 |
| n (Samp) | 143 | 5 | 143 | 17 | 143 | 5 |
| n (Pat) | 55 | 5 | 55 | 17 | 55 | 5 |
| sCr only | | | | | | |
| median | 9667.323 | 17667.044 | 9667.323 | 14461.942 | 9667.323 | 10861.325 |
| average | 10879.753 | 17667.044 | 10879.753 | 13982.601 | 10879.753 | 10861.325 |
| stdev | 4460.887 | 1089.089 | 4460.887 | 3496.355 | 4460.887 | 1616.735 |
| p (t-test) |  | 0.033 |  | 0.125 |  | 0.995 |
| min | 3586.165 | 16896.942 | 3586.165 | 9280.245 | 3586.165 | 9718.121 |
| max | 21494.904 | 18437.146 | 21494.904 | 18618.347 | 21494.904 | 12004.530 |
| n (Samp) | 178 | 2 | 178 | 5 | 178 | 2 |
| n (Pat) | 69 | 2 | 69 | 5 | 69 | 2 |
| UO only | | | | | | |
| median | 9494.640 | 14688.562 | 9494.640 | 9387.443 | 9494.640 | 10101.532 |
| average | 10348.364 | 15184.838 | 10348.364 | 10774.711 | 10348.364 | 11182.283 |
| stdev | 4266.467 | 1459.847 | 4266.467 | 3418.974 | 4266.467 | 3331.268 |
| p (t-test) |  | 0.026 |  | 0.711 |  | 0.700 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| min | 3586.165 | 14117.647 | 3586.165 | 6493.109 | 3586.165 | 8489.828 |
| max | 21494.904 | 17244.582 | 21494.904 | 17086.614 | 21494.904 | 16036.240 |
| n (Samp) | 111 | 4 | 111 | 15 | 111 | 4 |
| n (Pat) | 44 | 4 | 44 | 15 | 44 | 4 |

Soluble Tumor Necrosis Factor Ligand Superfamily Member 6:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 43.218 | 27.158 | 43.218 | 42.878 | 43.218 | 42.057 |
| average | 52.799 | 29.007 | 52.799 | 53.586 | 52.799 | 61.206 |
| stdev | 31.236 | 12.205 | 31.236 | 25.789 | 31.236 | 42.042 |
| p (t-test) |  | 0.094 |  | 0.948 |  | 0.602 |
| min | 9.201 | 14.357 | 9.201 | 29.390 | 9.201 | 36.579 |
| max | 140.754 | 41.424 | 140.754 | 95.808 | 140.754 | 124.129 |
| n (Samp) | 109 | 5 | 109 | 7 | 109 | 4 |
| n (Pat) | 27 | 5 | 27 | 7 | 27 | 4 |
| sCr only | | | | | | |
| median | 43.218 | 34.414 | 43.218 | 37.796 | 43.218 | 30.953 |
| average | 52.411 | 34.414 | 52.411 | 50.785 | 52.411 | 30.953 |
| stdev | 31.016 | 9.914 | 31.016 | 40.138 | 31.016 | 13.858 |
| p (t-test) |  | 0.415 |  | 0.929 |  | 0.332 |
| min | 9.201 | 27.404 | 9.201 | 18.750 | 9.201 | 21.154 |
| max | 140.754 | 41.424 | 140.754 | 95.808 | 140.754 | 40.752 |
| n (Samp) | 132 | 2 | 132 | 3 | 132 | 2 |
| n (Pat) | 32 | 2 | 32 | 3 | 32 | 2 |
| UO only | | | | | | |
| median | 52.010 | 23.915 | 52.010 | 42.878 | 52.010 | 43.362 |
| average | 56.406 | 25.903 | 56.406 | 48.300 | 56.406 | 68.024 |
| stdev | 32.233 | 11.592 | 32.233 | 21.322 | 32.233 | 48.707 |
| p (t-test) |  | 0.064 |  | 0.582 |  | 0.548 |
| min | 12.326 | 14.357 | 12.326 | 29.390 | 12.326 | 36.579 |
| max | 140.754 | 41.424 | 140.754 | 84.930 | 140.754 | 124.129 |
| n (Samp) | 81 | 4 | 81 | 5 | 81 | 3 |
| n (Pat) | 20 | 4 | 20 | 5 | 20 | 3 |

Soluble Intercellular Adhesion Molecule 2:

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| median | 368.071 | 389.854 | 368.071 | 261.327 | 368.071 | 319.807 |
| average | 441.140 | 503.002 | 441.140 | 372.348 | 441.140 | 319.807 |
| stdev | 292.394 | 244.962 | 292.394 | 379.558 | 292.394 | 159.493 |
| p (t-test) |  | 0.549 |  | 0.656 |  | 0.564 |
| min | 1.944 | 307.980 | 1.944 | 45.957 | 1.944 | 207.029 |
| max | 1343.415 | 933.659 | 1343.415 | 920.780 | 1343.415 | 432.585 |
| n (Samp) | 60 | 9 | 60 | 4 | 60 | 2 |
| n (Pat) | 37 | 9 | 37 | 4 | 37 | 2 |
| sCr only | | | | | | |
| median | 358.818 | 319.564 | 358.818 | 148.247 | 358.818 | 520.295 |
| average | 440.246 | 319.564 | 440.246 | 148.247 | 440.246 | 520.295 |
| stdev | 289.787 | 178.125 | 289.787 | 144.659 | 289.787 | 443.025 |
| p (t-test) |  | 0.561 |  | 0.161 |  | 0.703 |
| min | 1.944 | 193.610 | 1.944 | 45.957 | 1.944 | 207.029 |
| max | 1343.415 | 445.517 | 1343.415 | 250.537 | 1343.415 | 833.561 |
| n (Samp) | 79 | 2 | 79 | 2 | 79 | 2 |
| n (Pat) | 49 | 2 | 49 | 2 | 49 | 2 |
| UO only | | | | | | |
| median | 354.483 | 389.854 | 354.483 | 596.449 | 354.483 | 34.681 |
| average | 468.680 | 503.002 | 468.680 | 596.449 | 468.680 | 432.585 |
| stdev | 301.539 | 244.962 | 301.539 | 458.673 | 301.539 | na |
| p (t-test) |  | 0.750 |  | 0.566 |  | na |
| min | 34.681 | 307.980 | 34.681 | 272.118 | 34.681 | 432.585 |
| max | 1343.415 | 933.659 | 1343.415 | 920.780 | 1343.415 | 432.585 |
| n (Samp) | 45 | 9 | 45 | 2 | 45 | 1 |
| n (Pat) | 26 | 9 | 26 | 2 | 26 | 1 |

Heat Shock Protein Beta-1:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 77.927 | 25.248 | 77.927 | 78.317 | 77.927 | 41.287 |
| average | 120.234 | 81.591 | 120.234 | 66.833 | 120.234 | 41.287 |
| stdev | 122.931 | 146.704 | 122.931 | 32.285 | 122.931 | 22.975 |
| p (t-test) |  | 0.382 |  | 0.391 |  | 0.369 |
| min | 3.449 | 9.813 | 3.449 | 19.454 | 3.449 | 25.041 |
| max | 683.847 | 469.182 | 683.847 | 91.246 | 683.847 | 57.533 |
| n (Samp) | 82 | 9 | 82 | 4 | 82 | 2 |
| n (Pat) | 59 | 9 | 59 | 4 | 59 | 2 |
| sCr only | | | | | | |
| median | 77.308 | 271.435 | 77.308 | 83.108 | 77.308 | 435.515 |
| average | 118.486 | 271.435 | 118.486 | 83.108 | 118.486 | 435.515 |
| stdev | 123.934 | 370.581 | 123.934 | 11.509 | 123.934 | 534.547 |
| p (t-test) |  | 0.099 |  | 0.689 |  | 0.001 |
| min | 3.449 | 9.395 | 3.449 | 74.970 | 3.449 | 57.533 |
| max | 683.847 | 533.475 | 683.847 | 91.246 | 683.847 | 813.496 |
| n (Samp) | 101 | 2 | 101 | 2 | 101 | 2 |
| n (Pat) | 71 | 2 | 71 | 2 | 71 | 2 |
| UO only | | | | | | |
| median | 78.528 | 25.248 | 78.528 | 50.559 | 78.528 | 8.406 |
| average | 124.114 | 81.591 | 124.114 | 50.559 | 124.114 | 25.041 |
| stdev | 126.609 | 146.704 | 126.609 | 43.989 | 126.609 | na |
| p (t-test) |  | 0.358 |  | 0.418 |  | na |
| min | 8.406 | 9.813 | 8.406 | 19.454 | 8.406 | 25.041 |
| max | 683.847 | 469.182 | 683.847 | 81.664 | 683.847 | 25.041 |
| n (Samp) | 64 | 9 | 64 | 2 | 64 | 1 |
| n (Pat) | 46 | 9 | 46 | 2 | 46 | 1 |

Soluble Epidermal Growth Factor Receptor:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 10786.081 | 12379.349 | 10786.081 | 12714.333 | 10786.081 | na |
| average | 11450.960 | 12172.479 | 11450.960 | 12334.421 | 11450.960 | na |
| stdev | 3589.071 | 2833.018 | 3589.071 | 4187.377 | 3589.071 | na |
| p (t-test) |  | 0.607 |  | 0.464 |  | na |
| min | 6765.100 | 8232.414 | 6765.100 | 5676.691 | 6765.100 | na |
| max | 21698.024 | 16778.200 | 21698.024 | 21272.844 | 21698.024 | na |
| n (Samp) | 26 | 8 | 26 | 17 | 26 | 0 |
| n (Pat) | 25 | 8 | 25 | 17 | 25 | 0 |
| sCr only | | | | | | |
| median | 11118.118 | 9665.092 | 11118.118 | 10305.909 | 11118.118 | 6765.100 |
| average | 11998.860 | 9665.092 | 11998.860 | 12086.926 | 11998.860 | 6339.341 |
| stdev | 3653.295 | 2026.112 | 3653.295 | 5299.697 | 3653.295 | na |
| p (t-test) |  | 0.377 |  | 0.951 |  | na |
| min | 6765.100 | 8232.414 | 6765.100 | 5676.691 | 6765.100 | 6339.341 |
| max | 21698.024 | 11097.769 | 21698.024 | 22866.557 | 21698.024 | 6339.341 |
| n (Samp) | 47 | 2 | 47 | 9 | 47 | 1 |
| n (Pat) | 44 | 2 | 44 | 9 | 44 | 1 |
| UO only | | | | | | |
| median | 10541.051 | 13660.928 | 10541.051 | 13735.459 | 10541.051 | 6765.100 |
| average | 11680.245 | 12735.345 | 11680.245 | 14394.423 | 11680.245 | 11884.006 |
| stdev | 4430.173 | 2531.142 | 4430.173 | 4142.066 | 4430.173 | na |
| p (t-test) |  | 0.552 |  | 0.090 |  | na |
| min | 6765.100 | 9355.404 | 6765.100 | 7026.751 | 6765.100 | 11884.006 |
| max | 24717.033 | 16778.200 | 24717.033 | 21272.844 | 24717.033 | 11884.006 |
| n (Samp) | 27 | 7 | 27 | 11 | 27 | 1 |
| n (Pat) | 25 | 7 | 25 | 11 | 25 | 1 |

In the following tables, the ability to distinguish cohort 1 (subjects remaining in RIFLE 0 or R) from Cohort 2 (subjects progressing to RIFLE I or F) was determined using ROC analysis.

Soluble p-Selectin:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | nd | nd | 46 | 0 | 0.211 |
| 24 hours | 0.47 | 0.090 | 46 | 13 | 1.233 |
| 48 hours | 0.54 | 0.301 | 46 | 1 | 0.885 |
| Cohort 1 v Cohort 2, adjudicated on serum creatinine | | | | | |
| 0 hours | nd | nd | 59 | 0 | 0.211 |
| 24 hours | 0.53 | 0.175 | 59 | 3 | 0.859 |
| 48 hours | nd | nd | 59 | 0 | 0.211 |
| Cohort 1 v Cohort 2, adjudicated on urine output | | | | | |
| 0 hours | nd | nd | 40 | 0 | 0.211 |
| 24 hours | 0.44 | 0.090 | 40 | 13 | 1.491 |
| 48 hours | 0.55 | 0.303 | 40 | 1 | 0.869 |

Protein NOV Homolog:

| Time prior max stage | AUC | SE | $n_{Cohort\ 1}$ | $n_{Cohort\ 2}$ | p |
| --- | --- | --- | --- | --- | --- |
| Cohort 1 v Cohort 2, adjudicated on serum creatinine measurements or urine output | | | | | |
| 0 hours | 0.55 | 0.102 | 126 | 9 | 0.602 |
| 24 hours | 0.49 | 0.075 | 126 | 17 | 1.062 |
| 48 hours | 0.62 | 0.175 | 126 | 3 | 0.483 |

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine | | | | | |
| 0 hours | 0.93 | 0.128 | 157 | 2 | 0.001 |
| 24 hours | 0.77 | 0.125 | 157 | 5 | 0.028 |
| 48 hours | 0.82 | 0.185 | 157 | 2 | 0.088 |
| Cohort 1 v Cohort 2, adjudicated on urine output | | | | | |
| 0 hours | 0.53 | 0.102 | 102 | 9 | 0.786 |
| 24 hours | 0.41 | 0.075 | 102 | 15 | 1.792 |
| 48 hours | 0.55 | 0.212 | 102 | 2 | 0.809 |

Netrin 4:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.67 | 0.103 | 80 | 9 | 0.099 |
| 24 hours | 0.67 | 0.152 | 80 | 4 | 0.258 |
| 48 hours | 0.72 | 0.208 | 80 | 2 | 0.285 |
| Cohort 1 v Cohort 2, adjudicated on serum creatinine | | | | | |
| 0 hours | 0.80 | 0.190 | 98 | 2 | 0.113 |
| 24 hours | 0.89 | 0.154 | 98 | 2 | 0.012 |
| 48 hours | 0.69 | 0.211 | 98 | 2 | 0.372 |
| Cohort 1 v Cohort 2, adjudicated on urine output | | | | | |
| 0 hours | 0.71 | 0.102 | 62 | 9 | 0.041 |
| 24 hours | 0.51 | 0.210 | 62 | 2 | 0.969 |
| 48 hours | 0.73 | 0.291 | 62 | 1 | 0.421 |

Alpha-1-Antitrypsin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.36 | 0.054 | 356 | 23 | 1.991 |
| 24 hours | 0.28 | 0.045 | 356 | 25 | 2.000 |
| 48 hours | 0.24 | 0.054 | 356 | 13 | 2.000 |
| Cohort 1 v Cohort 2, adjudicated on serum creatinine | | | | | |
| 0 hours | 0.43 | 0.111 | 441 | 6 | 1.494 |
| 24 hours | 0.43 | 0.104 | 441 | 7 | 1.480 |
| 48 hours | 0.46 | 0.126 | 441 | 5 | 1.265 |
| Cohort 1 v Cohort 2, adjudicated on urine output | | | | | |
| 0 hours | 0.39 | 0.058 | 293 | 22 | 1.954 |
| 24 hours | 0.27 | 0.045 | 293 | 24 | 2.000 |
| 48 hours | 0.17 | 0.042 | 293 | 13 | 2.000 |

Leukocyte elastase:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.63 | 0.075 | 176 | 17 | 0.081 |
| 24 hours | 0.57 | 0.072 | 176 | 19 | 0.296 |
| 48 hours | 0.62 | 0.086 | 176 | 13 | 0.152 |

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine | | | | | |
| 0 hours | 0.94 | 0.094 | 230 | 3 | 0.000 |
| 24 hours | 0.61 | 0.136 | 230 | 5 | 0.417 |
| 48 hours | 0.69 | 0.133 | 230 | 5 | 0.155 |
| Cohort 1 v Cohort 2, adjudicated on urine output | | | | | |
| 0 hours | 0.57 | 0.076 | 154 | 17 | 0.333 |
| 24 hours | 0.56 | 0.072 | 154 | 19 | 0.410 |
| 48 hours | 0.60 | 0.089 | 154 | 12 | 0.269 |

Soluble Tumor Necrosis Factor Receptor Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.83 | 0.113 | 143 | 5 | 0.003 |
| 24 hours | 0.61 | 0.076 | 143 | 17 | 0.136 |
| 48 hours | 0.60 | 0.136 | 143 | 5 | 0.476 |
| Cohort 1 v Cohort 2, adjudicated on serum creatinine | | | | | |
| 0 hours | 0.90 | 0.149 | 178 | 2 | 0.008 |
| 24 hours | 0.72 | 0.131 | 178 | 5 | 0.093 |
| 48 hours | 0.58 | 0.213 | 178 | 2 | 0.721 |
| Cohort 1 v Cohort 2, adjudicated on urine output | | | | | |
| 0 hours | 0.84 | 0.125 | 111 | 4 | 0.007 |
| 24 hours | 0.55 | 0.081 | 111 | 15 | 0.530 |
| 48 hours | 0.59 | 0.153 | 111 | 4 | 0.535 |

Soluble Tumor Necrosis Factor Ligand Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.26 | 0.094 | 109 | 5 | 1.990 |
| 24 hours | 0.53 | 0.115 | 109 | 7 | 0.763 |
| 48 hours | 0.56 | 0.152 | 109 | 4 | 0.672 |
| Cohort 1 v Cohort 2, adjudicated on serum creatinine | | | | | |
| 0 hours | 0.35 | 0.174 | 132 | 2 | 1.623 |
| 24 hours | 0.46 | 0.164 | 132 | 3 | 1.213 |
| 48 hours | 0.29 | 0.154 | 132 | 2 | 1.831 |
| Cohort 1 v Cohort 2, adjudicated on urine output | | | | | |
| 0 hours | 0.19 | 0.084 | 81 | 4 | 2.000 |
| 24 hours | 0.45 | 0.129 | 81 | 5 | 1.320 |
| 48 hours | 0.56 | 0.175 | 81 | 3 | 0.734 |

Soluble Intercellular Adhesion Molecule 2:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.60 | 0.106 | 60 | 9 | 0.365 |
| 24 hours | 0.38 | 0.134 | 60 | 4 | 1.632 |
| 48 hours | 0.41 | 0.193 | 60 | 2 | 1.365 |

-continued

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine | | | | | |
| 0 hours | 0.40 | 0.189 | 79 | 2 | 1.407 |
| 24 hours | 0.14 | 0.091 | 79 | 2 | 2.000 |
| 48 hours | 0.53 | 0.212 | 79 | 2 | 0.881 |
| Cohort 1 v Cohort 2, adjudicated on urine output | | | | | |
| 0 hours | 0.59 | 0.108 | 45 | 9 | 0.419 |
| 24 hours | 0.59 | 0.218 | 45 | 2 | 0.683 |
| 48 hours | 0.62 | 0.306 | 45 | 1 | 0.689 |

Heat Shock Protein Beta-1:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.30 | 0.080 | 82 | 9 | 1.989 |
| 24 hours | 0.42 | 0.140 | 82 | 4 | 1.415 |
| 48 hours | 0.26 | 0.147 | 82 | 2 | 1.895 |
| Cohort 1 v Cohort 2, adjudicated on serum creatinine | | | | | |
| 0 hours | 0.51 | 0.208 | 101 | 2 | 0.962 |
| 24 hours | 0.53 | 0.211 | 101 | 2 | 0.870 |
| 48 hours | 0.70 | 0.210 | 101 | 2 | 0.333 |
| Cohort 1 v Cohort 2, adjudicated on urine output | | | | | |
| 0 hours | 0.28 | 0.079 | 64 | 9 | 1.995 |
| 24 hours | 0.32 | 0.168 | 64 | 2 | 1.714 |
| 48 hours | 0.14 | 0.129 | 64 | 1 | 1.995 |

Soluble Epidermal Growth Factor Receptor:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.60 | 0.119 | 26 | 8 | 0.398 |
| 24 hours | 0.58 | 0.091 | 26 | 17 | 0.369 |
| 48 hours | nd | nd | 26 | 0 | 0.211 |
| Cohort 1 v Cohort 2, adjudicated on serum creatinine | | | | | |
| 0 hours | 0.31 | 0.167 | 47 | 2 | 1.749 |
| 24 hours | 0.48 | 0.105 | 47 | 9 | 1.188 |
| 48 hours | 0.00 | 0.000 | 47 | 1 | n/a |
| Cohort 1 v Cohort 2, adjudicated on urine output | | | | | |
| 0 hours | 0.67 | 0.123 | 27 | 7 | 0.176 |
| 24 hours | 0.73 | 0.097 | 27 | 11 | 0.019 |
| 48 hours | 0.63 | 0.309 | 27 | 1 | 0.675 |

Various threshold (or "cutoff") concentrations were selected, and the associated sensitivity and specificity for distinguishing cohort 1 from cohort 2, as shown in the following tables. OR is the odds ratio calculated for the particular cutoff concentration, and 95% CI is the confidence interval for the odds ratio.

Soluble p-Selectin:

| Time prior AKI stage | Cutoff value | sens | spec | Quartile | OR | 95% CI of OR |
|---|---|---|---|---|---|---|
| sCr or UO | | | | | | |
| 0 hours | 0 | na | na | 1 | | |
|  | 0 | na | na | 2 | na | na na |
|  | 0 | na | na | 3 | na | na na |
|  | 0 | na | na | 4 | na | na na |
|  | 0 | na | na | | | |
|  | 0 | na | na | | | |
| 24 hours | 41.57990997 | 77% | 24% | 1 | | |
|  | 41.16807386 | 85% | 24% | 2 | 0.4 | 0.1 2.6 |
|  | 36.15698737 | 92% | 15% | 3 | 1.0 | 0.3 3.8 |
|  | 85.18918315 | 31% | 72% | 4 | 0.8 | 0.2 3.4 |
|  | 98.6629192 | 23% | 80% | | | |
|  | 116.8580315 | 0% | 91% | | | |
| 48 hours | 71.26241682 | 100% | 54% | 1 | | |
|  | 71.26241682 | 100% | 54% | 2 | na | na na |
|  | 71.26241682 | 100% | 54% | 3 | na | na na |
|  | 85.18918315 | 0% | 72% | 4 | na | na na |
|  | 98.6629192 | 0% | 80% | | | |
|  | 116.8580315 | 0% | 91% | | | |
| sCr only | | | | | | |
| 0 hours | 0 | na | na | 1 | | |
|  | 0 | na | na | 2 | na | na na |
|  | 0 | na | na | 3 | na | na na |
|  | 0 | na | na | 4 | na | na na |
|  | 0 | na | na | | | |
|  | 0 | na | na | | | |
| 24 hours | 45.08916942 | 100% | 27% | 1 | | |
|  | 45.08916942 | 100% | 27% | 2 | na | na na |
|  | 45.08916942 | 100% | 27% | 3 | na | na na |
|  | 84.57719926 | 33% | 71% | 4 | na | na na |
|  | 98.6629192 | 33% | 81% | | | |
|  | 115.1555728 | 0% | 92% | | | |
| 48 hours | 0 | na | na | 1 | | |
|  | 0 | na | na | 2 | na | na na |
|  | 0 | na | na | 3 | na | na na |
|  | 0 | na | na | 4 | na | na na |
|  | 0 | na | na | | | |
|  | 0 | na | na | | | |
| UO only | | | | | | |
| 0 hours | 0 | na | na | 1 | | |
|  | 0 | na | na | 2 | na | na na |
|  | 0 | na | na | 3 | na | na na |
|  | 0 | na | na | 4 | na | na na |
|  | 0 | na | na | | | |
|  | 0 | na | na | | | |
| 24 hours | 41.57990997 | 77% | 25% | 1 | | |
|  | 39.57955124 | 85% | 25% | 2 | 0.7 | 0.1 4.9 |
|  | 36.15698737 | 92% | 18% | 3 | 2.3 | 0.5 10.0 |
|  | 85.18918315 | 23% | 70% | 4 | 1.1 | 0.2 5.9 |
|  | 100.9858993 | 15% | 80% | | | |
|  | 116.8580315 | 0% | 90% | | | |
| 48 hours | 71.26241682 | 100% | 55% | 1 | | |
|  | 71.26241682 | 100% | 55% | 2 | na | na na |
|  | 71.26241682 | 100% | 55% | 3 | na | na na |
|  | 85.18918315 | 0% | 70% | 4 | na | na na |
|  | 100.9858993 | 0% | 80% | | | |
|  | 116.8580315 | 0% | 90% | | | |

Protein NOV Homolog:

| Time prior AKI stage | Cutoff value | sens | spec | Quartile | OR | 95% CI of OR |
|---|---|---|---|---|---|---|
| sCr or UO | | | | | | |
| 0 hours | 5128.205128 | 78% | 25% | 1 | | |
|  | 2895.095368 | 89% | 17% | 2 | 0.5 | 0.0 10.0 |
|  | 1542.207792 | 100% | 9% | 3 | 1.5 | 0.3 8.7 |
|  | 13232.42188 | 44% | 71% | 4 | 1.5 | 0.3 8.7 |

-continued

| Time prior AKI stage | Cutoff value | sens | spec | Quartile | OR | 95% CI of OR | |
|---|---|---|---|---|---|---|---|
| | 16845.70313 | 22% | 80% | | | | |
| | 30886.85015 | 22% | 90% | | | | |
| 24 hours | 5128.205128 | 71% | 25% | 1 | | | |
| | 2282.016349 | 82% | 13% | 2 | 1.3 | 0.5 | 3.5 |
| | 1542.207792 | 94% | 9% | 3 | 0.7 | 0.2 | 2.6 |
| | 13232.42188 | 35% | 71% | 4 | 1.3 | 0.5 | 3.7 |
| | 16845.70313 | 18% | 80% | | | | |
| | 30886.85015 | 0% | 90% | | | | |
| 48 hours | 8560.92437 | 100% | 47% | 1 | | | |
| | 8560.92437 | 100% | 47% | 2 | na | na | na |
| | 8560.92437 | 100% | 47% | 3 | na | na | na |
| | 13232.42188 | 33% | 71% | 4 | na | na | na |
| | 16845.70313 | 0% | 80% | | | | |
| | 30886.85015 | 0% | 90% | | | | | sCr only

| Time prior AKI stage | Cutoff value | sens | spec | Quartile | OR | 95% CI of OR | |
|---|---|---|---|---|---|---|---|
| 0 hours | 29816.51376 | 100% | 90% | 1 | | | |
| | 29816.51376 | 100% | 90% | 2 | na | na | na |
| | 29816.51376 | 100% | 90% | 3 | na | na | na |
| | 13330.07813 | 100% | 70% | 4 | na | na | na |
| | 16845.70313 | 100% | 80% | | | | |
| | 29816.51376 | 100% | 90% | | | | |
| 24 hours | 14404.29688 | 80% | 73% | 1 | | | |
| | 14404.29688 | 80% | 73% | 2 | na | na | na |
| | 9339.08046 | 100% | 50% | 3 | na | na | na |
| | 13330.07813 | 80% | 70% | 4 | na | na | na |
| | 16845.70313 | 60% | 80% | | | | |
| | 29816.51376 | 20% | 90% | | | | |
| 48 hours | 12978.4689 | 100% | 68% | 1 | | | |
| | 12978.4689 | 100% | 68% | 2 | na | na | na |
| | 12978.4689 | 100% | 68% | 3 | na | na | na |
| | 13330.07813 | 50% | 70% | 4 | na | na | na |
| | 16845.70313 | 50% | 80% | | | | |
| | 29816.51376 | 50% | 90% | | | | |

UO only

| Time prior AKI stage | Cutoff value | sens | spec | Quartile | OR | 95% CI of OR | |
|---|---|---|---|---|---|---|---|
| 0 hours | 5128.205128 | 78% | 20% | 1 | | | |
| | 2895.095368 | 89% | 14% | 2 | 0.3 | 0.0 | 4.7 |
| | 1542.207792 | 100% | 6% | 3 | 1.0 | 0.2 | 4.2 |
| | 13916.01563 | 44% | 71% | 4 | 0.6 | 0.1 | 3.7 |
| | 17165.07177 | 22% | 80% | | | | |
| | 30886.85015 | 22% | 90% | | | | |
| 24 hours | 2588.555858 | 73% | 11% | 1 | | | |
| | 2158.938172 | 80% | 10% | 2 | 1.0 | 0.2 | 4.4 |
| | 1542.207792 | 93% | 6% | 3 | 0.7 | 0.1 | 3.9 |
| | 13916.01563 | 20% | 71% | 4 | 2.9 | 1.0 | 8.6 |
| | 17165.07177 | 13% | 80% | | | | |
| | 30886.85015 | 0% | 90% | | | | |
| 48 hours | 8560.92437 | 100% | 41% | 1 | | | |
| | 8560.92437 | 100% | 41% | 2 | na | na | na |
| | 8560.92437 | 100% | 41% | 3 | na | na | na |
| | 13916.01563 | 0% | 71% | 4 | na | na | na |
| | 17165.07177 | 0% | 80% | | | | |
| | 30886.85015 | 0% | 90% | | | | |

Netrin 4:

| Time prior AKI stage | Cutoff value | sens | spec | Quartile | OR | 95% CI of OR | |
|---|---|---|---|---|---|---|---|
| | | | sCr or UO | | | | |
| 0 hours | 0.013020833 | 78% | 51% | 1 | | | |
| | 0.01171875 | 89% | 46% | 2 | 2.1 | 0.1 | 48.1 |
| | 0.006669207 | 100% | 9% | 3 | 2.1 | 0.1 | 48.1 |
| | 0.018843157 | 67% | 70% | 4 | 4.4 | 0.3 | 62.4 |
| | 0.03671875 | 22% | 80% | | | | |
| | 0.06171875 | 11% | 90% | | | | |
| 24 hours | 0.019901762 | 75% | 74% | 1 | | | |
| | 0.007727812 | 100% | 19% | 2 | 0.0 | 0.0 | 65535.0 |
| | 0.007727812 | 100% | 19% | 3 | 1.0 | 0.0 | 61.3 |
| | 0.018843157 | 75% | 70% | 4 | 2.1 | 0.1 | 48.7 |
| | 0.03671875 | 50% | 80% | | | | |
| | 0.06171875 | 25% | 90% | | | | |
| 48 hours | 0.01640625 | 100% | 68% | 1 | | | |
| | 0.01640625 | 100% | 68% | 2 | na | na | na |
| | 0.01640625 | 100% | 68% | 3 | na | na | na |
| | 0.018843157 | 50% | 70% | 4 | na | na | na |
| | 0.03671875 | 0% | 80% | | | | |
| | 0.06171875 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.020431064 | 100% | 72% | 1 | | | |
| | 0.020431064 | 100% | 72% | 2 | na | na | na |
| | 0.020431064 | 100% | 72% | 3 | na | na | na |
| | 0.019901762 | 100% | 70% | 4 | na | na | na |
| | 0.031546409 | 50% | 81% | | | | |
| | 0.06171875 | 0% | 91% | | | | |
| 24 hours | 0.0375 | 100% | 83% | 1 | | | |
| | 0.0375 | 100% | 83% | 2 | na | na | na |
| | 0.0375 | 100% | 83% | 3 | na | na | na |
| | 0.019901762 | 100% | 70% | 4 | na | na | na |
| | 0.031546409 | 100% | 81% | | | | |
| | 0.06171875 | 50% | 91% | | | | |
| 48 hours | 0.01640625 | 100% | 63% | 1 | | | |
| | 0.01640625 | 100% | 63% | 2 | na | na | na |
| | 0.01640625 | 100% | 63% | 3 | na | na | na |
| | 0.019901762 | 50% | 70% | 4 | na | na | na |
| | 0.031546409 | 0% | 81% | | | | |
| | 0.06171875 | 0% | 91% | | | | |

UO only

| Time prior AKI stage | Cutoff value | sens | spec | Quartile | OR | 95% CI of OR | |
|---|---|---|---|---|---|---|---|
| 0 hours | 0.0125 | 78% | 56% | 1 | | | |
| | 0.01171875 | 89% | 52% | 2 | 0.9 | 0.0 | 60.2 |
| | 0.006669207 | 100% | 10% | 3 | 0.9 | 0.0 | 60.2 |
| | 0.015625 | 67% | 71% | 4 | 8.0 | 0.6 | 104.8 |
| | 0.019901762 | 67% | 81% | | | | |
| | 0.06171875 | 11% | 90% | | | | |
| 24 hours | 0.007727812 | 100% | 21% | 1 | | | |
| | 0.007727812 | 100% | 21% | 2 | 0.0 | 0.0 | 65535.0 |
| | 0.007727812 | 100% | 21% | 3 | 0.0 | 0.0 | 65535.0 |
| | 0.015625 | 50% | 71% | 4 | 1.0 | 0.0 | 65.5 |
| | 0.019901762 | 50% | 81% | | | | |
| | 0.06171875 | 0% | 90% | | | | |
| 48 hours | 0.01640625 | 100% | 73% | 1 | | | |
| | 0.01640625 | 100% | 73% | 2 | na | na | na |
| | 0.01640625 | 100% | 73% | 3 | na | na | na |
| | 0.015625 | 100% | 71% | 4 | na | na | na |
| | 0.019901762 | 0% | 81% | | | | |
| | 0.06171875 | 0% | 90% | | | | |

Alpha-1-Antitrypsin:

| Time prior AKI stage | Cutoff value | sens | spec | Quartile | OR | 95% CI of OR | |
|---|---|---|---|---|---|---|---|
| | | | sCr or UO | | | | |
| 0 hours | 1.93 | 74% | 17% | 1 | | | |
| | 1.77 | 83% | 12% | 2 | 0.5 | 0.1 | 2.2 |
| | 1.46 | 91% | 4% | 3 | 2.4 | 1.1 | 5.1 |
| | 4.02 | 17% | 70% | 4 | 2.1 | 1.0 | 4.6 |
| | 4.67 | 13% | 80% | | | | |
| | 5.53 | 4% | 90% | | | | |
| 24 hours | 1.76 | 72% | 12% | 1 | | | |
| | 1.54 | 80% | 5% | 2 | 1.0 | 0.1 | 7.5 |
| | 1.19 | 92% | 1% | 3 | 4.9 | 1.4 | 17.0 |
| | 4.02 | 8% | 70% | 4 | 6.8 | 2.1 | 22.3 |
| | 4.67 | 8% | 80% | | | | |
| | 5.53 | 4% | 90% | | | | |
| 48 hours | 1.22 | 77% | 1% | 1 | | | |
| | 1.2 | 85% | 1% | 2 | 1.0 | 0.0 | 53.2 |
| | 1.19 | 92% | 1% | 3 | 3.1 | 0.2 | 44.2 |
| | 4.02 | 8% | 70% | 4 | 8.8 | 0.9 | 83.1 |
| | 4.67 | 8% | 80% | | | | |
| | 0.06171875 | 0% | 90% | | | | | sCr only

| Time prior AKI stage | Cutoff value | sens | spec | Quartile | OR | 95% CI of OR | |
|---|---|---|---|---|---|---|---|
| 0 hours | 1.77 | 83% | 14% | 1 | | | |
| | 1.77 | 83% | 14% | 2 | 0.0 | 0.0 | 65535.0 |
| | 1.53 | 100% | 7% | 3 | 0.5 | 0.0 | 9.7 |
| | 3.84 | 33% | 70% | 4 | 1.5 | 0.3 | 8.1 |
| | 4.47 | 33% | 80% | | | | |
| | 5.36 | 17% | 90% | | | | |
| 24 hours | 1.81 | 71% | 15% | 1 | | | |
| | 1.54 | 86% | 7% | 2 | 0.5 | 0.0 | 9.7 |
| | 1.08 | 100% | 2% | 3 | 0.5 | 0.0 | 9.7 |
| | 3.84 | 29% | 70% | 4 | 1.5 | 0.3 | 8.0 |
| | 4.47 | 29% | 80% | | | | |
| | 5.36 | 14% | 90% | | | | |
| 48 hours | 2.34 | 80% | 32% | 1 | | | |
| | 2.34 | 80% | 32% | 2 | 1.0 | 0.0 | 52.7 |
| | 1.67 | 100% | 10% | 3 | 2.0 | 0.1 | 39.6 |
| | 3.84 | 20% | 70% | 4 | 1.0 | 0.0 | 52.7 |
| | 4.47 | 20% | 80% | | | | |
| | 5.36 | 20% | 90% | | | | |

UO only

| Time prior AKI stage | Cutoff value | sens | spec | Quartile | OR | 95% CI of OR | |
|---|---|---|---|---|---|---|---|
| 0 hours | 1.99 | 73% | 19% | 1 | | | |
| | 1.71 | 82% | 9% | 2 | 0.5 | 0.1 | 2.2 |
| | 1.46 | 91% | 3% | 3 | 2.4 | 1.1 | 5.2 |
| | 3.84 | 18% | 71% | 4 | 1.8 | 0.8 | 4.2 |
| | 4.4 | 18% | 80% | | | | |
| | 5.3 | 9% | 90% | | | | |
| 24 hours | 1.77 | 71% | 12% | 1 | | | |
| | 1.49 | 83% | 4% | 2 | 2.1 | 0.1 | 40.8 |
| | 1.2 | 92% | 1% | 3 | 10.2 | 1.1 | 94.5 |
| | 3.84 | 4% | 71% | 4 | 14.1 | 1.6 | 124.8 |
| | 4.4 | 4% | 80% | | | | |
| | 5.3 | 4% | 90% | | | | |
| 48 hours | 1.22 | 77% | 1% | 1 | | | |
| | 1.2 | 85% | 1% | 2 | na | na | na |
| | 1.08 | 92% | 1% | 3 | na | na | na |
| | 3.84 | 0% | 71% | 4 | na | na | na |
| | 4.4 | 0% | 80% | | | | |
| | 5.3 | 0% | 90% | | | | |

Leukocyte Elastase:

sCr or UO

| Time prior AKI stage | Cutoff value | sens | spec | Quartile | OR | 95% CI of OR | |
|---|---|---|---|---|---|---|---|
| 0 hours | 256.5466448 | 71% | 52% | 1 | | | |
| | 198.9247312 | 82% | 38% | 2 | 0.7 | 0.1 | 3.6 |
| | 117.2808765 | 94% | 16% | 3 | 2.1 | 0.7 | 6.2 |
| | 335.1920694 | 53% | 70% | 4 | 2.1 | 0.7 | 6.1 |
| | 449.1945477 | 29% | 80% | | | | |
| | 561.0655738 | 18% | 90% | | | | |
| 24 hours | 206.9935691 | 74% | 38% | 1 | | | |
| | 116.4772727 | 84% | 16% | 2 | 0.7 | 0.2 | 2.5 |
| | 93.49593496 | 95% | 10% | 3 | 1.0 | 0.3 | 2.8 |
| | 335.1920694 | 47% | 70% | 4 | 2.1 | 0.9 | 4.9 |
| | 449.1945477 | 21% | 80% | | | | |
| | 561.0655738 | 16% | 90% | | | | |
| 48 hours | 222.421671 | 77% | 43% | 1 | | | |
| | 215.5913978 | 85% | 40% | 2 | 4.3 | 0.3 | 54.2 |
| | 161.5932642 | 92% | 27% | 3 | 3.1 | 0.2 | 46.7 |
| | 335.1920694 | 54% | 70% | 4 | 5.3 | 0.5 | 61.4 |
| | 449.1945477 | 23% | 80% | | | | |
| | 561.0655738 | 8% | 90% | | | | | sCr only

| Time prior AKI stage | Cutoff value | sens | spec | Quartile | OR | 95% CI of OR | |
|---|---|---|---|---|---|---|---|
| 0 hours | 512.704918 | 100% | 87% | 1 | | | |
| | 512.704918 | 100% | 87% | 2 | na | na | na |
| | 512.704918 | 100% | 87% | 3 | na | na | na |
| | 373.605948 | 100% | 70% | 4 | na | na | na |
| | 450.4337051 | 100% | 80% | | | | |
| | 561.0655738 | 67% | 90% | | | | |
| 24 hours | 237.4631268 | 80% | 43% | 1 | | | |
| | 237.4631268 | 80% | 43% | 2 | na | na | na |
| | 218.1788512 | 100% | 37% | 3 | na | na | na |
| | 373.605948 | 60% | 70% | 4 | na | na | na |
| | 450.4337051 | 0% | 80% | | | | |
| | 561.0655738 | 0% | 90% | | | | |
| 48 hours | 328.9962825 | 80% | 63% | 1 | | | |
| | 328.9962825 | 80% | 63% | 2 | na | na | na |
| | 240.6088083 | 100% | 44% | 3 | na | na | na |
| | 373.605948 | 60% | 70% | 4 | na | na | na |
| | 450.4337051 | 20% | 80% | | | | |
| | 561.0655738 | 0% | 90% | | | | |

UO only

| Time prior AKI stage | Cutoff value | sens | spec | Quartile | OR | 95% CI of OR | |
|---|---|---|---|---|---|---|---|
| 0 hours | 234.5132743 | 71% | 46% | 1 | | | |
| | 189.7845953 | 82% | 36% | 2 | 1.3 | 0.4 | 4.6 |
| | 117.2808765 | 94% | 15% | 3 | 2.1 | 0.7 | 6.2 |
| | 376.8939394 | 35% | 70% | 4 | 1.3 | 0.4 | 4.6 |
| | 463.747646 | 24% | 81% | | | | |
| | 563.8166047 | 12% | 90% | | | | |
| 24 hours | 198.9247312 | 74% | 37% | 1 | | | |
| | 116.4772727 | 84% | 15% | 2 | 0.6 | 0.2 | 1.8 |
| | 93.49593496 | 95% | 10% | 3 | 1.0 | 0.4 | 2.4 |
| | 376.8939394 | 42% | 70% | 4 | 1.2 | 0.5 | 2.7 |
| | 463.747646 | 26% | 81% | | | | |
| | 563.8166047 | 21% | 90% | | | | |
| 48 hours | 221.8264249 | 75% | 42% | 1 | | | |
| | 215.5913978 | 83% | 40% | 2 | 4.2 | 0.3 | 54.0 |
| | 161.5932642 | 92% | 26% | 3 | 3.2 | 0.2 | 47.6 |
| | 376.8939394 | 42% | 70% | 4 | 4.2 | 0.3 | 54.0 |
| | 463.747646 | 25% | 81% | | | | |
| | 563.8166047 | 17% | 90% | | | | |

Soluble Tumor Necrosis Factor Receptor Superfamily Member 6:

sCr or UO

| Time prior AKI stage | Cutoff value | sens | spec | Quartile | OR | 95% CI of OR | |
|---|---|---|---|---|---|---|---|
| 0 hours | 14117.64706 | 80% | 80% | 1 | | | |
| | 14117.64706 | 80% | 80% | 2 | na | na | na |
| | 14086.68731 | 100% | 80% | 3 | na | na | na |
| | 12329.41176 | 100% | 71% | 4 | na | na | na |
| | 14241.48607 | 60% | 80% | | | | |
| | 17689.69422 | 0% | 90% | | | | |
| 24 hours | 8865.41471 | 71% | 46% | 1 | | | |
| | 8145.539906 | 82% | 38% | 2 | 6.9 | 0.6 | 75.5 |
| | 7165.217391 | 94% | 27% | 3 | 4.3 | 0.3 | 55.8 |
| | 12329.41176 | 47% | 71% | 4 | 6.9 | 0.6 | 75.5 |
| | 14241.48607 | 29% | 80% | | | | |
| | 17689.69422 | 6% | 90% | | | | |
| 48 hours | 9710.485133 | 80% | 56% | 1 | | | |
| | 9710.485133 | 80% | 56% | 2 | na | na | na |
| | 8367.071525 | 100% | 42% | 3 | na | na | na |
| | 12329.41176 | 20% | 71% | 4 | na | na | na |
| | 14241.48607 | 20% | 80% | | | | |
| | 17689.69422 | 0% | 90% | | | | | sCr only

| Time prior AKI stage | Cutoff value | sens | spec | Quartile | OR | 95% CI of OR | |
|---|---|---|---|---|---|---|---|
| 0 hours | 16824.14698 | 100% | 87% | 1 | | | |
| | 16824.14698 | 100% | 87% | 2 | na | na | na |
| | 16824.14698 | 100% | 87% | 3 | na | na | na |
| | 12894.11765 | 100% | 70% | 4 | na | na | na |
| | 15572.75542 | 100% | 80% | | | | |
| | 17689.69422 | 50% | 90% | | | | |
| 24 hours | 12043.34365 | 80% | 65% | 1 | | | |
| | 12043.34365 | 80% | 65% | 2 | na | na | na |
| | 9257.759784 | 100% | 46% | 3 | na | na | na |
| | 12894.11765 | 60% | 70% | 4 | na | na | na |
| | 15572.75542 | 20% | 80% | | | | |
| | 17689.69422 | 20% | 90% | | | | |

| Time prior AKI stage | Cutoff value | sens | spec | Quartile | OR | 95% CI of OR | |
|---|---|---|---|---|---|---|---|
| 48 hours | 9710.485133 | 100% | 51% | 1 | | | |
| | 9710.485133 | 100% | 51% | 2 | na | na | na |
| | 9710.485133 | 100% | 51% | 3 | na | na | na |
| | 12894.11765 | 0% | 70% | 4 | na | na | na |
| | 15572.75542 | 0% | 80% | | | | |
| | 17689.69422 | 0% | 90% | | | | |
| UO only | | | | | | | |
| 0 hours | 14117.64706 | 75% | 81% | 1 | | | |
| | 14047.05882 | 100% | 81% | 2 | na | na | na |
| | 14047.05882 | 100% | 81% | 3 | na | na | na |
| | 12043.34365 | 100% | 70% | 4 | na | na | na |
| | 13937.00787 | 100% | 80% | | | | |
| | 16611.76471 | 25% | 90% | | | | |
| 24 hours | 8145.539906 | 73% | 35% | 1 | | | |
| | 7366.003063 | 80% | 32% | 2 | 8.4 | 0.8 | 91.1 |
| | 7136.294028 | 93% | 27% | 3 | 2.1 | 0.1 | 44.7 |
| | 12043.34365 | 40% | 70% | 4 | 5.6 | 0.5 | 67.0 |
| | 13937.00787 | 20% | 80% | | | | |
| | 16611.76471 | 7% | 90% | | | | |
| 48 hours | 9710.485133 | 75% | 54% | 1 | | | |
| | 8361.408882 | 100% | 39% | 2 | na | na | na |
| | 8361.408882 | 100% | 39% | 3 | na | na | na |
| | 12043.34365 | 25% | 70% | 4 | na | na | na |
| | 13937.00787 | 25% | 80% | | | | |
| | 1611.76471 | 0% | 90% | | | | |

Soluble Tumor Necrosis Factor Ligand Superfamily Member 6:

| Time prior AKI stage | Cutoff value | sens | spec | Quartile | OR | 95% CI of OR | |
|---|---|---|---|---|---|---|---|
| sCr or UO | | | | | | | |
| 0 hours | 20.39930556 | 80% | 13% | 1 | | | |
| | 20.39930556 | 80% | 13% | 2 | na | na | na |
| | 13.36805556 | 100% | 4% | 3 | na | na | na |
| | 60.06205674 | 0% | 71% | 4 | na | na | na |
| | 81.75505051 | 0% | 81% | | | | |
| | 105.8362369 | 0% | 91% | | | | |
| 24 hours | 39.2287234 | 71% | 43% | 1 | | | |
| | 37.54844961 | 86% | 38% | 2 | 3.2 | 0.2 | 51.0 |
| | 28.64583333 | 100% | 25% | 3 | 1.0 | 0.0 | 58.0 |
| | 60.06205674 | 29% | 71% | 4 | 2.1 | 0.1 | 45.2 |
| | 81.75505051 | 29% | 81% | | | | |
| | 105.8362369 | 0% | 91% | | | | |
| 48 hours | 40.11524823 | 75% | 44% | 1 | | | |
| | 36.09496124 | 100% | 33% | 2 | na | na | na |
| | 36.09496124 | 100% | 33% | 3 | na | na | na |
| | 60.06205674 | 25% | 71% | 4 | na | na | na |
| | 81.75505051 | 25% | 81% | | | | |
| | 105.8362369 | 25% | 91% | | | | |
| sCr only | | | | | | | |
| 0 hours | 27.34375 | 100% | 22% | 1 | | | |
| | 27.34375 | 100% | 22% | 2 | na | na | na |
| | 27.34375 | 100% | 22% | 3 | na | na | na |
| | 60.06205674 | 0% | 70% | 4 | na | na | na |
| | 81.75505051 | 0% | 80% | | | | |
| | 103.8510101 | 0% | 90% | | | | |
| 24 hours | 17.78846154 | 100% | 11% | 1 | | | |
| | 17.78846154 | 100% | 11% | 2 | 0.0 | 0.0 | 65535.0 |
| | 17.78846154 | 100% | 11% | 3 | 1.0 | 0.0 | 56.8 |
| | 60.06205674 | 33% | 70% | 4 | 1.0 | 0.0 | 58.6 |
| | 81.75505051 | 33% | 80% | | | | |
| | 103.8510101 | 0% | 90% | | | | |
| 48 hours | 20.39930556 | 100% | 13% | 1 | | | |
| | 20.39930556 | 100% | 13% | 2 | na | na | na |
| | 20.39930556 | 100% | 13% | 3 | na | na | na |
| | 60.06205674 | 0% | 70% | 4 | na | na | na |
| | 81.75505051 | 0% | 80% | | | | |
| | 103.8510101 | 0% | 90% | | | | |
| UO only | | | | | | | |
| 0 hours | 20.39930556 | 75% | 14% | 1 | | | |
| | 12.32638889 | 100% | 1% | 2 | na | na | na |
| | 12.32638889 | 100% | 1% | 3 | na | na | na |
| | 61.18881119 | 0% | 70% | 4 | na | na | na |
| | 90.59233449 | 0% | 80% | | | | |
| | 112.804878 | 0% | 90% | | | | |
| 24 hours | 39.2287234 | 80% | 35% | 1 | | | |
| | 39.2287234 | 80% | 35% | 2 | 0.0 | 0.0 | 65535.0 |
| | 27.40384615 | 100% | 22% | 3 | 3.3 | 0.2 | 55.1 |
| | 61.18881119 | 20% | 70% | 4 | 1.1 | 0.0 | 64.1 |
| | 90.59233449 | 0% | 80% | | | | |
| | 112.804878 | 0% | 90% | | | | |
| 48 hours | 36.09496124 | 100% | 26% | 1 | | | |
| | 36.09496124 | 100% | 26% | 2 | na | na | na |
| | 36.09496124 | 100% | 26% | 3 | na | na | na |
| | 61.18881119 | 33% | 70% | 4 | na | na | na |
| | 90.59233449 | 33% | 80% | | | | |
| | 112.804878 | 33% | 90% | | | | |

Soluble Intercellular Adhesion Molecule 2:

| Time prior AKI stage | Cutoff value | sens | spec | Quartile | OR | 95% CI of OR | |
|---|---|---|---|---|---|---|---|
| sCr or UO | | | | | | | |
| 0 hours | 354.4827586 | 78% | 50% | 1 | | | |
| | 316.6502463 | 89% | 35% | 2 | na | na | na |
| | 296.9458128 | 100% | 32% | 3 | na | na | na |
| | 516.8780488 | 33% | 70% | 4 | na | na | na |
| | 690.1463415 | 22% | 80% | | | | |
| | 750.4390244 | 22% | 90% | | | | |
| 24 hours | 239.6166134 | 75% | 23% | 1 | | | |
| | 43.61702128 | 100% | 5% | 2 | 0.0 | 0.0 | 65535.0 |
| | 43.61702128 | 100% | 5% | 3 | 1.0 | 0.0 | 65.5 |
| | 516.8780488 | 25% | 70% | 4 | 2.1 | 0.1 | 53.1 |
| | 690.1463415 | 25% | 80% | | | | |
| | 750.4390244 | 25% | 90% | | | | |
| 48 hours | 205.8785942 | 100% | 18% | 1 | | | |
| | 205.8785942 | 100% | 18% | 2 | na | na | na |
| | 205.8785942 | 100% | 18% | 3 | na | na | na |
| | 516.8780488 | 0% | 70% | 4 | na | na | na |
| | 690.1463415 | 0% | 80% | | | | |
| | 750.4390244 | 0% | 90% | | | | |
| sCr only | | | | | | | |
| 0 hours | 191.5294118 | 100% | 16% | 1 | | | |
| | 191.5294118 | 100% | 16% | 2 | na | na | na |
| | 191.5294118 | 100% | 16% | 3 | na | na | na |
| | 525.91133 | 0% | 71% | 4 | na | na | na |
| | 693.6585366 | 0% | 81% | | | | |
| | 889.1707317 | 0% | 91% | | | | |
| 24 hours | 45.31914894 | 100% | 5% | 1 | | | |
| | 45.31914894 | 100% | 5% | 2 | na | na | na |
| | 45.31914894 | 100% | 5% | 3 | na | na | na |
| | 525.91133 | 0% | 71% | 4 | na | na | na |
| | 693.6585366 | 0% | 81% | | | | |
| | 889.1707317 | 0% | 91% | | | | |
| 48 hours | 205.8785942 | 100% | 18% | 1 | | | |
| | 205.8785942 | 100% | 18% | 2 | 0.0 | 0.0 | 65535.0 |
| | 205.8785942 | 100% | 18% | 3 | 0.0 | 0.0 | 65535.0 |
| | 525.91133 | 50% | 71% | 4 | 1.0 | 0.0 | 58.5 |
| | 693.6585366 | 50% | 81% | | | | |
| | 889.1707317 | 0% | 91% | | | | |
| UO only | | | | | | | |
| 0 hours | 354.4827586 | 78% | 51% | 1 | | | |
| | 316.6502463 | 89% | 33% | 2 | na | na | na |
| | 296.9458128 | 100% | 29% | 3 | na | na | na |
| | 557.8536585 | 22% | 71% | 4 | na | na | na |
| | 703.6097561 | 22% | 80% | | | | |
| | 783.804878 | 22% | 91% | | | | |

-continued

| Time prior AKI stage | Cutoff value | sens | spec | Quartile | OR | 95% CI of OR | |
|---|---|---|---|---|---|---|---|
| 24 hours | 271.3300493 | 100% | 24% | 1 | | | |
| | 271.3300493 | 100% | 24% | 2 | na | na | na |
| | 271.3300493 | 100% | 24% | 3 | na | na | na |
| | 557.8536585 | 50% | 71% | 4 | na | na | na |
| | 703.6097561 | 50% | 80% | | | | |
| | 783.804878 | 50% | 91% | | | | |
| 48 hours | 422.6600985 | 100% | 62% | 1 | | | |
| | 422.6600985 | 100% | 62% | 2 | na | na | na |
| | 422.6600985 | 100% | 62% | 3 | na | na | na |
| | 557.8536585 | 0% | 71% | 4 | na | na | na |
| | 703.6097561 | 0% | 80% | | | | |
| | 783.804878 | 0% | 91% | | | | |

Heat Shock Protein Beta-1:

| Time prior AKI stage | Cutoff value | sens | spec | Quartile | OR | 95% CI of OR | |
|---|---|---|---|---|---|---|---|
| | | | sCr or UO | | | | |
| 0 hours | 16.34933775 | 78% | 12% | 1 | | | |
| | 14.76753049 | 89% | 9% | 2 | 0.0 | 0.0 | 65535.0 |
| | 8.860518293 | 100% | 4% | 3 | 3.3 | 0.2 | 54.3 |
| | 135.1610429 | 11% | 72% | 4 | 6.5 | 0.5 | 83.4 |
| | 184.5735786 | 11% | 80% | | | | |
| | 273.1137088 | 11% | 90% | | | | |
| 24 hours | 74.06850962 | 75% | 46% | 1 | | | |
| | 16.34933775 | 100% | 12% | 2 | na | na | na |
| | 16.34933775 | 100% | 12% | 3 | na | na | na |
| | 135.1610429 | 0% | 72% | 4 | na | na | na |
| | 184.5735786 | 0% | 80% | | | | |
| | 273.1137088 | 0% | 90% | | | | |
| 48 hours | 24.96936275 | 100% | 16% | 1 | | | |
| | 24.96936275 | 100% | 16% | 2 | na | na | na |
| | 24.96936275 | 100% | 16% | 3 | na | na | na |
| | 135.1610429 | 0% | 72% | 4 | na | na | na |
| | 184.5735786 | 0% | 80% | | | | |
| | 273.1137088 | 0% | 90% | | | | |
| | | | sCr only | | | | |
| 0 hours | 8.860518293 | 100% | 3% | 1 | | | |
| | 8.860518293 | 100% | 3% | 2 | 0.0 | 0.0 | 65535.0 |
| | 8.860518293 | 100% | 3% | 3 | 0.0 | 0.0 | 65535.0 |
| | 126.3420245 | 50% | 70% | 4 | 1.0 | 0.0 | 56.8 |
| | 184.5735786 | 50% | 80% | | | | |
| | 273.1137088 | 50% | 90% | | | | |
| 24 hours | 74.06850962 | 100% | 49% | 1 | | | |
| | 74.06850962 | 100% | 49% | 2 | na | na | na |
| | 74.06850962 | 100% | 49% | 3 | na | na | na |
| | 126.3420245 | 0% | 70% | 4 | na | na | na |
| | 184.5735786 | 0% | 80% | | | | |
| | 273.1137088 | 0% | 90% | | | | |
| 48 hours | 57.1192053 | 100% | 41% | 1 | | | |
| | 57.1192053 | 100% | 41% | 2 | na | na | na |
| | 57.1192053 | 100% | 41% | 3 | na | na | na |
| | 126.3420245 | 50% | 70% | 4 | na | na | na |
| | 184.5735786 | 50% | 80% | | | | |
| | 273.1137088 | 50% | 90% | | | | |
| | | | UO only | | | | |
| 0 hours | 16.34933775 | 78% | 11% | 1 | | | |
| | 14.76753049 | 89% | 6% | 2 | 0.0 | 0.0 | 65535.0 |
| | 8.40585443 | 100% | 2% | 3 | 3.6 | 0.2 | 62.4 |
| | 135.1610429 | 11% | 72% | 4 | 6.9 | 0.5 | 94.3 |
| | 184.5735786 | 11% | 81% | | | | |
| | 290.1168969 | 11% | 91% | | | | |
| 24 hours | 16.34933775 | 100% | 11% | 1 | | | |
| | 16.34933775 | 100% | 11% | 2 | na | na | na |
| | 16.34933775 | 100% | 11% | 3 | na | na | na |
| | 135.1610429 | 0% | 72% | 4 | na | na | na |
| | 184.5735786 | 0% | 81% | | | | |
| | 290.1168969 | 0% | 91% | | | | |
| 48 hours | 24.96936275 | 100% | 14% | 1 | | | |
| | 24.96936275 | 100% | 14% | 2 | na | na | na |
| | 24.96936275 | 100% | 14% | 3 | na | na | na |
| | 135.1610429 | 0% | 72% | 4 | na | na | na |
| | 184.5735786 | 0% | 81% | | | | |
| | 290.1168969 | 0% | 91% | | | | |

Soluble Epidermal Growth Factor Receptor:

| Time prior AKI stage | Cutoff value | sens | spec | Quartile | OR | 95% CI of OR | |
|---|---|---|---|---|---|---|---|
| | | | sCr or UO | | | | |
| 0 hours | 10541.05124 | 75% | 46% | 1 | | | |
| | 8828.351099 | 88% | 23% | 2 | 0.4 | 0.0 | 12.6 |
| | 8202.74857 | 100% | 15% | 3 | 0.4 | 0.0 | 14.9 |
| | 11934.01788 | 50% | 73% | 4 | 2.4 | 0.3 | 21.4 |
| | 12761.28396 | 50% | 81% | | | | |
| | 15460.1643 | 13% | 92% | | | | |
| 24 hours | 10001.60234 | 71% | 42% | 1 | | | |
| | 8358.83336 | 82% | 19% | 2 | 0.6 | 0.1 | 3.1 |
| | 6977.052258 | 94% | 8% | 3 | 0.9 | 0.2 | 4.2 |
| | 11934.01788 | 53% | 73% | 4 | 1.8 | 0.4 | 8.4 |
| | 12761.28396 | 47% | 81% | | | | |
| | 15460.1643 | 18% | 92% | | | | |
| 48 hours | 0 | na | na | 1 | | | |
| | 0 | na | na | 2 | na | na | na |
| | 0 | na | na | 3 | na | na | na |
| | 0 | na | na | 4 | na | na | na |
| | 0 | na | na | | | | |
| | 0 | na | na | | | | |
| | | | sCr only | | | | |
| 0 hours | 8202.74857 | 100% | 13% | 1 | | | |
| | 8202.74857 | 100% | 13% | 2 | na | na | na |
| | 8202.74857 | 100% | 13% | 3 | na | na | na |
| | 13660.92774 | 0% | 70% | 4 | na | na | na |
| | 14168.09234 | 0% | 81% | | | | |
| | 16778.19999 | 0% | 91% | | | | |
| 24 hours | 8358.83336 | 78% | 15% | 1 | | | |
| | 7655.774622 | 89% | 11% | 2 | 0.3 | 0.0 | 5.3 |
| | 0 | 100% | 0% | 3 | 0.6 | 0.1 | 4.4 |
| | 13660.92774 | 33% | 70% | 4 | 1.0 | 0.2 | 5.3 |
| | 14168.09234 | 33% | 81% | | | | |
| | 16778.19999 | 11% | 91% | | | | |
| 48 hours | 0 | 100% | 0% | 1 | | | |
| | 0 | 100% | 0% | 2 | na | na | na |
| | 0 | 100% | 0% | 3 | na | na | na |
| | 13660.92774 | 0% | 70% | 4 | na | na | na |
| | 14168.09234 | 0% | 81% | | | | |
| | 16778.19999 | 0% | 91% | | | | |
| | | | UO only | | | | |
| 0 hours | 10870.7146 | 71% | 63% | 1 | | | |
| | 10541.05124 | 86% | 52% | 2 | 0.9 | 0.0 | 74.5 |
| | 8377.470829 | 100% | 26% | 3 | 2.3 | 0.1 | 81.0 |
| | 11909.00287 | 57% | 70% | 4 | 3.5 | 0.1 | 87.6 |
| | 13862.95214 | 29% | 81% | | | | |
| | 20361.99567 | 0% | 93% | | | | |
| 24 hours | 12714.33315 | 73% | 78% | 1 | | | |
| | 12624.87324 | 82% | 78% | 2 | 0.9 | 0.0 | 71.2 |
| | 10001.60234 | 91% | 48% | 3 | 6.4 | 0.3 | 140.2 |
| | 11909.00287 | 82% | 70% | 4 | 8.0 | 0.4 | 158.9 |
| | 13862.95214 | 45% | 81% | | | | |
| | 20361.99567 | 9% | 93% | | | | |
| 48 hours | 10870.7146 | 100% | 63% | 1 | | | |
| | 10870.7146 | 100% | 63% | 2 | na | na | na |
| | 10870.7146 | 100% | 63% | 3 | na | na | na |
| | 11909.00287 | 0% | 70% | 4 | na | na | na |
| | 13862.95214 | 0% | 81% | | | | |
| | 20361.99567 | 0% | 93% | | | | |

Example 11

Kidney Injury Markers for Evaluating Renal Status in Patients Progressing from Stage R to Stages I and F Patients were classified and analyzed as described in Example 9, but only those patients that reached Stage R were included in this example. Cohort 1 contained patients that reached stage R but did not progress to stage I or F within 10 days, and Cohort 2 included only patients that progressed to stage I or F. Marker concentrations in the plasma component from blood samples collected within 12 hours of reaching stage R were included in the analysis for both Cohort 1 and 2.

The following descriptive statistics were obtained

Alpha-1-Antitrypsin:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 2.250 | 1.770 | 2.250 | 1.770 | 2.250 | 1.770 |
| average | 2.493 | 2.201 | 2.493 | 2.201 | 2.493 | 2.201 |
| stdev | 0.954 | 1.240 | 0.954 | 1.240 | 0.954 | 1.240 |
| p (t-test) |  | 0.395 |  | 0.395 |  | 0.395 |
| min | 1.310 | 0.748 | 1.310 | 0.748 | 1.310 | 0.748 |
| max | 4.900 | 5.090 | 4.900 | 5.090 | 4.900 | 5.090 |
| n (Samp) | 28 | 15 | 28 | 15 | 28 | 15 |
| n (Pat) | 28 | 15 | 28 | 15 | 28 | 15 |
| sCr only | | | | | | |
| median | 2.295 | 2.340 | 2.295 | 2.340 | 2.295 | 2.340 |
| average | 2.456 | 2.518 | 2.456 | 2.518 | 2.456 | 2.518 |
| stdev | 0.950 | 1.524 | 0.950 | 1.524 | 0.950 | 1.524 |
| p (t-test) |  | 0.919 |  | 0.919 |  | 0.919 |
| min | 1.280 | 1.220 | 1.280 | 1.220 | 1.280 | 1.220 |
| max | 4.020 | 5.090 | 4.020 | 5.090 | 4.020 | 5.090 |
| n (Samp) | 12 | 5 | 12 | 5 | 12 | 5 |
| n (Pat) | 12 | 5 | 12 | 5 | 12 | 5 |
| UO only | | | | | | |
| median | 2.250 | 2.070 | 2.250 | 2.070 | 2.250 | 2.070 |
| average | 2.526 | 2.342 | 2.526 | 2.342 | 2.526 | 2.342 |
| stdev | 0.977 | 1.282 | 0.977 | 1.282 | 0.977 | 1.282 |
| p (t-test) |  | 0.635 |  | 0.635 |  | 0.635 |
| min | 1.310 | 0.748 | 1.310 | 0.748 | 1.310 | 0.748 |
| max | 4.900 | 5.090 | 4.900 | 5.090 | 4.900 | 5.090 |
| n (Samp) | 22 | 13 | 22 | 13 | 22 | 13 |
| n (Pat) | 22 | 13 | 22 | 13 | 22 | 13 |

Leukocyte Elastase:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 262.275 | 351.301 | 262.275 | 351.301 | 262.275 | 351.301 |
| average | 306.017 | 407.321 | 306.017 | 407.321 | 306.017 | 407.321 |
| stdev | 196.187 | 223.977 | 196.187 | 223.977 | 196.187 | 223.977 |
| p (t-test) |  | 0.159 |  | 0.159 |  | 0.159 |
| min | 48.240 | 125.972 | 48.240 | 125.972 | 48.240 | 125.972 |
| max | 874.180 | 861.088 | 874.180 | 861.088 | 874.180 | 861.088 |
| n (Samp) | 25 | 13 | 25 | 13 | 25 | 13 |
| n (Pat) | 25 | 13 | 25 | 13 | 25 | 13 |
| sCr only | | | | | | |
| median | 313.934 | 316.320 | 313.934 | 316.320 | 313.934 | 316.320 |
| average | 383.175 | 289.483 | 383.175 | 289.483 | 383.175 | 289.483 |
| stdev | 233.049 | 150.491 | 233.049 | 150.491 | 233.049 | 150.491 |
| p (t-test) |  | 0.476 |  | 0.476 |  | 0.476 |
| min | 79.573 | 98.357 | 79.573 | 98.357 | 79.573 | 98.357 |
| max | 874.180 | 426.933 | 874.180 | 426.933 | 874.180 | 426.933 |
| n (Samp) | 10 | 4 | 10 | 4 | 10 | 4 |
| n (Pat) | 10 | 4 | 10 | 4 | 10 | 4 |
| UO only | | | | | | |
| median | 230.894 | 436.205 | 230.894 | 436.205 | 230.894 | 436.205 |
| average | 249.531 | 466.498 | 249.531 | 466.498 | 249.531 | 466.498 |
| stdev | 141.086 | 236.312 | 141.086 | 236.312 | 141.086 | 236.312 |
| p (t-test) |  | 0.004 |  | 0.004 |  | 0.004 |
| min | 48.240 | 125.972 | 48.240 | 125.972 | 48.240 | 125.972 |
| max | 524.180 | 861.088 | 524.180 | 861.088 | 524.180 | 861.088 |
| n (Samp) | 18 | 12 | 18 | 12 | 18 | 12 |
| n (Pat) | 18 | 12 | 18 | 12 | 18 | 12 |

Soluble Tumor Necrosis Factor Receptor Superfamily Member 6:

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| median | 13485.572 | 9900.459 | 13485.572 | 9900.459 | 13485.572 | 9900.459 |
| average | 12626.602 | 11194.423 | 12626.602 | 11194.423 | 12626.602 | 11194.423 |
| stdev | 4299.336 | 3620.104 | 4299.336 | 3620.104 | 4299.336 | 3620.104 |
| p (t-test) |  | 0.406 |  | 0.406 |  | 0.406 |
| min | 6747.826 | 6493.109 | 6747.826 | 6493.109 | 6747.826 | 6493.109 |
| max | 18935.447 | 17259.343 | 18935.447 | 17259.343 | 18935.447 | 17259.343 |
| n (Samp) | 10 | 12 | 10 | 12 | 10 | 12 |
| n (Pat) | 10 | 12 | 10 | 12 | 10 | 12 |
| sCr only | | | | | | |
| median | 9099.309 | 15136.444 | 9099.309 | 15136.444 | 9099.309 | 15136.444 |
| average | 10218.561 | 15136.444 | 10218.561 | 15136.444 | 10218.561 | 15136.444 |
| stdev | 2958.891 | 4155.386 | 2958.891 | 4155.386 | 2958.891 | 4155.386 |
| p (t-test) |  | 0.160 |  | 0.160 |  | 0.160 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| min | 8161.189 | 12198.142 | 8161.189 | 12198.142 | 8161.189 | 12198.142 |
| max | 14514.436 | 18074.745 | 14514.436 | 18074.745 | 14514.436 | 18074.745 |
| n (Samp) | 4 | 2 | 4 | 2 | 4 | 2 |
| n (Pat) | 4 | 2 | 4 | 2 | 4 | 2 |
| | | | UO only | | | |
| median | 14241.486 | 11083.757 | 14241.486 | 11083.757 | 14241.486 | 11083.757 |
| average | 13099.883 | 11634.034 | 13099.883 | 11634.034 | 13099.883 | 11634.034 |
| stdev | 4274.913 | 3817.593 | 4274.913 | 3817.593 | 4274.913 | 3817.593 |
| p (t-test) |  | 0.441 |  | 0.441 |  | 0.441 |
| min | 6747.826 | 6493.109 | 6747.826 | 6493.109 | 6747.826 | 6493.109 |
| max | 18935.447 | 17259.343 | 18935.447 | 17259.343 | 18935.447 | 17259.343 |
| n (Samp) | 9 | 10 | 9 | 10 | 9 | 10 |
| n (Pat) | 9 | 10 | 9 | 10 | 9 | 10 |

In the following tables, the ability to distinguish cohort 1 (subjects remaining in RIFLE R) from Cohort 2 (subjects progressing to RIFLE I or F) was determined using ROC analysis.

Alpha-1-Antitrypsin:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.38 | 0.088 | 28 | 15 | 1.842 |
| 24 hours | 0.38 | 0.088 | 28 | 15 | 1.842 |
| 48 hours | 0.38 | 0.088 | 28 | 15 | 1.842 |
| Cohort 1 v Cohort 2, adjudicated on serum creatinine | | | | | |
| 0 hours | 0.43 | 0.154 | 12 | 5 | 1.336 |
| 24 hours | 0.43 | 0.154 | 12 | 5 | 1.336 |
| 48 hours | 0.43 | 0.154 | 12 | 5 | 1.336 |
| Cohort 1 v Cohort 2, adjudicated on urine output | | | | | |
| 0 hours | 0.43 | 0.100 | 22 | 13 | 1.538 |
| 24 hours | 0.43 | 0.100 | 22 | 13 | 1.538 |
| 48 hours | 0.43 | 0.100 | 22 | 13 | 1.538 |

Leukocyte Elastase:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.64 | 0.098 | 25 | 13 | 0.163 |
| 24 hours | 0.64 | 0.098 | 25 | 13 | 0.163 |
| 48 hours | 0.64 | 0.098 | 25 | 13 | 0.163 |
| Cohort 1 v Cohort 2, adjudicated on serum creatinine | | | | | |
| 0 hours | 0.43 | 0.171 | 10 | 4 | 1.339 |
| 24 hours | 0.43 | 0.171 | 10 | 4 | 1.339 |
| 48 hours | 0.43 | 0.171 | 10 | 4 | 1.339 |
| Cohort 1 v Cohort 2, adjudicated on urine output | | | | | |
| 0 hours | 0.79 | 0.090 | 18 | 12 | 0.001 |
| 24 hours | 0.79 | 0.090 | 18 | 12 | 0.001 |
| 48 hours | 0.79 | 0.090 | 18 | 12 | 0.001 |

Soluble Tumor Necrosis Factor Receptor Superfamily Member 6:

| Time prior max stage | AUC | SE | $n_{Cohort\ 1}$ | $n_{Cohort\ 2}$ | p |
|---|---|---|---|---|---|
| Cohort 1 v Cohort 2, adjudicated on serum creatinine measurements or urine output | | | | | |
| 0 hours | 0.39 | 0.124 | 10 | 12 | 1.619 |
| 24 hours | 0.39 | 0.124 | 10 | 12 | 1.619 |
| 48 hours | 0.39 | 0.124 | 10 | 12 | 1.619 |
| Cohort 1 v Cohort 2, adjudicated on serum creatinine | | | | | |
| 0 hours | 0.88 | 0.185 | 4 | 2 | 0.043 |
| 24 hours | 0.88 | 0.185 | 4 | 2 | 0.043 |
| 48 hours | 0.88 | 0.185 | 4 | 2 | 0.043 |
| Cohort 1 v Cohort 2, adjudicated on urine output | | | | | |
| 0 hours | 0.38 | 0.132 | 9 | 10 | 1.646 |
| 24 hours | 0.38 | 0.132 | 9 | 10 | 1.646 |
| 48 hours | 0.38 | 0.132 | 9 | 10 | 1.646 |

Various threshold (or "cutoff") concentrations were selected, and the associated sensitivity and specificity for distinguishing cohort 1 from cohort 2, as shown in the following tables. OR is the odds ratio calculated for the particular cutoff concentration, and 95% CI is the confidence interval for the odds ratio:

Alpha-1-Antitrypsin:

| Time prior AKI stage | Cutoff value | sens | spec | Quartile | OR | 95% CI of OR |
|---|---|---|---|---|---|---|
| | sCr or UO | | | | | |
| 0 hours | 1.48 | 73% | 11% | 1 | | |
|  | 1.2 | 80% | 0% | 2 | 1.0 | 0.2   6.0 |
|  | 0.748 | 93% | 0% | 3 | 1.0 | 0.2   6.0 |
|  | 2.89 | 20% | 71% | 4 | 4.0 | 0.7   22.2 |
|  | 3.03 | 20% | 82% |  |  |  |
|  | 4.02 | 13% | 93% |  |  |  |
| 24 hours | 1.48 | 73% | 11% | 1 | | |
|  | 1.2 | 80% | 0% | 2 | 1.0 | 0.2   6.0 |
|  | 0.748 | 93% | 0% | 3 | 1.0 | 0.2   6.0 |
|  | 2.89 | 20% | 71% | 4 | 4.0 | 0.7   22.2 |
|  | 3.03 | 20% | 82% |  |  |  |
|  | 4.02 | 13% | 93% |  |  |  |
| 48 hours | 1.48 | 73% | 11% | 1 | | |
|  | 1.2 | 80% | 0% | 2 | 1.0 | 0.2   6.0 |
|  | 0.748 | 93% | 0% | 3 | 1.0 | 0.2   6.0 |

| Time prior AKI stage | Cutoff value | sens | spec | Quartile | OR | 95% CI of OR | |
|---|---|---|---|---|---|---|---|
| | 2.89 | 20% | 71% | 4 | 4.0 | 0.7 | 22.2 |
| | 3.03 | 20% | 82% | | | | |
| | 4.02 | 13% | 93% | | | | |
| | sCr only | | | | | | |
| 0 hours | 1.53 | 80% | 17% | 1 | | | |
| | 1.53 | 80% | 17% | 2 | 4.0 | 0.0 | 329.1 |
| | 0 | 100% | 0% | 3 | 0.0 | 0.0 | 65535.0 |
| | 2.96 | 20% | 75% | 4 | 4.0 | 0.0 | 329.1 |
| | 3.28 | 20% | 83% | | | | |
| | 3.84 | 20% | 92% | | | | |
| 24 hours | 1.53 | 80% | 17% | 1 | | | |
| | 1.53 | 80% | 17% | 2 | 4.0 | 0.0 | 329.1 |
| | 0 | 100% | 0% | 3 | 0.0 | 0.0 | 65535.0 |
| | 2.96 | 20% | 75% | 4 | 4.0 | 0.0 | 329.1 |
| | 3.28 | 20% | 83% | | | | |
| | 3.84 | 20% | 92% | | | | |
| 48 hours | 1.53 | 80% | 17% | 1 | | | |
| | 1.53 | 80% | 17% | 2 | 4.0 | 0.0 | 329.1 |
| | 0 | 100% | 0% | 3 | 0.0 | 0.0 | 65535.0 |
| | 2.96 | 20% | 75% | 4 | 4.0 | 0.0 | 329.1 |
| | 3.28 | 20% | 83% | | | | |
| | 3.84 | 20% | 92% | | | | |
| | UO only | | | | | | |
| 0 hours | 1.65 | 77% | 23% | 1 | | | |
| | 0.818 | 85% | 0% | 2 | 1.0 | 0.1 | 7.1 |
| | 0.748 | 92% | 0% | 3 | 1.6 | 0.2 | 10.3 |
| | 2.89 | 23% | 73% | 4 | 1.2 | 0.2 | 9.1 |
| | 3.03 | 23% | 82% | | | | |
| | 3.49 | 15% | 91% | | | | |
| 24 hours | 1.65 | 77% | 23% | 1 | | | |
| | 0.818 | 85% | 0% | 2 | 1.0 | 0.1 | 7.1 |
| | 0.748 | 92% | 0% | 3 | 1.6 | 0.2 | 10.3 |
| | 2.89 | 23% | 73% | 4 | 1.2 | 0.2 | 9.1 |
| | 3.03 | 23% | 82% | | | | |
| | 3.49 | 15% | 91% | | | | |
| 48 hours | 1.65 | 77% | 23% | 1 | | | |
| | 0.818 | 85% | 0% | 2 | 1.0 | 0.1 | 7.1 |
| | 0.748 | 92% | 0% | 3 | 1.6 | 0.2 | 10.3 |
| | 2.89 | 23% | 73% | 4 | 1.2 | 0.2 | 9.1 |
| | 3.03 | 23% | 82% | | | | |
| | 3.49 | 15% | 91% | | | | |

Leukocyte Elastase:

| Time prior AKI stage | Cutoff value | sens | spec | Quartile | OR | 95% CI of OR | |
|---|---|---|---|---|---|---|---|
| | sCr or UO | | | | | | |
| 0 hours | 221.1787565 | 77% | 40% | 1 | | | |
| | 188.805483 | 85% | 32% | 2 | 1.5 | 0.2 | 13.4 |
| | 170.0160772 | 92% | 28% | 3 | 2.8 | 0.3 | 23.8 |
| | 422.6677578 | 46% | 72% | 4 | 2.3 | 0.3 | 18.6 |
| | 449.1945477 | 31% | 80% | | | | |
| | 563.8166047 | 23% | 92% | | | | |
| 24 hours | 221.1787565 | 77% | 40% | 1 | | | |
| | 188.805483 | 85% | 32% | 2 | 1.5 | 0.2 | 13.4 |
| | 170.0160772 | 92% | 28% | 3 | 2.8 | 0.3 | 23.8 |
| | 422.6677578 | 46% | 72% | 4 | 2.3 | 0.3 | 18.6 |
| | 449.1945477 | 31% | 80% | | | | |
| | 563.8166047 | 23% | 92% | | | | |
| 48 hours | 221.1787565 | 77% | 40% | 1 | | | |
| | 188.805483 | 85% | 32% | 2 | 1.5 | 0.2 | 13.4 |
| | 170.0160772 | 92% | 28% | 3 | 2.8 | 0.3 | 23.8 |
| | 422.6677578 | 46% | 72% | 4 | 2.3 | 0.3 | 18.6 |
| | 449.1945477 | 31% | 80% | | | | |
| | 563.8166047 | 23% | 92% | | | | |
| | sCr only | | | | | | |
| 0 hours | 239.3134715 | 75% | 40% | 1 | | | |
| | 79.57317073 | 100% | 10% | 2 | na | na | na |
| | 79.57317073 | 100% | 10% | 3 | na | na | na |
| | 449.1945477 | 0% | 70% | 4 | na | na | na |
| | 563.8166047 | 0% | 80% | | | | |
| | 564.2389525 | 0% | 90% | | | | |
| 24 hours | 239.3134715 | 75% | 40% | 1 | | | |
| | 79.57317073 | 100% | 10% | 2 | na | na | na |
| | 79.57317073 | 100% | 10% | 3 | na | na | na |
| | 449.1945477 | 0% | 70% | 4 | na | na | na |
| | 563.8166047 | 0% | 80% | | | | |
| | 564.2389525 | 0% | 90% | | | | |
| 48 hours | 239.3134715 | 75% | 40% | 1 | | | |
| | 79.57317073 | 100% | 10% | 2 | na | na | na |
| | 79.57317073 | 100% | 10% | 3 | na | na | na |
| | 449.1945477 | 0% | 70% | 4 | na | na | na |
| | 563.8166047 | 0% | 80% | | | | |
| | 564.2389525 | 0% | 90% | | | | |
| | UO only | | | | | | |
| 0 hours | 326.1047463 | 75% | 78% | 1 | | | |
| | 251.6366612 | 83% | 61% | 2 | 2.0 | 0.1 | 72.7 |
| | 170.0160772 | 92% | 33% | 3 | 4.5 | 0.1 | 138.9 |
| | 297.3977695 | 75% | 72% | 4 | 18.0 | 0.5 | 654.4 |
| | 422.6677578 | 58% | 83% | | | | |
| | 478.2786885 | 42% | 94% | | | | |
| 24 hours | 326.1047463 | 75% | 78% | 1 | | | |
| | 251.6366612 | 83% | 61% | 2 | 2.0 | 0.1 | 72.7 |
| | 170.0160772 | 92% | 33% | 3 | 4.5 | 0.1 | 138.9 |
| | 297.3977695 | 75% | 72% | 4 | 18.0 | 0.5 | 654.4 |
| | 422.6677578 | 58% | 83% | | | | |
| | 478.2786885 | 42% | 94% | | | | |
| 48 hours | 326.1047463 | 75% | 78% | 1 | | | |
| | 251.6366612 | 83% | 61% | 2 | 2.0 | 0.1 | 72.7 |
| | 170.0160772 | 92% | 33% | 3 | 4.5 | 0.1 | 138.9 |
| | 297.3977695 | 75% | 72% | 4 | 18.0 | 0.5 | 654.4 |
| | 422.6677578 | 58% | 83% | | | | |
| | 478.2786885 | 42% | 94% | | | | |

Soluble Tumor Necrosis Factor Receptor Superfamily Member 6:

| Time prior AKI stage | Cutoff value | sens | spec | Quartile | OR | 95% CI of OR | |
|---|---|---|---|---|---|---|---|
| | sCr or UO | | | | | | |
| 0 hours | 8367.071525 | 75% | 30% | 1 | | | |
| | 7442.572741 | 83% | 20% | 2 | 0.7 | 0.0 | 12.6 |
| | 7366.003063 | 92% | 20% | 3 | 2.0 | 0.1 | 32.1 |
| | 14514.4357 | 25% | 70% | 4 | 1.5 | 0.1 | 28.4 |
| | 15433.07087 | 17% | 80% | | | | |
| | 17742.78215 | 0% | 90% | | | | |
| 24 hours | 8367.071525 | 75% | 30% | 1 | | | |
| | 7442.572741 | 83% | 20% | 2 | 0.7 | 0.0 | 12.6 |
| | 7366.003063 | 92% | 20% | 3 | 2.0 | 0.1 | 32.1 |
| | 14514.4357 | 25% | 70% | 4 | 1.5 | 0.1 | 28.4 |
| | 15433.07087 | 17% | 80% | | | | |
| | 17742.78215 | 0% | 90% | | | | |
| 48 hours | 8367.071525 | 75% | 30% | 1 | | | |
| | 7442.572741 | 83% | 20% | 2 | 0.7 | 0.0 | 12.6 |
| | 7366.003063 | 92% | 20% | 3 | 2.0 | 0.1 | 32.1 |
| | 14514.4357 | 25% | 70% | 4 | 1.5 | 0.1 | 28.4 |
| | 15433.07087 | 17% | 80% | | | | |
| | 17742.78215 | 0% | 90% | | | | |
| | sCr only | | | | | | |
| 0 hours | 9831.546708 | 100% | 75% | 1 | | | |
| | 9831.546708 | 100% | 75% | 2 | na | na | na |
| | 9831.546708 | 100% | 75% | 3 | na | na | na |
| | 9831.546708 | 100% | 75% | 4 | na | na | na |
| | 14514.4357 | 50% | 100% | | | | |
| | 14514.4357 | 50% | 100% | | | | |
| 24 hours | 9831.546708 | 100% | 75% | 1 | | | |
| | 9831.546708 | 100% | 75% | 2 | na | na | na |
| | 9831.546708 | 100% | 75% | 3 | na | na | na |
| | 9831.546708 | 100% | 75% | 4 | na | na | na |

-continued

| Time prior AKI stage | Cutoff value | sens | spec | Quartile | OR | 95% CI of OR | |
|---|---|---|---|---|---|---|---|
|  | 14514.4357 | 50% | 100% |  |  |  |  |
|  | 14514.4357 | 50% | 100% |  |  |  |  |
| 48 hours | 9831.546708 | 100% | 75% | 1 |  |  |  |
|  | 9831.546708 | 100% | 75% | 2 | na | na | na |
|  | 9831.546708 | 100% | 75% | 3 | na | na | na |
|  | 9831.546708 | 100% | 75% | 4 | na | na | na |
|  | 14514.4357 | 50% | 100% |  |  |  |  |
|  | 14514.4357 | 50% | 100% |  |  |  |  |
|  |  |  | UO only |  |  |  |  |
| 0 hours | 8897.396631 | 70% | 22% | 1 |  |  |  |
|  | 7442.572741 | 80% | 22% | 2 | 1.0 | 0.0 | 26.2 |
|  | 7366.003063 | 90% | 22% | 3 | 6.0 | 0.1 | 356.1 |
|  | 15433.07087 | 20% | 78% | 4 | 1.5 | 0.0 | 54.5 |
|  | 17742.78215 | 0% | 89% |  |  |  |  |
|  | 18935.44734 | 0% | 100% |  |  |  |  |
| 24 hours | 8897.396631 | 70% | 22% | 1 |  |  |  |
|  | 7442.572741 | 80% | 22% | 2 | 1.0 | 0.0 | 26.2 |
|  | 7366.003063 | 90% | 22% | 3 | 6.0 | 0.1 | 356.1 |
|  | 15433.07087 | 20% | 78% | 4 | 1.5 | 0.0 | 54.5 |
|  | 17742.78215 | 0% | 89% |  |  |  |  |
|  | 18935.44734 | 0% | 100% |  |  |  |  |
| 48 hours | 8897.396631 | 70% | 22% | 1 |  |  |  |
|  | 7442.572741 | 80% | 22% | 2 | 1.0 | 0.0 | 26.2 |
|  | 7366.003063 | 90% | 22% | 3 | 6.0 | 0.1 | 356.1 |
|  | 15433.07087 | 20% | 78% | 4 | 1.5 | 0.0 | 54.5 |
|  | 17742.78215 | 0% | 89% |  |  |  |  |
|  | 18935.44734 | 0% | 100% |  |  |  |  |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating a risk of future acute kidney injury in a subject and treating the subject based on the evaluation, the method comprising:
    detecting soluble tumor necrosis factor receptor superfamily member 6 in a urine sample with an antibody which specifically binds to the soluble tumor necrosis factor receptor superfamily member 6 using an immunoassay; and generating an assay result indicative of binding of the soluble tumor necrosis factor receptor superfamily member 6 to the antibody;
    correlating the assay result to an increased risk of the subject developing a future acute kidney injury meeting the definition of RIFLE I or F when the assay result is above a predetermined threshold value; and
    treating the subject having the increased risk of developing a future acute kidney injury meeting the definition of RIFLE I or F with a compatible treatment regimen comprising one or more of initiating renal replacement therapy and withdrawing delivery of compounds that are known to be damaging to the kidney.

2. The method according to claim 1, wherein said assay result comprises a measured concentration of the soluble tumor necrosis factor receptor superfamily member 6.

3. The method of claim 1, wherein the treatment regimen comprises the renal replacement therapy.

4. The method of claim 3, wherein the renal replacement therapy comprises hemodialysis, peritoneal dialysis, hemofiltration, and/or renal transplantation.

5. A method of treating a subject at increased risk of a future acute kidney injury, the method comprising:
    determining the subject is at increased risk of a future acute kidney injury by performing an assay to detect soluble tumor necrosis factor receptor superfamily member 6 in a urine sample obtained from the subject, wherein the level of the soluble tumor necrosis factor receptor superfamily member 6 in the urine is above a predetermined threshold level; and
    treating the subject having an increased risk of future acute kidney injury with a compatible treatment regimen comprising one or more of initiating renal replacement therapy and withdrawing delivery of compounds that are known to be damaging to the kidney.

6. The method of claim 5, wherein the assay comprises (i) contacting the urine sample with an antibody which specifically binds soluble tumor necrosis factor receptor superfamily member 6, and (ii) generating an assay result indicative of binding of soluble tumor necrosis factor receptor superfamily member 6 to the antibody.

7. The method of claim 5, wherein the treatment regimen comprises the renal replacement therapy.

8. The method of claim 7, wherein the renal replacement therapy comprises hemodialysis, peritoneal dialysis, hemofiltration, and/or renal transplantation.

* * * * *